US007279557B2

(12) United States Patent
Hilton et al.

(10) Patent No.: US 7,279,557 B2
(45) Date of Patent: Oct. 9, 2007

(54) THERAPEUTIC AND DIAGNOSTIC AGENTS

(75) Inventors: Douglas J. Hilton, Warrandyte (AU); Warren S. Alexander, Moonee Pounds (AU); Elizabeth M. Viney, Bundoora (AU); Tracy A. Willson, North Balwyn (AU); Rachael T. Richardson, East Brighton (AU); Robyn Starr, Carlton (AU); Sandra E. Nicholson, Newport (AU); Donald Metcalf, Balwyn (AU); Nicos A. Nicola, Mont Albert (AU)

(73) Assignee: The Walter and Eliza Hall Institute of Medical Research, Parkville, Victoria (AU)

( * ) Notice: Subject to any disclaimer, the term of this patent is extended or adjusted under 35 U.S.C. 154(b) by 41 days.

(21) Appl. No.: 10/991,181

(22) Filed: Nov. 17, 2004

(65) Prior Publication Data

US 2005/0208521 A1 Sep. 22, 2005

Related U.S. Application Data

(63) Continuation of application No. 08/962,560, filed on Oct. 31, 1997, now Pat. No. 6,905,842.

(30) Foreign Application Priority Data

Nov. 1, 1996 (AU) .................................... PO3384
Feb. 14, 1997 (AU) .................................... PI5117

(51) Int. Cl.
*C07K 14/00* (2006.01)
*C07H 17/00* (2006.01)

(52) U.S. Cl. .................................... 530/350; 536/23.1

(58) Field of Classification Search ................ 530/350; 536/23.1

See application file for complete search history.

(56) References Cited

U.S. PATENT DOCUMENTS 5,871,960 A 2/1999 Smith et al.
6,323,317 B1 11/2001 Hilton et al.

FOREIGN PATENT DOCUMENTS

| | | |
|---|---|---|
| EP | 0 989 186 A1 | 3/2000 |
| WO | 94/28156 | 12/1994 |
| WO | WO98/30688 | 7/1998 |
| WO | WO99/03993 | 1/1999 |

OTHER PUBLICATIONS

Yoshimura et al. 1995; A novel cytokine inducible gene CIS encodes an SH2-containing protein that binds to tyrosine-phosphorylated interleukin 3 and erythropoietin receptors. EMBO J. 14 (12): 2816-2826.*

Mashura et al. Oct. 1997; Cloning and characterization of novel CIS family genes. Biochem. Biophys. Res. Commun. 239: 439-446.*

Accession No. Z4752, ID:MMPRMGNS (1995), XDP-002165867 (Abstract).

Schluter, G. et al., "Sequence Analysis of the Conserved Protamine Gene Cluster Shows That it Contains a Fourth Expressed Gene", *Molecular Reproduction and Development 43*:1-6 (1996), XP-000993037.

Accession No. Z46940; ID: HSPRMTNP2 (1995), XP-002165868 (Abstract).

Accession No. Z46939; ID: BTPRMTNP2 (1995) (Abstract).

Yoshimura, A. et al., "A Novel Cytokine-Inducible Gene CIS Encodes an SH2-Containg Protein that Binds to Tyrosine-Phosphorylated Interleukin 3 and Erythropoietin Receptors", *The EMBO Journal 14*(12):2816-2826 (1995), XP-002088456.

Minamoto, S. et al., "Cloning and Functional Analysis of New Members of STAT Induced STAT Inhibitor (SSI) Family: SSI-2 and SSI-3", *Biochemical and Biophysical Research Communications 237*:79-83 (1997), XP-002095406.

Accession No. U72673, ID: MMU72673 (1997), XP-002172403 (Abstract).

Fu, X., et al., "E2a-Pbx1 Induces Aberrant Expression of Tissue-Specific and Developmentally Regulated Genes When Expressed in NIH 3T3 Fibroblasts", *Molecular and Cellular Biology 17*(3): 1503-1512 (1997), XP-002172402.

Starr, R. et al., "A Family of Cytokine-Inducible Inhibitors of Signalling", *Nature 387*: 917-921 (1997), XP-002085491.

Endo, T.A. et al., "A New Protein Containing an SH2 Domain that Inhibits JAK Kinases", *Nature 387*: 921-924 (1997), XP-002085492.

Naka, T. et al., "Structure and Function of a New STAT-Induced STAT Inhibitor", *Nature 387*: 924-928 (1997), XP-002088455.

Accession No. AA189608, ID: MMAA81160 (1997), XP-002172404 (Abstract).

Hilton, D.J. et al., "Twenty Proteins Containing a C-Terminal SOCS Box Form Five Structural Classes", *Proceedings of the National Academy of Sciences of USA 95*: 114-119 (1998), XP-002085497.

Watson et al. *Molecular Biology of the Gene*, 4th edition. Inside cover (1987).

Hilton et al. Twenty proteins containing a C-terminal SOCS box form five structural classes. *Proc. Natl Acad Sci USA 95*:114-119 (1998).

* cited by examiner

*Primary Examiner*—Karen Cochrane Carlson
(74) *Attorney, Agent, or Firm*—Scully, Scott, Murphy & Presser, P.C.

(57) ABSTRACT

The present invention relates generally to therapeutic and diagnostic agents. More particularly, the present invention provides therapeutic molecules capable of modulating signal transduction such as but not limited to cytokine-mediated signal transduction. The molecules of the present invention are useful, therefore, in modulating cellular responsiveness to cytokines as well as other mediators of signal transduction such as endogenous or exogenous molecules, antigens, microbes and microbial products, viruses or components thereof, ions, hormones and parasites.

12 Claims, 89 Drawing Sheets

```
-159                                  cgaggctcaagctccgggcggattctgcgtgccgctctcg
-120      ctccttggggtctgttggccggcctgtgccacccggacgcccggctcactgcctctgtct
-60       cccccatcagcgcagccccggacgctatggcccacccctccagctggcccctcgagtagg

1         ATGGTAGCACGCAACCAGGTGGCAGCCGACAATGCGATCTCCCCGGCAGCAGAGCCCCGA
1         MetValAlaArgAsnGlnValAlaAlaAspAsnAlaIleSerProAlaAlaGluProArg

61        CGGCGGTCAGAGCCCTCCTCGTCCTCGTCTTCGTCCTCGCCAGCGGCCCCCGTGCGTCCC
21        ArgArgSerGluProSerSerSerSerSerSerSerSerProAlaAlaProValArgPro

121       CGGCCCTGCCCGGCGGTCCCAGCCCCAGCCCCTGGCGACACTCACTTCCGCACCTTCCGC
41        ArgProCysProAlaValProAlaProAlaProGlyAspThrHisPheArgThrPheArg

181       TCCCACTCCGATTACCGGCGCATCACGCGGACCAGCGCGCTCCTGGACGCCTGCGGCTTC
61        SerHisSerAspTyrArgArgIleThrArgThrSerAlaLeuLeuAspAlaCysGlyPhe

241       TATTGGGGACCCCTGAGCGTGCACGGGGCGCACGAGCGGCTCCTGGACGCCTGCGGCTTC
81        TyrTrpGlyProLeuSerValHisGlyAlaHisGluArgLeuArgAlaGluProValGly

301       ACCTTCTTGGTGCGCGACAGTCGTCAACGGAACTGCTTCTTCGCGCTCAGCGTGAAGATG
101       ThrPheLeuValArgAspSerArgGlnArgAsnCysPhePheAlaLeuSerValLysMet
```

```
361     GCTTCGGGCCCCACGAGCATCCGCGTGCACTTCCAGGCCGGCCGCTTCCACTTGGACGGC
121     AlaSerGlyProThrSerIleArgValHisPheGlnAlaGlyArgPheHisLeuAspGly

421     AGCCGCGAGACCTTCGACTGCCTTTTCGAGCTGCTGGAGCACTACGTGGCGGCGCCGCGC
141     SerArgGluThrPheAspCysLeuPheGluLeuLeuGluHisTyrValAlaAlaProArg

491     CGCATGTTGGGGGCCCCGCTGCGGCCAGCGCCGCGTGCGGCCGCTGCAGGAGCTGTGCGC
161     ArgMetLeuGlyAlaProLeuArgGlnArgArgValArgProLeuGlnGluLeuCysArg

541     CAGCGCATCGTGGCCGCCGTGGGTCGCGAGAACCTGG GCGCATCCCTCTTAACCCGGTA
191     GlnArgIleValAlaAlaValGlyArgGluAsnLeuAlaArgIleProLeuAsnProVal

601     CTCCGTGACTACCTGAGTTCCTTCCCCTTCCAGATCtgaccggctgccgctgtgccgcag
201     LeuArgAspTyrLeuSerSerPheProPheGluIle*
```

```
661     cattaagtggggcgccttattatttcttattattaattattattatttttctggaacca
721     cgtgggagccctccccgcctgggtcggagggagtggttgtggagggtgagatgcctccca
781     cttctggctggagacctcatcccacctctcaggggtgggggtgctcccctcctggtgctc
841     cctccgggtccccccctggttgtagcagcttgtgtctggggccaggacctgaattccactc
901     ctacctctccatgtttacatattcccagtatctttgcacaaaccaggggtcggggagggt
961     ctctggcttcatttttctgctgtgcagaatatcctattttatatttttacagccagttta
1021    ggtaataaactttattatgaaagtttttttttaaaagaaaaaaaaaaaaaaaaaa
```

Figure 3B(3)

```
hsSOCS.1  (1)  MVAHNQVAADNAVSTAAEPRRRPEPSSSSSSS.PAAPARPRPCPAVPAPA  (49)
rrSOCS.1  (1)  MVABNQVEADNAISPASEPRRRPEPSSSSSSSSPAAPARPRPCPVVPAPA  (50)
mmSOCS.1  (1)  MVARNQVAADNAISPAAEPRRRSEPSSSSSSSSPAAPVRPRPCPAVPAPA  (50)
mmSOCS.2  (1)  MTLRCLEPSGNGADRTRSQWGTAGLPEEQSPEA.................  (33)
mmSOCS.3  (1)  MVTHSKFPAAGMSR....................................  (14)
mmCIS     (1)  MVLCVQGSCPLLAVEQIGRRPLWAQSLELPGPAMQPLPTGAFPEEVTEET  (50)

hsSOCS.1 (50)  PGDTHF..RTFRSHADYRRITRASALLDACGFYWGPLSVHGAHERLRAEP  (97)
rrSOCS.1 (51)  PGDTHF..RTFRSHSDYRRITRTSALLDACGFYWGPLSVHGAHERLRSEP  (98)
mmSOCS.1 (51)  PGDTHF..RTFRSHSDYRRITRTSALLDACGFYWGPLSVHGAHERLRAEP  (98)
mmSOCS.2 (34)  .................ARLAKALRELSQTGWYWGSMTVNEAKEKLKEAP  (66)
mmSOCS.3 (15)  PLDTSLRLKTFSSKSEYQLVVHAVRKLQESGFYWSAVTGGEANLLLSAEP  (64)
mmCIS    (51)  PVQAENEPKVLDPEGDLLCIAKTFSYLRESGWYWGSITASEARQHLQKMP  (100)
```

```
hsSOCS.1  (98)  VGTFLVRDSRQRNCFFALSVKMASGPTSIRVHFQAGRFHLD......GSR  (141)
rrSOCS.1  (99)  VGTFLVRDSRQRNCFFALSVKMASGPTSIRVHFQAGRFHLD......GNR  (142)
mmSOCS.1  (99)  VGTFLVRDSRQRNCFFALSVKMASGPTSIRVHFQAGRFHLD......GSR  (142)
mmSOCS.2  (67)  EGTFLIRDSSHSDYLLTISVKTSAGPTNLRIEYQDGKFRLDSIICVKSKL  (116)
mmSOCS.3  (65)  AGTFLIRDSSDQRHFFTLSVKTQSGTKNLRIQCEGGSFSLQSDPRSTQPV  (117)
mmCIS     (101) EGTFLVRDSTHPSYLFTLSVKTTRGPTNVRIEYADSSFRLDSNCLSRPRI  (150)

hsSOCS.1  (142) ESFDCLFELLEHYVAAPRRMLGAP..........................  (165)
rrSOCS.1  (143) ETFDGLFELLEHYVAAPRRMLGAP..........................  (166)
mmSOCS.1  (143) ETFDCLFELLEHYVAAPRRMLGAP..........................  (166)
mmSOCS.2  (117) KQFDSVVHLIDYYVQMCKQKRTGP..........................  (140)
mmSOCS.3  (115) PRFDCVLKLVHHYMPPPGTPSFSLPPTEPSSEVPEQPPAQALPGSTPKRA  (164)
mmCIS     (151) LAFPDVVSLVQHYVASCAADTRSDSPDPAPTPALPMSKQDAPSDSVLPIP  (200)
```

```
hsSOCS.1  (166)  ................LRQRRVRPLQELCRQRIVATVGR.ENLARIPLNP  (198)
rrSOCS.1  (167)  ................LRQRRVRPLQELCRQRIVAAVGR.ENLARIPLNP  (199)
mmSOCS.1  (167)  ................LRQRRVRPLQELCRQRIVAAVGR.ENLARIPLNP  (199)
mmSOCS.2  (141)  ..EAPRNGTVHLYLTKPLYTSAPTLQHFCRLAINKCTGT...IWGLPLPT  (185)
mmSOCS.3  (165)  YYIYSGGEKIPLVLSRPLSSNVATLQHLCRKTVNGHLDSYEKVTQLPGP.  (213)
mmCIS     (201)  ...VATAVHLKLVQPFVRRSSARSLQHLCRLVINRLVAD...VDCLPLPR  (244)

hsSOCS.1  (199)  VLRDYLSSFPFQI  (211)
rrSOCS.1  (200)  VLRDYLSSFPFQI  (212)
mmSOCS.1  (200)  VLRDYLSSFPFQI  (212)
mmSOCS.2  (186)  RLKDYLEEYKFQV  (198)
mmSOCS.3  (214)  .IREFLDQYDAPL  (225)
mmCIS     (245)  RMADYLRQYDFQL  (257)
```

Figure 9(III)

Bone Marrow

```
mmSOCS-1    SH2  MVARNQVAADNAISPAAEPRRRSEPSSSSSSSPAAPVRP
mSOCS-3     SH2  MVTHSKFPAAGMSR.........................
mSOCS-2     SH2  MTLRCLEPSGNGADRTRSQWGTAGLPEEQSPEA.......
mCIS        SH2  MVLCVQGSCPLLAVEQIGRRPLWAQSLELPGPAMQPLPTG
mSOCS-5     SH2  MDKVGKMWNNLKYRCQNLFSHEGGSRNENVEMNPNRCPSV
mSOCS-14    SH2  SGGGPWRAGGGSGKSDSGLTVEPGRGLTARPPPGGSRTRS
mmSOCS-4    WD   MASFPPRVNE
mmSOCS-6    WD   ME
mmSOCS-15   WD   MGQTAL

mSOCS-5     SH2  AEIPQVVEISIEKDSDSGATPGTRLARRDSYSRHAPWGGK
mSOCS-14    SH2  NFLLEKLKNTVFITLEIVKNLFKMAENNSKNVDVRPKTSR

mSOCS-5     SH2  VSSRAVGSRSLRQRLQDTVGLCFPMRTYSKQSKPLFSNKR
mSOCS-14    SH2  SQERQLSCSSIELDLDHSCGHRFLGRSLKQKLQDAVGQCF

mSOCS-5     SH2  TFFDTFDPSLVSTEDEEDRLRERRRLSIEEGVDPPPNAQI
mSOCS-14    SH2  IKRHTVPMSPNSDEWVSADLSERKLRDAQLKRRNTEDDIP

mSOCS-5     SH2  SEEDSTTLCLQSRRQKQRQVSGDSHAHVSRQGAWKVHTQI
mSOCS-14    SH2  SEDEIITLCTSSRKRNKPRWEMEEEILQLEAPP KFHTQI
```

FIG. 13 A (i)

```
mmSOCS-1    SH2  R P C P A V P A P A
mSOCS-3     SH2  . . . . . . . . . .
mSOCS-2     SH2  . . . . . . . . . .
mCIS        SH2  . . . . . . . . . .
mSOCS-5     SH2  K E K S I S L G E A A P Q Q E S S P L R E N V A L Q L G L S P S K T F S R R N Q N C A
mSOCS-14    SH2  G S G R A S L P R L S E R R V M A V V M A A G A R T A P L E L S S E R S V Q K V P R R
mmSOCS-4    WD
mmSOCS-6    WD
mmSOCS-15   WD

mSOCS-5     SH2  K K H S C S T K T Q S S L D T E K K F G R T R S G L Q R R E R R Y G V S S M Q D M D S
mSOCS-14    SH2  S R S A D R K D G Y V W S G K K L S W S K K S E S C S E S E A I G T V E N V E I P L R

mSOCS-5     SH2  K I H L S E L M L E K C P F P A G S D L A Q K W H L I K Q H T A P V S         P H S
mSOCS-14    SH2  P I K N C S G R H S P G L P S K R K I H I S E L M L D K C P F P P R S D L A F R W H F

mSOCS-5     SH2  H T F E A T A Q V N P L Y K         G P K L A P G M T E I S G D G S A I P Q X N C D
mSOCS-14    SH2  C F S H T N G Q P C V I T A N S A S C T G G H I T G S M M N L V T N N S I E D S D M D

mSOCS-5     SH2  D Y I H C L V P D L L Q I T G N P
mSOCS-14    SH2  D Y V H C L V P D L L Q I S N N P
```

FIG. 13 A (ii)

```
                    YFH    T                         T       D              T
CONSENSUS           GWYoG oS     o  EbaL          GSFLoRES              oSo
mSOCS-1     SH2     GFYWGPLSVHGAHERLRAEPVGTFLVRDSRQRNCFALSVK
mSOCS-3     SH2     GFYWSAVTGGEANLLLSAEPAGTFLIRDSSDQRHFTLSVK
mSOCS-2     SH2     GWYWGSMTVNEAKEKLKEAPEGTFLIRDSSHSDYLTISVK
mCIS        SH2     GWYWGSITASEARQHLQKMPEGTFLVRDSTHPSYFTLSVK
mSOCS-5     SH2     PCYWGVMDRYEAEALLEGKPEGTFLLRDSAQEDYFSVSFR
mSOCS-14    SH2     PCYWGVMDXYAAEALLEGKPEGTFLLRDSAQEDYFSVSFR
hSOCS-9     SH2     GWYWGPITRWEAEGKLANVPDGSFLVRDSSDDRYLSCDFR
hSOCS-11    SH2     GWYWGPMNWEDAEMKLKGKPDGSFLVRDSSDPRYLSLSFR
```

FIG. 13 B (i)

```
                              R        T                        E        Y H
                       G    o K o    G  F S o                   D o o    H Y
CONSENSUS
mSOCS-1    SH2   M A S G P T S I R V H F Q A G R F H L D G S R E T F                D C L F E L L E H Y
mSOCS-3    SH2   T Q S G T K N L R I Q C E G G S F S L Q S D P R S T Q P V P R F    D C V L K L V H H Y
mSOCS-2    SH2   T S A G P T N L R I E Y Q D G K F R L D S I I C V K S K L K Q F    D S V V H L I D Y Y
mCIS       SH2   T T R G P T N V R I E Y A D S S F R L D S N C L S R P R I L A F P  D V V   S L V Q H Y
mSOCS-5    SH2   R Y N R S L H A R I E Q W N H N F S F D A H D P C V F H S S        T V T G   L L E H Y
mSOCS-14   SH2   R Y S R S L H A R I E Q W N H N F S F D A H D P C V F H S P        D I T G   L L E H Y
hSOCS-9    SH2   S H G K T L H T R I E H S N G R F S F Y E Q X D V E G H T S I V    D L I G A F N Q G L
hSOCS-11   SH2   S Q G I T H H T R M E H Y R G T F S L W C H P K F E D R C Q S V V  E F I K R A I M H S
```

FIG. 13 B (ii)

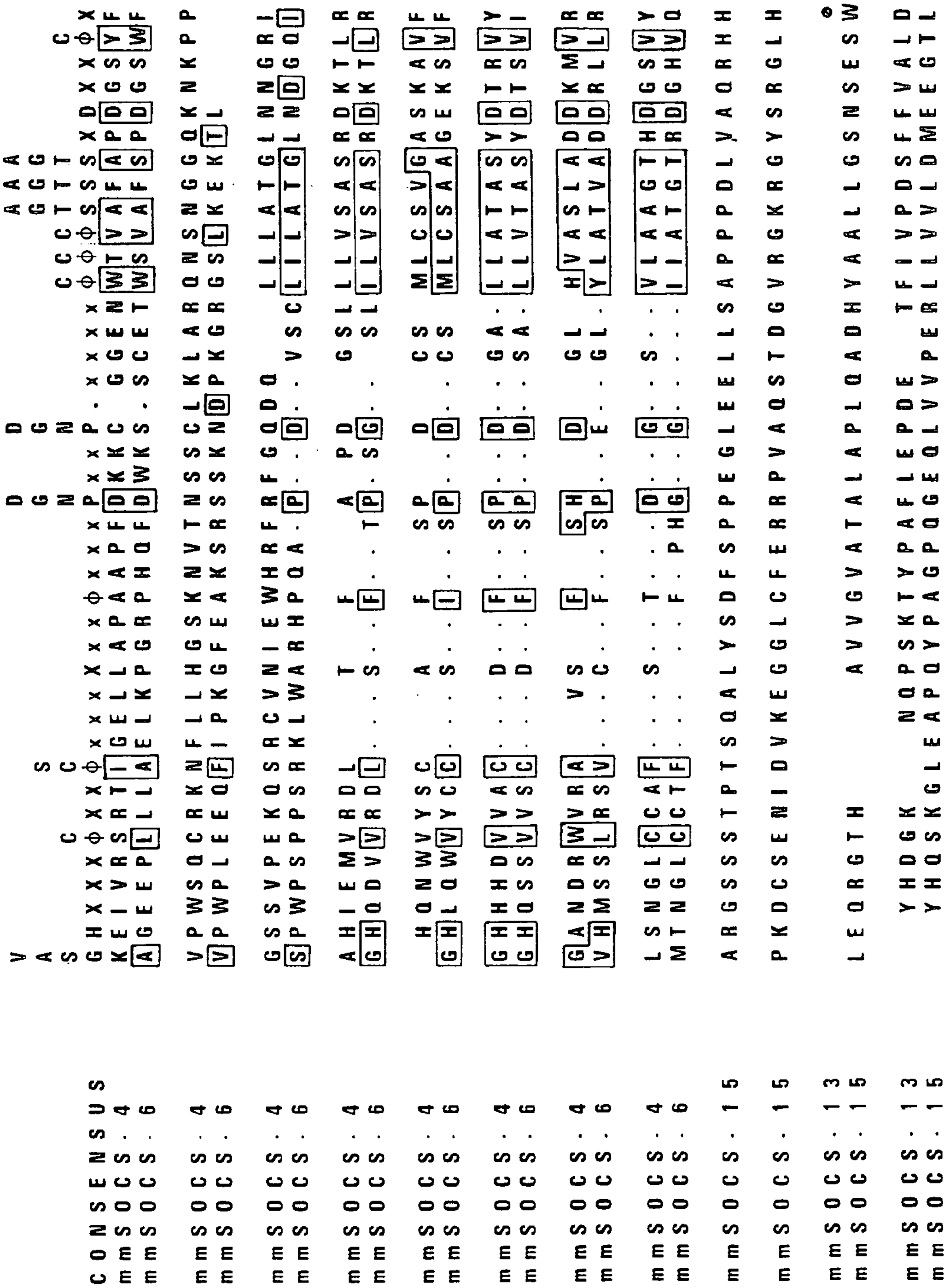
FIG. 13C (ii)

```
              K
            Y N
          C F R
CONSENSUS Φ W D
mmSOCS-4  A W S Q G Y R I V K L
mmSOCS-6  A W S Q G H C V V K L

mmSOCS-4  E H V I D C G D I V W S L A F
mmSOCS-6        D C G Q I V W G V A F

mmSOCS-4  K I W D V Y T G K L L L L N L V D
mmSOCS-6  K I W E V Q T G L   L L L N L S

mmSOCS-4  V W D L K D D G N M V K V L R
mmSOCS-6  I W D L N K H G K Q I Q V L S

mmSOCS-4  L W N M D K Y T M I R K L E
mmSOCS-6  L W S M R S Y T L I R K L E

mmSOCS-4  V W D P H N G D L L M E F G H L F P S P T P I F A G
mmSOCS-6  M W D P Y T G A R L R S L H H T Q L E P T M D D S D

mmSOCS-4  F Y R I D E D C P V Q V A P
mmSOCS-6  I W A · L E L K A P V A F A P

mmSOCS-4  F W A
mmSOCS-6  F W T

mmSOCS-15 G W N

mmSOCS-15 A W E

mmSOCS-13 G W D I S W P L G R N R L
mmSOCS-15 G W D         I G R G K L

mmSOCS-13 M X D
mmSOCS-15 G Y S
```

FIG. 13 C (iii)

```
                           T                          po
ONSENSUS                   S  L H φ A φ               φ φ φ    G  po
SOCS-7        ANK    • P C T P L R I A A T A G H G N C V D F L I R K G A E V D L V D V
SOCS-7        ANK    K G Q T A L Y V A V V N G H L E S T E I L L E A G A D P N G S R H
SOCS-7        ANK    H R S T P V Y H A X R V G R D D I L K A L I R Y G A D V D V N H H L N S D T R P P F S R R L T S
SOCS-7        ANK    L V V C P L Y I S A A Y H N L Q C F R L L L Q A G A N P D F N C N G P V N T Q E F Y R G S
SOCS-7        ANK    P G C V M D A V L R H G C E A A F V S L L V E F G A N L N

SOCS-10       ANK    • E E T A L Y L A T C R E H L D C L L S L L Q A G A E P D I S N K
SOCS-10       ANK    S R E T P L Y K A C E R K N A E A V R I L V R Y N A D A N H R C N
SOCS-10       ANK    R G W T A L H E S V S R N D L E V M E I L V S G G A K V E A K N V
SOCS-10       ANK    Y S I T P L F V A A Q S G Q L E A L R F L A K H G A D I N T Q A S
SOCS-10       ANK    D S A S A L Y E A S K N E H E D V V E F L L S Q G A D A N K A N K
SOCS-10       ANK    D G L L P L H V A S K K G N Y R I V Q M L L P V T S R T R V R R
SOCS-10       ANK    S G I S P L H L A A E R N H D A V L E A L L A A R F D V N A P L A P E R A R L Y
SOCS-10       ANK    E D R R S S A L Y F A V N N V Y A T E L L L L A G A D P N R
SOCS-10       ANK    D V I S P L L V A I R H G C L R T M Q L L L D H G A N I D A •
```

FIG. 13 D

| | | |
|---|---|---|
| mSOCS-1 | SH2 | |
| mSOCS-3 | SH2 | MPPPGTPSFSLPPTEPSSEVPEQPPAQALPGSTPKRAYYI |
| mSOCS-2 | SH2 | VQMCKDKRTGPE |
| mCIS | SH2 | VASCAADTRSDSPDPAPTPALPMSKQDAPSDSVLPIP |
| mSOCS-5 | SH2 | KDP |
| mSOCS-14 | SH2 | KDP |
| hSOCS-9 | SH2 | .... CYSRSQLP |
| hSOCS-11 | SH2 | KNGKFLYFLRSRVP |
| mSOCS-4 | WD | |
| mSOCS-6 | WD | |
| mSOCS-13 | WD | GTLSFIVDGQYMGVAFRGLKGKKLYPVVSAV |
| mSOCS-15 | WD | IGGTYLGPAFRGLKGRTLYPSVSAV |
| mSOCS-7 | ANK | LVKWESLGPEARGRRKMDPEALQVFKEARSI |

FIG. 13 E (i)

| | | |
|---|---|---|
| | | QRR |
| mSOCS-1 | SH2 | SSN |
| mSOCS-3 | SH2 | VAAPRRMLGAPLRYTS |
| mSOCS-2 | SH2 | YSGGEKIPLVLSRPLRSS |
| mCIS | SH2 | APRNGTVHLYLTKPLRTF |
| mSOCS-5 | SH2 | VATAVHLKLVQPFVRRTF |
| mSOCS-14 | SH2 | SSCMFFEPLLTISLNFXX |
| hSOCS-9 | SH2 | SACMFFEPLLSTPLIFSN |
| hSOCS-11 | SH2 | GSATYLVRLAKPVSRPRQ |
| mSOCS-4 | WD | GLPPTPVQLLYPVSRPRV |
| mSOCS-6 | WD | TDPE |
| mSOCS-13 | WD | TAVEE |
| mSOCS-15 | WD | WGHCEIRMRYL NGL |
| mSOCS-7 | ANK | WGQCQVRIRYMGERR |

FIG. 13 E (ii)

```
                   P
             P T  H         T                      F
CONSENSUS    φ SL Yφ CR  φ   φ          φ  φPφP  φ  Yφ
mSOCS-1  SH2 VRPLQELCRQRIVAAVGREN......LARIPLNPVLRDYL
mSOCS-3  SH2 VATLQHLCRKTVNGHLDSYEK.....VTQLPGP  IREFL
mSOCS-2  SH2 APTLQHFCRLAINKCTGT........IWGLPLPTRLKDYL
mCIS     SH2 ARSLQHLCRLVINRLVAD........VDCLPLPRRMADYL
mSOCS-5  SH2 PFSLQYICRAVICRCTTYDG......IDGLPLPSMLQDFL
mSOCS-14 SH2 PFSLQHICRTVICNCTTYDG......IDALPIPSPMKLYL
hSOCS-9  SH2 VRSLQYLCRFVICQYTRIDL......IQKLPLPNKMKDYL
hSOCS-11 SH2 VKSLQHLCRFRIRQYTRIDH......IPDLPLPKPLISYI
mSOCS-4  WD  VPSLQHICRMSIRRVMSTQE......VQKLPVPSKILAFL
mSOCS-6  WD  LSSLKHLCRKALRSFLTTYQ......VLALPIPKKMKEFL
mSOCS-13 WD  PLPLMDLCRRSVRLALGKERLGA...IPALPLPASLKAYL
mSOCS-15 WD  PQSLLHLSRLCVRHALGDTRLGQ...ISTLPLPPAMKRYL
mSOCS-7  ANK PRTLLSLCRVAVRRALGKYRLHL...VPSLPLPDPIKKFL
mSOCS-10 ANK PRPLAHLCRLRVRKAIGKYRIKL...LDTLPLPGRLIRYL
mSOCS-12 ANK VPSLTHLCRLEIRASLKAEHLHSDIFIHQLPLPRSLQNYL
mSOCS-8  ?   PRSLQHLCRCALRSHLEGCLPHA...LPRLPLPPRMLRFL
```

FIG. 13 F (i)

| | | |
|---|---|---|
| ONSENSUS | | |
| SOCS-1 | SH2 | SSFPFQI* |
| SOCS-3 | SH2 | DQYDAP* |
| SOCS-2 | SH2 | EEYKFQV* |
| CIS | SH2 | RQYPFQL* |
| SOCS-5 | SH2 | KEYHYKQKVRVRWLE |
| SOCS-14 | SH2 | KEYHYKSKVRLLRIDLKEAQRQFPNRSKRWNPPRSEGLPAGHHQGHLV* |
| SOCS-9 | SH2 | QEKHY* |
| SOCS-11 | SH2 | RKFYYYDPQEEVYLS |
| SOCS-4 | WD | SYRG* |
| SOCS-6 | WD | TYRTF* |
| SOCS-13 | WD | LYQ* |
| SOCS-15 | WD | LY* |
| SOCS-7 | ANK | YE* |
| SOCS-10 | ANK | KYENTQ* |
| SOCS-12 | ANK | LYEEVLRMNEILEPA |
| SOCS-8 | ? | QLDFEDLLY* |

FIG. 13 F (ii)

cgaattccgggcgggctgtgtgagtctgtgagtggaaggcgcgccggctcttttgtctgagtgtgacccggtggctttgtt
ccaggcattccggtgatttcctccgggcagtccgcagaagccgcagcggccgcccgcgctctctctgcagtctccacacc
cgggagagcctgagcccgcgtcacgcccctcagcccccgctgagtcccttctctgttgtcgcgtccgaatcgagttcccg
gaatcagacggtgccccatagATGGCCAGCTTTCCCCCGAGGGTTAACGAGAAAGAGATCGTGAGATCACGTACTATAGG
GGAACTCTTGGCTCCAGCAGCTCCTTTTGACAAGAAATGTGGTGGTGAGAACTGGACGGTTGCTTTTGCTcCTGATGGTT
CCTACTTTGCGTGGTCACAAGGATATCGCATAGTGAAGCTTGTCCCGTGGTCCCAGTGCCGTAAGAACTTTCTTTTGCAT
GGTTCCAAAAATGTTACCAATTCAAGCTGTCTAAAATTGGCAAGACAAAACAGTAATGGTGGTCAGAAAAACAAGCCTCC
TGAGCACGTTATAGACTGTGGAGACATAGTCTGGAGTCTTGCTTTTGGGTCTTCAGTTCCAGAAAAACAGAGTCGTTGCG
TTAATATAGAATGGCATCGGTTCCGATTTGGACAGGATCAGCTACTCCTTGCCACAGGATTAAACAATGGTCGCATCAAA
ATCTGGGATGTATATACAGGAAAACTCCTCCTTAATTTGGTAGACCACATTGAAATGGTTAGAGATTTAACTTTTGCTCC
AGATGGGAGCTTACTCCTTGTATCAGCTTCAAGAGACAAAACTCTAAGAGTGTGGGACCTGAAAGATGATGGAAACATGG
TGAAAGTATTGCGGGCACATCAGAATTGGGtGtACAGTTGTGCATTcTCTCCcGACTGTTcTATGCTGTGTTCAGTgGGC
GCCAGTAAAGCAGTTTTcCTTTGGAATATGGATAAAtACACCATGATTAGGAAGcTGGAAGGTCATCACCATGATGTTGT
AGCTTGTGACTTTTCTCCTGATGGAGCATTGCTAgCTACTGCATCCTATGACACTCGTGTGTATGTCTGGGATCCACACA
ATGGAGACCTTCTGATGGAGTTTGGGCACCTGTTTCCCTCGCCCACTCCAATATTTGCTGGAGGAGCAAATGACCGATGG
GTGAGAGCTGTGTCTTTCAGTCATGATGGACTGCATGTTGCCAGCCTTGCTGATGATAAAATGGTGAgGTTCTGGAGAAT
CGATGAGGATTGTCCGGTACAAGTTGCACCTTTGAGCAATGGTCTTTGCTGTGCCTTTTCTACTGATGGCAGTGTTTTAG
CTGCTGGGACACATGATGGAAGTGTGTATTTTTGGGCCACTCCAAGGCAAGTCCCTAgCCTTCAACATATATGTCGCATG
TCAATCCGAAGAGTGATGTCCACCCAAGAAGTCCAAAAACTGCCTGTTCCTTCCAAAATATTGGCGTTTCTCTCCTACCG
CGGTTAGactgaagactgcctttcctggtaggcctgccagacagagcgcccttacaagacacacctcaagctttacctc
gtgccgaatt

Figure 15

MASFPPRVNEKEIVRSRTIGELLAPAAPFDKKCGGENWTVAFAPDGSYFAWSQGYRIVKLVPWSQCRKNFLLHGSKNVTN
SSCLKLARQNSNGGQKNKPPEHVIDCGDIVWSLAFGSSVPEKQSRCVNIEWHRFRFGQDQLLLATGLNNGRIKIWDVYTG
KLLLNLVDHIEMVRDLTFAPDGSLLLVSASRDKTLRVWDLKDDGNMVKVLRAHQNWVYSCAFSPDCSMLCSVGASKAVFL
WNMDKYTMIRKLEGHHHDVVACDFSPDGALLATASYDTRVYVWDPHNGDLLMEFGHLFPSPTPIFAGGANDRWVRAVSFS
HDGLHVASLADDKMVRFWRIDEDCPVQVAPLSNGLCCAFSTDGSVLAAGTHDGSVYFWATPRQVPSLQHICRMSIRRVMS
TQEVQKLPVPSKILAFLSYRG*

Figure 16 h4.1

CTGTCTTCCTCCGCAGCGCGAGGCTGGGTACAGGGTCTATTGTCTGTGGTTGACTCCGTA
CTTTGGTCTGAGGCCTTCGGGAGCTTTCCCGAGGCAGTTAGCAGAAGCCGCAGCGACCGC
CCCCGCCCGTCTCCTCTGTCCCTGGCCCGGGAGACAAACTTGGCGTCACGCCCTCAGCG
GTCGCCACTCTCTTCTCTGTTGTTGGGTCCGCATCGTATTCCCGGAATCAGACGGTGCCC
CATAGATGGCCAGCTTTCCCCCGAGGGTCAACGAGAAAGAGATCGTGAGATCACGTACTA
TAGGTGAACTTTTAGCTCCTGCAGCTCCTTTTGACAAGAAATGTGGTCGTGAAAATTGGA
CTGTTGCTTTTGCTCCAGATGGTTCATACTTTGCTTGGTCACAAGGACATCGCACAGTAA
AGCTTGTTCCGTGGTCCCAGTGCCTTCAGAACTTTCTCTTGCATGGCACCAAGAATGTTA
CCAATTCAAGCAGTTTAAGATTGCCAAGACAAAATAGTGATGGTGGTCAGAAAAATAAGC
CTCGTGACATATTATAGACTGTGGAGATATAGTCTGGAGTCTTGCTTTTGGGTCATCAGT
TCCAGAAAAACAGAGTCGCTGTGTAAATATAGAATGGCATCGCTTCAGATTTGGACAAGA
TCAGCTACTTCTTGCTACAGGGTTGAACAATGGGCGTATCAAAATATGGGATGTATATCA
GGAAACTCCTCCTTAACTTGGTAGATCATACTGAAGTGGTCAGAGATTTAACTTTTGCTC
CAG h4.2

CTCTGTATGTCTGAATGAAGCTATAACATTTGCCTTTTTATTGCAGGTTTTCCTTTGGAA
TATGGATAAATACACCATGATACGGAAACTAGAAGGACATCACCATGATGTGGTAGCTTG
TGACTTTTCTCCTGATGGAGCATTACTGGCTACTGCATCTTATGATACTCGAGTATATAT
CTGGGATCCACATAATGGAGACATTCTGATGGAATTTGGGCACCTGTTTCCCCCACCTAC
TCCAATATTTGCTGGAGGAGCAAATGACCGGTGGGTACGATCTGTATCTTTTAGCCATGA
TGGACTGCATGTTGCAAGCCTTGCTGATGATAAAATGGTGAGGTTCTGGAGAATTGATGA
GGATTATCCAGTGCAAGTTGCACCTTTGAGCAATGGTCTTTGCTGTGCCTTCTCTACTGA
TGGCAGTGTTTTAGCTGCTGGGACACATGACGGAAGTGTGTATTTTTGGGCCACTCCACG
GCAGGTCCCTAGCCTGCAACATTTATGTCGCATGTCAATCCGAAGAGTGATGCCCACCCA
AGAAGTTCAGGAGCTGCCGATTCCTTCCAAGCTTTTGGAGTTTCTCTCGTATCGTATTTA
GAAGATTCTGCCTTCCCTAGTAGTAGGGACTGACAGAATACACTTAACACAAACCTCAAG
CTTTACTGACTTCAATTATCTGTTTTTAAAGACGTAGAAGATTTATTTAATTTGATATGT
TCTTGTACTGCATTTTGATCAGTTGAGCTTTTAAAATATTATTTATAGACAATAGAAGTA
TTTCTGAACATATCAAATATAAATTTTTTTAAAGATCTAACTGTGAAAACATACATACCT
GTACATATTTAGATATAAGCTGCTATATGTTGAATGGACCCTTTTGCTTTTCTGATTTTT
AGTTCTGACATGTATATATTGCTTCAGTAGAGCCACAATATGTATCTTTGCTGTAAAGTG
CAAGGAAATTTTAAATTCTGGGACACTGAGTTAGATGGTAAATACTGACTTACGAAAGTT
GAATTGGGTGAGGCGGGCAAATCACCTGAGGTCAGCAGTTTGAGACTAGCCTGGCAAACA
TGATGAAACCCTGTCTCTACTAAAAATACAAAAAAAAAAAAA

Figure 18 cggcacgagccgggctccgtccggaggaagcgaggctgcgccgccggcccggcaggagcggaggacgg
gamgcgcgggcggtcgcgctcgccctgtcgctgactgcgctgccccggcccatccttgcctggccgca
ggtgccctggatgaggccgccgcgcgtgtcccggccgctgagtgtcccccgcggtcgcccggcgcctg
ccctcaagcggccgcctctccttgcccgggtccccgtttcccccggcgcagtcctcctccggtgggc
gcctccgcacctcggcgcaggcggcacggccctcgggccgggatggatccgccgggaagaggaagaca
agccggggcgttgagcccctgcgcacggtgccgccgcgcgtagtgggagcttactcgcagtaggctct
cgctcttctaatcaATGGATAAAGTGGGGAAAATGTGGAACAACTTAAAATACAGATGCCAGAATCTC
TTCAGCCACGAGGGAGGAAGCCGTAATGAGAACGTGGAGATGAACCCCAACAGATGTCCGTCTGTCAA
AGAGAAAAGCATCAGTCTGGGAGAGGCAGCTCCCCAGCAAGAGAGCAGTCCCTTAAGAGAAAATGTT
GCCTTACAGCTGGGACTGAGCCCTTCCAAGACCTTTTCCAGGCGGAACCAAAACTGTGCCGCAGAGAT
CCCTCAAGTGGTTGAAATCAGCATCGAGAAAGACAGTGACTCGGGTGCCACCCCAGGAACGAGGCTTG
CACGGAGAGACTCCTACTCGCGGCACGCCCCGTGGGGAGGAAAGAAGAAACATTCCTGTTCCACAAAG
ACCCAGAGTTCATTGGATACCGAGAAAAAGTTTGGTAGAACTCGAAGCGGCCTTCAGAGGCGAGAGCG
GCGCTATGGAGTCAGCTCCATGCAGGACATGGACAGCGTTTCTAGCCGCGCGGTCGGGAGCCGCTCCC
TGAGGCAGAGGCTCCAGGACACGGTGGGTTTGTGTTTTCCCATGAGAACTTACAGCAAGCAGTCAAAG
CCACTCTTTTCCAATAAAAGAAAAATACATCTTTCTGAATTAATGCTGGAGAAATGCCCTTTTCCTGC
TGGCTCGGATTTAGCACAAAAGTGGCATTTGATTAAACAGCATACCGCCCCTGTGAGCCCACACTCAA
CATTTTTTGATACATTTGATCCATCACTGGTGTCTACAGAAGATGAAGAAGATAGGCTTCGCGAGAGA
AGACGGCTTAGTATCGAAGAAGGGGTGGATCCCCCTCCCAACGCACAAATACACACCTTTGAAGCTAC
TGCACAGGTCAACCCATTGTATAAGCTGGGACCAAAGTTAGCTCCTGGGATGACAGAGATAAGTGGAG
ATGGTTCTGCAATTCCACAAGCSAATTGTGACTCAGAAGAGGATTCAACCACCCTATGTCTGCAGTCA
CGGAGGCAGAAGCAGCGCCAGGTGTCCGGGGACAGCCACGCGCACGTTAGCAGACAGGGAGCTTGGAA
AGTTCATACGCAGATCGATTACATACACTGCCTCGTGCCAGATTTGCTTCAGATCACAGGGAATCCCT
GTTACTGGGGCGTGATGGACCGATACGAGGCCGAAGCCCTTCTAGAAGGGAAACCGGAAGGCACGTTC
TTGCTCAGGGACTCTGCACAGGAGGACTACCTCTTCTCTGTGAGCTTCCGCCGCTACAACAGGTCTCT
GCACGCCCGGATCGAGCAGTGGAACCACAACTTCAGCTTCGATGCCCATGACCCCTGCGTGTTTCACT
CCTCCACWGTCACGGGGCTTCTCGAACACTATAAAGACCCCAGCTCTTGCATGTTTTTTGAACCGTTG
CTAACGATATCACTGAATAGAACTTTCCCTTTCAGCCTGCAGTATATCTGCCGCGCAGTGATCTGCAG
ATGCACTACGTATGATGGGATTGACGGGCTCCCGCTACCGTCGATGTTACAGGATTTTTTAAAAGAGT
ATCATTATAAACAAAAAGTTAGGGTTCGCTGGTTAGAACGAGARCCAGTCAAAGCAAAGtaactcctg
tccccaaagggcactaactaagtctgctcctcccgtgcatcmgaactgcacccataggraggcagtca
gctgctaggatttcccacccagaatgggagcttagtcattagcctctgccctatggggtccgctgttc
ctcagacaaaggtgcctagggacagcaagatggcttgcaggtgttcggtgggctgtgacaactgaggg
aggcaactctggggcatttgctatgaagaattctatttcttaccgaagaacaaattattaatattgga
tgggtatttcaatagtgtgactaatgtttgaaattatttttctaagaatttttctataaccttcaga
aaaagtagtgatgtttgtagttactataaatcaagctttgaaagttcaaaacaaacaagttaaataa
agactaccttccttttagagaaaacaaatgcaagttttcccagccacaggcattgtgcactgttaatg
ttagcttgttatcagctcctttctcctcc

Figure 20A

MDKVGKMWNNLKYRCQNLFSHEGGSRNENVEMNPNRCPSVKEKSISLGEAAPQQESSPLRENVALQLGLSPSKTFSRRNQ
NCAAEIPQVVEISIEKDSDSGATPGTRLARRDSYSRHAPWGGKKKHSCSTKTQSSLDTEKKFGRTRSGLQRRERRYGVSS
MQDMDSVSSRAVGSRSLRQRLQDTVGLCFPMRTYSKQSKPLFSNKRKIHLSELMLEKCPFPAGSDLAQKWHLIKQHTAPV
SPHSTFFDTFDPSLVSTEDEEDRLRERRRLSIEEGVDPPPNAQIHTFEATAQVNPLYKLGPKLAPGMTEISGDGSAIPQX
NCDSEEDSTTLCLQSRRQKWRWVSGDSHAHVSRQGAWKVHTQIDYIHCLVPDLLQITGNPCYWGVMDRYEAEALLEGKPE
GTFLLRDSAQEDYLFSVSFRRYNRSLHARIEQWNHNFSFDAHDPCVFHSSXVTGLLEHYKDPSSCMFFEPLLTISLNRTF
PFSLQYICRAVICRCTTYDGIDGLPLPSMLQDFLKEYHYKQKVRVRWLERXPVKAK*

Figure 20B

GATTAAACAGCATACAGCTCCTGTGAGCCCACATTCAACATTTTTTGATACTTTGATCCATCTTTGG
TTTCTACAGAAGATGAAGAAGATAGGCTTAGAGAGAGAAGGCGGCTTAGTATTGAAGAAGGGGTTGA
TCCCCCTCCCAATGCACAAATACATACATTTGAAGCTACTGCACAGGTTAATCCATTATTAAACTGG
GACCAAAATTAGCTCCTGGAATGACTGAAATAAGTGGGGACAGTTCTGCAATTCCACAAGCTAATTG
TGACTCGGAAGAGGATACAACCACCCTGTGTTGCAGTCACGGAGGCAGAAGCAGCGTCAGATATCTG
GAGACAGCCATACCCATGTTAGCAGACAGGGAGCTTGGAAAGTCCACACACAGATTGATTACATACA
CTGCTTCGTGCCTGATTTGCTTCAAATTACAGGGAATCCCTGTTACTGGGGAGTGATGGACCGTTAT
GAAGCAGAAGCCCTTCTCGAAGGGAAACCTGAAGGCACGTTTTTGCTCAGGGACTCTGCGCAAGAGG
ACTACTTCTTCTCTGTGAGCTTCCGCCGATACAACAGATCCCTGCATGCCCGAATTGAGCAGTGGAA
TCACAACTTTAGTTTCGACGCCCATGACCCGTGTGTATTTCACTCCTCCACTGTAACGGACTTTTA
GAACATTATAAAGATCCCAGTTCGTGCATGTTTTTTGAACCATTGCTTACTATATCACTAAATAGGA
CTTTCCCTTTTAGCCTGCAGTATATCTGTCGCGCGGTAATCTGCAGGTGCACTACGTATGATGGAAT
TGATGGGCTCCCTCTACCCTCAATGTTACAGGATTTTTTAAAAGAGTATCATTATAAACAAAAAGTT
AGAGTTCGCTGGTTGGAACGAGAACCAGTCAAGGCAAAGTAAACTCTCCGGTCCCCAAAGGGTGTTA
ACTAGGTCCGCTTTCATGTGCATCAGACAGTACACCTATAGCAAGCACACGTAGCAGTGTTAGGCTT
TTTCATACAGTATGTAAGCTTAGTGTTAGTATCTGTCAGATGCTACCTGCTGTTACTTATTCAGATA
AACATGGTGCCTATTGGAACAATAGCGGATAGAGCTACAGGTGTTCAGTAAGACTACAAAAACATTT
TGCCTATTTCGCTAACAGTTTGGTTTTTAATGGCTGTGGTATTTGAGTGAGGCAACTCTGGGGCATT
TGTTATGAAGAAATG

Figure 21 cacgaggcggtggtggcggcggcgggcgcggccgcggcggggcgggcgcggaatgaaggcccacggccctgggggctgaggcgcccgccgcctggg
gggccgcgcgtcctcATGGAGGCCGGAGAGGAGCCGCTGCTGCTGGCTGAACTCAAGCCTGGGCGCCCCCACCAGTTCGACTGGAAGTCAAGCTGC
GACCTGGAGCGTGGCCTTCTCGCCAGACGGTTCCTGGTTCGCCTGGTCTCAAGGACACTGCGTGGTCAAGCTGGTCCCCTGGCCCTTAGAGGAACA
TCATCCCTAAAGGATTCGAAGCCAAGAGCCGAAGCAGCAAGAATGACCCAAAAGGACGGGGCAGTCTGAAGGAGAAGACGCTGGACTGTGGCCAGA
GTGTGGGGGCTGGCCTTCAGCCCGTGGCCCTCTCCACCCAGCAGGAAACTCTGGGCACGTCACCATCCCCAGGCGCCTGATGTTTCTTGCCTGATC
GGCCACAGGTCTCAACGATGGGCAGATCAAGATTTGGGAGGTACAGACAGGCCTCCTGCTTCTGAATCTTTCTGGCCACCAAGACGTCGTGAGAGA
TGAGCTTCACGCCCAGCGGCAGTTTGATTTTGGTCTCTGCATCCCGGGATAAGACACTTCGAATTTGGGACCTGAATAAACACGGTAAGCAGATCC
GTGTTATCCGGCCATCTGCAGTGGGTTTACTGCTGCTCCATCTCCCCTGACTGTAGCATGCTGTGCTCTGCAGCTGGGGAGAAGTCGGTCTTTCTG
GAGCATGCGGTCCTACACACTAATCCGGAAACTAGAAGGCCACCAAAGCAGTGTTGTCTCCTGTGATTTCTCTCCTGATTCAGCCTTGCTTGTCAC
CTTCGTATGACACCAGTGTGATTATGTGGACCCCTACACCGGCGCGAGGCTGAGGTCACTTCATCACACACAACTTGAACCCACCATGGATGACA
GACGTCCACATGAGCTCCCTGAGGTCCGTGTGCTTCTCACCTGAAGGCTTGTATCTCGCTACGGTGGCAGATGACAGGCTGCTCAGGATCTGGGCT
GGAACTGAAGGCTCCGGTTGCCTTTGCTCCGATGACCAATGGTCTTTGCTGCACGTTCTTCCCACACGGTGGAATTATTGCCACAGGGACGAGAGA
GCCATGTCCAGTTCTGGACAGCTCCCCGGGTCCTGTCCTCACTGAAGCACTTATGCAGGAAAGCCCTCCGAAGTTTCCTGACAACGTATCAAGTCC
GCACTGCCAATCCCCAAGAAGATGAAAGAGTTCCTCACATACAGGACTTTCTAGcagtgccggctcccccacctcctgcagcagcagcagtacaag
actggctaggatggagtcaggcagctcacactggaccagtgtggaccttccttcctcccatggcatgtgcaagtaggtctgcgtgaccccacttct
ggtgccggccttacctcgtcttcatccgtggtgagcagccttcgtcagtctagttgtgttgaagccaagtgcagttgtggatgttgctggggtaat
aggcaagcgggctccagagcctctctggtggcggccaagccacactcccttaactgggaagtacctgccacgtagggcatttctgctgcctatttc
gccagcggctgcatggtttgaagttcctccgttgtggtcagaagaactctggtgtttggttccctgctcagctgcgcgtggactgggctgagctcc
accatacactagtgccggcttttgtttcctgtaaacagtggttgcatgtgtagagaagtaacaagcgagtattcagatcatacgaggaggcgttcc
ggtgcatgacggtcagatggccatttatcagcatatttatttgtatttctcagcacatagtaaggtacaactgtgttttctcaattgtctcgaaa
acagagttcttaagtggcccagttgtggagccaagtctaagtcgtgtggagtcagtgctgacatcactggcttgtgctgtctgtcacatgtgtttg
tctgctgcttgacctcatgggatgtaccctccagttcaactgcccaaaacagacagccccttccaagcaccgttctttgacagcggtagcagctac
attcaagacgcctcacacaaaatctgccttagaaagttaatatatttaaattattttaaaagaaactcaacatcttattctttggcctttcttaa
gatgctttatggaggcagtgttaacattgtacagtgtatgcatagaggagtctcctctatttgaagaacaatgcaaaatgaggctttcattgaagg
aaaaaaaaaaaaaaa

Figure 23A

MEAGEEPLLLAELKPGRPHQFDWKSSCETWSVAFSPDGSWFAWSQGHCVVKLVPWPLEEQFIPKGFEAKSRSSKNDPKGRG
SLKEKTLDCGQIVWGLAFSPWPSPPSRKLWARHHPQAPDVSCLILATGLNDGQIKIWEVQTGLLLLNLSGHQDVVRDLSFT
PSGSLILVSASRDKTLRIWDLNKHGKQIQVLSGHLQWVYCCSISPDCSMLCSAAGEKSVFLWSMRSYTLIRKLEGHQSSVV
SCDFSPDSALLVTASYDTSVIMWDPYTGARLRSLHHTQLEPTMDDSDVHMSSLRSVCFSPEGLYLATVADDRLLRIWALEL
KAPVAFAPMTNGLCCTFFPHGGIIATGTRDGHVQFWTAPRV<u>LSSLKHLCRKALRSFLTTYQVLALPIPKKMKEFL</u>TYRTF*

Figure 23B h6.1

GACACTGCATCGTCAAACTGATCCCCTGGCCGTTGGAGGAGCAGTTCATCCCTAAAGGGTTTGAAGCC
AAAAGCCGAAGTAGCAAAAATGAGACGAAAGGGCGGGGCAGCCCAAAAGAGAAGACGCTGGACTGTGG
TCAGATTGTCTGGGGGCTGGCCTTCAGCCTGTGCTTTCCCCACCCAGCAGGAAGCTCTGGGCACGCCA
CCACCCCCAAGTGCCCGATGTCTCTTGCCTGGTTCTTGCTACGGGACTCAACGATGGGCAGATCAAGA
TCTGGGAGGTGCAGACAGGGCTCCTGCTTTTGAATCTTTCCGGCCACCAAGATGTCGTGAGAGATCTG
AGCTTCACACCCAGTGGCAGTTTGATTTTGGTCTCCGCGTCACGGGATAAGACTCTTCGCATCTGGGA
CCTGAATAAACACGGTAAACAGATTCAAGTGTTATCGGGCCACCTGCAGTGGGTTTACTGCTGTTCCA
TCTCCCCAGACTGCAGCATGCTGTGCTCTGCAGCTGGAGAGAAGTCGGTCTTTCTATGGAGCATGAGG
TCCTACACGTTAATTCGGAAGCTAGAGGGCCATCAAAGCAGTGTTGTCTCTTGTGACTTCTCCCCCGA
CTCTGCCCTGCTTGTCACGGCTTCTTACGATACCAATGTGATTATGTGGGACCCCTACACCGGCGAAA
GGCTGAGGTCACTCCACCACACCCAGGTTGACCCCGCCATGGATGACAGTGACGTCCACATTAGCTCA
CTGAGATCTGTGTGCTTCTCTCCAGAAGGCTTGTACCTTGCCACGGTGGCAGATGACAGACTCCTCAG
GATCTGGGCCCTGGAACTGAAAACTCCCATTGCATTTGCTCCTATGACCAATGGGCTTTGCTGGCACA
TTTTTTCCACATGGTGGAGTCATTGCCACAGGGACAAGAGATGGCCACGTCCAGTTCTGGACAGCTCC
TAGGGTCCTGTCCTCACTGAAGCACTTATGCCGGAAAGCCCTTCGAAGTTTCCTAACAACTTACCAAG
TCCTAGCACTGCCAATCCCCAAGAAAATGAAAGAGTTCCTCACATACAGGACTTTTTAAGCAACACCA
CATCTTGTGCTTCTTTGTAGCAGGGTAAATCGTCCTGTCAAAGGGAGTTGCTGGAATAATGGGCCAAA
CATCTGGTCTTGCATTGAAATAGCATTTCTTTGGGATTGTGAATAGAATGTAGCAAAACCAGATTCCA
GTGTACTAGTCATGGATTTTTC h6.2

ACCATGGTTCCAAGTCCTCTCCCCTGTGGTCAAGTTGCCCGAATGTTGGGCCCAAGTGCCTTTTCCTC
CTTGGGCCTCCCCTTCTGACCTGCAGGACAGTTTTCCGGAGCCCATTTGGTATGAGGTATTAATTAGC
CTTAACTAAATTACAGGGGACTCAGAGGCCGTGCTCCTGACCGATCCAGACACTATTTTTTTTTTTTT
TTTTTAACAATGGTGTGCATGTGCAGGAAATGACAAATTTGTATGTCAGATTATACAAGGATGTATTC
TTAAACCGCATGACTATTCAGATGGCTACTGAGTTATCAGTGGCCATTTATTAGCATCATATTTATTT
GTATTTTCTCAACAGATGTTAAGGTACAACTGTGTTTTTCTCGATTATCTAAAAACCATAGTACTTAA
ATTGAAAAAAAAAA

Figure 24

GGCACGAGGCGGGGTCAGGGCGGAGGCTGAGGACCAAGTAGGCATGGCGGAGGGCGGGACCGGCCCCG
ATGGACGGGCCGGCCCGGGACCCGCAGGTCCTAATCTGAAGGAGTGGCTGAGGGAGCAGTTCTGTGAC
CATCCACTGGAGCACTGTGACGATACAAGACTCCATGATGCAGCCTATGTAGGGGACCTCCAGACCCT
CAGGAACCTACTGCAAGAGGAGAGCTACCGGAGCCGCATCAATGAGAAGTCTGTCTGGTGCTGCGGCT
GGCTTCCCTGCACACCACTGAGGATCGCAGCCACTGCAGGCCATGGGAACTGTGTGGACTTCCTCATA
CGCAAAGGGGCCGAGGTGGACCTGGTGGATGTCAAGGGGCAGACTGCCCTGTATGTGGCTGTAGTGAA
CGGGCACTTGGAGAGCACTGAGATCCTTTTGGAAGCTGGTGCTGATCCCAACGGCAGCCGGCACCACC
GCAGCACTCCTGTGTACCATGCCTYTCGTGTGGGTAGGGACGACATCCTGAAGGCTCTTATCAGGTAT
GGGGCAGATGTTGATGTCAACCATCATCTGAATTCTGACACCCGGCCCCCTTTTTCACGGCGGCTAAC
CTCCTTGGTGGTCTGTCCTCTATACATCAGTGCTGCCTACCATAACCTTCAGTGCTTCAGGCTGCTCT
TGCAGGCTGGGGCAAATCCTGACTTCAATTGCAATGGCCCTGTCAACACCCAGGAGTTCTACAGGGGA
TCCCCTGGGTGTGTCATGGATGCTGTCCTGCGCCATGGCTGTGAAGCAGCCTTCGTGAGTCTGTTGGT
AGAGTTTGGAGCCAACCTGAACCTGGTGAAGTGGGAATCCCTGGGCCCAGAGGCAAGAGGCAGAAGAA
AGATGGATCCTGAGGCCTTGCAGGTCTTTAAAGAGGCCAGAAGTATTCCCAGGACCTTGCTGAGTTTG
TGCCGGGTGGCTGTGAGAAGAGCTCTTGGCAAATACCGACTGCATCTGGTTCCCTCGCTGCCGCTGCC
AGACCCCATAAAGAAGTTTTTGCTTTATGAGTAGcattcacatgcagtgctgactgcaatgtggaagc
cgatcacctgcagtgaaaactgacacagactctggcatcctgggaaccatggcctgtgctgccagctt
gatccttggctgtcagtgaagaaaaaacggctgtgttctcttggactgtgattctatctcaggtgctt
gggccatcgaacgctccttgagtcattgtcaactgagaggcacatacaaacttaattttgttcctctt
cagtctctctgttttggattcttcctggcaatgtgtgcagcatgggctgagcctggtgattgccctag
tggggaaggctttttctccaggctatgcatctatttatgttcctactttgcaatttattgttctttt
aaggcttgatatcaaaacagaaagaggtttgttaagaaaagatatagggagaaaggaattccggttcc
gtgcacttgctagcctgctttccttgcctgggtttgtctgtctatgctgcctggtgcacatcccttct
ctttgctgccactgttctattttgggagttgtcttccgtctaagatggcttctggggttctatcttat
tgcacagaggtcccagaacagtgttcatagggcaccatctgctctgccaagggttttctgatgtctta
ccctggggatcttcagacagtggttacctttaggagacccacctggaactaaccattaagtgactgcc
cacattcagatcagggaccatcttaatagtactcactgccagtcctcacaagagaagatgacacgggt
gctctcttcagacactcccatacaggaagttggaaaatgtcttggtcacctgggttgttcccaggcta
caacttcttggtgttccactaaraccagratatcctagtttttgggttgactgttccctccccactt
tccttgaancccaatgcccntttgtktnggttgcttccctaaaaktt

Figure 26A

....ARGGVRAEAEDQVGMAEGGTGPDGRAGPGPAGPNLKEWLREQFCDHPLEHCDDTRLHDAAYVGDLQTLRNLLQEESY
RSRINEKSVWCCGWLPCTPLRIAATAGHGNCVDFLIRKGAEVDLVDVKGQTALYVAVVNGHLESTEILLEAGADPNGSRHH
RSTPVYHAXRVGRDDILKALIRYGADVDVNHHLNSDTRPPFSRRLTSLVVCPLYISAAYHNLQCFRLLLQAGANPDFNCNG
PVNTQEFYRGSPGCVMDAVLRHGCEAAFVSLLVEFGANLNLVKWESLGPEARGRRKMDPEALQVFKEARSIPRTLLSLCRV
AVRRALGKYRLHLVPSLPLPDPIKKFLLYE*

Figure 26B h7.1

GCATCCATGGCGGAGGGCGGCAGCACGACGGGCGGGCAGGGCCGGGCTCCGCAGGTCGTAATCTGAAG
GAGTGGCTGAGGGAGCAATTTTGTGATCATCCGCTGGAGCACTGTGAGGACACGAGGCTCCATGATGC
AGCTTACGTCGGGGACCTCCAGACCCTCAGGAGCCTATTGCAAGAGGAGAGCTACCGGAGCCGCATCA
ACGAGAAGTCTGTCTGGTGCTGTGGCTGGCTCCCCTGCACACCGTTGCGAATCGCGGCCACTGCAGGC
CATGGGAGCTGTGTGGACTTCCTCATCCGGAAGGGGGCCGAGGTGGATCTGGTGGACGTAAAAGGACA
GACGGCCCTGTATGTGGCTGTGGTGAACGGGCACCTAGAGAGTACCCAGATCCTTCTCGAAGCTGGCG
CGGACCCCAAC h7.2

GAGGAAGAAGAAAAGTGGACCCTGAGGCCTTGCAGGTCTTTAAAGAGGCCAGAAGTGTTCCCAGAACC
TTGCTGTGTCTGTGCCGTGTGGCTGTGAGAAGAGCTCTTGGCAAAACCGGCTTCATCTGATTCCTTCG
CTGCCTCTGCCAGACCCCATAAAGAAGTTTCTACTCCATGAGTAGACTCCAAGTGCTGCGGTTGATTC
CAGTGAGGGAGAAAGTGATCTGCAGGGAGGTGGACACCGAGCCCTGAGTGCTGTGCTGCTGCTGGTCT
CCTGATGGCTGTTGCTGCAGAAGATGTCCTCGTAGACTGTCATTGCTCCTCAGGTGCCTGGGCCGCTG
AACAGTCCTTGGGTCATTGTCAGCTGAGAGGCTTATACTAAAGTTATTATTGTTTTTCCCAAGTTCTC
TGTTCTGGATTTTCAGTTGCATATTAATGTAACGGGCCATGGGGTATGTACATGTAGGGGCTGAGGTT
GGAGGCCTACTAATTTCCTGTAGGGAAGACTCCCAGCACTTCTGGAACTGTGCTTCTCTTTATTTTTC
TACTTCTCAATTTGATGGTTCGATTAAAGCCTTCTAGTATCTCAATGAAAA

Figure 27

CTGATGTCCGCAATTCTGAAGGTTGGACACCACTGCTGGCTGCCTGTGACATCCGCTGTCAATCCCC
AAAGGATGCTGAGGCCACCACCAACCGCTGTTTTCAACTGTGCCGCTTGCTGCTGTCTGTGGGGGCA
GATGCTGATGAATACATACCGTGTAGTTCAGCTTCCTGAGGAGGCCAAGGGCTTGGTGCCACCAGAG
ATTCTACAGAAGTACCATGGATTCTACTCTTCCCTCTTTGCCTTGGTGAGGCAGCCCAGGTCGCTGC
AGCATCTCTGCCGTTGTGCGCTCCGCAGTCACCTGGAGGGCTGTCTGCCCCATGCACTACCGCGCCT
TCCCCTGCCACCGCGCATGCTCCGCTTTCTGCAGCTGGACTTTGAGGATCTGCTCTACTAGgcttgc
tgccctgtgaacaaagcagaccccacccccaccccaagggcatctctcagcaatgaatgatgcaagg
cggtctgtcttcaagtcaggagtggacgccttgatccacacttgagagaagaggccagatcagcacc
yggctggtagtgatngcagagggcacctgtgcagatctgtgtgcgcactggaaatctctaggctgaa
ggcyagagcaaatggtgcargtgttagtccttgggangagagacaganggtgagaaagcaagacaga
ggtgagagtgcacatgtcaagtggtagattgccttaaaagaaagctaaaaaaagaaaaagattcggg
cgaacttctttaggggtaatgctgcagcgtgttaaactgactgaccagcgtccatatctttggaccc
ttcccgggtgaaaaagccccttcatcctccagcgctccccaagggtgcttagcaataccgggtgctt
ttctgccgcaaagtgagttaccaaa

Figure 29A

....MSAILKVGHHCWLPVTSAVNPQRMLRPPPTAVFNCAACCCLWGQMLMNTYRVVQLPEEAKGLVPPEILQKYHGFYS
SLFALVRQPRSLQHLCRCALRSHLEGCLPHALPRLPLPPRMLRFLQLDFEDLLY*

Figure 29B

GTGGGGGCGTCATCATGACCTCCTCTAGGGCTCTGCAACATGACTCCTGTGGTGCAAATCAACAAAT
TGTTCACTGATGAATCCACAAGGATCTCTGGGCCTACAACCAGGTCCTGGTCCACATGACTGTCGTC
TTCGGAGAAGGCACCACTCGCCCCCGGCAGGTACGGCTGACACCTCCATGGGAGAAGACGTATCCAG
GCAGCAGCTGCGCGGCCCTTCAAGAGGGCACATCCCGTCATCTAAAGGCACGGTGTACTGAAGGTAG
TCCTGAGACATGAGTCCGATTACTACAGGCACGTGTTCCTCCAGGTGGAGGCTCAGGTCCCCGGGTG
AGCTGGGGCTGCAGCGGGACTCAGGGCGCGGCTCTGGCTGCAGGTCTCGCAGCTCCCTGGGCTGTAG
CTCCCGCAGATCCTTGCGCACACCGTTGACTGGT

Figure 31

TTAATAGTACCTACATAGTAGAAAATTATAACTCCACTTTAAAACAATGTTTTCTTTCTATTCAAATCAATTTAAAACTTTTTATAAACATTAATGTTGCAAGAG
AATCCAGTCCATTTATGAAAATTAGTTGACAATCAAGTTCACCCAAGAAAATGTTGACTAAGCTAAAGAAATCACAGATAAAACATTTTACCAAAAGGATAGGTA
ACACACAAAAAAATGCTATCACAGGAAGCTATGATCATCTAATATTTCTTTAATAATAATTCTAGTTCCATAGGTTTTCATGTTATGCCAATTTGTACCCGAGTT
TAATTACAGAAAAGGCAACAATTTCTAAATTGGTGGTATACATTTCTTTACAATTTTTAATGTAAGGCCATTTATTAAAATAGACAAACTAGAAGATGAAAACG
AAGGCAACAGAAAAATTCAACTTTTCACAACCAAAAGAATTAGCACAACCTTAGAAATAATTTAGAAAAAAGTGTTGTTAAAAGATATGTTGCAGATCTCCGTTC
CATTACCCAAGATTATGTCAATTCACGATTCTAAATAAATCTTTTTAAAGTAAGAGATTAAAAACTCATCTTCAGTGTATATGTAAATTCCGTGGTTTTATCACA
CAGGTATGTTTATTCAACACTGCTTTGGAAATGGACCATTTAAAAGGACATGGCAATTTCCATTCTGTTAAGTTTCATTCAACCTTTACTTAGGGGTTGATTACC
ACATGAAATGTGCTTTTAATGCATAAAAATCACAGTGGATTAGCCAGCAAAAGGGACTGGGCGGGGGGGGCATTGAGGAGAATTTGATAATTCACATTGTGATTA
TTCTGCACATTGATGAAACATAATTCACACCTCTAAAACCTCAAGACTTCCCTTTTTTAAAGAACCAAAATAAACCCAAGACACCTTGCTGACACTTCCCCACCC
CTAAACAAACTGATGACTCTTTTACACATAAAACTGAAATAGTTATGGCAGCAAAAGATTTTGATGGCAATGAAAGTTTGTAAACTGTATTTCAATCTCTTGTTC
TTATTCCCAAAGTGCAAGATGCAGGGTTCTCAATCTTTCAGTAGTGCTTCTCCTGTAAATAATCCTTCATTTTGTTTGGCAAAGGCAGTTTCTGAATTAAGTCTA
TTCTGGTATACTGACGTATAACAAAACGACACAGGTACTGCAACGAGCGCACCTATGAACCCCGGAACACTGGTTGGCAAGTTCTGACGGAAGTGCAGATTCCAG
GCAGCGAGACCTTGAATAACAAAAAGCTCCCATTTTCAGAGTCCCTGATTGAATGCTCCAATTAGATCAACTATGGACGTATGTCCTTCCACATCGGCTGTTCAT
AAAAGCTAAACCTACCATTTGAGTGCTCAATTCTAGTGTGAAGTGTTTTACCATGGGAGCGAAAGTCACAGCTTAAAAGGTAACGGTCGTCAGAACTGTCCCGAA
CAAGAAAAGAACCATCTGGCACGTTTGCTAGCTTCCCTTCTGCCTCCCAACGTGTGATTGGTCCCCAGTACCATCCTTGCTTTGCAAGTTTTTTCAGCTCCTCTG
TAAGGCTTGTCACAACCATGGGACCACTACTTTGCACTGAGTCATAAACTCTTGCAACCCCAGGAGCAGAGTTCGGATCAAAATTCAAATGACAGCGCATAACTT
TCAGCCACGTGGGGCTTTCTGTCCAGTGAGTCCACTGAAAGTTCCCCTTTGGGATTTGGATTATTCCTGCATTGGAGTAACCAATGGTGAAGATTGGAGGGACAT
CCATCGTGAACCCGCTCTCCGGGGTTCTGCAACATGACTCCCGTGGTGCCAATCAACAAGCCATTCACCGGACTGATCCACGAAGATCTCTGGGGCGACAACTAG
GTCCTGGTCTACCTGACTCTCATCCTCGGGGAAAGCGCGCCCTCCCACTTGAGGAGGAACCGCAGAGACTTCCATGGGAGAAGAGCTGTCCAGACAATAGCTCCG
TGATCCTTCCAAAGGATACATCCCCTCATCTAAAGGCACAGTATACTGAATGTAGTCCTGAGGCATAAGTCCAATAACGACAGGCACATGTTCATCCAGGTGAAG
ATGCAGGTCTCCATTATGAGAAGCCGAGCTCTTCAGTGAATTGGCTTGCTCCTGGCACGTGGTCTCAGACTGGAGGTCGT

Figure 32

GGCACGAGGCTGTGTCCAGCACACAGAGAGGGCCCGGCCATCTGCTTTGGTTCAGAGCCCTGTGTCTGTCTGTCACTTAGACTCTTCCTCCCGGCT
CGCAGCTCACCCTCCATCCTCCTTACTGGCTCCAGCATGACTCGCTTCTCTTATGCAGAGTACTTTGCTCTGTTTCACTCTGGCTCTGCACCTTCC
AGGTCCCCTTCGTCTCCCGAGAACCCACCGGCCCGCGCACCCCTGGGTCTGTTCCAAGGGGTCATGCAGAAGTATAGCAGCAACCTGTTCAAGACC
TCCCAGATGGCGGCTATGGACCCCGTGCTGAAGGCCATCAAGGAAGGGGATGAAGAGGCCTTGAAGATCATGATCCAGGATGGGAAGAATCTTGCA
GAGCCCAACAAGGAGGGCTGGCTGCCGCTCCACGAGGCTGCCTACTATGGCCAGCTGGGCTGCCTGAAAGTCCTGCAGCAAGCCTACCCAGGGACC
ATTGACCAACGCACACTGCAGGAAGAGACAGCATTATACCTGGCCACATGCAGAGAACACCTGGATTGCCTCCTGTCGCTGCTCCAGGCGGGGGCA
GAGCCTGACATCTCTAACAAATCCAGGGAGACTCCACTTTACAAAGCCTGTGAGCGCAAGAACGCGGAGGCGGTGAGGATATTGGTGCGATACAAC
GCAGACGCCAACCACCGCTGTAACAGGGGCTGGACCGCACTGCACGAGTCTGTCTCCCGCAATGACCTGGAGGTCATGGAGATCCTAGTGAGTGGC
GGGGCCAAGGTGGAGGCCAAGAATGTCTACAGCATCACCCCTTTGTTTGTGGCTGCCCAGAGTGGGCAGCTGGAGGCCCTGAGGTTCCTGGCCAAG
CATGGTGCAGACATCAACACGCAGGCCAGTGACAGTGCATCAGCCCTCTACGAGGCCAGCAAGAATGAGCATGAAGACGTGGTAGAGTTTCTTCTC
TCTCAGGGCGCCGATGCTAACAAAGCCAACAAGGACGGCCTGCTCCCCCTGCATGTTGCCTCCAAGAAGGGCAACTATAGAATAGTGCAGATGCTG
CTGCCTGTGACCAGCCGCACGCGCGTGCGCCGTAGCGGCATCAGCCCGCTGCACCTAGCGGCCGAGCGCAACCACGACGCGGTGCTGGAGGCGCTG
CTGGCCGCGCGCTTCGACGTGAACGCACCTCTGGCTCCCGAGCGCGCCCGCCTCTACGAGGACCGCCGCAGTTCTGCGCTCTACTTCGCTGTGGTC
AACAACAATGTGTACGCCACCGAGCTGTTGCTGCTGGCGGGCGCGGACCCCAACCGCGATGTCATCAGCCCTCTGCTCGTGGCCATCCGCCACGGC
TGCCTGCGCACCATGCAGCTGCTGTTGGACCATGGCGCCAACATCGACGCCTACATCGCCACTCACCCCACCGCCTTTCCAGCCACCATCATGTTT
GCCATGAAGTGCCTGTCGTTACTCAAGTTCCTTATGGACCTCGGCTGCGATGGCGAGCCCTGCTTCTCCTGCCTGTACGGCAACGGGCCGCACCAC
CCGCCCCGCGACCTGGCCGCTTCCACGACGCACCCGTGGACGACAAGGCACCTAGCGTGGTGCAGTTCTGTGAGTTCCTGTCGGCCCCGGAAGTGA
GCCGCTGGGCGGGACCCATCATCGATGTCCTCCTGGACTATGTGGGCAACGTGCAGCTGTGCTCCCGGCTGAAGGAGCACATCGACAGCTTTGAGG
ACTGGGCTGTCATCAAGGAGAAGGCAGAACCTCCGAGACCTCTGGCTCACCTCTGCCGGCTGCGGGTTCGGAAGGCCATAGGAAAATACCGGATAA
AACTCCTGGACACACTGCCGCTTCCCGGCAGGCTAATCAGATACTTGAAATATGAGAATACACAGTAAccagcctggagaggagatgtggccttca
gactgtttccgggacgccccaggtggcctgcatccaggacccccctggggtcagaacaggtgtgaccttgctggttctttgctggagcttcacccaa
agtgagaacctgatgtggggagtggacgtggaacctctgctttcacactgtcagcggatcgcagacccgctctgcttctggccatagccagagacc
ttcaacctggggccaggggagagctggtctgggcaaggtggcccaggcaggaatcctggccttaagctggagaacttgtaggaatccctcactgga
ccctcagctttcaggctgcgagggagacgcccagcccaagtattttatttccgtgacacaataacgttgtatcagaaaaaaaaaaaacatgggcg
cagcttattccttagtagggtatttacttgcatgcgcgcttaaagctactggaaacatgcgttccactatgcttgagaatccccttgcactggtaa
acgagagccgacgtgcttcaaggttggattttggttgcccctttggcgttccgcgggtttgtccgacgtaattgaccccgtgttttgtcactttc
gagtgttccgactattggggggcttttggttgtccccaaaattgtgggtggtgtgcggacgccacgagaagtggttcatgggcgataatcattact
ggagaatgtagagcggcggttttacgaataaatatttttaagccgccttcccaaaa

Figure 34 h10.1
CCTCCTGAGAGTTCGCCGGCCCGGGCCCAATGGGnTTGTTCCAAGGGGTCATGCAGAAATACAGCAGCAGCTTGTTCAAG
ACCTCCCAGCTGGCGCCTGCGGACCCCTTGATAAAGGCCATCAAGGATGnCGATGAAGAGGCCTTGAAGACCATGATCAA
GGAAGGGAAGAATCTCGCAGAGCCCAACAAGGAGGGCTGGCTGCCGCTGCACGAGGCCGCATACTATGGCCAGGTGGGCT
GCCTGAAAGTCCTGCAGCGAGCGTACCCAGGGACCATCGACCAGCGCACCCTGCAGGAGGAAACAGCCGTTTACTTGGCA
ACGTGCAGGGGCCACCTGGACTGTCTCCTGTCACTGCTCCAAGCAGGGGCAGAGCGGGACATCTCCAACAAATCCCGAGA
GAnACCGCTCTACAAAGCCTGTGAGCGCAAGAACGCGGAAGCCGTGAAGATTCTTGGTGCAGCACAACGCAGACACCAAC
AACGCTGCAACCGGGCTG h10.2
GTGCAGCTCTGCTCGCGGCTGAAGGAACACATCGACAGCTTTGAGGACTGGGCCGTCATCAAGGAGAAGGCAGAACCTCC
AAGACCTCTGGCTCACCTTTGCCGACTGCGGGTTCGAAAGGCCATTGGGAAATACCGTATAAAACTCCTAGACACCTTGC
CGCTCCCAGGCAGGCTGATTAGATACCTGAAATACGAGAACACCCAGTAACTGGGGCCACGGGGAGAGAGGAGTAGCCCC
TCAGACTCTTCTTACTAAGTCTCAGGACGTCGGTGTTCCCAACTCCAAGGGGACCTGGTGACAGAcGAGGCTGCAGGCTG
CCTCCCTCTCAGCCTGGACAGCTACCAGGATCTCACTGGGTCTCAGGGcCCAGAGCTTTGGCCAGAGCAGAGAACAGAAT
GTGTCAAGGAGAAGAATCATTTGTTTACAAACTGATGAGCAGATCCCAGACCTTCTCTACCTTCAGGAATGGCAGAAACC
TCTATTCCTGGGGCCAGGGCAGAGCTTGAGGTGTTCTGGGGAAGGTGGTGCTCAGAGCCTTCCCTGTGCCCCTCCACTTG
TTCTGGAAAACTCACCACTTGACTTCAGAGCTTTCTCTCCAAAGACTAAGATGAAGACGTGGCCCAAGGTAGGGGGTAGG
GGGAGCCTGGGTCTTGGAGGGCTTTGTTAAGTATTAATATAATAAATGTTACACATGTGAAAAAAAAAA

Figure 35

TTGGAGAAGTGTGGTTGGTATTGGGGGCCAATGAATTGGGAAGATGCAGAGATGAAGCTGAAAGGGA
AACCAGATGGTTCTTTCCTGGTACGAGACAGTTCTGATCCTCGTTACATCCTGAGCCTCAGTTTCCG
ATCACAGGGTATCACCCACCACACTAGAATGGAGCACTACAGAGGAACCTTCAGCCTGTGGTGTCAT
CCCAAGTTTGAGGACCGCTGTCAATCTGTTGTAGAGTTTATTAAGAGAGCCATTATGCACTCCAAGA
ATGGAAAGTTTCTCTATTTCTTAAGATCCAGGGTTCCAGGACTGCCACCAACTCCTGTCCAGCTGCT
CTATCCAGTGTCCCGATTCAGCAATGTCAAATCCCTCCAGCACCTTTGCAGATTCCGGATACGACAG
CTCGTCAGGATAGATCACATCCCAGATCTCCCACTGCCTAAACCTCTGATCTCTTATATCCGAAAGT
TCTACTACTATGATCCTCAGGAAGAGGTATACCTGTCTCTAAAGGAAGCGCAGCGTCAGTTTCCAAA
CAGAAGCAAGAGGTGGAACCCTCCACGTAGCGAGGGGCTCCCTGCTGGTCACCACCAAGGGCATTTG
GTTGCCAAGCTCCAGCTTTGAagaaccaaattaagctaccatgaaaagaagaggaaaagtgagggaa
caggaaggttgggattctctgtgcagagactttggttccccacgcaagccctggggcttggaagaag
cacatgaccgtactctgcgtggggctccacctcacacccacccctgggcatcttaggactggagggg
ctccttggaaaactggaagaagtctcaacactgtttctttttca

Figure 36A

....LEKCGWYWGPMNWEDAEMKLKGKPDGSFLVRDSSDPRYILSLSFRSQGITHHTRMEHYRGTFSLWCHPKFEDRCQSV
VEFIKRAIMHSKINGKFLYFLRSRVPGLPPTPVQLYPVSRFSNVKSLQHLCRFRIRQLVRIDHIPDLPLPKPLISYIRKFY
YYDPQEEVYLSLKEAQRQFPNRSKRWNPPRSEGLPAGHHQGHLVAKLQL*

Figure 36B

GTTCCAAGCCTAACCCATCTTTGTCGTTTGGAAATTCGGGCCAGTCTAAAAGCAGAGCACCTTCACT
CTGACATTTTCATCCATCAGTTGCCACTTCCCAGAAGTCTGCAGAACTATTTGCTCTATGAAGAGGT
TTTAAGAATGAATGAGATTCTAGAACCAGCAGCTAATCAGGATGGAGAAACCAGCAAGGCCACCTGA
cacaggtcctttaattctgtttagtcacaaaagacggcttgtgtgactgtttggatttggtgatcaa
atgtccatgtttacagttgcttttcccagtttgtgtctttcccaatattgtgaaccttatccatctt
gccttactcagttttatttctagtgcactttgttgtgtattatttgtttacctgaccattttctact
ttattctgctaataaactgtaattctgaaaaaaaaaaaaaaaaaaaaaaaaaaaaaaaaaa

Figure 39 h12.1

GGGGATCGAAAGCGGGGGCTTCTGGGACGCAGCTCTGGAGACGCGGCCTCGGACCAGCCATTTCGGT
GTAGAAGTGGCAGCACGGCAGACTGGTCAAACAAATGGATTTTACAGAGGCTTACGCGGACACGTGC
TCTACAGTTGGACTTGCTGCCAGGGAAGGCAATGTTAAAGTCTTAAGGAAACTGCTCAAAAAGGGCC
GAAGTGTCGATGTTGCTGATAACAGGGGATGGATGCCAATTCATGAAGCAGCTTATCACAACTCTGT
AGAATGTTTGCAAATGTTAATTAATGCAGATTCATCTGAAAACTACATTAAGATGAAGACCTTTGAA
GGTTTCTGTGCTTTGCATCTCGCTGCAAGTCAAGGACATTGGAAAATCGTACAGATTCTTTTAGAAG
CTGGGGCAGATCCTAATGCAACTACTTTAGAAGAAACGACACCATTGTTTTTAGCTGTTGAAAATGG
ACAGATAGATGTGTTAAGGCTGTTGCTTCAACACGGAGCAAATGTTAATGGATCCCATTCTATGTGT
GGATGGAACTCCTTGCACCAGGCTTCTTTTCAGGAAAATGCTGAGATCATAAAATTGCTTCTTAGAA
AAGGAGCAAACAAGGAATGCCAGGATGACTTTGGAATCACACCTTTATTTGTGGCTGCTCAGTATGG
CCAAGCTAGAAAGCTTTGAAGCATACTTATTTCATCCGGGTGCAAATGTCAATTGTCAAGCCTTGGA
CAAAGCTACC h12.2

CACAAATGGGACCATACAAAAATCTTGGACTTGTTAATAACCACTTACTAACCGGGACCTGTGACAC
TGGGCTAAACAAAGTAAGTCCCTGTTTACTCAGCAGTGTTTGGGGGACATGAAGGATTGCCTAGAAA
TATTACTCCGGAATGGTCTACAGCCCAGACGCCCAGGCGTGCCTTGTTTTTGGATTCAGTTCTCCTG
TGTGCATGGCTTTCCAAAAGGAGGTGGAGCTGTAGTTCTTTGGAATTGTGAACATTCTTTTGAAATA
TGGAGCCCAGATAAATGAACTTCATTTGGCATACTGCCTGAAGTACGAGAAGTTTTCGATATTTCGC
TACTTTTTGAGGAAAGGTTGCTCATTGGGACCATGGAACCATATATATGAATTTGTAAATCATGCAA
TTAAAGCACAAGCAAAATATAAGGAGTGGTTGCCACATCTTCTGGTTGCTGGATTTGACCCACTGAT
TCTACTGTGCAATTCTTGGATTGACTCAGTCAGCATTGACACCCTTATCTTCACTTTGGAGTTTACT
AATTGGAAGACACTTGCACCAGCTGTTGAAAGGATGCTCTCTGCTCGTGCCTCAAACGCTTGGATTC
TACAGCAACATATTGCCCACTGTTCCATCCCTGACCCATCTTTGTCGTTTGGAAATTCGGTCCAGTC
TAAAATCAGAACGTCTACGGTCTGACAGTTATATTAGTCAGCTGCCACTTCCCAGAAGCCTACATAA
TTATTTGCTCTATGAAGACGTTCTGAGGATGTATGAAGTTCCAGAACTGGCAGCTATTCAAGATGGA
TAAATCAGTGAAACTACTTAACACAGCTAATTTTTTCTCTGAAAAATCATCGAGACAAAAGAGCCA
CAGAGTACAAGTTTTTATGATTTTATAGTCAAAAGATGATTATTGATTGTCAGATAGGTTAGGTTTT
GGGGGGCCAGTAGTTCAGTGAGAATGTTTATGTTTACAACTAGCCTTCCCAGTAAAAAAAAAAAAAA
AAAAAAAAAAAAA

Figure 40

CGGGGGGCTGGGACCTGGGGCGTAACCGTCTCTACCACGACGGCAAGAACCAGCCAAGTAAAACATA
CCCAGCCTTTCTGGAGCCGGACGAGACATTCATTGTCCCTGACTCCTTTTTCGTGGCCCTGGACATG
RATGATGGGACCTTAAGTTTCATCGTGGATGGACAGTACATGGGAGTGGCTTTCCGGGGACTCAAGG
GTAAAAAGCTGTATCCTGTAGTGAGTGCCGTCTGGGGCCACTGTGAGATCCGCATGCGCTACTTGAA
CGGACTTGATCCTGAGCCCCTGCCACTCATGGACCTGTGCCGGCGTTCGGTGCGCCTAGCGCTGGGA
AAAGAGCGCCTGGGTGCCATCCCCGCTCTGCCGCTACCTGCCTCCCTCAAAGCCTACCTCCTCTACC
AGTGAtccacatcccaggaccgccatacgacagccatctggtgccaartcactgagcccgttggggt
ccgccgacccctgcgcctgggatggaagcccacctcagccatgggcagacgtgccccctcatcctac
cggctgcctctgctgggggaacctatgccaacggacttctcccttcccaacactggctgaagcagca
gcacccaggcccttccctgaaccagatgcagagaataaactatgaaaacctctctcaggcgccttct
gctctcaggtggagtgggctgccccccactctctgcagagagaggctacacccacctgggggtcct
gggaggtaagactagtaggaggtgccagggctgartccaaaagcaggaatggccaggamcaggccat
acagatgaagctcaggatgtcacataccatggacamtgagacagaaccccaggttggamttcccttg
ggccaacgagtgccagctttaatgtcagctgcmggtgctctgtggcctgtatttattctttaaacag
tagcaaaggccatttatttattccacttagaaaggaaaccttggtgggtggyttccctcgatgtgct
ttcccccacctccctggaatgtgtgtgccacacctgtccttgtcccaggccaggactgtggcacatg
agctggtgtgcacagatacacgtatgtcgtcgtgcatgacccctgactagttcctaagtagccctgc
accaagcaccagagcagaccccaagagaggcccgtgcaagtccccatgtccccaggtccctgcttct
gttgccttgggactcatacaccggcacacgtgtttcagcctcttgacttccatgagcttcgaatttt
gcccccgattcttctgatatttcccattggcatcctccaaagctctgggcctggagggcattaggac
acatggaatgagtggggtctccagcccctgggaaagccactggcaaggcaggattagaaagaccaag
agcagggtggggcgccatgaagcctgtatgcctctcaggctcaagaccccgccacacacccactcaa
gcctcagaagtggtgtgtagggcagccccaggagaggaatgcctgtcctagcagcacgtacatggag
caccccacatgtgctccagccctctggctgtttctcttgctctagaatcaactccctacattgggaa
tgtagccatttggtagaggacttgcctagcctgcaggaagctcacgttccatcccctgcaccaagga
gaatcaaagctcaggaggctgaggcaggaggattgctgtcagtggtgtacagaggtcatggccatcc
tgggctatattaaaccttgtcctttaagaaaaagaaaagaaatcaacttccattgaatctgagttct
gctcatttctgcacaggtacaatagatgacttkatttgttgaaaaatgkttaatatatttacmtata
tatatatttgtaagaagcatt

Figure 42A

....GGWDLGRNRLYHDGKNQPSKTYPAFLEPDETFIVPDSFFVALDMXDGTLSFIVDGQYMGVAFRGLKGKKLYPVVSAV
WGHCEIRMRYLNGLDPEPLPLMDLCRRSVRLALGKERLGAIPALPLPASLKAYLLYQ*

Figure 42B

AAGGGTAAAAAACTGTATCCTGTAGTGAGTGCCGTCTGGGGCCACTGTNAGATCCGAATGCGCTACT
TGAACGGACTCGATCCCGAGACNTGCCGCTCATGGATTTGTGCCGTCGCTCGGTGCGCCTGGCCCTG
GGGAGGGAGCGCCTGGGGGAGAACCANCACCTGCCGCTGCCGGCTTCCCTCAAGGCCTACCTCCTCT
ACCAGTGACGTTCGCCATCATACCGCCAGCGCGACAGCCACCTGGTGCCAACTCACTGAGCCGCCTG

Figure 43

....AAGTGGCGGCGGTCCCTGGAGAGCAGGCGGAGGCAGCGGCAAGTCTGACTCTGGGCTGACCGTGGAGCCGGGGCGGGGGCTGACAGCCAGGCCT
CCGCCTGGCGGGAGCCGCACGAGGAGCGGGAGTGGCCGGGCCTCTCTTCCGCGCTTGAGCGAGCGCCGGGTGATGGCGGTGGTGATGGCGGCAGGC
GCTCGGACAGCTCCGCTTGAGCTGAGCTCGGAGAGATCCGTCCAGAAAGTGCCCAGAAGAAACTTCCTCTTAGAAAAGCTGAAAAACACARTATTT
ATAACACTGGAAATTGTAAAGAATTTGTTTAAAATGGCTGAAAACAATAGTAAAAATGTAGATGTACGGCCTAAAACAAGTCGGAGTCGAAGTGCT
GACAGGAAGGATGGTTATGTGTGGAGTGGAAAGAAGTTGTCTTGGTCCAAAAAGAGTGAGAGTTGTTCTGAATCTGAAGCCATAGGTACTGTTGAG
AATGTTGAAATTCCTCTAAGAAGCCAAGAAAGGCAGCTTAGCTGTTCGTCCATTGAGTTGGACTTAGATCATTCCTGTGGGCATAGATTTTTAGGC
CGATCCCTTAAACAGAAACTGCAAGATGCGGTGGGGCAGTGTTTTCCAATAAAGAATTGTAGTGGCCGACACTCTCCAGGGCTTCCATCTAAAAGA
AAGATTCATATCAGTGAACTCATGTTAGATAAGTGCCCTTTCCCACCTCGCTCAGATTTAGCCTTTAGGTGGCATTTTATTAAACGACACACTGTT
CCTATGAGTCCCAACTCAGATGAATGGGTGAGTGCAGACCTGTCTGAGAGGAAACTGAGAGATGCTCAGCTGAAACGAAGAAACACAGAAGATGAC
ATACCCTGTTTCTCACATACCAATGGCCAGCCTTGTGTCATAACTGCCAACAGTGCTTCGTGTACAGGTGGTCACATAACTGGTTCTATGATGAAC
TTGGTCACAAACAACAGCATAGAAGACAGTGACATGGATTCAGAGGATGAAATTATAACGCTGTGCACAAGCTCCAGAAAAAGGAATAAGCCCAGG
TGGGAAATGGAAGAGGAGATCCTGCAGTTGGAGGCACCTCCTAAGTTCCACACCCAGATCGACTACGTCCACTGCCTTGTTCCAGACCTCCTTCAG
ATCAGTAACAATCCGTGCTACTGGGGTGTCATGGACAAATATGCAGCCGAAGCTCTGCTGGAAGGAAAGCCAGAGGGCACCTTTTTACTTCGAGAT
TCAGCGCAGGAAGATTATTTATTCTCTGTTAGTTTTAGACGCTACAGTCGTTCTCTTCATGCTAGAATTGAGCAGTGGAATCATAACTTTAGCTTT
GATGCCCATGATCCTTGTGTCTTCCATTCTCCTGATATTACTGGGCTCCTGGAACACTATAAGGACCCCAGTGCCTGTATGTTCTTTGAGCCGCTC
TTGTCCACTCCCTTAATCCGGACGTTCCCCTTTTCCTTGCAGCATATTTGCAGAACGGTTATTTGTAATTGTACGACTTACGATGGCATCGATGCC
CTTCCCATTCCTTCGCCTATGAAATTGTATCTGAAGGAATACCATTATAAATCAAAAGTTAGGTTACTCAGGATTGATGTGCCAGAGCAGCAGTGA
tgcggagaggttagaatgtcgacctgcatacatatttcatttaatatttatttttcttatgcctctttgaatttttgtacaaaggcagttgaat
caaataaaactgtgccctaagttttaattccagatcaatttattttttttatgatacacttgttatatattttaagcaggtgtttggttttgttt
ttaccatataaatttacatatggtccaggcatatttacaatttcaaggcattgcatatacatttgaatattctgtatttttaaataatcttttgt
tctttcctatgtgtgaaatattttgctaatctatgctatcagtattcttgtatgaccgaatagttacctattctcttttcatcttgaagattttca
gtaaagagtgttgtaatcaatccattataatgtaattgacttttgtaatttgccaataggagtgttaaacaacaaaatgatttaaaatgaaactta
atgtattttcatttaaatattaactaaaccaagtttgtttgttagttattctagccaataagaaaagagaatgtagcatcctagaggtgtatttg
ttctgcagtttggcaggaccgtcagttagtccaaataaacatcccctcagcgtggaggcgaatggaacctgtgctcctttcttacgggaagctttg
caaagcaaaatagcagggttacaagcttggagttgttaaggcaactagagttttctctattaatttatagactgttgttgcacctacttagctctt
ttttgggaactctagttcccaggggaaaatacctcgtgcc

Figure 45A

....SGGGPWRAGGGSGKSDSGLTVEPGRGLTARPPPGGSRTRSGSGRASLPRLSERRVMAVVMAAGARTAPLELSSERS
VQKVPRRNFLLEKLKNTXFITLEIVKNLFKMAENNSKNVDVRPKTSRSRSADRKDGYVWSGKKLSWSKKSESCSESEAIG
TVENVEIPLRSQERQLSCSSIELDLDHSCGHRFLGRSLKQKLQDAVGQCFPIKNCSGRHSPGLPSKRKIHISELMLDKCP
FPPRSDLAFRWHFIKRHTVPMSPNSDEWVSADLSERKLRDAQLKRRNTEDDIPCFSHTNGQPCVITANSASCTGGHITGS
MMNLVTNNSIEDSDMDSEDEIITLCTSSRKRNKPRWEMEEEILQLEAPPKFHTQIDYVHCLVPDLLQISNNPCYWGVMDK
YAAEALLEGKPEGTFLLRDSAQEDYLFSVSFRRYSRSLHARIEQWNHNFSFDAHDPCVFHSPDITGLLEHYKDPSACMFF
EPLLSTPLIRTFPFSLQHICRTVICNCTTYDGIDALPIPSPMKLYLKEYHYKSKVRLLRIDVPEQQ*

Figure 45B ccctctgggcaagccgcccccccccacccatctaccacacacacacacacacacacacacattcagaccttgggg
caaaaacaaagcaaaataacaacaacaaaaacactgcctgtggaaagtccttacttcaggaaggttggcagatgaggagc
aagggaacattttatcaggactgccacaaaggagtctttttttttaatggttttcaagacagggtttctctgtatagcc
ctggctgtcctggagctcactttgtagaccaggctggcctcgaactcagaaattcgcctgcctctgcctcctgagtgctg
ggattaaaggcgtgcagcaccatgtccaactggcattttctcaattaaggttcgttcctttcagataactctaggttctg
ggtcaagctgacacaaggctacacagcacagtttgtatgccacattcagttcagaagacacccaacctccctggaactgg
aacttatgcacatttgtgagcttccacttgggagtgggaacctgaactgggtcctctgcaagagcagccgtgctcttaac
tgctgagccatttcagcagcctcacatcagaattaagttaaaattagccgggtatgaatcatacccttagaatcctagca
tctgaaagcagagctaagagaaacagggattcaagaccagctcttggctacagagcccgtcctgtcctaggatgggctac
aagagactatttcaaagccatccaaacaacaataactacaacaacaacaaggttaaaattaggctgggcacagggtacac
acctttaatgccaacactcaggaggcagaggcaggctgatcagtgtgagtttgagttcaacgtggtctacatagggagtt
ctaggccagcagaggttacagtctctctctctctctctctctctctctctcacacacacacacacacacacaca
cacacacacacacacacggtggcattatgggatttttttgggataaggtttctctgtctagccctggcatagattcactc
tgtagactaggctagccttgaactcagagatccgcctgcctctgcctcccaagtgctgggattataggtgttgcaccacc
actgcccagccactttgggattttttgaactgttatcaagaggctttcgaggaggtcaaacttcaacagcaacctctccat
gataatgtagctaatgatcaaacgacactcaaaacttaacccttaaagcacacatccaccagacagcgtgcccactcgta

A - - - - - - - - - - - - - - - - - - - - A gttccattactcaggaggctgaagcaggaggatgaaggactaaggcttcagcaacctagggagccgcaggggacagtagt
ctcaatccctacattctcctgaacacaggagcaggagttcaggaagggtgtcaaggccgcttactgatcttagggcctca
ggaatgactagctcaggcagagagagcaaaggtctccagtggagaagtctacacacacacacacacacacacacacac
acacacacacagaatccaaggcgatgacgtcatcaaagggttaattctagtctgggatgggggggagggtggggcacgca
gctgtcaggtggctttggaaaaataaactgctgaagagtctgacgccagggagtcctgggagggacaagaggttacccac
tcaaagagtgtgctccacaaagcatgcgcgcttgtccacgtctggagtcgtcacttatttttgcctggattctttgtag
ccggtgggttctcaaggcggtaagtggtgtggccgccgtggtctgggaggtgacgatagggttaatcgtccacagagccc
aggggcggagcgcgggcgggcgtccgcagccccgctggagccggaagcagtggctggtcaggggcgcttctagccttccc
tatctgtacttccacagaggtctctgcgagctagggggacagtgaggtgcggggtaggggcccggcgttagagccagcaa
ggggacggttcacggtaaggtctgagggagagagagctcctgagaaacttgggggcgcgacacagatagggtgaaagca
gagtgatagacctgggatggttaggggaccaagggaagaccaggctggttggcatacaccggtgaacggatgggagtcct
agggaaagatgatgcgcctaacagtcctttctgtctccacaccactccaggggacgatccggagctcaactttcaaaagc
gagacgccccagcaagcctgttttgagaagttcttcagcggctctcctcATGGGCCAGACGGCCCTGGCAAGGGGCAGCA
GCAGCACCCCTACCTCGCAGGCTCTGTACTCGGACTTCTCTCCTCCCGAGGGCTTGGAGGAGCTCCTGTCTGCTCCCCCT
CCTGACCTGGTTGCCCAACGGCACCACGGCTGGAACCCCAAGGATTGCTCCGAGAACATCGATGTCAAGGAAGGGGGTCT

GTGCTTTGAGCGGCGCCCTGTGGCCCAGAGCACTGATGGAGTCCGGGGAAACGGGGCTATTCGAGAGGTCTGCACGCCT
GGGAGATCAGCTGGCCCCTGGAGCAAAGGGGCACACACGCCGTGGTGGGCGTGGCCACCGCCCTCGCCCCGCTGCAGGCT
GACCACTATGCGGCGCTTTTGGGCAGCAACAGCGAGTCCTGGGGCTGGGATATTGGGCGGGGAAAATTGTATCATCAGAG
TAAGGGCCTCGAGGCCCCCCAGTATCCAGCTGGACCTCAGGGTGAGCAGCTAGTGGTGCCAGAGAGACTGCTGGTGGTTC
TGGACATGGAGGAGGGGACTCTTGGCTACTCTATTGGGGGCACGTACCTGGGACCAGCCTTCCGTGGACTGAAGGGGAGG
ACCCTCTATCCCTCTGTAAGTGCTGTTTGGGGCCAGTGCCAGGTCCGCATCCGCTACATGGGCGAAAGAAGAGgtgagat
acggactaggtgtggggagatcactactcttggcaatggtttgggctggaaactcatggttggagcacaggaagtaggct
tcttgtcactttggcctgtcacttagatggccttggatctagcttcactcccaatccctattggatgtgatgcacaaatt
cagagcctttgggtctccctcagctgaggtggcggtggaaatggaggaagaaggaagggtgcctgagcaggatctcaagt
tcaaggatgcctggagttgcttacttaccttgtcttccttctctctccgcagTGGAGGAACCACAATCCCTTCTGCACCT
GAGCCGCCTGTGTGTGCGCCATGCTCTGGGGGACACCCGGCTGGGTCAAATATCCACTCTGCCTTTGCCCCCTGCCATGA
AGCGCTATCTGCTCTACAAATGAcccagtagtacagggtgtgctggcaccctaccgtggggacaggtggagaggcacccg
ctggcctagacaactttaaaaagctggtgaagctggggggggggctggaccccttcacctccccttctcacaggagca
agacatatagaaatgatattaaacaccatggcagcctgggacaaagaggtttttgaagtaaaaaatgagatgtattgtca
caacctgtttcattattgtttttgttttgttttacactcccccaccccaggctagagccccatcactgtcttaaggaat
tatgacaacccacaaagctcaggcccaggtgtttatttcccttacatgtaggatggttcacaaacacaatacaggggctt
tggcaccgtgggggaggggactatcccaggcctcttagggtctcatgtataccgaattcagacccgaaagctctgaattt

C - - - - - - - - - - - - - - - - - - - - - - - - - - - - - - C

Figure 47A(iii)

C - - - - - - - - - - - - - - - - - - - - - - - - - - - - - - - - - - - - - - C ctgcatcagacatccagtagaacttgggagtgaagctagagccaaggccatctaagtgacaggccaaagtgacacgaagc
ccacttcctgtgctccaaccatgagtttccagcccaaaccaatggaaggtgatttcacttgtcagggcccaaagggacag
tcagttctactccctcccctcactaggagccaccttggtgacagttgattctacccactgtaagtggtaaagggattggc
ctggtcccaaccataatagggcggtggaaacggctcaggagggtacagcgtggattaggccacaagatggggcagatgat
gtcatcagaagcatgtgaccggtgggagcagttactaaacttctgggcaacctagtccatgctatgcaggcaggtagagg
gatgggcagtgctcattgtttggcattgatgatgtccacaaattcaggcttgagagatgcgccacccacaaggaagccgt
ccacgtcaggctggcttgccagctctttgcaggttgctccagtcacagaacctgtaccaggaacaagaagacagtttggt
caggtctatgatcagaacacttaagccccacctctctgtgcaaggcagcctcagtctgtcttagcccatttccgtcttag
ctagagccaaagccactcacctccataaatgatccgggtgctctgagccaccccatcattgacattggatttcagccatc
cccggagcttctcgtgtacttcctgtgcctagaaggaggaggcagagctactaagtaagctccttcctatctatcattca
aggagtaaaaaccactggttctcacatagagttgagtttccagaaaagccccgggaccagagagtggcaaggctccaatc
ccaccaggcttggaatgaacattttggcaaagtcactctccttggtgagtttgggggccctctgtctctaaaggggctt
ggatgggctccatagctgtgtgagtctgttaaagccggacaggctgaggagctctgggtagttacctgctgaggggttgc
cgtcttgccagtcccaatggcccacacaggttcataggccaggaccaccttgctccagtctttcacattatctgtggggc
agagaggagagtgagtaggaaggagctgacccgccaagc]

Figure 47A(iv)

MGQTALARGSSSTPTSQALYSDFSPPEGLEELLSAPPPDLVAQRHHGWNPKDCSENIDVKEGGLCFERRPVAQSTDGVRGK
RGYSRGLHAWEISWPLEQRGTHAVVGVATALAPLQADHYAALLGSNSESWGWDIGRGKLYHQSKGLEAPQYPAGPQGEQLV
VPERLLVVLDMEEGTLGYSIGGTYLGPAFRGLKGRTLYPSVSAVWGQCQVRIRYMGERRVEEPOSLLHLSRLCVRHALGDT
RLGQISTLPLPPAMKRYLLYK

Figure 47B gtactttctttatatctccataattttatttactattactacatgatacattattttataaaagtctttgtaacctcctt
aaggattcactgcttaatctccagtgcttagcacaaatcattaaatgcgaaccagaaactcttccaaatgtgttacatct
ataacctcattggattctcactaccaaccccatgcaatagatactaatgtgatctctgtcttacagaggaagaaacaggc
acagggaggttcagtaatttgcccaaggtcatacacacactggccttcaggtattcatgcccggggagtctggtcccaca
gctggcatgtttgccattatattatattgcctccttatagtgtcggcactcattaagcacattgacagctatgcttggtg
agtgactactatgtacccagctctgtgctacatgctttacctggattatttcaactgcacaacaaccctgtgaggtaact
accatcattgctcctatttacataacagaaaactacagaaatctggggctgggcgtagtggctcatgcctgaaatccca
gcactttgggagaccctgtctctaaaaaaatttttttttggccggacgtggtggctcacacctgtaatctcagcacttt
gggaggctaaggcaggcagatcacaaggtcaggagttctagaccagcctggccaacatggcaaaaccctgtgtctactaa
aaatacaaaaaatagctaggcgtggtggcaggtgcctgtaatcccagctactcaggaggctgaggcaggagaatcccctg
aacctgggagatggaggttacagagagccgagatcgtgccgctgcactccagcctgggcaacaagagcaagactctgtct
cgaaaaaaataaaaataaaaataaaaatatttttttaaaaattagctgggtgtggtagcacatgcctgtagtcccagcta
cttgggaggctgaggtaggaggatcacttgagcccaggaggtcaaggctgcagtgggctgtgatggcgccactgcactct
agccttggtgacagcaagaccctgtctcaaaaaaaaaaaaaagagaaatcgggcaacttccccaagatcgcgcagttaac
tagtggcatagcttcactcaaactcgaagtcttaatcaggacactctaccaaatgagatcaacggctcagtaatggattg

A - - - - - - - - - - - - - - - - - - - - - - A gcatccagtatgaagactggaccagcagggagaactatgatgcgtacagcctagagcctgaagcagatttcacagcctca
gaggtggcacaggctgactcacaacccggggcagaaagggaccagcccagaaacagtgacccagaatcacagggaagtag
aaatgggattcggcacaatgaagcccctccttgaccccatgctccttaccctcaggggcgcaggagttagtcgctcaggc
ggctcaaaggtcttgacggtggagaacaccatccccagggattcccgacgcggtgatgccatcaaagcgttaattctgag
atgggcctgcccgggtgcggactctgccgcagcaagagaagggttaactgccccgggccttcgccgtgggggcggggcct
cggggagggtcacagcccgggactgagacccgaggttaaccgcccggggtgggctccacgggggcggggcatgctctccg
cggctgctgccggtatagagcggtaactgcccaggagggggcggggccccacaggggcgtggcctcggagctgcacggcc
gtgggcggcgatgagagggttaagccccagagggccctggagggcggggccgcgggacgggctcggcccaagggaggag
ctgggggcggaagcggccggcggtctgcgccctgcgcgcctcggcttctttccgcccggctccttcagaggcccggcgac
ctccagggctgggaagtcaaccgaggttcgggggcagcggcgagggctccgggcgagtaagggggatggtccatgctgag
gcccaaatggggcgaactcgcgagagtctctggcgacctggatcagatggggcgagggcagatgaagggcccaggagctt
tggggcagcgaggagggaggagcgggcccgttggcaaacttgggtgaaaggatggggtacctgggtgacgagcccccgcc
aggattctgctcttcacgccccttttctcccagctcccttccaggtcaatccaaactggagctcaactttcagaagagaa
agacgccccagcaagcctctttcggggagtcctctagctcctcacctccATGGGCCAGACAGCTCTGGCAGGGGGCAGCA

GCAGCACCCCCACGCCACAGGCCCTGTACCCTGACCTCTCCTGTCCCGAGGGCTTGGAAGAGCTGCTGTCTGCACCCCCT
CCTGACCTGGGGGCCCAGCGGCGCCACGGTTGGAACCCCAAAGACTGTTCAGAGAACATCGAGGTCAAGGAAGGAGGGTT
GTACTTTGAGCGGCGGCCCGTGGCCCAGAGCACTGATGGGGCCCGGGGTAAGAGGGGCTATTCAAGGGGCCTGCACGCCT
GGGAGATCAGCTGGCCCCTAGAGCAGAGGGGCACGCATGCCGTGGTGGGCGTGGCCACGGCCCTCGCCCCGCTGCAGACT
GACCACTACGCGGCGCTGCTGGGCAGCAACAGCGAGTCGTGGGGCTGGGACATCGGGCGGGGGAAGCTGTACCATCAGAG
CAAGGGGCCCGGAGCCCCCCAGTATCCAGCGGGAACTCAGGGTGAGCAGCTGGAGGTGCCAGAGAGACTGCTGGTGGTTC
TGGACATGGAGGAGGGAACTCTGGGCTACGCTATTGGGGGCACCTACCTGGGGCCAGCATTCCGCGGACTGAAGGGCAGG
ACCCTCTATCCGGCAGTAAGCGCTGTCTGGGGCCAGTGCCAGGTCCGCATCCGCTACCTGGGCGAAAGGAGAGgtgaggc
ctggggcagacgtggggagaactttctgtccctggtggcagtggtttgggatggaaactcttctgacaagagcagagggg
atggaccttcatccagcctgcctcaacctctgttcagtgctgggaaaggctaggggtcttcacagctgttatttaattta
acccaacagcaatagaggtgaaacaggcttgagaaagcaactttctcaagttctcttggccagtaaatggtgaaccttca
gaatggagggaggaactgcagggatgagagaattcaggagatatcaacccctgagcaagaggtgcaaagcgttaggtact
gggtttgatgtacaggtccaaaagaaggatgggcagagccaggtacccaggctgtataccggattccctgggctctaacc
tgtctctgtgccacatacctacttccttcctcagccacacctctggatggagacactggggccctgggcaccagggagga

C - - - - - - - - - - - - - - - - - - - - - - - - - - - - - - C

Figure 48A(iii)

C ----------------------------------------- C gtcaaagcctgggccagctccaccactgtcagagccaccttggcctgttgtttagagggccttagccagctcttcacccc
cagctctgactagggatgtgtgaaatcttatctgggaggcagaacttccgggtatctcaaattcccctttcagccaggtg
ggcacactcgaagcaggaaagcagaaaggcatctgagtaggaccccgtagtttgaggacatctggctggtggctgcaccc
atacttacattcccctccttctctctcccagCGGAGCCACACTCCCTTCTGCACCTGAGCCGCCTGTGTGTGCGCCACAA
CCTGGGGGATACCCGGCTCGGCCAGGTGTCTGCCCTGCCCTTGCCCCCTGCCATGAAGCGCTACCTGCTCTACCAGTGAg
ccctgtgataccacagactgtgctgaggtcttgccaccacccctccccttggggaggtggggaggcactgctggcctaga
ccagctgctgaaagctggtgaggctgagcccctaccccaacccaagctctgcggaaatcaacagccccagagccacttgg
agggaggaagaaagggagccggcgttcaaggctatgacagtctgctacgcaaaacatttttcaagtaaaaatagtaaga
gatgttgttatagaaacctgttcttgtttttttttttcttgcacaaatgatcatttatatagctgcctcaaaaaggaa
gattatctgggcaagtccagtgaaggcagacaaaccacaagacctagtgccaggtttattccctcacatgggtggttcac
atacacagcacagaggcacgggcaccatgggagagggcagcactcctgccttctgaggggatcttggcctcacggtgtaa
gaagggagaggatggtttctcttctgccctcactagggcctagggaacccaggagcaaatcccaccacgccttccatctc
tcagccaaggagaagccaccttggtgacgtttagttccaaccattatagtaagtggagaagggattggcctggtcccaac

D - - - - - - - - - - - - - - - - - - - - - - - - - - - - - - - - D cattacagggtgaagatataaacagtaaaggaagatacagtttggatgaggccacaggaaggagcagatgacaccatcag
aagcatatgcagggaaagggcagttactgggcttctgggctgcttagtccctggcttggcaggaagggtagggaagatgg
atggggctcattgtttggcattgatgatgtccacgaattcgggcttgagggaagcaccacccacaaggaagccatccaca
tcaggctggctggccagctccttgcaggttgccccagtcacagagcctgggaagggagcagaacaagggcttggtcaaga
atgggatgagtctgccccatccccacctccatgtccgagggctcagtctagtcctcagcccactccacctcagccgggaa
ccaaagccactcacctccataaatgatacgggtgctctgagccaccgcatcagagacgttggacttcagccatcctcgga
gcttctcgtgtacttcctgggcctagaacaagaagctggcctaagtaagacctttctgcctctctaagaggaaaaatca
ctggcaccagtggacacttagtgtggtttctgactgagtcagagtaccagggctctgatccaagccaggccctggactgg
atgcccttggacaagtcactgtctctgggttcaaggtctctgtgtctttgaaataaggggttgccccatgtgggctgtgt
ctgtccaaacctattgaggcaggctgggatgagggcagggctcctgggcccggttacctgttggggtgttgcagtcttgc
cagtaccaatggcccacacaggctcataggccaggacgaccttgctccagtccttcacgttatctgcagggcagagatac
agatggagggaagggtgaacaagaaagagctctccagccaggttctccggagtacgaagaacggtggcctactgcccccct
agtggacattggggg

Figure 48A(v)

MGQTALAGGSSSTPTPQALYPDLSCPEGLEELLSAPPPDLGAQRRHGWNPKDCSENIEVKEGGLYFERRPVAQSTDGARGK
RGYSRGLHAWEISWPLEQRGTHAVVGVATALAPLQTDHYAALLGSNSESWGWDIGRGKLYHQSKGPGAPQYPAGTQGEQLE
VPERLLVVLDMEEGTLGYAIGGTYLGPAFRGLKGRTLYPAVSAVWGQCQVRIRYLGERRAEPHSLLHISRLCVRHNLGDTR
LGOVSALPLPPAMKRYLLYQ

Figure 48B

5'x3' SOCS-1 Arms in pBgalpAloxNeoTK

THERAPEUTIC AND DIAGNOSTIC AGENTS

CROSS-REFERENCE TO RELATED APPLICATIONS

This application is a continuation of U.S. patent application Ser. No. 08/962,560, filed Oct. 31, 1997, now U.S. Pat. No. 6,905,842, which claims priority from Australian Application No. P03384/96, filed Nov. 1, 1996 and Australian Application No. P05117/97, filed Feb. 14, 1997.

FIELD OF THE INVENTION

The present invention relates generally to therapeutic and diagnostic agents. More particularly, the present invention provides therapeutic molecules capable of modulating signal transduction such as but not limited to cytokine-mediated signal transduction. The molecules of the present invention are useful, therefore, in modulating cellular responsiveness to cytokines as well as other mediators of signal transduction such as endogenous or exogenous molecules, antigens, microbes and microbial products, viruses or components thereof, ions, hormones and parasites.

Bibliographic details of the publications referred to in this specification by author are collected at the end of the description. Sequence Identity Numbers (SEQ ID NOs.) for the nucleotide and amino acid sequences referred to in the specification are defined after the bibliography. A summary of the SEQ ID NOs is given in Table 1.

Throughout this specification and the claims which follow, unless the context requires otherwise, the word “comprise”, or variations such as “comprises” or “comprising”, will be understood to imply the inclusion of a stated integer or group of integers but not the exclusion of any other integer or group of integers.

BACKGROUND OF THE INVENTION

Cells continually monitor their environment in order to modulate physiological and biochemical processes which in turn affects future behaviour. Frequently, a cell’s initial interaction with its surroundings occurs via receptors expressed on the plasma membrane. Activation of these receptors, whether through binding endogenous ligands (such as cytokines) or exogenous ligands (such as antigens), triggers a biochemical cascade from the membrane through the cytoplasm to the nucleus.

Of the endogenous ligands, cytokines represent a particularly important and versatile group. Cytokines are proteins which regulate the survival, proliferation, differentiation and function of a variety of cells within the body [Nicola, 1994]. The haemopoietic cytokines have in common a four-alpha helical bundle structure and the vast majority interact with a structurally related family of cell surface receptors, the type I and type II cytokine receptors [Bazan, 1990; Sprang, 1993]. In all cases, ligand-induced receptor aggregation appears to be a critical event in initiating intracellular signal transduction cascades. Some cytokines, for example growth hormone, erythropoietin (Epo) and granulocyte-colony-stimulating factor (G-CSF), trigger receptor homodimerisation, while for other cytokines, receptor heterodimerisation or heterotrimerisation is crucial. In the latter cases, several cytokines share common receptor subunits and on this basis can be grouped into three subfamilies with similar patterns of intracellular activation and similar biological effects [Hilton, 1994]. Interleukin-3 (IL-3), IL-5 and granulocyte-macrophage colony-stimulating factor (GM-CSF) use the common β-receptor subunit (βc) and each cytokine stimulates the production and functional activity of granulocytes and macrophages. IL-2, IL-4, IL-7, IL-9, and IL-15 each use the common γ-chain (γc), while IL-4 and IL-13 share an alternative γ-chain (γc or IL-13 receptor α-chain). Each of these cytokines plays an important role in regulating acquired immunity in the lymphoid system. Finally, IL-6, IL-11, leukaemia inhibitory factor (LIF), oncostatin-M (OSM), ciliary neurotrophic factor (CNTF) and cardiotrophin (CT) share the receptor subunit gp130. Each of these cytokines appears to be highly pleiotropic, having effects both within and outside the haemopoietic system [Nicola, 1994].

In all of the above cases at least one subunit of each receptor complex contains the conserved sequence elements, termed box1 and box2, in their cytoplasmic tails [Murakami, 1991]. Box1 is a proline-rich motif which is located more proximal to the transmembrane domain than the acidic box 2 element. The box-1 region serves as the binding site for a class of cytoplasmic tyrosine kinases termed JAKs (Janus kinases). Ligand-induced receptor dimerisation serves to increase the catalytic activity of the associated JAKs through cross-phosphorylation. Activated JAKs then tyrosine phosphorylate several substrates, including the receptors themselves. Specific phosphotyrosine residues on the receptor then serve as docking sites for SH2-containing proteins, the best characterised of which are the signal transducers and activators of transcription (STATs) and the adaptor protein, shc. The STATs are then phosphorylated on tyrosines, probably by JAKs, dissociate from the receptor and form either homodimers or heterodimers through the interaction of the SH2 domain of one STAT with the phosphotyrosine residue of the other. STAT dimers then translocate to the nucleus where they bind to specific cytokine-responsive promoters and activate transcription [Darnell, 1994; Ihle, 1995; Ihle, 1995]. In a separate pathway, tyrosine phosphorylated shc interacts with another SH2 domain-containing protein, Grb-2, leading ultimately to activation of members of the MAP kinase family and in turn transcription factors such as fos and jun [Sato, 1993; Cutler, 1993]. These pathways are not unique to members of the cytokine receptor family since cytokines that bind receptor tyrosine kinases also being able to activate STATs and members of the MAP kinase family [David, 1996; Leaman, 1996; Shual, 1993; Sato, 1993; Cutler, 1993].

Four members of the JAK family of cytoplasmic tyrosine kinases have been described, JAK1, JAK2, JAK3 and TYK2, each of which binds to a specific subset of cytokine receptor subunits. Six STATs have been described (STAT1 through STAT6), and these too are activated by distinct cytokine/receptor complexes. For example, STAT1 appears to be functionally specific to the interferon system, STAT4 appears to be specific to IL-12, while STAT6 appears to be specific for IL-4 and IL-13. Thus, despite common activation mechanisms some degree of cytokine specificity may be achieved through the use of specific JAKs and STATs [Thierfelder, 1996; Kaplan, 1996; Takeda, 1996; Shimoda, 1996; Meraz, 1996; Durbin, 1996].

In addition to those described above, there are clearly other mechanisms of activation of these pathways. For example, the JAK/STAT pathway appears to be able to activate MAP kinases independent of the shc-induced pathway [David, 1995] and the STATs themselves can be activated without binding to the receptor, possibly by direct interaction with JAKs [Gupta, 1996]. Conversely, full activation of STATS may require the action of MAP kinase in addition to that of JAKs [David, 1995; Wen, 1995].

While the activation of these signalling pathways is becoming better understood, little is known of the regulation of these pathways, including employment of negative or positive feedback loops. This is important since once a cell has begun to respond to a stimulus, it is critical that the intensity and duration of the response is regulated and that signal transduction is switched off. It is likewise desirable to increase the intensity of a response systemically or even locally as the situation requires.

In work leading up to the present invention, the inventors sought to isolate negative regulators of signal transduction. The inventors have now identified a new family of proteins which are capable of acting as regulators of signalling. The new family of proteins is defined as the suppressor of cytokine signalling (SOCS) family based on the ability of the initially identified SOCS molecules to suppress cytokine-mediated signalling. It should be noted, however, that not all members of the SOCS family need necessarily share suppressor function nor target solely cytokine mediated signalling. The SOCS family comprises at least three classes of protein molecules based on amino acid sequence motifs located N-terminal of a C-terminal motif called the SOCS box. The identification of this new family of regulatory molecules permits the generation of a range of effector or modulator molecules capable of modulating signal transduction and, hence, cellular responsiveness to a range of molecules including cytokines. The present invention, therefore, provides therapeutic and diagnostic agents based on SOCS proteins, derivatives, homologues, analogues and mimetics thereof as well as agonists and antagonists of SOCS proteins.

SUMMARY OF THE INVENTION

The present invention provides inter alia nucleic acid molecules encoding members of the SOCS family of proteins as well as the proteins themselves. Reference hereinafter to "SOCS" encompasses any or all members of the SOCS family. Specific SOCS molecules are defined numerically such as, for example, SOCS1, SOCS2 and SOCS3. The species from which the SOCS has been obtained may be indicated by a preface of a single letter abbreviation where "h" is human, "m" is murine and "r" is rat. Accordingly, "mSOCS1" is a specific SOCS from a murine animal. Reference herein to "SOCS" is not to imply that the protein solely suppresses cytokine-mediated signal transduction, as the molecule may modulate other effector-mediated signal transductions such as by hormones or other endogenous or exogenous molecules, antigens, microbes and microbial products, viruses or components thereof, ions, hormones and parasites. The term "modulates" encompasses up-regulation, down-regulation as well as maintenance of particular levels.

One aspect of the present invention provides a nucleic acid molecule comprising a sequence of nucleotides encoding or complementary to a sequence encoding a protein or a derivative, homologue, analogue or mimetic thereof or a nucleotide sequence capable of hybridizing thereto under low stringency conditions at 42° C. wherein said protein comprises a SOCS box in its C-terminal region Another aspect of the present invention provides a nucleic acid molecule comprising a sequence of nucleotides encoding or complementary to a sequence encoding a protein or a derivative, homologue, analogue or mimetic thereof or a nucleotide sequence capable of hybridizing thereto under low stringency conditions at 42° C. wherein said protein comprises a SOCS box in its C-terminal region and a protein:molecule interacting region.

Yet another aspect of the present invention is directed to a nucleic acid molecule comprising a sequence of nucleotides encoding or complementary to a sequence encoding a protein or a derivative, homologue, analogue or mimetic thereof or a nucleotide sequence capable of hybridizing thereto under low stringency conditions at 42° C. wherein said protein comprises a C-terminal region and a protein:molecule interacting region located in a region N-terminal of the SOCS box.

Preferably, the protein:molecule interacting region is a protein:DNA or protein:protein binding region.

Still a further aspect of the present invention provides a nucleic acid molecule comprising a sequence of nucleotides encoding or complementary to a sequence encoding a protein or a derivative, homologue, analogue or mimetic thereof or a nucleotide sequence capable of hybridizing thereto under low stringency conditions at 42° C. wherein said protein comprises a SOCS box in its C-terminal region and one or more of an SH2 domain, WD-40 repeats or ankyrin repeats N-terminal of the SOCS box.

Even still a further aspect of the present invention is directed to a nucleic acid molecule comprising a sequence of nucleotides encoding or complementary to a sequence encoding a protein or a derivative, homologue, analogue or mimetic thereof or a nucleotide sequence capable of hybridizing thereto under low stringency conditions at 42° C. wherein said protein comprises a SOCS box in its C-terminal region wherein the SOCS box comprises the amino acid sequence:

(SEQ ID NO: 51)

$X_1\ X_2\ X_3\ X_4\ X_5\ X_6\ X_7\ X_8\ X_9\ X_{10}\ X_{11}\ X_{12}\ X_{13}\ X_{14}\ X_{15}$
$X_{16}\ [X_i]_n\ X_{17}\ X_{18}\ X_{19}\ X_{20}\ X_{21}\ X_{22}\ X_{23}$
$[X_j]_n\ X_{24}\ X_{25}\ X_{26}\ X_{27}\ X_{28}$ wherein:

$X_1$ is L, I, V, M, A or P;
$X_2$ is any amino acid residue;
$X_3$ is P, T or S;
$X_4$ is L, I, V, M, A or P;
$X_5$ is any amino acid;
$X_6$ is any amino acid;
$X_7$ is L, I, V, M, A, F, Y or W;
$X_8$ is C, T or S;
$X_9$ is R, K or H;
$X_{10}$ is any amino acid;
$X_{11}$ is any amino acid;
$X_{12}$ is L, I, V, M, A or P;
$X_{13}$ is any amino acid;
$X_{14}$ is any amino acid;
$X_{15}$ is any amino acid;
$X_{16}$ is L, I, V, M, A, P, G, C, T or S;
$[X_i]_n$ is a sequence of n amino acids wherein n is from 1 to 50 amino acids and wherein the sequence $X_i$ may comprise the same or different amino acids selected from any amino acid residue;
$X_{17}$ is L, I, V, M, A or P;
$X_{18}$ is any amino acid;
$X_{19}$ is any amino acid;
$X_{20}$ L, I, V, M, A or P;
$X_{21}$ is P;
$X_{22}$ is L, I, V, M, A, P or G;
$X_{23}$ is P or N;
$[X_j]_n$ is a sequence of n amino acids wherein n is from 0 to 50 amino acids and wherein the sequence $X_j$ may comprise the same or different amino acids selected from any amino acid residue;

$X_{24}$ is L, I, V, M, A or P;
$X_{25}$ is any amino acid;
$X_{26}$ is any amino acid;
$X_{27}$ is Y or F;
$X_{28}$ is L, I, V, M, A or P;

and a protein:molecule interacting region such as but not limited to one or more of an SH2 domain, WD-40 repeats and/or ankyrin repeats N-terminal of the SOCS box.

Another aspect of the present invention is directed to a nucleic acid molecule comprising a sequence of nucleotides encoding or complementary to a sequence encoding a protein or a derivative, homologue, analogue or mimetic thereof or a nucleotide sequence capable of hybridizing thereto under low stringency conditions at 42° C. wherein said protein exhibits the following characteristics:

(i) comprises a SOCS box in its C-terminal region having the amino acid sequence:

(SEQ ID NO: 51)
$X_1$ $X_2$ $X_3$ $X_4$ $X_5$ $X_6$ $X_7$ $X_8$ $X_9$ $X_{10}$ $X_{11}$ $X_{12}$ $X_{13}$ $X_{14}$ $X_{15}$ $X_{16}$ $[X_i]_n$ $X_{17}$ $X_{18}$ $X_{19}$ $X_{20}$ $X_{21}$ $X_{22}$ $X_{23}$ $[X_j]_n$ $X_{24}$ $X_{25}$ $X_{26}$ $X_{27}$ $X_{28}$ wherein:
$X_1$ is L, I, V, M, A or P;
$X_2$ is any amino acid residue;
$X_3$ is P, T or S;
$X_4$ is L, I, V, M, A or P;
$X_5$ is any amino acid;
$X_6$ is any amino acid;
$X_7$ is L, I, V, M, A, F, Y or W;
$X_8$ is C, T or S;
$X_9$ is R, K or H;
$X_{10}$ is any amino acid;
$X_{11}$ is any amino acid;
$X_{12}$ is L, I, V, M, A or P;
$X_{13}$ is any amino acid;
$X_{14}$ is any amino acid;
$X_{15}$ is any amino acid;
$X_{16}$ is L, I, V, M, A, P, G, C, T or S;
$[X_i]_n$ is a sequence of n amino acids wherein n is from 1 to 50 amino acids and wherein the sequence $X_i$ may comprise the same or different amino acids selected from any amino acid residue;
$X_{17}$ is L, I, V, M, A or P;
$X_{18}$ is any amino acid;
$X_{19}$ is any amino acid;
$X_{20}$ L, I, V, M, A or P;
$X_{21}$ is P;
$X_{22}$ is L, I, V, M, A, P or G;
$X_{23}$ is P or N;
$[X_j]_n$ is a sequence of n amino acids wherein n is from 0 to 50 amino acids and wherein the sequence $X_j$ may comprise the same or different amino acids selected from any amino acid residue;
$X_{24}$ is L, I, V, M, A or P;
$X_{25}$ is any amino acid;
$X_{26}$ is any amino acid;
$X_{27}$ is Y or F;
$X_{28}$ is L, I, V, M, A or P; and (ii) comprises at least one of a SH2 domain, WD-40 repeats and/or ankyrin repeats or other protein:molecule interacting domain in a region N-terminal of the SOCS box.

Preferably, the SOCS molecules modulate signal transduction such as from a cytokine or hormone or other endogenous or exogenous molecule, a microbe or microbial product, an antigen or a parasite.

More preferably, the SOCS molecule modulate cytokine mediated signal transduction.

Still another aspect of the present invention comprises a nucleic acid molecule comprising a sequence of nucleotides encoding or complementary to a sequence encoding a protein or a derivative, homologue, analogue or mimetic thereof or comprises a nucleotide sequence capable of hybridizing thereto under low stringency conditions at 42° C. wherein said protein exhibits the following characteristics;

(i) is capable of modulating signal transduction;

(ii) comprises a SOCS box in its C-terminal region having the amino acid sequence:

(SEQ ID NO: 51)
$X_1$ $X_2$ $X_3$ $X_4$ $X_5$ $X_6$ $X_7$ $X_8$ $X_9$ $X_{10}$ $X_{11}$ $X_{12}$ $X_{13}$ $X_{14}$ $X_{15}$ $X_{16}$ $[Xi]_n$ $X_{17}$ $X_{18}$ $X_{19}$ $X_{20}$ $X_{21}$ $X_{22}$ $X_{23}$ $[X_j]_n$ $X_{24}$ $X_{25}$ $X_{26}$ $X_{27}$ $X_{28}$ wherein:
$X_1$ is L, I, V, M, A or P;
$X_2$ is any amino acid residue;
$X_3$ is P, T or S;
$X_4$ is L, I, V, M, A or P;
$X_5$ is any amino acid;
$X_6$ is any amino acid;
$X_7$ is L, I, V, M, A, F, Y or W;
$X_8$ is C, T or S;
$X_9$ is R, K or H;
$X_{10}$ is any amino acid;
$X_{11}$ is any amino acid;
$X_{12}$ is L, I, V, M, A or P;
$X_{13}$ is any amino acid;
$X_{14}$ is any amino acid;
$X_{15}$ is any amino acid;
$X_{16}$ is L, I, V, M, A, P, G, C, T or S;
$[X_i]_n$ is a sequence of n amino acids wherein n is from 0 to 50 amino acids and wherein the sequence $X_i$ may comprise the same or different amino acids selected from any amino acid residue;
$X_{17}$ is L, I, V, M, A or P;
$X_{18}$ is any amino acid;
$X_{19}$ is any amino acid;
$X_{20}$ L, I, V, M, A or P;
$X_{21}$ is P;
$X_{22}$ is L, I, V, M, A, P or G;
$X_{23}$ is P or N;
$[X_j]_n$ is a sequence of n amino acids wherein n is from 0 to 50 amino acids and wherein the sequence $X_j$ may comprise the same or different amino acids selected from any amino acid residue;
$X_{24}$ is L, I, V, M, A or P;
$X_{25}$ is any amino acid;
$X_{26}$ is any amino acid;
$X_{27}$ is Y or F;
$X_{28}$ is L, I, V, M, A or P; and (iii) comprises at least one of a SH2 domain, WD-40 repeats and/or ankyrin repeats or other protein:molecule interacting domain in a region N-terminal of the SOCS box.

Preferably, the signal transduction is mediated by a cytokine such as one or more of EPO, TPO, G-CSF, GM-CSF, IL-3, IL-2, IL-4, IL-7, IL-13, IL-6, LIF, IL-12, IFNα, TNFα, IL-1 and/or M-CSF.

Preferably, the signal transduction is mediated by one or more of Interleukin 6 (IL-6), Leukaemia Inhibitory Factor (LIF), Oncostatin M (OSM), Interferon (IFN)-α and/or thrombopoietin.

Preferably, the signal transduction is mediated by IL-6.

Particularly preferred nucleic acid molecules comprise nucleotide sequences substantially set forth in SEQ ID NO:3 (mSOCS1), SEQ ID NO:5 (mSOCS2), SEQ ID NO:7 (mSOCS3), SEQ ID NO:9 (hSOCS1), SEQ ID NO:11 (rSOCS1), SEQ ID NO:13 (mSOCS4), SEQ ID NO:15 and SEQ ID NO:16 (hSOCS4), SEQ ID NO:17 (mSOCS5), SEQ ID NO:19 (hSOCS5), SEQ ID NO:20 (mSOCS6), SEQ ID NO:22 and SEQ ID NO:23 (hSOCS6), SEQ ID NO:24 (mSOCS7), SEQ ID NO:26 and SEQ ID NO:27 (hSOCS7), SEQ ID NO:28 (mSOCS8), SEQ ID NO:30 (mSOCS9), SEQ ID NO:31 (hSOCS9), SEQ ID NO:32 (mSOCS10), SEQ ID NO:33 and SEQ ID NO:34 (hSOCS10), SEQ ID NO:35 (hSOCS11), SEQ ID NO:37 (mSOCS12), SEQ ID NO:38 and SEQ ID NO:39 (hSOCS12), SEQ ID NO:40 (mSOCS13), SEQ ID NO:42 (hSOCS13), SEQ ID NO:43 (mSOCS14), SEQ ID NO:45 (mSOCS15) and SEQ ID NO:47 (hSOCS15) or a nucleotide sequence having at least about 15% similarity to all or a region of any of the listed sequences or a nucleotide acid molecule capable of hybridizing to any one of the listed sequences under low stringency conditions at 42° C.

Another aspect of the present invention relates to a protein or a derivative, homologue, analogue or mimetic thereof comprising a SOCS box in its C-terminal region.

Yet another aspect of the present invention is directed to a protein or a derivative, homologue, analogue or mimetic thereof comprising a SOCS box in its C-terminal region and a protein:molecule interacting region.

Even yet another aspect of the present invention provides a protein or a derivative, homologue, analogue or mimetic thereof comprising an interacting region located in a region N-terminal of the SOCS box.

Preferably, the protein:molecule interacting region is a protein:DNA or a protein:protein binding region.

Another aspect of the present invention contemplates a protein or a derivative, homologue, analogue or mimetic thereof comprising a SOCS box in its C-terminal region and a SH2 domain, WD-40 repeats or ankyrin repeats N-terminal of the SOCS box.

Still yet another aspect of the present invention provides a protein or a derivative, homologue, analogue or mimetic thereof exhibiting the following characteristics:

(i) comprises a SOCS box in its C-terminal region having the amino acid sequence:

(SEQ ID NO: 51)

$X_1$ $X_2$ $X_3$ $X_4$ $X_5$ $X_6$ $X_7$ $X_8$ $X_9$ $X_{10}$ $X_{11}$ $X_{12}$ $X_{13}$ $X_{14}$ $X_{15}$
$X_{16}$ $[X_i]_n$ $X_{17}$ $X_{18}$ $X_{19}$ $X_{20}$ $X_{21}$ $X_{22}$ $X_{23}$ $[X_j]_n$ $X_{24}$
$X_{25}$ $X_{26}$ $X_{27}$ $X_{28}$ wherein:

$X_1$ is L, I, V, M, A or P;
$X_2$ is any amino acid residue;
$X_3$ is P, T or S;
$X_4$ is L, I, V, M, A or P;
$X_5$ is any amino acid;
$X_6$ is any amino acid;
$X_7$ is L, I, V, M, A, F, Y or W;
$X_8$ is C, T or S;
$X_9$ is R, K or H;
$X_{10}$ is any amino acid;
$X_{11}$ is any amino acid;
$X_{12}$ is L, I, V, M, A or P;
$X_{13}$ is any amino acid;
$X_{14}$ is any amino acid;
$X_{15}$ is any amino acid;
$X_{16}$ is L, I, V, M, A, P, G, C, T or S;
$[X_i]_n$ is a sequence of n amino acids wherein n is from 1 to 50 amino acids and wherein the sequence $X_i$ may comprise the same or different amino acids selected from any amino acid residue;
$X_{17}$ is L, I, V, M, A or P;
$X_{18}$ is any amino acid;
$X_{19}$ is any amino acid;
$X_{20}$ L, I, V, M, A or P;
$X_{21}$ is P;
$X_{22}$ is L, I, V, M, A, P or G;
$X_{23}$ is P or N;
$[X_j]_n$ is a sequence of n amino acids wherein n is from 0 to 50 amino acids and wherein the sequence $X_j$ may comprise the same or different amino acids selected from any amino acid residue;
$X_{24}$ is L, I, V, M, A or P;
$X_{25}$ is any amino acid;
$X_{26}$ is any amino acid;
$X_{27}$ is Y or F;
$X_{28}$ is L, I, V, M, A or P; and (ii) comprises at least one of a SH2 domain, WD-40 repeats and/or ankyrin repeats or other protein:molecule interacting domain in a region N-terminal of the SOCS box.

Preferably, the proteins modulate signal transduction such as cytokine-mediated signal transduction.

Preferred cytokines are EPO, TPO, G-CSF, GM-CSF, IL-3, IL-2, IL-4, IL-7, IL-13, IL-6, LIF, IL-12, IFNγ, TNFα, IL-1 and/or M-CSF.

A particularly preferred cytokine is IL-6.

Even yet another aspect of the present invention provides a protein or derivative, homologue, analogue or mimetic thereof exhibiting the following characteristics:

(i) is capable of modulating signal transduction such as cytokine-mediated signal transduction;

(ii) comprises a SOCS box in its C-terminal region having the amino acid sequence:

(SEQ ID NO: 51)

$X_1$ $X_2$ $X_3$ $X_4$ $X_5$ $X_6$ $X_7$ $X_8$ $X_9$ $X_{10}$ $X_{11}$ $X_{12}$ $X_{13}$ $X_{14}$ $X_{15}$
$X_{16}$ $[X_i]_n$ $X_{17}$ $X_{18}$ $X_{19}$ $X_{20}$ $X_{21}$ $X_{22}$ $X_{23}$ $[X_j]_n$ $X_{24}$
$X_{25}$ $X_{26}$ $X_{27}$ $X_{28}$ wherein:

$X_1$ is L, I, V, M, A or P;
$X_2$ is any amino acid residue;
$X_3$ is P, T or S;
$X_4$ is L, I, V, M, A or P;
$X_5$ is any amino acid;
$X_6$ is any amino acid;
$X_7$ is L, I, V, M, A, F, Y or W;
$X_8$ is C, T or S;
$X_9$ is R, K or H;
$X_{10}$ is any amino acid;
$X_{11}$ is any amino acid;
$X_{12}$ is L, I, V, M, A or P;
$X_{13}$ is any amino acid;
$X_{14}$ is any amino acid;
$X_{15}$ is any amino acid;
$X_{16}$ is L, I, V, M, A, P, G, C, T or S;
$[X_i]_n$ is a sequence of n amino acids wherein n is from 1 to 50 amino acids and wherein the sequence $X_i$ may comprise the same or different amino acids selected from any amino acid residue;

$X_{17}$ is L, I, V, M, A or P;

$X_{18}$ is any amino acid;

$X_{19}$ is any amino acid;

$X_{20}$ L, I, V, M, A or P;

$X_{21}$ is P;

$X_{22}$ is L, I, V, M, A, P or G;

$X_{23}$ is P or N;

$[X_j]_n$ is a sequence of n amino acids wherein n is from 0 to 50 amino acids and wherein the sequence $X_j$ may comprise the same or different amino acids selected from any amino acid residue;

$X_{24}$ is L, I, V, M, A or P;

$X_{25}$ is any amino acid;

$X_{26}$ is any amino acid;

$X_{27}$ is Y or F;

$X_{28}$ is L, I, V, M, A or P; and (iii) comprises at least one of a SH2 domain, WD-40 repeats and/or ankyrin repeats or other protein-molecule interacting domain in a region N-terminal of the SOCS box.

Particularly preferred SOCS proteins comprise an amino acid sequence substantially as set forth in SEQ ID NO:4 (mSOCS1), SEQ ID NO:6 (mSOCS2), SEQ ID NO:8 (mSOCS3), SEQ ID NO:10 (hSOCS1), SEQ ID NO:12 (rSOCS1), SEQ ID NO:14 (mSOCS4), SEQ ID NO:18 (mSOCS5), SEQ ID NO:21 (mSOCS6), SEQ ID NO:25 (mSOCS7), SEQ ID NO:29 (mSOCS8), SEQ ID NO:36 (hSOCS11), SEQ ID NO:41 (mSOCS13), SEQ ID NO:44 (mSOCS14), SEQ ID NO:46 (mSOCS15) and SEQ ID NO:48 (hSOCS15) or an amino acid sequence having at least 15% similarity to all or a region of any one of the listed sequences.

Another aspect of the present invention contemplates a method of modulating levels of a SOCS protein in a cell said method comprising contacting a cell containing a SOCS gene with an effective amount of a modulator of SOCS gene expression or SOCS protein activity for a time and under conditions sufficient to modulate levels of said SOCS protein.

A related aspect of the present invention provides a method of modulating signal transduction in a cell containing a SOCS gene comprising contacting said cell with an effective amount of a modulator of SOCS gene expression or SOCS protein activity for a time sufficient to modulate signal transduction.

Yet a further related aspect of the present invention is directed to a method of influencing interaction between cells wherein at least one cell carries a SOCS gene, said method comprising contacting the cell carrying the SOCS gene with an effective amount of a modulator of SOCS gene expression or SOCS protein activity for a time sufficient to modulate signal transduction.

In accordance with the present invention, n in $[X_i]_n$ and $[X_j]_n$ may, in addition from being 1-50, be from 1-30, 1-20, 1-10 and 1-5.

A summary of the SEQ ID NOs referred to in the subject specification is given in Table 1.

TABLE 1

SUMMARY OF SEQUENCE IDENTITY NUMBERS

| SEQUENCE | SEQ ID NO. |
|---|---|
| PCR Primer | 1 |
| PCR Primer | 2 |
| Mouse SOCS1 (nucleotide) | 3 |
| Mouse SOCS1 (amino acid) | 4 |
| Mouse SOCS2 (nucleotide) | 5 |
| Mouse SOCS2 (amino acid) | 6 |
| Mouse SOCS3 (nucleotide) | 7 |
| Mouse SOCS3 (amino acid) | 8 |
| Human SOCS1 (nucleotide) | 9 |
| Human SOCS1 (amino acid) | 10 |
| Rat SOCS1 (nucleotide) | 11 |
| Rat SOCS1 (amino acid) | 12 |
| nucleotide sequence of murine SOCS4 | 13 |
| amino acid sequence of murine SOCS4 | 14 |
| nucleotide sequence of SOCS4 cDNA human contig 4.1 | 15 |
| nucleotide sequence of SOCS4 cDNA human contig 4.2 | 16 |
| nucleotide sequence of murine SOCS5 | 17 |
| amino acid sequence of murine SOCS5 | 18 |
| nucleotide sequence of human SOCS5 | 19 |
| nucleotide sequence of murine SOCS6 | 20 |
| amino acid of murine SOCS6 | 21 |
| nucleotide sequence of human SOCS6 contig h6.1 | 22 |
| nucleotide sequence of human SOCS6 contig h6.2 | 23 |
| nucleotide sequence of murine SOCS7 | 24 |
| amino acid sequence of murine SOCS7 | 25 |
| nucleotide sequence of human SOCS7 contig h7.1 | 26 |
| nucleotide sequence of human SOCS7 contig 17.2 | 27 |
| nucleotide sequence of murine SOCS8 | 28 |
| amino acid sequence of murine SOCS 8 | 29 |
| nucleotide sequence of murine SOCS9 | 30 |
| nucleotide sequence of human SOCS9 | 31 |
| nucleotide sequence of murine SOCS10 | 32 |
| nucleotide sequence of human SOCS10 contig h10.1 | 33 |
| nucleotide sequence of human SOCS10 contig h10.2 | 34 |
| nucleotide sequence of human SOCS11 | 35 |
| amino acid sequence of human SOCS11 | 36 |
| nucleotide sequence of mouse SOCS12 | 37 |
| nucleotide sequence of human SOCS12 contig h12.1 | 38 |
| nucleotide sequence of human SOCS12 contig h12.2 | 39 |
| nucleotide sequence of murine SOCS13 | 40 |
| amino acid sequence of murine SOCS13 | 41 |
| nucleotide sequence of human SOCS13 cDNA contig h13.1 | 42 |
| nucleotide sequence of murine SOCS14 cDNA | 43 |
| amino acid sequence of murine SOCS14 | 44 |
| nucleotide sequence of murine SOCS15 cDNA | 45 |
| amino acid sequence of murine SOCS15 | 46 |
| nucleotide sequence of human SOCS15 | 47 |
| amino acid sequence of human SOCS15 | 48 |

Single and three letter abbreviations are used to denote amino acid residues and these are summarized in Table 2.

TABLE 2

| Amino Acid | Three-letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |

TABLE 2-continued

| Amino Acid | Three-letter Abbreviation | One-letter Symbol |
|---|---|---|
| Tyrosine | Tyr | Y |
| Valine | Val | V |
| Any residue | Xaa | X |

BRIEF DESCRIPTION OF THE DRAWINGS

In some of the Figures, abbreviations are used to denote SOCS proteins with certain binding motifs. SOCS proteins which contain WD-40 repeats are referred to as WSB1-WSB4. SOCS proteins with ankyrin repeats are referred to as ASB1-ASB3.

FIG. 3A-3B(3) is a representation of the nucleotide sequence and structure of the SOCS1 gene. A. The genomic context of SOCS1 in relation to the protamine gene cluster on murine chromosome 16. The accession number of this locus is MMPRMGNS (direct submission; G. Schlueter, 1995) for the mouse and BTPRMTNP2 for the rat (direct submission; G. Schlueter, 1996). B(1)-(3). The nucleotide sequence of the SOCS1 cDNA and deduced amino acid sequence. Conventional one letter abbreviations are used for the amino acid sequence and the asterisk indicates the stop codon. The polyadenylation signal sequence is underlined. The coding region is shown in uppercase and the untranslated region is shown in lower case.

FIG. 9(I)-9(III) is a representation of a comparison of the amino acid sequences of SOCS1, SOCS2, SOCS3 and CIS. Alignment of the predicted amino acid sequence of mouse (mm), human (hs) and rat (rr) SOCS1, SOCS2, SOCS3 and CIS. Those residues shaded are conserved in three or four mouse SOCS family members. The SH2 domain is boxed in solid lines, while the SOCS box is bounded by double lines.

(11A) Northern analysis of mRNA from a range of mouse organs showing constitutive expression of SOCS family members in a limited number of tissues.

(11B) Norther analysis of mRNA from liver and M1 cells showing induction of expression of SOCS family members following exposure to IL-6.

(11C) Reverse transcriptase PCR analysis of mRNA from bone marrow showing induction of expression of SOCS family members by a range of cytokines.

Figure 12A:
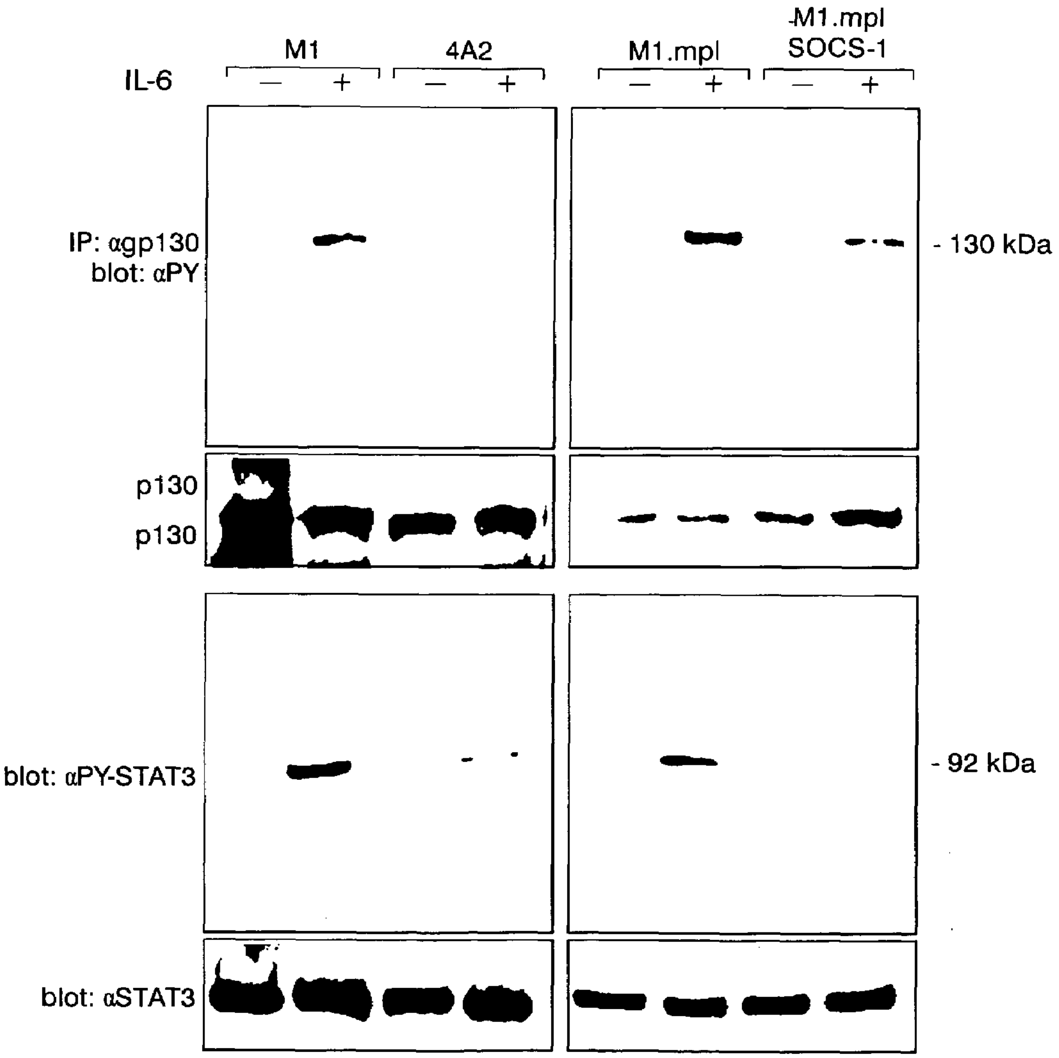
Figure 12B:
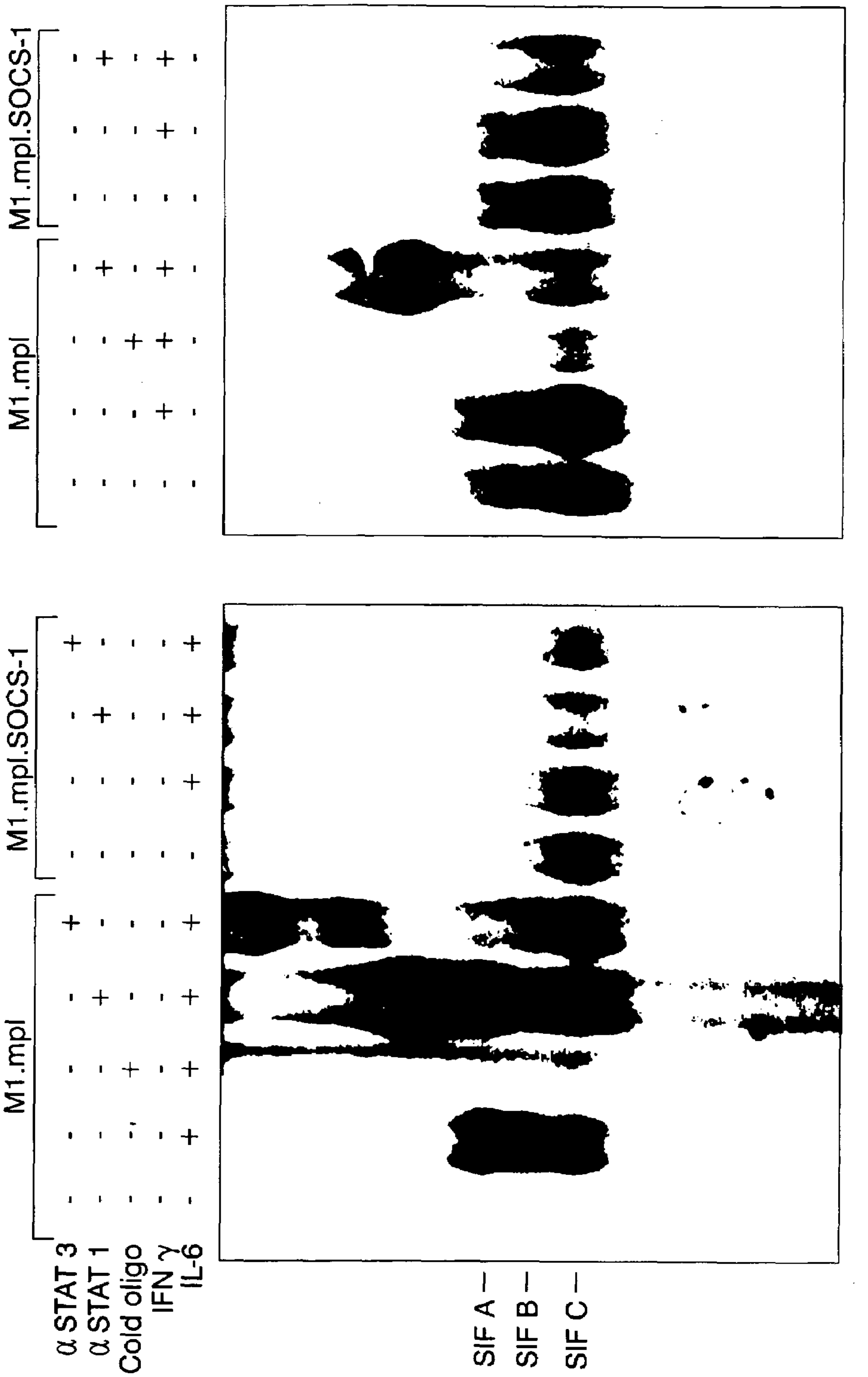

FIG. 12A-12B is a photographic representation showing SOCS1 suppresses the phosphorylation and activation of gp130 and STAT-3.

(12A) Western blots of extracts from parental M1 cells (M1 and M1.mpl) and M1 cells expressing SOCS1 (4A2 and M1.mpl.SOCS1) stimulated with (+) or without (−) 100 ng/ml IL-6. Top: Extracts immunoprecipitated with antu-gp130 (αgp130) and immunoblotted with anti-phosphotyrosine (αPY-STAT3), or for STAT3

(αSTAT3) to demonstrate equal loading of protein. The molecular weights of the bands are shown on the right.

(12B) EMSA of M1.mpl and M1.mpl.SOCS1 cells stimulated with (+) and without (−) 100 ng/ml IL-6 or 100 ng/ml IFNγ. The DNA-binding complexes SIF A, B, and C are indicated at the left.

FIG. 13A(i)-13F(ii) is a representation of a comparison of the amino acid sequence of the SOCS proteins (13A(i)-(ii)) Schematic representation of structures of SOCS proteins including proteins which contain WD-40 repeats (WSB) and ankyrin repeats (ASB). (13B(i)-(ii)) Alignment of N-terminal regions of SOCS proteins. (13C(i)-(ii)) Alignment of the SH2 domains of CIS, SOCS1, 2, 3, 5, 9, 11 and 14. (13D) Alignment of the WD-40 repeats of SOCS4, SOCS6, SOCS13 and SOCS15. (13E(i)-(ii)) Alignment of the ankyrin repeats of SOCS7 and SOCS10. (13F(i)-(ii)) Alignment of the regions between SH2, WD-40 and ankyrin repeats and the SOCS box. In each case the conventional one letter abbreviations for amino acids are used, with X denoting residues of uncertain identity and ○○○ denoting the beginning and the end of contigs. Amino acid sequence obtained from conceptual translation of nucleic acid sequence derived from isolated cDNAs is shown in upper case while amino acid sequence obtained by conceptual translation of ESTs is shown in lower case and is approximate only. Conserved residues, defined as (LIVMA), (FYW), (DE), (QN), (C, S, T), (KRH), (PG) are shaded in the SH2 domain, WD-40 repeats, ankyrin repeats and the SOCS box. For the alignment of SH2 domains, WD-40 repeats and ankyrin repeats a consensus sequence is shown above. In each case this has been derived from examination of a large and diverse set of domains (Neer et al, 1994; Bork, 1993).

Figure 14A:
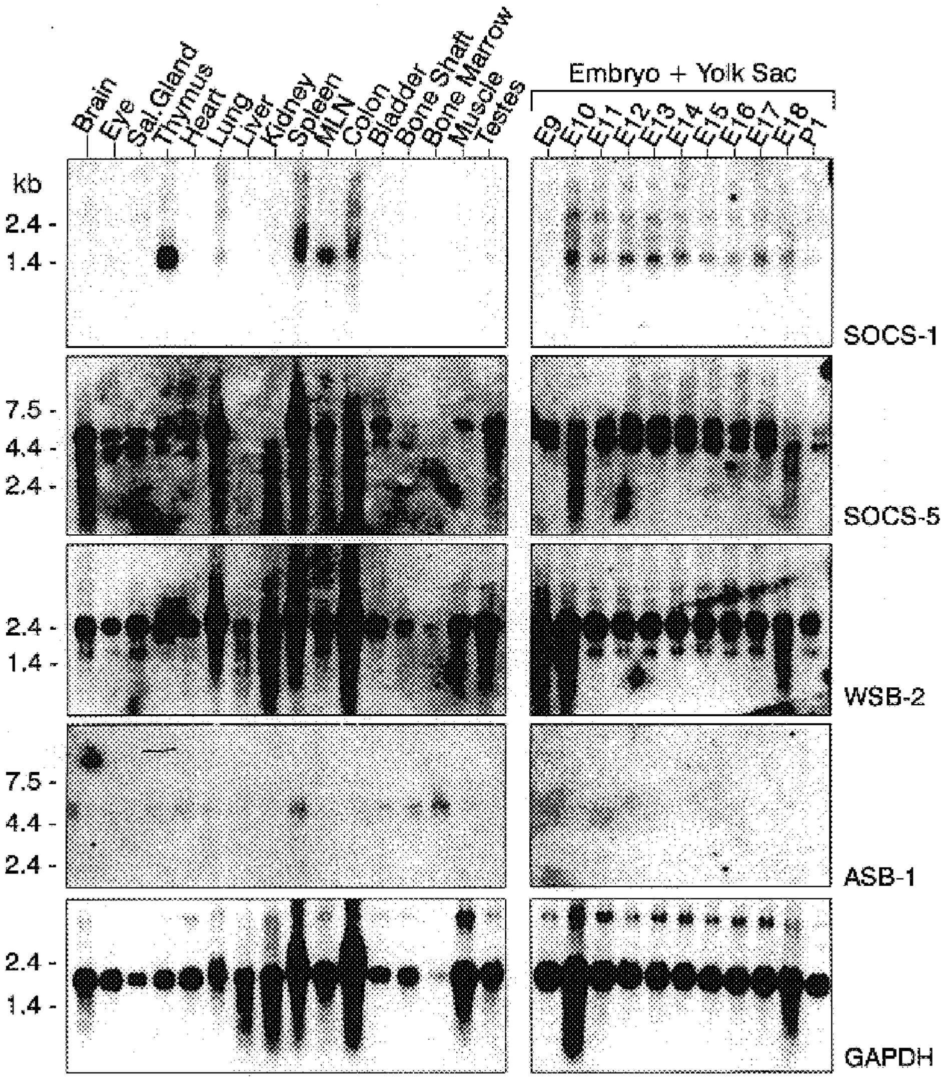

FIGS. 14(A) and (B) are photographic representations showing analysis of mRNA expression of mouse SOCS1 and SOCS5 and SOCS containing a WD-40 repeat (WSB2) and ankyrin repeats (ASB1).

FIG. 15 is a representation showing the nucleotide sequence of the mouse SOCS4 cDNA. The nucleotides encoding the mature coding region from the predicted ATG “start” codon to the stop codon is shown in upper case, while the predicted 5' and 3' untranslated regions are shown in lower case. The relationship of mouse cDNA sequence to mouse and human EST contigs is illustrated in FIG. 17.

FIG. 16 is a representation showing the predicted amino acid sequence of the mouse SOCS4 protein, derived from the nucleotide sequence in FIG. 15. The SOCS box, which also shown in FIG. 13, is underlined.

Figure 17:
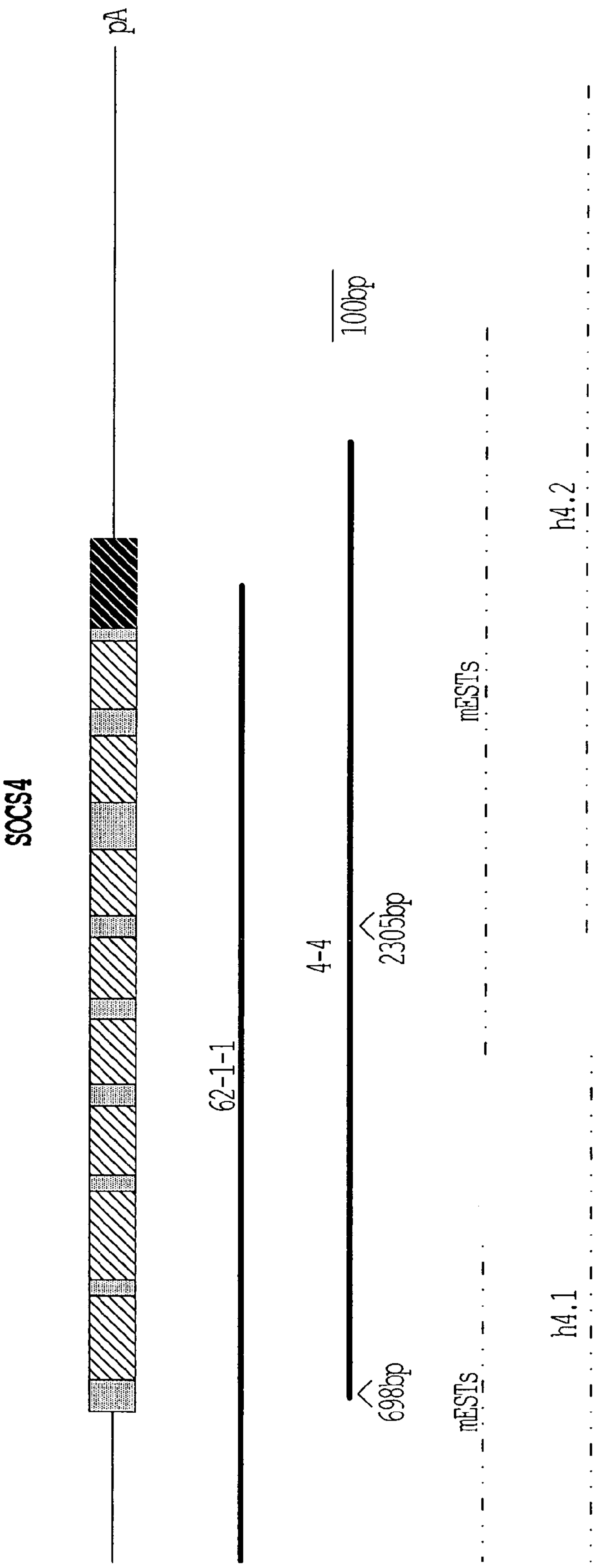

FIG. 17 is a representation showing the relationship of two cDNA clones encoding mouse SOCS4 (62-1-1 and 4-4) to contigs derived from analysis of mouse ESTs (Table 4.1) and human SOCS4 cDNA contigs h4.1 and h4.2. The structure of the mouse SOCS4 protein is shown schematically, with the WD-40 repeats indicated by open white hatched boxes, and the SOCS box by the solid black hatched box. The 5' and 3' untranslated regions are shown by the thin solid line.

FIG. 18 is a representation showing the nucleotide sequence of human SOCS4 cDNA contigs h4.1 and h4.2, derived from analysis of ESTs listed in Table 4.1. The relationship of these contigs to the mouse cDNA sequence is illustrated in FIG. 17.

Figure 19:
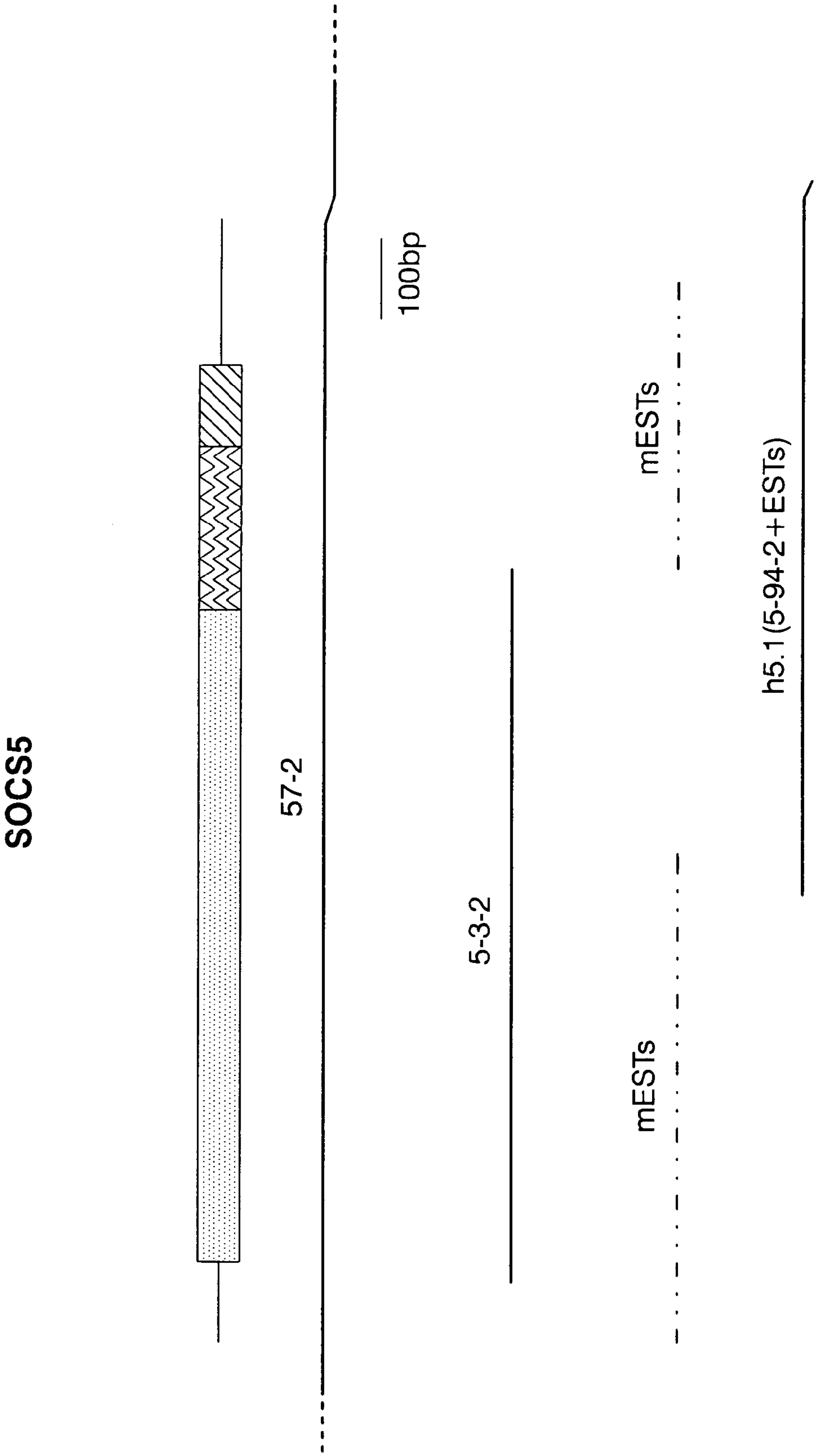

FIG. 19 is a diagrammatic representation showing the relationship of mouse SOCS5 genomic (57-2) and cDNA (5-3-2) clones to contigs derived from analysis of mouse ESTs (Table 5.1) and human cDNA clone (5-94-2) and ESTs (Table 5.2). The nucleotide sequence of the mouse SOCS5 contig is shown in FIG. 20, with the sequence of human SOCS5 contig (h5.1) being shown in FIG. 21. The deduced amino acid sequence of mouse SOCS5 is shown in FIG. 20B. The structure of the protein is shown schematically, with the SH2 domain indicated by the open white wave box and the SOCS box by the solid black hatched box. The putative 5' and 3' translated regions are shown by the thin solid line.

FIG. 20A is a representation showing the nucleotide sequence of the mouse SOCS5 derived from analysis of genomic and cDNA clones. The nucleotides encoding the mature coding region from the predicted ATG “start” codon to the stop codon is shown in upper case, while the predicted 5' and 3' untranslated regions are shown in lower case. The relationship of mouse cDNA sequence to mouse and human EST contigs is illustrated in FIG. 19.

FIG. 20B is a representation of the predicted amino acid sequence of mouse SOCS5 protein, derived from the nucleotide sequence in FIG. 20A. The SOCS box, which also shown in FIG. 13 is underlined.

FIG. 21 is a representation showing the nucleotide sequence of human SOCS5 cDNA contig h5.1, derived from analysis of cDNA clone 5-94-2 and the ESTs listed in Table 5.2. The relationship of these contigs to the mouse cDNA sequence is illustrated in FIG. 19.

Figure 22:
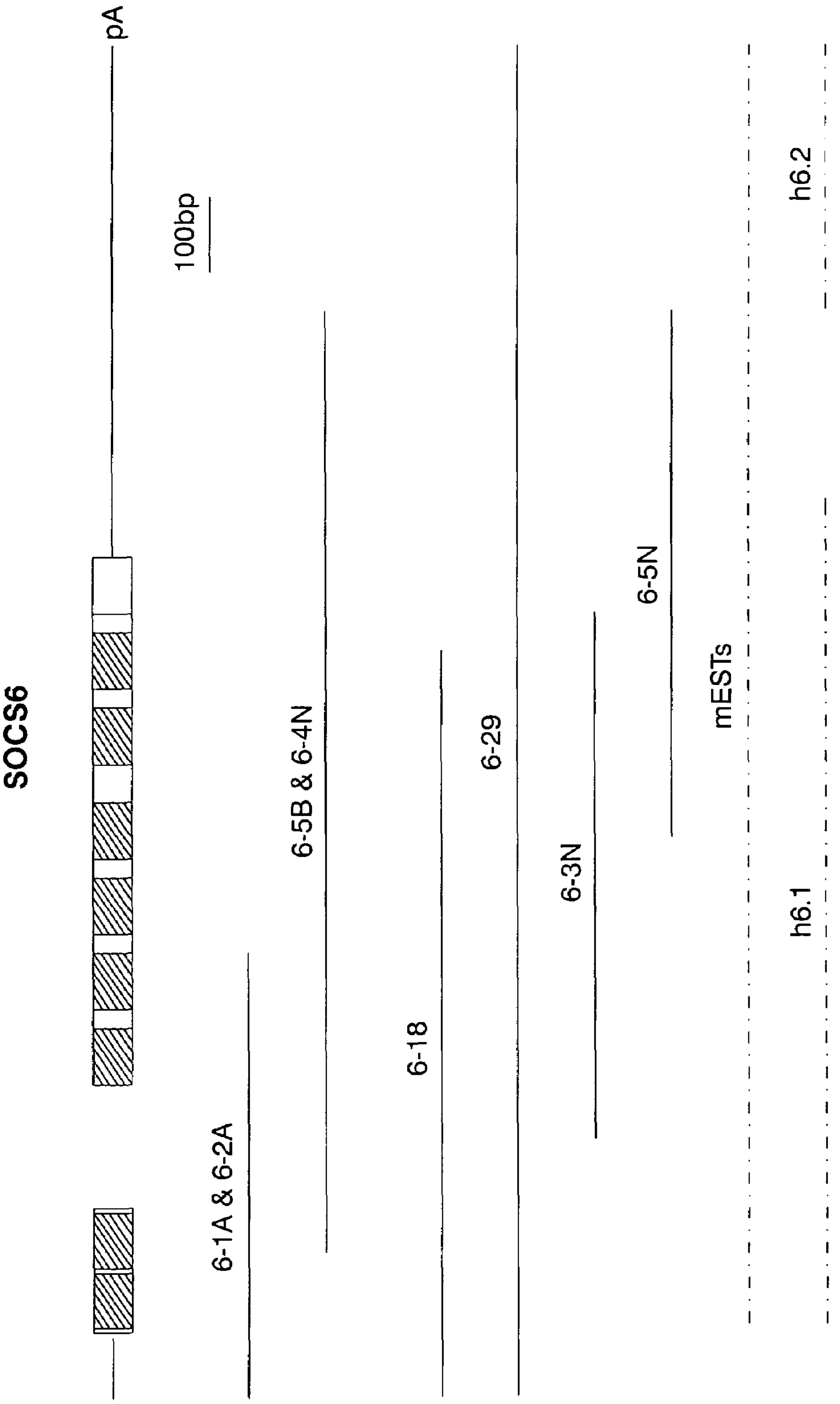

FIG. 22 is a diagrammatic representation showing the relationship of mouse SOCS6 cDNA clones (6-1A, 6-2A, 6-5B, 6-4N, 6-18, 6-29, 6-3N and 6-SN) to contigs derived from analysis of mouse ESTs (Table 6.1) and human ESTs (Table 6.2). The nucleotide sequence of the mouse SOCS-6 contig is shown in FIG. 23, with the sequence of human SOCS6 contigs (h6.1 and h6.2) being shown in FIG. 24. The deduced amino acid sequence of mouse SOCS6 is shown in FIG. 23B. The structure of the protein is shown schematically, while the WD-40 repeats indicated by open white hatched boxes and the SOCS box by the solid black hatched box. The putative 5' and 3' untranslated regions are shown by the thin solid line.

FIG. 23A is a representation showing the nucleotide sequence of the mouse SOCS6 derived from analysis of cDNA clone 64-10A-11. The nucleotides encoding the part of the predicted coding region, ending in the stop codon are shown in upper case, while the predicted 3' untranslated regions are shown in lower case. The relationship of mouse cDNA sequence to mouse and human EST contigs is illustrated in FIG. 22.

FIG. 23B is a representation showing the predicted amino acid sequence of mouse SOCS6 protein, derived from the nucleotide sequence in FIG. 23A. The SOCS box, which also shown in FIG. 13 is underlined.

FIG. 24 is a representation showing the nucleotide sequence of human SOCS6 cDNA contig h6.1, derived from analysis of cDNA clone 5-94-2 and the ESTs listed in Table 6.2. The relationship of these contigs to the mouse cDNA sequence is illustrated in FIG. 22

Figure 25:
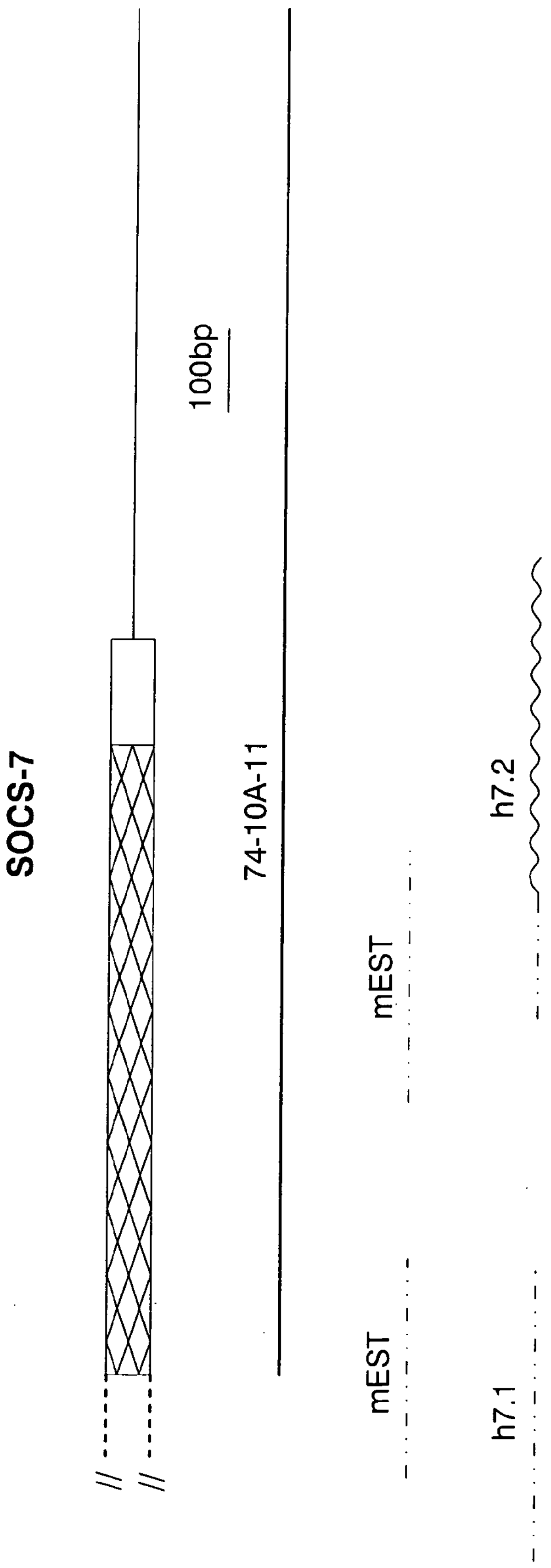

FIG. 25 is a diagrammatic representation showing the relationship of mouse SOCS7 cDNA clone (74-10A-11) to contigs derived from analysis of mouse ESTs (Table 7.1) and human ESTs (Table 7.2). The nucleotide sequence of the mouse SOCS7 contig is shown in FIG. 26 with the sequence of human SOCS7 contigs (h7.1 and h7.2) being shown in FIG. 27. The deduced amino acid sequence of mouse SOCS7 is shown in FIG. 26B. The structure of the protein is shown schematically, with the ankyrin repeats indicated by the cross hatched box and the SOCS box by the solid black hatched box. The putative 5' and 3' untranslated regions are shown by the thin solid line in the mouse and by the wavy line in h7.2. Based on analysis of clones isolated to date and ESTs the 3' untranslated regions of mSOCS7 and hSOCS7 share little similarity.

FIG. 26A is a representation showing the nucleotide sequence of the mouse SOCS7 derived from analysis of cDNA clone 74-10A-11. The nucleotides encoding the part of the predicted coding region, ending in the stop codon are shown in upper case, while the predicted 3' untranslated regions are shown in lower case. The relationship of mouse cDNA sequence to mouse and human EST contigs is illustrated in FIG. 25.

FIG. 26B is a representation showing the predicted amino acid sequence of mouse SOCS7 protein, derived from the nucleotide sequence in FIG. 26A. The SOCS box, which also shown in FIG. 13 is underlined.

FIG. 27 is a representation showing the nucleotide sequence of human SOCS7 cDNA contig h7.1 and h7.2 derived from analysis of the ESTs listed in Table 7.2. The relationship of these contigs to the mouse cDNA sequence is illustrated in FIG. 25.

Figure 28:
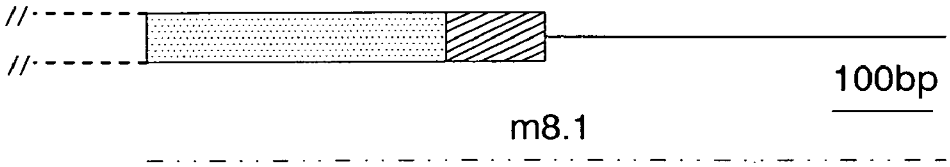

FIG. 28 is a diagrammatic representation of the relationship of sequence derived from analysis of mouse SOCS8 ESTs (Table 8.1 and FIG. 29A) to the predicted protein structure of mouse SOCS8. The deduced partial amino acid sequence of mouse SOCS8 is shown in FIG. 29B. The structure of the protein is shown schematically with the SOCS box highlighted by the solid black hatched box. The predicted 3' untranslated region is shown by the thin line.

FIG. 29A is a representation showing the partial nucleotide sequence of mouse SOCS8 cDNA (contig 8.1) derived from analysis of ESTs. The nucleotides encoding the part of the predicted coding region, ending in the STOP codon are shown in upper case, while the predicted 3' untranslated regions are shown in lower case.

FIG. 29B is a representation showing the partial predicted amino acid sequence of the mouse SOCS8 protein, derived from the nucleotide sequence in FIG. 29A. The SOCS box, which also shown in FIG. 13 is underlined.

Figure 30:
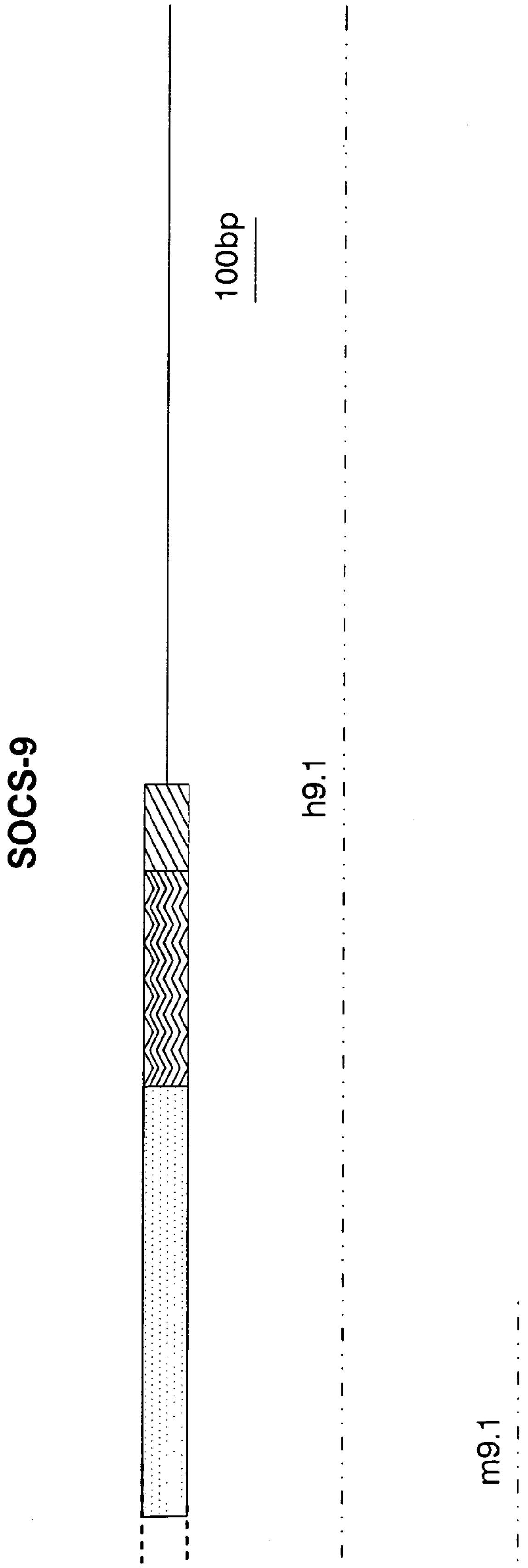

FIG. 30 is a diagrammatic representation showing the relationship of mouse SOCS9 ESTs (Table 9.1) and human SOCS9 ESTs (Table 9.2). The nucleotide sequence of the mouse SOCS9 contig (m9.1) is shown in FIG. 31, with the sequence of human SOCS9 contig (h9.1) being shown in FIG. 32. The deduced amino acid sequence of human SOCS9 is shown schematically, with the SH2 domain indicated by the open white wave box and the SOCS box by the solid black hatched box. The putative 3' untranslated region is shown by the thin solid line.

FIG. 31 is a representation showing the partial nucleotide sequence of mouse SOCS9 cDNA (contig m9. 1), derived from analysis of the ESTs listed in Table 9.1. The relationship of these contigs to the mouse cDNA sequence is illustrated in FIG. 30.

FIG. 32 is a representation showing the partial nucleotide sequence of human SOCS9 cDNA (contig h9.1), derived from analysis of the ESTs listed in Table 9.2. Although it is clear that contig h9.1 encodes a protein with an SH2 domain and a SOCS box, the quality of the sequence is not high enough to derive a single unambiguous open reading frame. The relationship of these contigs to the mouse cDNA sequence is illustrated in FIG. 30.

Figure 10:
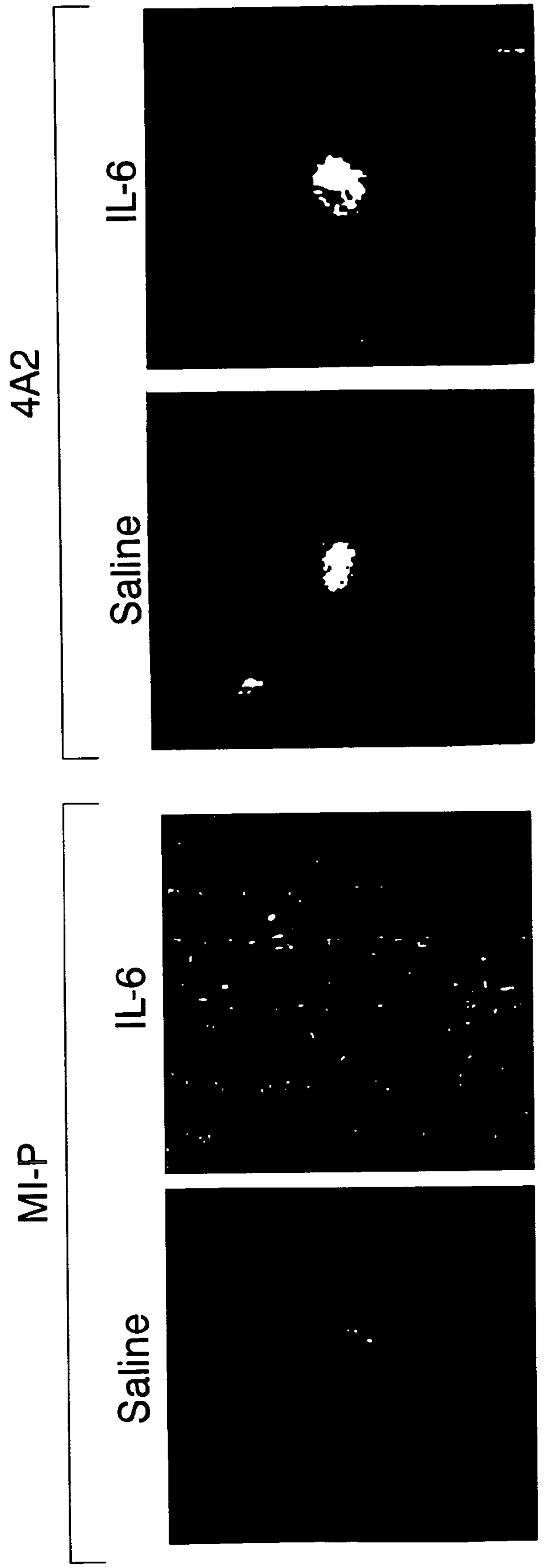
FIG. 10 is a photographic representation showing the phenotype of IL-6 unresponsive M1 cell clone, 4A2. Colonies of parental M1 cells (left panel) and clone 4A2 (right panel) cultured in semi-solid agar for 7 days in saline or 100 ng/ml IL-6.
Figure 33:
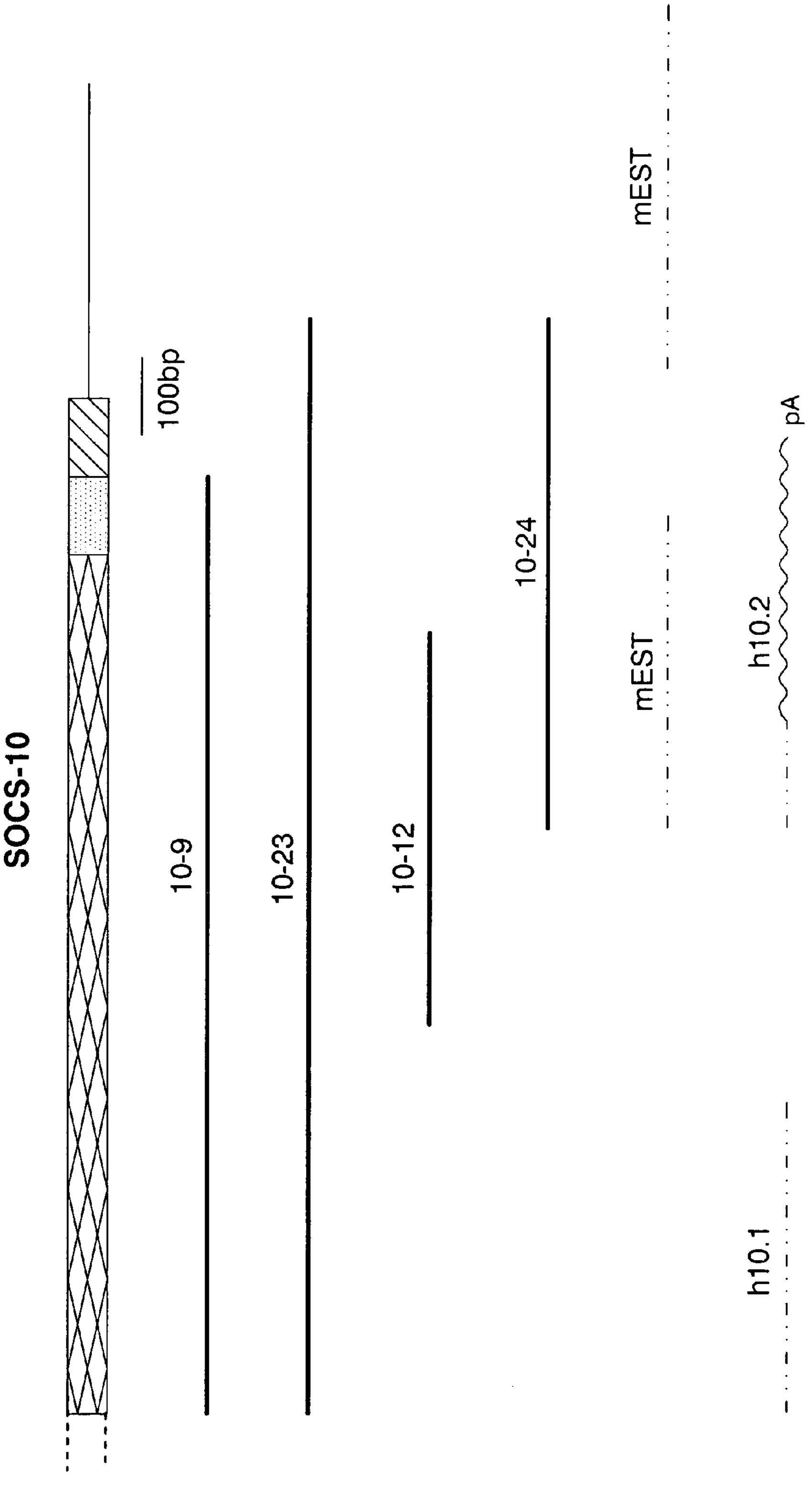

FIG. 33 is a representation showing the relationship of mouse SOCS10 cDNA clones (10-9, 10-12, 10-23 and 10-24) to contigs derived from analysis of mouse ESTs (Table 10.1) and human ESTs (Table 10.2). The nucleotide sequence of the mouse SOCS10 contig is shown in FIG. 10.2, with the sequence of human SOCS10 contigs (h10.1 and h10.2) being shown in FIG. 35. The predicted structure of the protein is shown schematically, with the ankyrin repeats indicated by the cross hatched box and the SOCS box by the solid black hatched box. The putative 3' untranslated regions is shown by the thin line solid line in the mouse and by the wavy line in h10.2. Based on analysis of clones isolated to date and ESTs the 3' untranslated regions of mSOCS-10 and hSOCS-10 share little similarity.

FIG. 34 is a representation showing the nucleotide sequence of the mouse SOCS10 derived from analysis of cDNA clone 10-9, 10-12, 10-23 and 10-24. The nucleotides encoding the part of the predicted coding region, ending in the stop codon are shown in upper case, while the predicted 3' untranslated regions are shown in lower case. Although it is clear that contig m10.1 encodes a protein with a series of ankyrin repeats and a SOCS box, the quality of the sequence is not high enough to derive a single unambiguous open reading frame. The relationship of mouse cDNA sequence to mouse and human EST contigs is illustrated in FIG. 33.

FIG. 35 is a representation showing the nucleotide sequence of human SOCS10 cDNA contig h10.2 and h10.2 derived from analysis of the ESTs listed in Table 10.2. The relationship of these contigs to the mouse cDNA sequence is illustrated in FIG. 33.

FIG. 36A is a representation showing the partial nucleotide sequence of the human SOCS11 cDNA derived from analysis of ESTs listed in Table 11.1 The nucleotides encoding the mature coding region from the predicted ATG "start" codon to the stop codon is shown in upper case, while the predicted 5' and 3' untranslated regions are shown in lower case. The relationship of the partial cDNA sequence, derived from ESTs, to the predicted protein is shown in FIG. 37.

FIG. 36B is a representation showing the partial predicted amino acid sequence of human SOCS11 protein, derived from the nucleotide sequence in FIG. 36A. The SOCS box, which also shown in FIG. 13, is underlined.

Figure 37:
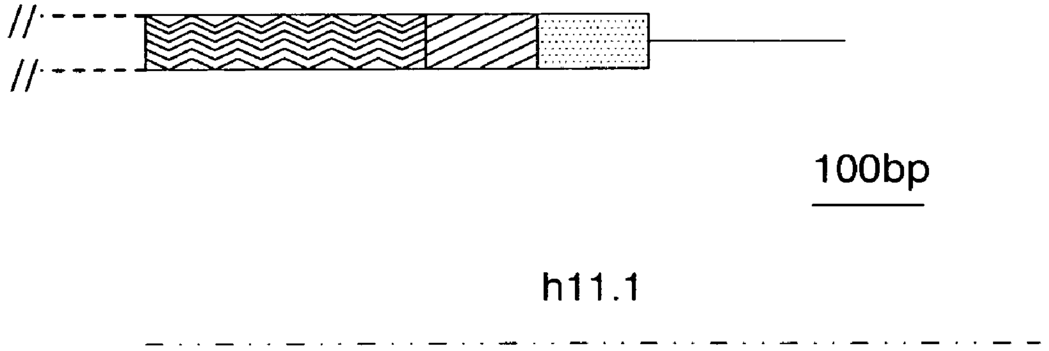

FIG. 37 is a diagrammatic representation showing the relationship of sequence derived from analysis of human SOCS-11 ESTs (Table 11.1 and FIG. 36A) to the predicted protein structure of human SOCS11. The deduced partial amino acid sequence of human SOCS11 is shown in FIG. 36B. The structure of the protein is shown schematically with the SH2 domain shown by the open white wave box and the SOCS box highlighted by the solid black hatched box. The predicted 3' untranslated region is shown by the thin line.

Figure 38:
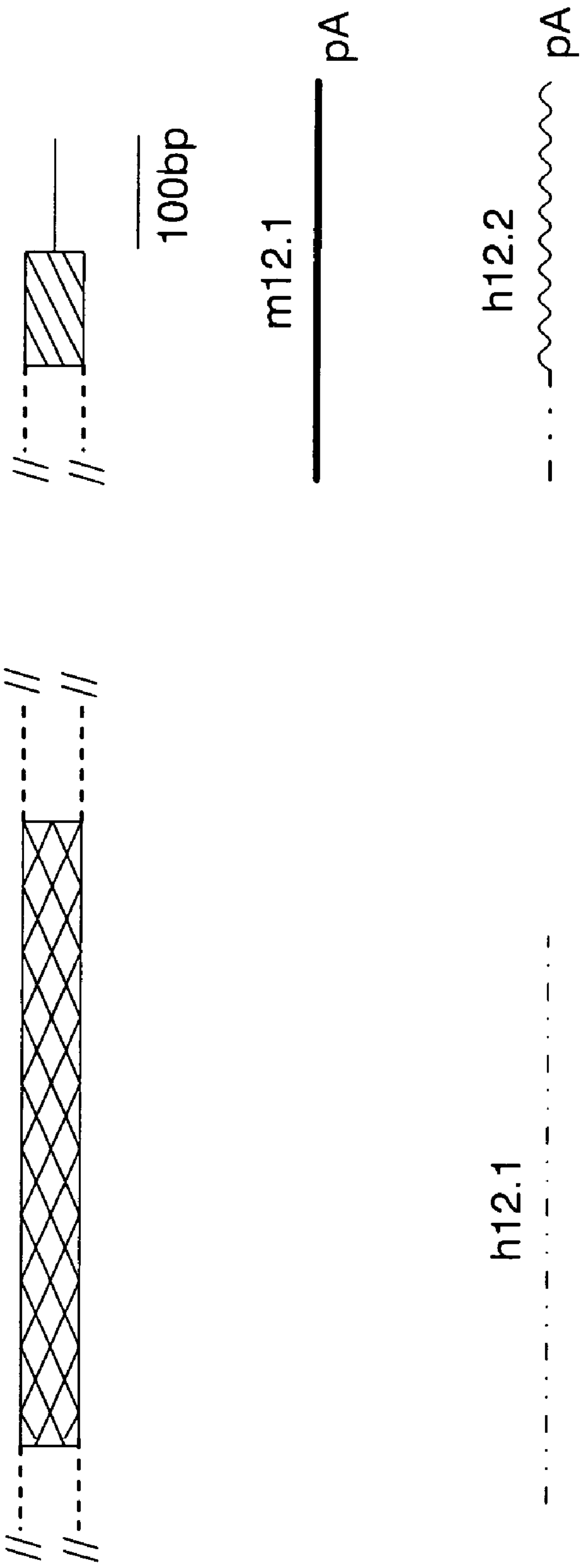

FIG. 38 is a diagrammatic representation showing the relationship of mouse SOCS12 cDNA clones (12-1) to contigs derived from analysis of mouse ESTs (Table 12.1) and human ESTs (Table 12.2). The nucleotide sequence of the mouse SOCS12 contig is shown in FIG. 12.2, with the sequence of human SOCS12 contigs (h12.1 and h12.2) being shown in FIG. 40. The deduced partial amino acid sequence of mouse SOCS12 is shown in FIG. 39. The structure of the protein is sown schematically, with the ankyrin repeats indicated by the cross hatched box and the SOCS box by the solid black hatched box. The putative 3' untranslated region is shown by the thin line solid line in the mouse and by the wavy line in hl 2.2. Based on analysis of clones isolated to date and ESTs the 3' untranslated regions of mSOCS12 and hSOCS12 share little similarity.

FIG. 39 is a representation showing the nucleotide sequence of the mouse SOCS12 derived from analysis of cDNA clone 12-1 and the ESTs listed in Table 12.1. The nucleotides encoding the part of the predicted coding region, including the stop codon are shown in upper case, while the predicted 3' untranslated region is shown in lower case. By homology with human SOCS12 it is clear that contig m12.1 encodes a protein with a series of ankyrin repeats and a SOCS box, the quality of the sequence is not high enough to derive a single unambiguous open reading frame. The relationship of mouse cDNA sequence to mouse and human EST contigs is illustrated in FIG. 38.

FIG. 40 is a representation showing the nucleotide sequence of human SOCS12 cDNA contig h12.1 and h12.2 derived from analysis of the ESTs listed in Table 12.2. The relationship of these contigs to the mouse cDNA sequence is illustrated in FIG. 38.

Figure 41:
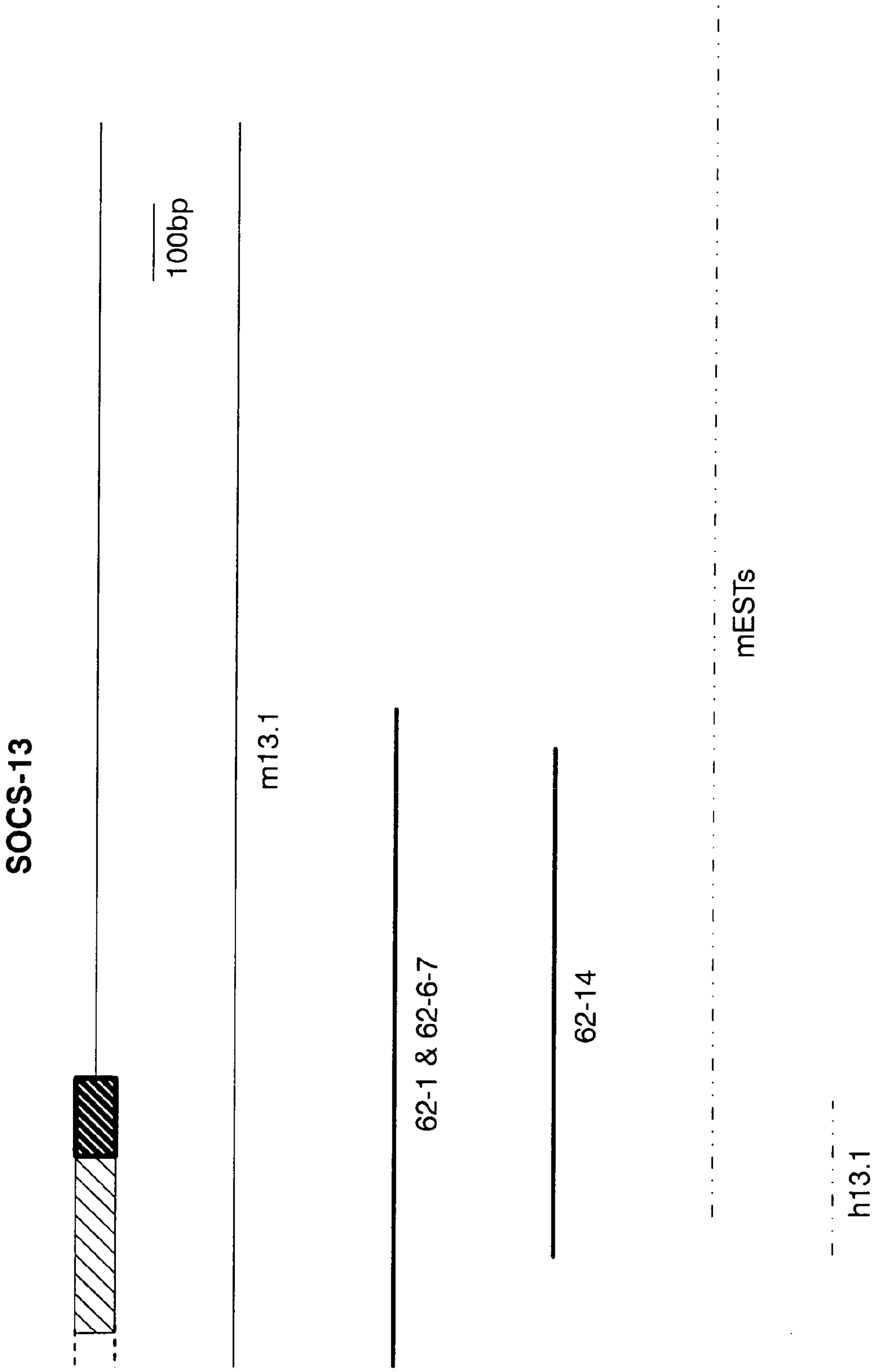

FIG. 41 is a diagrammatic representation showing the relationship of contig m13.1 derived from analysis of mouse SOCS13 cDNA clones (62-1, 62-6-7, 62-14) and mouse ESTs (Table 13.1) to contig h13.1 derived from analysis of human ESTs (Table 13.2). The nucleotide sequence of the mouse SOCS13 contig is shown in FIG. 42, with the sequence of human SOCS13 contig (h13.1) being shown in FIG. 43. The deduced amino acid sequence of mouse SOCS13 is shown in FIG. 42B. The structure of the protein is shown schematically, with the WD-40 repeats highlighted by the open white hatched box and the SOCS box highlighted by the solid black hatched box. The 3' untranslated region is shown by the thin line solid line.

FIG. 42A is a representation showing the nucleotide sequence of the mouse SOCS13 derived from analysis of cDNA clones 62-1, 62-6-7 and 62-14. The nucleotides encoding part of the predicted coding region, ending in the stop codon are shown in upper case, while those encoding the predicted 3' untranslated regions are shown in lower case. The relationship of mouse cDNA sequence to mouse and human EST contigs is illustrated in FIG. 41.

FIG. 42B is a representation showing the predicted amino acid sequence of mouse SOCS13 protein, derived from the nucleotide sequence in FIG. 42A. The SOCS box, which also shown in FIG. 13 is underlined.

FIG. 43 is a representation showing the nucleotide sequence of human SOCS13 cDNA contig h13.1 derived from analysis of the ESTs listed in Table 13.2. The relationship of these contigs to the mouse cDNA sequence is illustrated in FIG. 41.

Figure 44:
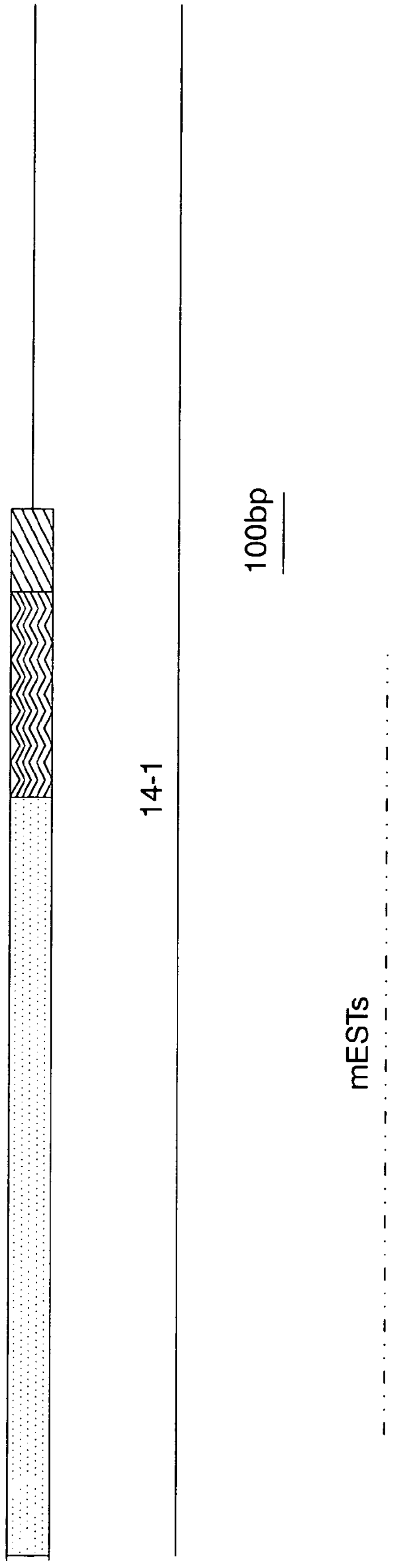

FIG. 44 is a diagrammatic representation showing the relationship of a partial mouse SOCS14 cDNA clone (14-1) to contigs derived from analysis of mouse ESTs (Table 14.1). The nucleotide sequence of the mouse SOCS14 contig is shown in FIG. 45. The deduced partial amino acid sequence of mouse SOCS14 is shown in FIG. 45B. The structure of the protein is shown schematically, with the SH3 domain indicated by the open white wave box and the SOCS box by the solid black hatched box. The putative 3' untranslated region is shown by the thin line.

FIG. 45A is a representation showing the nucleotide sequence of the mouse SOCS14 derived from analysis of genomic and cDNA clones. The nucleotides encoding the mature coding region from the predicted ATG "start" codon to the stop codon is shown in upper case, while the predicted 5' and 3' untranslated regions are shown in lower case. The relationship of mouse cDNA sequence to mouse and human EST contigs is illustrated in FIG. 44.

FIG. 45B is a representation showing the predicted amino acid sequence of mouse SOCS14 protein, derived from the nucleotide sequence in FIG. 45B. The SOCS box, which also shown in FIG. 13 is underlined.

Figure 46:
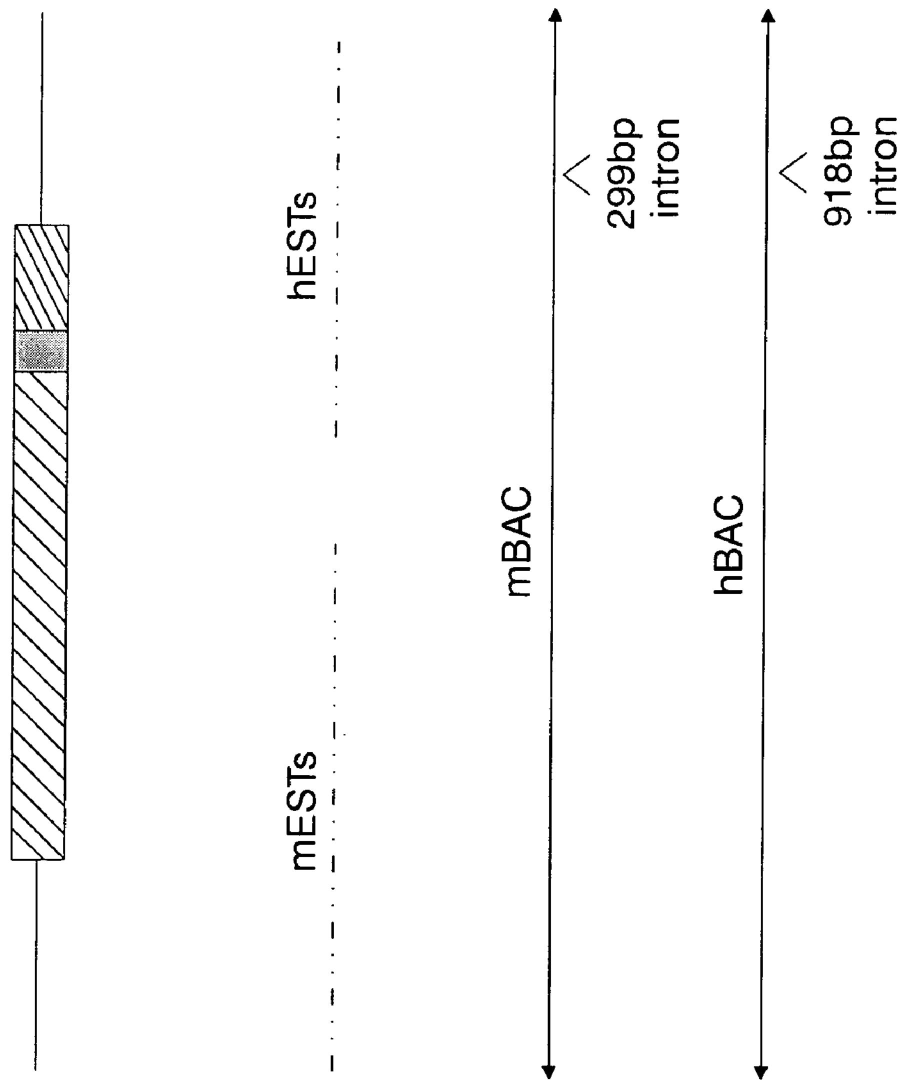

FIG. 46 is a diagrammatic representation showing the relationship of contig m15.1 derived from analysis of mouse BAC and mouse ESTs (Table 15.1) to contig h15.1 derived from analysis of the human BAC and human ESTs (Table 15.2). The nucleotide sequence of the mouse SOCS15 contig is shown in FIG. 47, with the sequence of human SOCS15 contig (h15.1) being shown in FIG. 47. The deduced amino acid sequence of mouse SOCS15 is shown in FIG. 47B. The structure of the protein is shown schematically, with the WD-40 repeats highlighted by the open white hatched box and the SOCS box highlighted by the solid black hatched box. The 5' and 3' untranslated region are shown by the thin line solid line. The introns which interrupt the coding region are shown by ^.

FIG. 47A(i)-(iv) is a representation showing the nucleotide sequence covering the mouse SOCS15 gene derived from analysis the mouse BAC listed in Table 15.1. The nucleotides encoding the predicted coding region, beginning with the ATG and ending in the stop codon are shown in upper case, while those encoding the predicted 5' untranslated region, the introns and the 3' untranslated region are shown in lower case. The relationship of mouse BAC to mouse and human ESTs contigs is illustrated in FIG. 46.

FIG. 47B is a representation showing the predicted amino acid sequence of mouse SOCS15 protein, derived from the nucleotide sequence in FIG. 47A(i)-(iv). The SOCS box, which also shown in FIG. 13 is underlined.

FIG. 48A(i)-(v) is a representation showing the nucleotide sequence covering the human SOCS15 gene derived from analysis the human BAC listed in Table 15.2. The nucleotides encoding the predicted coding region, beginning with the ATG and ending in the stop codon are shown in upper case, while those encoding the predicted 5' untranslated region, the introns and the 3' untranslated region are shown in lower case. The relationship of the human BAC to mouse and human ESTs contigs is illustrated in FIG. 46.

FIG. 48B is a representation showing the predicted amino acid sequence of human SOCS15 protein, derived from the nucleotide sequence in FIG. 48A(i)-(v). The SOCS box, which also shown in FIG. 13 is underlined.

Figure 49:
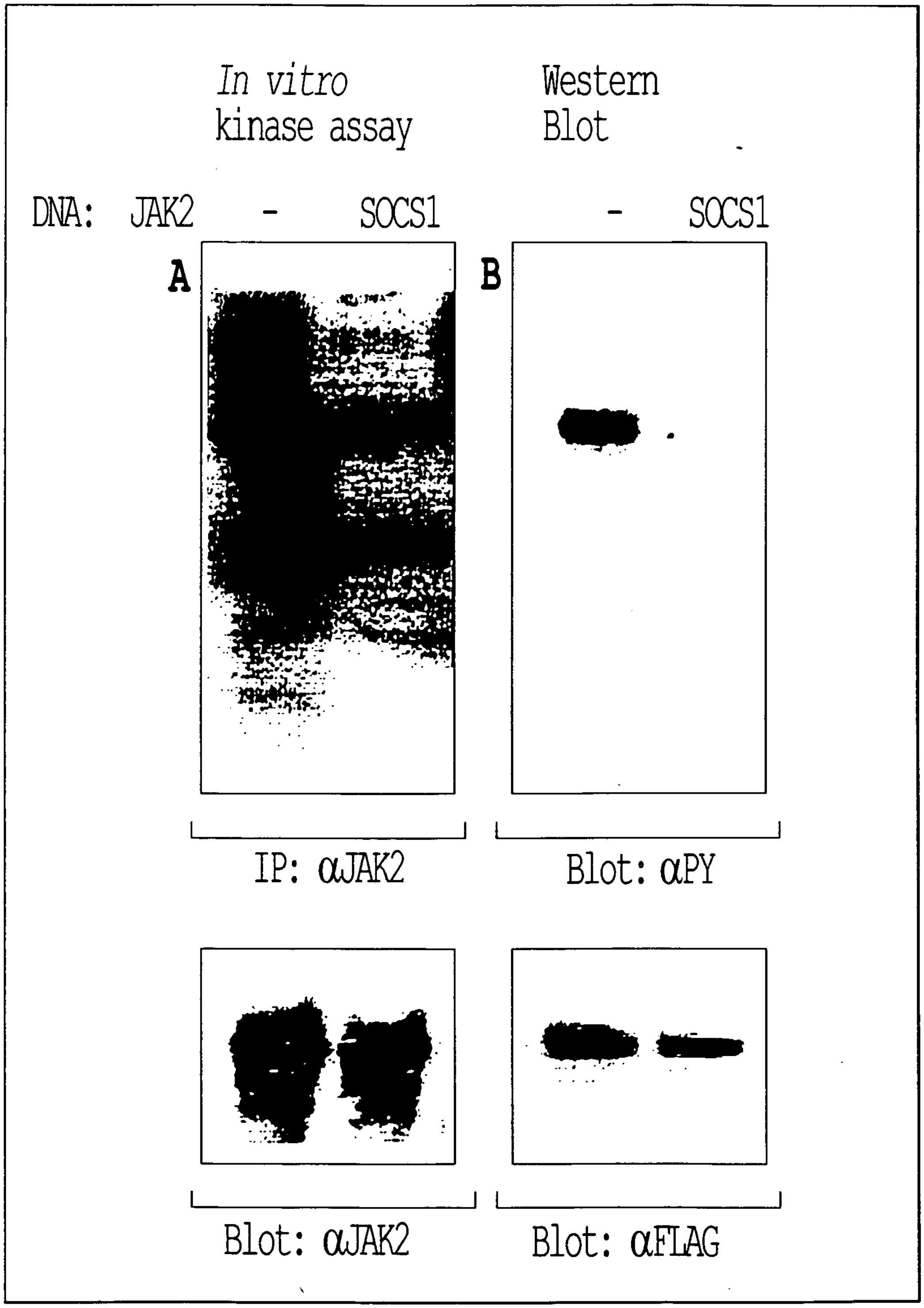

FIG. 49 is a photographic representation showing SOCS1 inhibition of JAK2 kinase activity. (A) Upper panel. Cos M6 cells were transiently transfected with either Flag-tagged mJAK2 and mSOCS-1 DNA (SOCS1) or Flag-mJAK2 DNA alone (−), lysed, JAK2 proteins immunoprecipitated using anti-JAK2 antibody and subjected to an in vitro kinase assay. Lower panel. A portion of the JAK2 immunoprecipitates were Western blotted with anti-JAK2 antibody. (B) Upper panel. Cos M6 cells were transiently transfected with Flag-mJAK2 and Flag-mSOCS-1 DNA or Flag-mJAK2 DNA alone, lysed, JAK2 proteins immunoprecipitated using anti-JAK2 (UBI) and separated by SDS/PAGE gel. Immunoprecipitates were then analysed by Western blot with anti-phosphotyrosine antibody. Lower panel; JAK2 expression. Cos cell lysates were separated by SDS/PAGE gel and analysed by Western blot with anti-FLAG antibody (M2).

Figure 50:
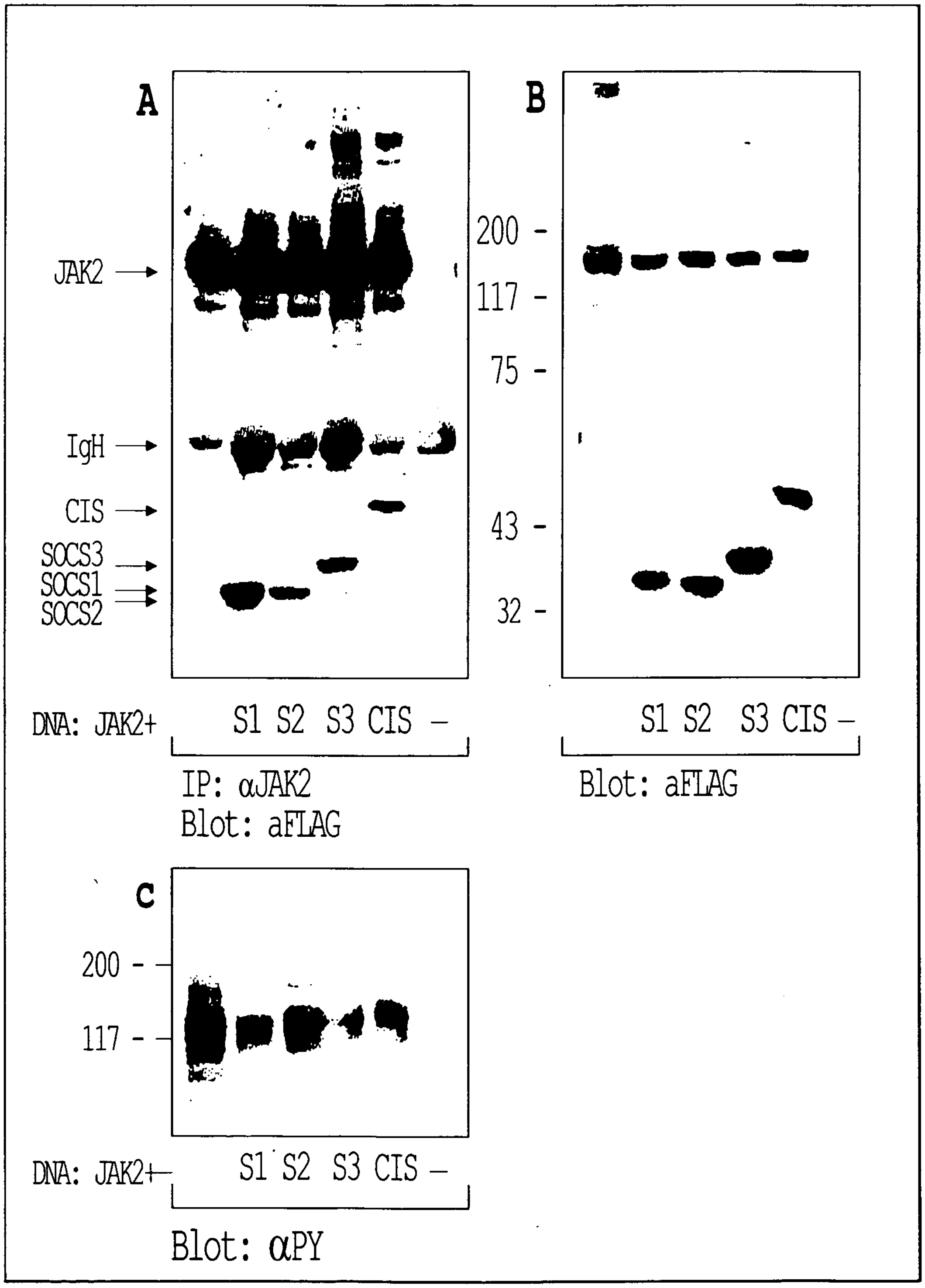

FIG. 50 is a photographic representation showing interaction between JAK2 and SOCS protein. (A) Cos M6 cells were transiently transfected with Flag-tagged mJAK2 and various Flag-tagged SOCS DNAs (SOCS-1;S1, SOCS-2;S2, SOCS-3;S3, CIS) or flag-mJAK2 alone, lysed, JAK2 proteins immunoprecipitated using anti-JAK2 (UBI) and separated by SDS/PAGE. Immunoprecipitates were then analysed by Western blot with anti-FLAG antibody (M2). (B) Cos cell lysates described in (A) were separated by SDS/PAGE and expression levels of the various proteins were determined by Western blot with anti-FLAG antibody (M2). (C) JAK2 tyrosine phosphorylation. Cos cell lysates described in (A) were separated by SDS/PAGE and proteins analysed by Western blot with anti-phosphotyrosine antibody.

Figure 51:
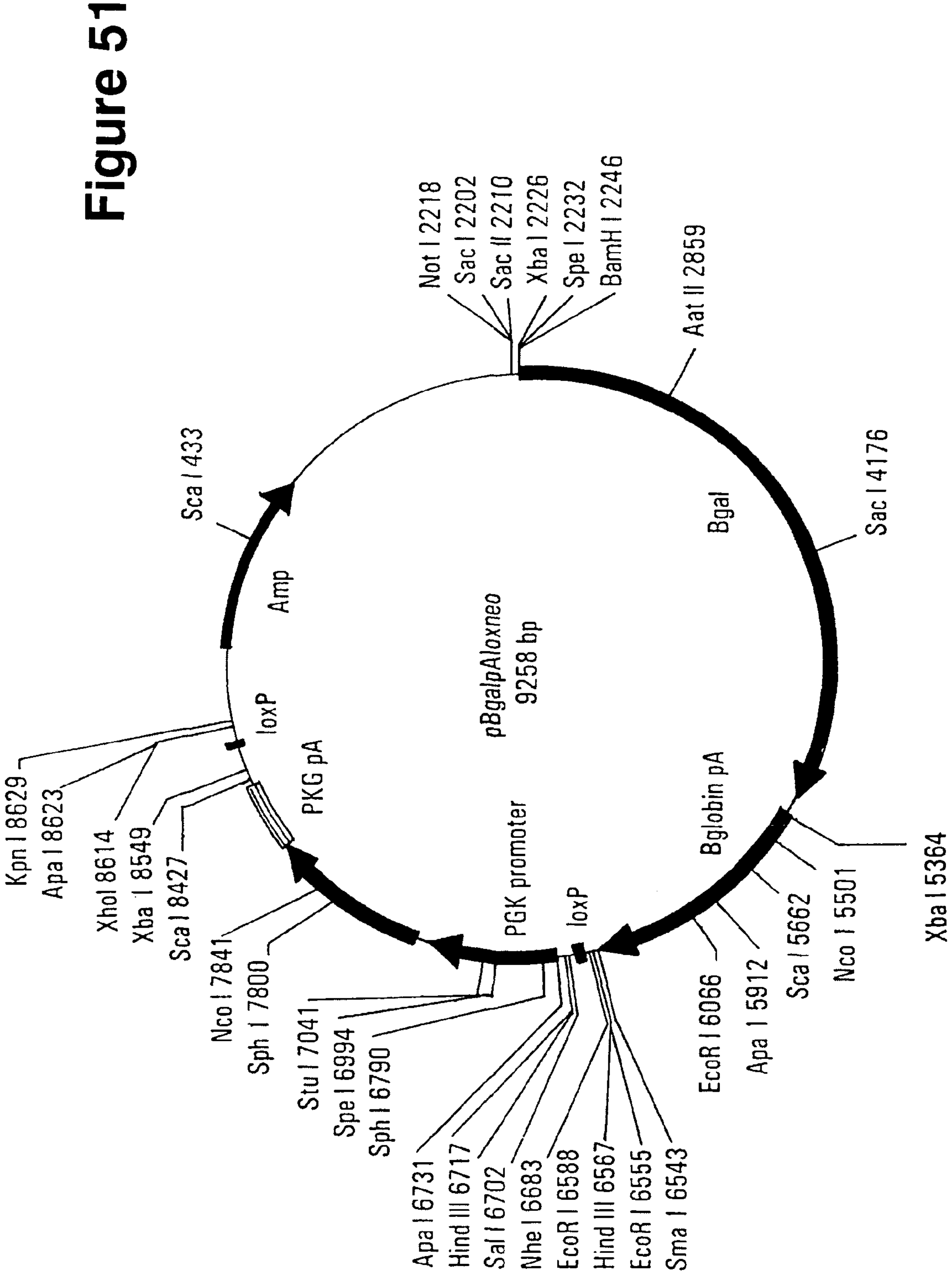

FIG. 51 is a diagrammatic representation of pβgalpAloxneo.

Figure 52:
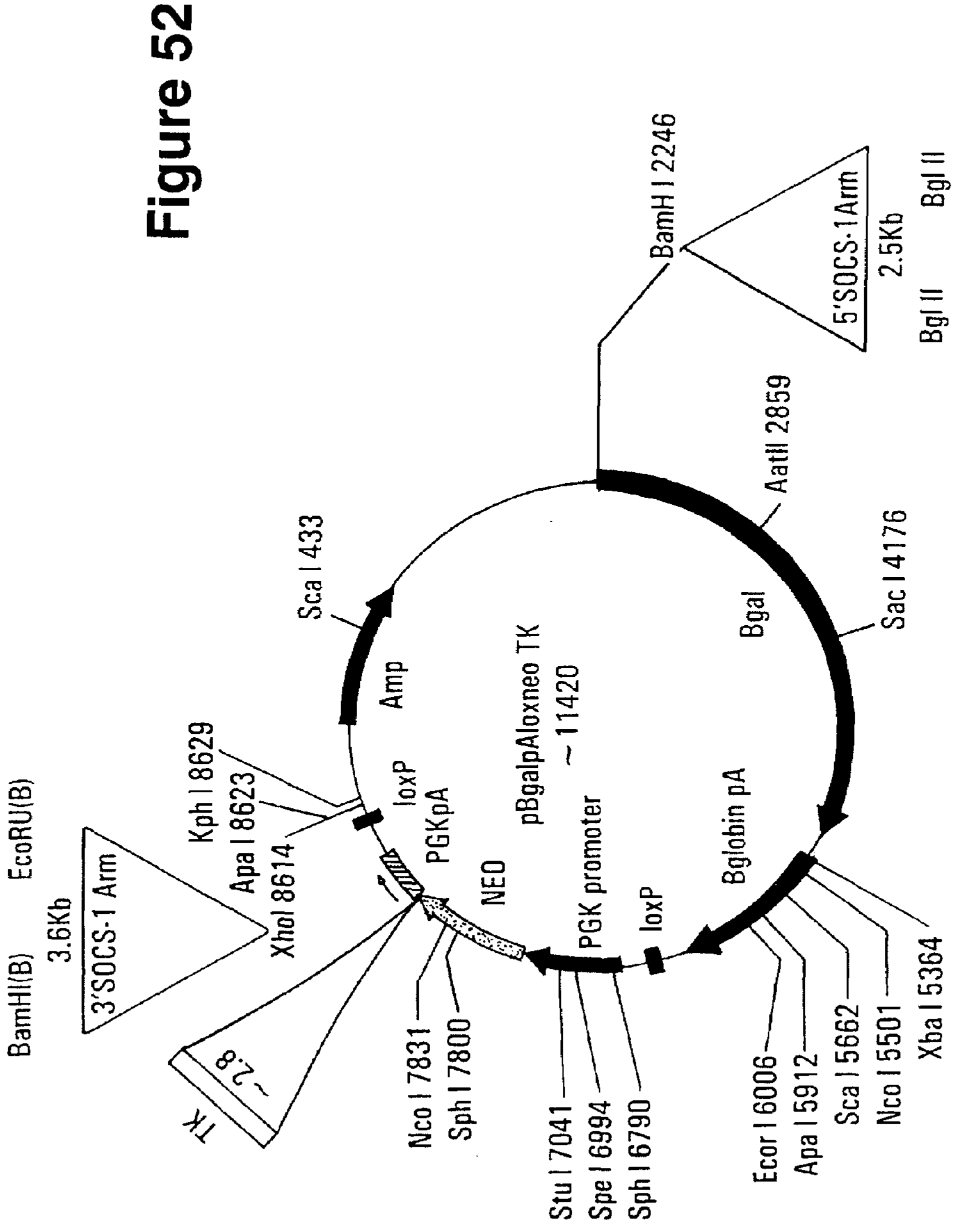

FIG. 52 is a diagrammatic representation of pβgalpAloxneoTK.

Figure 53:
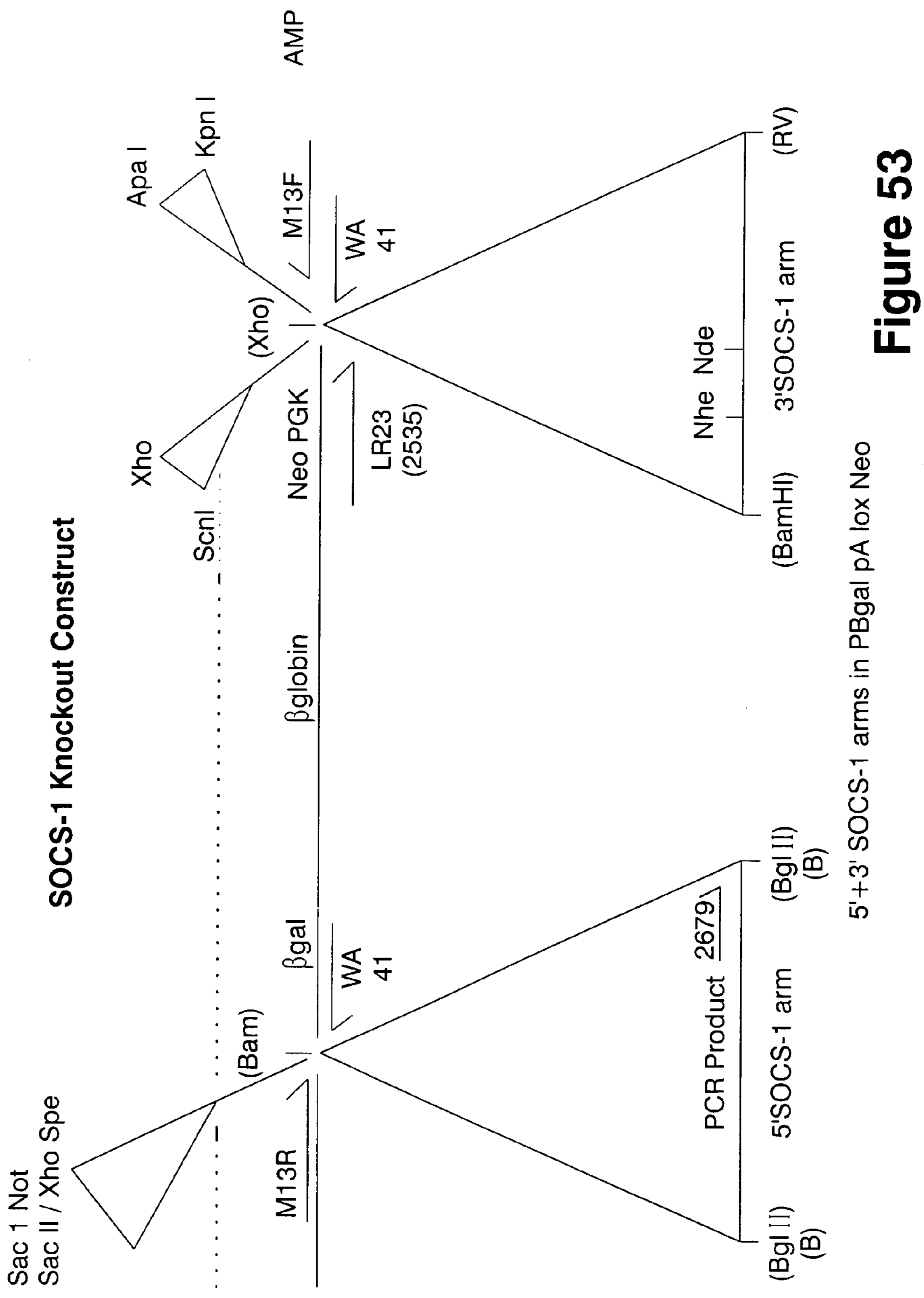

FIG. 53 is a diagrammatic representation of SOCS1 knockout construct.

DETAILED DESCRIPTION OF PREFERRED EMBODIMENTS

The present invention provides a new family of modulators of signal transduction. As the initial members of this family suppressed cytokine signalling, the family is referred to as the "suppressors of cytokine signalling" family of "SOCS". The SOCS family is defmed by the presence of a C-terminal domain referred to as a "SOCS box". Different classes of SOCS molecules are defmed by a motif generally but not exclusively located N-terminal to the SOCS box and which is involved by protein:molecule interaction such as protein:DNA or protein:protein interaction. Particularly preferred motifs are selected from an SH2 domain, WD-40 repeats and ankyrin repeats.

WD-40 repeats were originally recognised in the β-subunit of G-proteins. WD-40 repeats appear to form a β-propeller-like structure and may be involved in protein-protein interactions. Ankyrin repeats were originally recognised in the cytoskeletal protein ankryin.

Members of the SOCS family may be identified by any number of means. For example, SOCS1 to SOCS3 were identified by their ability to suppress cytokine-mediated signal transduction and, hence, were identified based on activity. SOCS4 to SOCS15 were identified as nucleotide sequences exhibiting similarity at the level of the SOCS box.

The SOCS box is a conserved motif located in the C-terminal region of the SOCS molecule. In accordance with the present invention, the amino acid sequence of the SOCS box is:

(SEQ ID NO: 51)

$X_1$ $X_2$ $X_3$ $X_4$ $X_5$ $X_6$ $X_7$ $X_8$ $X_9$ $X_{10}$ $X_{11}$ $X_{12}$ $X_{13}$ $X_{14}$ $X_{15}$ $X_{16}$ $[X_i]_n$ $X_{17}$ $X_{18}$ $X_{19}$ $X_{20}$ $X_{21}$ $X_{22}$ $X_{23}$ $[X_j]_n$ $X_{24}$ $X_{25}$ $X_{26}$ $X_{27}$ $X_{28}$ wherein:

$X_1$ is L, I, V, M, A or P;
$X_2$ is any amino acid residue;
$X_3$ is P, T or S;
$X_4$ is L, I, V, M, A or P;
$X_5$ is any amino acid;
$X_6$ is any amino acid;
$X_7$ is L, I, V, M, A, F, Y or W;
$X_8$ is C, T or S;
$X_9$ is R, K or H;
$X_{10}$ is any amino acid;
$X_{11}$ is any amino acid;
$X_{12}$ is L, I, V, M, A or P;
$X_{13}$ is any amino acid;
$X_{14}$ is any amino acid;
$X_{15}$ is any amino acid;
$X_{16}$ is L, I, V, M, A, P, G, C, T or S;
$[X_i]_n$ is a sequence of n amino acids wherein n is from 1 to 50 amino acids and wherein the sequence $X_i$ may comprise the same or different amino acids selected from any amino acid residue;
$X_{17}$ is L, I, V, M, A or P;
$X_{18}$ is any amino acid;
$X_{19}$ is any amino acid;
$X_{20}$ L, I, V, M, A or P;
$X_{21}$ is P;
$X_{22}$ is L, I, V, M, A, P or G;
$X_{23}$ is P or N;
$[X_j]_n$ is a sequence of n amino acids wherein n is from 0 to 50 amino acids and wherein the sequence $X_j$ may comprise the same or different amino acids selected from any amino acid residue;
$X_{24}$ is L, I, V, M, A or P;
$X_{25}$ is any amino acid;
$X_{26}$ is any amino acid;
$X_{27}$ is Y or F; and
$X_{28}$ is L, I, V, M, A or P.

As stated above and in accordance with the present invention, SOCS proteins are divided into separate classes based on the presence of a protein:molecule interacting region such as but not limited to an SH2 domain, WD-40 repeats and ankyrin repeats located N-terminal of the SOCS box. The latter three domains are protein:protein interacting domains.

Examples of SH2 containing SOCS proteins include SOCS1, SOCS2, SOCS3, SOCS5, SOCS9, SOCS11 and SOCS14. Examples of SOCS containing WD-40 repeats include SOCS4, SOCS6 and SOCS15. Examples of SOCS containing ankyrin repeats include SOCS7, SOCS10 and SOCS12.

The present invention provides inter alia nucleic acid molecules encoding SOCS proteins, purified naturally occurring SOCS proteins as well as recombinant forms of SOCS proteins and methods of modulating signal transduction by modulating activity of SOCS proteins or expression of SOCS genes. Preferably, signal transduction is mediated by a cytokine, examples of which include EPO, TPO, G-CSF, GM-CSF, IL-3, IL-2, IL-4, IL-7, IL-13, IL-6, LIF, IL-12, IFNγ, TNFα, IL-1 and/or M-CSF. Particularly preferred cytokines include IL-6, LIF, OSM, IFN-γ and/or thrombopoietin.

Accordingly, one aspect of the present invention provides an isolated nucleic acid molecule comprising a sequence of nucleotides encoding or complementary to a sequence encoding a protein or a derivative, homologue, analogue or mimetic thereof or comprises a nucleotide sequence capable of hybridizing thereto under low stringency conditions at 42° C. wherein said protein comprises a SOCS box in its C-terminal region and optionally a protein:molecule interacting domain N-terminal of the SOCS box.

Preferably, the protein:molecule interacting domain is a protein:DNA or protein:protein interacting domain. Most preferably, the protein:molecule interacting domain is one of an SH2 domain, WD-40 repeats and/or ankyrin repeats.

As stated above, preferably the subject SOCS modulate cytokine-mediated signal transduction. The present invention extends, however, to SOCS molecules modulating other effector-mediated signal transduction such as mediated by other endogenous or exogenous molecules, antigens, microbes and microbial products, viruses or components thereof, ions, hormones and parasites. Endogenous molecules in this context are molecules produced within the cell carrying the SOCS molecule. Exogenous molecules are produced by other cells or are introduced to the body.

Preferably, the nucleic acid molecule or SOCS protein is in isolated or purified form. The terms "isolated" and "purified" mean that a molecule has undergone at least one purification step away from other material.

Preferably, the nucleic acid molecule is in isolated form and is DNA such as cDNA or genomic DNA. The DNA may encode the same amino acid sequence as the naturally occurring SOCS or the SOCS may contain one or more amino acid substitutions, deletions and/or additions. The nucleotide sequence may correspond to the genomic coding sequence (including exons and introns) or to the nucleotide sequence in cDNA from mRNA transcribed from the genomic gene or it may carry one or more nucleotide substitutions, deletions and/or additions thereto.

In a preferred embodiment, the nucleic acid molecule comprises a sequence of nucleotide encoding or complementary to a sequence encoding a SOCS protein or a derivative, homologue, analogue or mimetic thereof wherein the amino acid sequence of said SOCS protein is selected from SEQ ID NO:4 (mSOCS1), SEQ ID NO:6 (mSOCS2), SEQ ID NO:8 (mSOCS3), SEQ ID NO:10 (hSOCS1), SEQ ID NO:12 (rSOCS1), SEQ ID NO:14 (mSOCS4), SEQ ID NO:18 (mSOCS5), SEQ ID NO:21 (mSOCS6), SEQ ID NO:25 (mSOCS27), SEQ ID NO:29 (mSOCS8), SEQ ID NO:36 (hSOCS11), SEQ ID NO:41 (mSOCS13), SEQ ID NO:44 (mSOCS14), SEQ ID NO:46 (mSOCS15) and SEQ ID NO:48 (mSOCS15) or encodes an amino acid sequence with a single or multiple amino acid substitution, deletion and/or addition to the listed sequences or is a nucleotide sequence capable of hybridizing to the nucleic acid molecule under low stringency conditions at 42▯C.

In an even more preferred embodiment, the present invention provides a nucleic acid molecule comprising a sequence of nucleotides encoding or complementary to a sequence encoding a SOCS protein or a derivative, homologue, analogue or mimetic thereof wherein the nucleotide sequence is selected from a nucleotide sequence substantially set forth in SEQ ID NO:3 (mSOCS1), SEQ ID NO:5 (mSOCS2), SEQ ID NO:7 (mSOCS3), SEQ ID NO:9 (hSOCS11), SEQ ID NO:11 (rSOCS1), SEQ ID NO:13 (mSOCS4), SEQ ID NO:15 and SEQ ID NO:16 (hSOCS4), SEQ ID NO:17 (mSOCS5), SEQ ID NO:19 (hSOCS5), SEQ ID NO:20 (mSOCS6), SEQ ID NO:22 and SEQ ID NO:23 (hSOCS6), SEQ ID NO:24 (mSOCS7), SEQ ID NO:26 and SEQ ID NO:27 (hSOCS7), SEQ ID NO:28 (mSOCS8), SEQ ID NO:30 (mSOCS9), SEQ ID NO:31 (hSOCS9), SEQ ID NO:32 (mSOCS10), SEQ ID NO:33 and SEQ ID NO:34 (hSOCS10), SEQ ID NO:35 (hSOCS11), SEQ ID NO:37 (mSOCS12), SEQ ID NO:38 and SEQ ID NO:39 (hSOCS12), SEQ ID NO:40 (mSOCS13), SEQ ID NO:42 (hSOCS13), SEQ ID NO:43 (mSOCS14), SEQ ID NO:45 (mSOCS15) and SEQ ID NO:47 (hSOCS15) or a nucleotide sequence having at least about 15% similarity to all or a region of any of the listed sequences or a nucleic acid molecule capable of hybridizing to any of the listed sequences under low stringency conditions at 42° C.

Reference herein to a low stringency at 42° C. includes and encompasses from at least about 1% v/v to at least about 15% v/v formamide and from at least about 1M to at least about 2M salt for hybridisation, and at least about 1M to at least about 2M salt for washing conditions. Alternative stringency conditions may be applied where necessary, such as medium stringency, which includes and encompasses from at least about 16% v/v to at least about 30% v/v formamide and from at least about 0.5M to at least about 0.9M salt for hybridisation, and at least about 0.5M to at least about 0.9M salt for washing conditions, or high stringency, which includes and encompasses from at least about 31% v/v to at least about 50% v/v formamide and from at least about 0.01M to at least about 0.15M salt for hybridisation, and at least about 0.01M to at least about 0.15M salt for washing conditions.

In another embodiment, the present invention is directed to a SOCS protein or a derivative, homologue, analogue or mimetic thereof wherein said SOCS protein is identified as follows:

- human SOCS4 characterised by EST81149, EST180909, EST182619, ya99H09, ye70co4, yh53c09, yh77g11, yh87h05, yi45h07, yj04e06, yq12h06, yq56a06, yq60e02, yq92g03, yq97h06, yr90f0, yt69c03, yv30a08, yv55f07, yv57h09, yv87h02, yv98e11, yw68d10, yw82a03, yx08a07, yx72h06, yx76b09, yy37h08, yy66b02, za81f08, zb18f07, zc06e08, zd14g06, zd51h12, zd52b09, ze25g11, ze69f02, zf54f03, zh96e07, zv66h12, zs83a08 and zs83g08;
- mouse SOCS-4 characterised by mc65f04, mf42e06, mp10c10, mr81g09, and mt19h12;
- human SOCS-5 characterised by EST15B103, EST15B105, EST27530 and zf50f01;
- mouse SOCS-5 characterised by mc55a01, mh98f09, my26h12 and ve24e06;
- human SOCS-6 characterised by yf61e08, yf93a09, yg05f12, yg41f04, yg45c02yh11f10, yh13b05, zc35a12, ze02h08, z109a03, z169e10, zn39d08 and zo39e06;
- mouse SOCS-6 characterised by mc04c05, md48a03, mf31d03, mh26b07, mh78e11, mh88h09, mh94h07, mi27h04 and mj29c05, mp66g04, mw75g03, va53b05, vb34h02, vc55d07, vc59e05, vc67d03, vc68d10, vc97h01, vc99c08, vd07h03, vd08c01, vd09b12, vd19b02, vd29a04 and vd46d06;
- human SOCS-7 characterised by STS WI30171, EST00939, EST12913, yc29b05, yp49f10, zt10f03 and zx73g04;
- mouse SOCS-7 characterised by mj39a01 and vi52h07;
- mouse SOCS-8 characterised by mj6e09 and vj27a029;
- human SOCS-9 characterised by CSRL-82f2-u, EST114054, yy06b07, yy06g06, zr40c09, zr72h01, yx92c08, yx93b08 and hfe0662;
- mouse SOCS-9 characterised by me65d05;
- human SOCS-10 characterised by aa48h10, zp35h01, zp97h12, zq08h01, zr34g05, EST73000 and HSDHEI005;
- mouse SOCS-10 characterised by mb14d12, mb40f06, mg89b11, mq89e12, mp03g12 and vh53c11;
- human SOCS-11 characterised by zt24h06 and zr43b02;
- human SOCS-13 characterised by EST59161;
- mouse SOCS-13 characterised by ma39a09, me60c05, mi78g05, mk10c11, mo48g12, mp94a01, vb57c07 and vh07c11; and
- human SOCS-14 characterised by mi75e03, vd29h11 and vd53g07;
- or a derivative or homologue of the above ESTs characterised by a nucleic acid molecule being capable of hybridizing to any of the listed ESTs under low stringency conditions at 42° C.

In another embodiment, the nucleotide sequence encodes the following amino acid sequence:

(SEQ ID NO: 51)

$X_1$ $X_2$ $X_3$ $X_4$ $X_5$ $X_6$ $X_7$ $X_8$ $X_9$ $X_{10}$ $X_{11}$ $X_{12}$ $X_{13}$ $X_{14}$ $X_{15}$
$X_{16}$ $[X_i]_n$ $X_{17}$ $X_{18}$ $X_{19}$ $X_{20}$ $X_{21}$ $X_{22}$ $X_{23}$ $[X_j]_n$ $X_{24}$
$X_{25}$ $X_{26}$ $X_{27}$ $X_{28}$ wherein:

$X_1$ is L, I, V, M, A or P;

$X_2$ is any amino acid residue;

$X_3$ is P, T or S;

$X_4$ is L, I, V, M, A or P;

$X_5$ is any amino acid;
$X_6$ is any amino acid;
$X_7$ is L, I, V, M, A, F, Y or W;
$X_8$ is C, T or S;
$X_9$ is R, K or H;
$X_{10}$ is any amino acid;
$X_{11}$ is any amino acid;
$X_{12}$ is L, I, V, M, A or P;
$X_{13}$ is any amino acid;
$X_{14}$ is any amino acid;
$X_{15}$ is any amino acid;
$X_{16}$ is L, I, V, M, A, P, G, C, T or S;
$[X_i]_n$ is a sequence of n amino acids wherein n is from 1 to 50 amino acids and wherein the sequence $X_i$ may comprise the same or different amino acids selected from any amino acid residue;
$X_{17}$ is L, I, V, M, A or P;
$X_{18}$ is any amino acid;
$X_{19}$ is any amino acid;
$X_{20}$ L, I, V, M, A or P;
$X_{21}$ is P;
$X_{22}$ is L, I, V, M, A, P or G;
$X_{23}$ is P or N;
$[X_j]_n$ is a sequence of n amino acids wherein n is from 0 to 50 amino acids and wherein the sequence $X_j$ may comprise the same or different amino acids selected from any amino acid residue;
$X_{24}$ is L, I, V, M, A or P;
$X_{25}$ is any amino acid;
$X_{26}$ is any amino acid;
$X_{27}$ is Y or F; and
$X_{28}$ is L, I, V, M, A or P.

The above sequence comparisons are preferably to the whole molecule but may also be to part thereof. Preferably, the comparisons are made to a contiguous series of at least about 21 nucleotides or at least about 5 amino acids. More preferably, the comparisons are made against at least about 21 contiguous nucleotides or at least 7 contiguous amino acids. Comparisons may also only be made to the SOCS box region or a region encompassing the protein:molecule interacting region such as the SH2 domain WD-40 repeats and/or ankyrin repeats.

Still another embodiment of the present invention contemplates an isolated polypeptide or a derivative, homologue, analogue or mimetic thereof comprising a SOCS box in its C-terminal region.

Preferably the polypeptide further comprises a protein: molecule interacting domain such as a protein:DNA or protein:protein interacting domain. Preferably, this domain is located N-terminal of the SOCS box. It is particularly preferred for the protein:molecule interacting domain to be at least one of an SH2 domain, WD-40 repeats and/or ankyrin repeats.

Preferably, the signal transduction is mediated by a cytokine selected from EPO, TPO, G-CSF, GM-CSF, IL-3, IL-2, IL-4, IL-7, IL-13, IL-6, LIF, IL-12, INFγ, TNFα, IL-1 and/or M-CSF. Preferred cytokines are IL-6, LIF, OSM, IFN-γ or thrombopoietin.

More preferably, the protein comprises a SOCS box having the amino acid sequence:

(SEQ ID NO: 51)

$X_1$ $X_2$ $X_3$ $X_4$ $X_5$ $X_6$ $X_7$ $X_8$ $X_9$ $X_{10}$ $X_{11}$ $X_{12}$ $X_{13}$ $X_{14}$ $X_{15}$
$X_{16}$ $[X_i]_n$ $X_{17}$ $X_{18}$ $X_{19}$ $X_{20}$ $X_{21}$ $X_{22}$ $X_{23}$ $[X_j]_n$ $X_{24}$
$X_{25}$ $X_{26}$ $X_{27}$ $X_{28}$ wherein:
$X_1$ is L, I, V, M, A or P;
$X_2$ is any amino acid residue;
$X_3$ is P, T or S;
$X_4$ is L, I, V, M, A or P;
$X_5$ is any amino acid;
$X_6$ is any amino acid;
$X_7$ is L, I, V, M, A, F, Y or W;
$X_8$ is C, T or S;
$X_9$ is R, K or H;
$X_{10}$ is any amino acid;
$X_{11}$ is any amino acid;
$X_{12}$ is L, I, V, M, A or P;
$X_{13}$ is any amino acid;
$X_{14}$ is any amino acid;
$X_{15}$ is any amino acid;
$X_{16}$ is L, I, V, M, A, P, G, C, T or S;
$[X_i]_n$ is a sequence of n amino acids wherein n is from 1 to 50 amino acids and wherein the sequence $X_i$ may comprise the same or different amino acids selected from any amino acid residue;
$X_{17}$ is L, I, V, M, A or P;
$X_{18}$ is any amino acid;
$X_{19}$ is any amino acid;
$X_{20}$ L, I, V, M, A or P;
$X_{21}$ is P;
$X_{22}$ is L, I, V, M, A, P or G;
$X_{23}$ is P or N;
$[X_j]_n$ is a sequence of n amino acids wherein n is from 0 to 50 amino acids and wherein the sequence $X_j$ may comprise the same or different amino acids selected from any amino acid residue;
$X_{24}$ is L, I, V, M, A or P;
$X_{25}$ is any amino acid;
$X_{26}$ is any amino acid;
$X_{27}$ is Y or F; and
$X_{28}$ is L, I, V, M, A or P.

Still another embodiment provides an isolated polypeptide or a derivative, homologue, analogue or mimetic thereof comprising a sequence of amino acids substantially as set forth in SEQ ID NO:4 (mSOCS1), SEQ ID NO:6 (mSOCS2), SEQ ID NO:8 (mSOCS3), SEQ ID NO:10 (hSOCS1), SEQ ID NO:12 (rSOCS1), SEQ ID NO:14 (mSOCS4), SEQ ID NO:18 (mSOCS5), SEQ ID NO:21 (mSOCS6), SEQ ID NO:25 (mSOCS7), SEQ ID NO:29 (mSOCS8), SEQ ID NO:36 (hSOCS11), SEQ ID NO:41 (mSOCS13), SEQ ID NO:44 (mSOCS14), SEQ ID NO:46 (mSOCS15) and SEQ ID NO:48 (hSOCS15) or an amino acid sequence having at least 15% similarity to all or a part of the listed sequences.

Preferred nucleotide percentage similarities include at least about 20%, at least about 40%, at least about 50%, at least about 60%, at least about 70%, at least about 80%, at least about 90% or above such as 93%, 95%, 98% or 99%.

Preferred amino acid similarities include at least about 20%, at least about 30%, at least about 40%, at least about 50%, at least about 60%, at least about 70%, at least about 80%, at least about 90%, at least about 95%, at least about 97% or 98% or above.

As stated above, similarity may be measured against an entire molecule or a region comprising at least 21 nucleotides or at least 7 amino acids. Preferably, similarity is measured in a conserved region such as SH2 domain, WD-40 repeats, ankyrin repeats or other protein:molecule interacting domains or a SOCS box.

The term "similarity" includes exact identity between sequences or, where the sequence differs, different amino acids are related to each other at the structural, functional, biochemical and/or conformational levels.

The nucleic acid molecule may be isolated from any animal such as humans, primates, livestock animals (e.g. horses, cows, sheep, donkeys, pigs), laboratory test animals (e.g. mice, rats, rabbits, hamsters, guinea pigs), companion animals (e.g. dogs, cats) or captive wild animals (e.g. deer, foxes, kangaroos).

The terms "derivatives" or its singular form "derivative" whether in relation to a nucleic acid molecule or a protein includes parts, mutants, fragments and analogues as well as hybrid or fusion molecules and glycosylation variants. Particularly useful derivatives comprise single or multiple amino acid substitutions, deletions and/or additions to the SOCS amino acid sequence.

Preferably, the derivatives have functional activity or alternatively act as antagonists or agonists. The present invention further extends to homologues of SOCS which include the functionally or structurally related molecule from different animal species. The present invention also encompasses analogues and mimetics. Mimetics include a class of molecule generally but not necessarily having a non-amino acid structure and which functionally are capable of acting in an analogous manner to the protein for which it is a mimic, in this case, a SOCS. Mimetics may comprise a carbohydrate, aromatic ring, lipid or other complex chemical structure or may also be proteinaceous in composition. Mimetics as well as agonists and antagonists contemplated herein are conveniently located through systematic searching of environments, such as coral, marine and freshwater river beds, flora and microorganisms.

This is sometimes referred to as natural product screening. Alternatively, libraries of synthetic chemical compounds may be screened for potentially useful molecules.

As stated above, the present invention contemplates agonists and antagonists of the SOCS. One example of an antagonist is an antisense oligonucleotide sequence. Useful oligonucleotides are those which have a nucleotide sequence complementary to at least a portion of the protein-coding or "sense" sequence of the nucleotide sequence. These antisense nucleotides can be used to effect the specific inhibition of gene expression. The antisense approach can cause inhibition of gene expression apparently by forming an anti-parallel duplex by complementary base pairing between the antisense construct and the targeted mRNA, presumably resulting in hybridisation arrest of translation. Ribozymes and co-suppression molecules may also be used. Antisense and other nucleic acid molecules may first need to be chemically modified to permit penetration of cell membranes and/or to increase their serum half life or otherwise make them more stable for in vivo administration. Antibodies may also act as either antagonists or agonists although are more useful in diagnostic applications or in the purification of SOCS proteins. Antagonists and agonists may also be identified following natural product screening or screening of libraries of chemical compounds or may be derivatives or analogues of the SOCS molecules.

Accordingly, the present invention extends to analogues of the SOCS proteins of the present invention. Analogues may be used, for example, in the treatment or prophylaxis of cytokine mediated dysfunction such as autoimmunity, immune suppression or hyperactive immunity or other condition including but not limited to dysfunctions in the haemopoietic, endocrine, hepatic and neural systems. Dysfunctions mediated by other signal transducing elements such as hormones or endogenous or exogenous molecules, antigens, microbes and microbial products, viruses or components thereof, ions, hormones and parasites are also contemplated by the present invention.

Analogues of the proteins contemplated herein include, but are not limited to, modification to side chains, incorporating of unnatural amino acids and/or their derivatives during peptide, polypeptide or protein synthesis and the use of crosslinkers and other methods which impose conformational constraints on the proteinaceous molecule or their analogues.

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural amino acid, contemplated herein is shown in Table 3.

TABLE 3

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane- | Cpro | L-N-methylasparagine | Nmasn |
| carboxylate | | L-N-methylaspartic acid | Nmasp |
| aminoisobutyric acid | Aib | L-N-methylcysteine | Nmcys |
| aminonorbornyl- | Norb | L-N-methylglutamine | Nmgln |
| carboxylate | | L-N-methylglutamic acid | Nmglu |
| cyclohexylalanine | | Chexa L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |

TABLE 3-continued

| Non-conventional amino acid | Code | Non-conventional amino acid | Code |
|---|---|---|---|
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl) carbamylmethyl)glycine | Nnbhm | N-(N-(3,3-diphenylpropyl) carbamylmethyl)glycine | Nnbhe |
| 1-carboxy-1-(2,2-diphenyl-ethylamino)cyclopropane | Nmbc | | |

Crosslinkers can be used, for example, to stabilise 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogues by introducing covalent bonds such as forming an amide bond between the N and C termini, between two side chains or between a side chain and the N or C terminus.

These types of modifications may be important to stabilise the cytokines if administered to an individual or for use as a diagnostic reagent.

Other derivatives contemplated by the present invention include a range of glycosylation variants from a completely unglycosylated molecule to a modified glycosylated molecule. Altered glycosylation patterns may result from expression of recombinant molecules in different host cells.

Another embodiment of the present invention contemplates a method for modulating expression of a SOCS protein in a mammal, said method comprising contacting a gene encoding a SOCS or a factor/element involved in controlling expression of the SOCS gene with an effective amount of a modulator of SOCS expression for a time and under conditions sufficient to up-regulate or down-regulate or otherwise modulate expression of SOCS. An example of a modulator is a cytokine such as IL-6 or other transcription regulators of SOCS expression.

Expression includes transcription or translation or both.

Another aspect of the present invention contemplates a method of modulating activity of SOCS in a human, said method comprising administering to said mammal a modulating effective amount of a molecule for a time and under conditions sufficient to increase or decrease SOCS activity. The molecule may be a proteinaceous molecule or a chemical entity and may also be a derivative of SOCS or a chemical analogue or truncation mutant of SOCS.

A further aspect of the present invention provides a method of inducing synthesis of a SOCS or transcription/translation of a SOCS comprising contacting a cell containing a SOCS gene with an effective amount of a cytokine capable of inducing said SOCS for a time and under conditions sufficient for said SOCS to be produced. For example, SOCS1 may be induced by IL-6.

Still a further aspect of the present invention contemplates a method of modulating levels of a SOCS protein in a cell said method comprising contacting a cell containing a SOCS gene with an effective amount of a modulator of SOCS gene expression or SOCS protein activity for a time and under conditions sufficient to modulate levels of said SOCS protein.

Yet a further aspect of the present invention contemplates a method of modulating signal transduction in a cell containing a SOCS gene comprising contacting said cell with an effective amount of a modulator of SOCS gene expression or SOCS protein activity for a time sufficient to modulate signal transduction.

Even yet a further aspect of the present invention contemplates a method of influencing interaction between cells wherein at least one cell carries a SOCS gene, said method comprising contacting the cell carrying the SOCS gene with an effective amount of a modulator of SOCS gene expression or SOCS protein activity for a time sufficient to modulate signal transduction.

As stated above, of the present invention contemplates a range of mimetics or small molecules capable of acting as agonists or antagonists of the SOCS. Such molecules may be obtained from natural product screening such as from coral, soil, plants or the ocean or antarctic environments. Alternatively, peptide, polypeptide or protein libraries or chemical libraries may be readily screened. For example, M1 cells expressing a SOCS do not undergo differentiation in the presence of IL-6. This system can be used to screen molecules which permit differentiation in the presence of IL-6 and a SOCS. A range of test cells may be prepared to screen for antagonists and agonists for a range of cytokines. Such molecules are preferably small molecules and may be of amino acid origin or of chemical origin. SOCS molecules interacting with signalling proteins (eg. JAKS) provide molecular screens to detect molecules which interfere or promote this interaction. Once such screening protocol involves natural product screening.

Accordingly, the present invention contemplates a pharmaceutical composition comprising SOCS or a derivative thereof or a modulator of SOCS expression or SOCS activity and one or more pharmaceutically acceptable carriers and/or diluents. These components are referred to as the "active ingredients". These and other aspects of the present invention apply to any SOCS molecules such as but not limited to SOCS1 to SOCS15.

The pharmaceutical forms containing active ingredients suitable for injectable use include sterile aqueous solutions (where water soluble) sterile powders for the extemporaneous preparation of sterile injectable solutions. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as licitin, by the maintenance of the required particle size in the case of dispersion and by the use of superfactants. The preventions of the action of microorganisms can be brought about by various antibacterial and antifungal agents, for example, parabens, chlorobutanol, phenol, sorbic acid, thirmerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the active ingredients are suitably protected they may be orally administered, for example, with an inert diluent or with an assimilable edible carrier, or it may be enclosed in hard or soft shell gelatin capsule, or it may be compressed into tablets. For oral therapeutic administration, the active compound may be incorporated with excipients and used in the form of ingestible tablets, buccal tablets, troches, capsules, elixirs, suspensions, syrups, wafers and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions in such that a suitable dosage will be obtained. Preferred compositions or preparations according to the present invention are prepared so that an oral dosage unit form contains between about 0.1 μg and 2000 mg of active compound.

The tablets, troches, pills, capsules and the like may also contain the components as listed hereafter. A binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations.

The present invention also extends to forms suitable for topical application such as creams, lotions and gels.

Pharmaceutically acceptable carriers and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from 0.5 μg to about 2000 mg. Expressed in proportions, the active compound is generally present in from about 0.5 μg to about 2000 mg/ml of carrier. In the case of compositions containing supplementary active ingredients, the dosages are determined by reference to the usual dose and manner of administration of the said ingredients. The effective amount may also be conveniently expressed in terms of an amount per kg of body weight. For example, from about 0.01 ng to about 10,000 mg/kg body weight may be administered.

The pharmaceutical composition may also comprise genetic molecules such as a vector capable of transfecting target cells where the vector carries a nucleic acid molecule capable of modulating SOCS expression or SOCS activity. The vector may, for example, be a viral vector. In this regard, a range of gene therapies are contemplated by the present invention including isolating certain cells, genetically manipulating and returning the cell to the same subject or to a genetically related or similar subject.

Still another aspect of the present invention is directed to antibodies to SOCS and its derivatives. Such antibodies may be monoclonal or polyclonal and may be selected from naturally occurring antibodies to SOCS or may be specifically raised to SOCS or derivatives thereof. In the case of the latter, SOCS or its derivatives may first need to be associated with a carrier molecule. The antibodies and/or recombinant SOCS or its derivatives of the present invention are particularly useful as therapeutic or diagnostic agents.

For example, SOCS and its derivatives can be used to screen for naturally occurring antibodies to SOCS. These may occur, for example in some autoimmune diseases. Alternatively, specific antibodies can be used to screen for SOCS. Techniques for such assays are well known in the art and include, for example, sandwich assays and ELISA. Knowledge of SOCS levels may be important for diagnosis of certain cancers or a predisposition to cancers or monitoring cytokine mediated cellular responsiveness or for monitoring certain therapeutic protocols.

Antibodies to SOCS of the present invention may be monoclonal or polyclonal. Alternatively, fragments of antibodies may be used such as Fab fragments. Furthermore, the present invention extends to recombinant and synthetic antibodies and to antibody hybrids. A "synthetic antibody" is considered herein to include fragments and hybrids of antibodies. The antibodies of this aspect of the present invention are particularly useful for immunotherapy and may also be used as a diagnostic tool for assessing apoptosis or monitoring the program of a therapeutic regimin.

For example, specific antibodies can be used to screen for SOCS proteins. The latter would be important, for example, as a means for screening for levels of SOCS in a cell extract or other biological fluid or purifying SOCS made by recombinant means from culture supernatant fluid. Techniques for the assays contemplated herein are known in the art and include, for example, sandwich assays and ELISA.

It is within the scope of this invention to include any second antibodies (monoclonal, polyclonal or fragments of antibodies or synthetic antibodies) directed to the first mentioned antibodies discussed above. Both the first and second antibodies may be used in detection assays or a first antibody may be used with a commercially available anti-immunoglobulin antibody. An antibody as contemplated herein includes any antibody specific to any region of SOCS.

Both polyclonal and monoclonal antibodies are obtainable by immunization with the enzyme or protein and either type is utilizable for immunoassays. The methods of obtaining both types of sera are well known in the art. Polyclonal sera are less preferred but are relatively easily prepared by injection of a suitable laboratory animal with an effective amount of SOCS, or antigenic parts thereof, collecting serum from the animal, and isolating specific sera by any of the known immunoadsorbent techniques. Although antibodies produced by this method are utilizable in virtually any type of immunoassay, they are generally less favoured because of the potential heterogeneity of the product.

The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art.

Another aspect of the present invention contemplates a method for detecting SOCS in a biological sample from a subject said method comprising contacting said biological sample with an antibody specific for SOCS or its derivatives or homologues for a time and under conditions sufficient for an antibody-SOCS complex to form and then detecting said complex.

The presence of SOCS may be accomplished in a number of ways such as by Western blotting and ELISA procedures. A wide range of immunoassay techniques are available as can be seen by reference to U.S. Pat. Nos. 4,016,043, 4,424,279 and 4,018,653. These, of course, include both single-site and two-site or "sandwich" assays of the non-competitive types, as well as in the traditional competitive binding assays. These assays also include direct binding of a labelled antibody to a target.

Sandwich assays are among the most useful and commonly used assays and are favoured for use in the present invention. A number of variations of the sandwich assay technique exist, and all are intended to be encompassed by the present invention. Briefly, in a typical forward assay, an unlabelled antibody is immobilized on a solid substrate and the sample to be tested brought into contact with the bound molecule. After a suitable period of incubation, for a period of time sufficient to allow formation of an antibody-antigen complex, a second antibody specific to the antigen, labelled with a reporter molecule capable of producing a detectable signal is then added and incubated, allowing time sufficient for the formation of another complex of antibody-antigen-labelled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of hapten. Variations on the forward assay include a simultaneous assay, in which both sample and labelled antibody are added simultaneously to the bound antibody. These techniques are well known to those skilled in the art, including any minor variations as will be readily apparent. In accordance with the present invention the sample is one which might contain SOCS including cell extract, tissue biopsy or possibly serum, saliva, mucosal secretions, lymph, tissue fluid and respiratory fluid. The sample is, therefore, generally a biological sample comprising biological fluid but also extends to fermentation fluid and supernatant fluid such as from a cell culture.

In the typical forward sandwich assay, a first antibody having specificity for the SOCS or antigenic parts thereof, is either covalently or passively bound to a solid surface. The solid surface Is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2-40 minutes or overnight if more convenient) and under suitable conditions (e.g. room temperature to 37° C.) to allow binding of any subunit present in the antibody. Following the incubation period, the antibody subunit solid phase is washed and dried and incubated with a second antibody specific for a portion of the hapten. The second antibody is linked to a reporter molecule which is used to indicate the binding of the second antibody to the hapten.

An alternative method involves immobilizing the target molecules in the biological sample and then exposing the immobilized target to specific antibody which may or may not be labelled with a reporter molecule. Depending on the amount of target and the strength of the reporter molecule signal, a bound target may be detectable by direct labelling with the antibody. Alternatively, a second labelled antibody, specific to the first antibody is exposed to the target-first antibody complex to form a target-first antibody-second antibody tertiary complex. The complex is detected by the signal emitted by the reporter molecule.

By "reporter molecule" as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (i.e. radioisotopes) and chemiluminescent molecules.

In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase and alkaline phosphatase, amongst others. The substrates to be used with the specific enzymes are generally chosen for the production, upon hydrolysis by the corresponding enzyme, of a detectable colour change. Examples of suitable enzymes include alkaline phosphatase and peroxidase. It is also possible to employ fluorogenic substrates, which yield a fluorescent product rather than the chromogenic substrates noted above. In all cases, the enzyme-labelled antibody is added to the first antibody hapten complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of hapten which was present in the sample. "Reporter molecule" also extends to use of cell agglutination or inhibition of agglutination such as red blood cells on latex beads, and the like.

Alternately, fluorescent compounds, such as fluorescein and rhodamine, may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic colour visually detectable with a light microscope. As in the EIA, the fluorescent labelled antibody is allowed to bind to the first antibody-hapten complex. After washing off the unbound reagent, the remaining tertiary complex is then exposed to the light of the appropriate wavelength the fluorescence observed indicates the presence of the hapten of interest. Immunofluorescene and EIA techniques are both very well established in the art and are particularly preferred for the present method. However, other reporter molecules, such as radioisotope, chemiluminescent or bioluminescent molecules, may also be employed.

The present invention also contemplates genetic assays such as involving PCR analysis to detect SOCS gene or its derivatives. Alternative methods or methods used in conjunction include direct nucleotide sequencing or mutation scanning such as single stranded conformation polymorphisms analysis (SSCP) as specific oligonucleotide hybridisation, as methods such as direct protein truncation tests.

Since cytokines are involved in transcription of some SOCS molecules, the detection of SOCS provides surrogate markers for cytokines or cytokine activity. This may be useful in assessing subjects with a range of conditions such as those will autoimmune diseases, for example, rheumatoid arthritis, diabetes and stiff man syndrome amongst others.

The nucleic acid molecules of the present invention may be DNA or RNA. When the nucleic acid molecule is in DNA form, it may be genomic DNA or cDNA. RNA forms of the nucleic acid molecules of the present invention are generally mRNA.

Although the nucleic acid molecules of the present invention are generally in isolated form, they may be integrated into or ligated to or otherwise fused or associated with other genetic molecules such as vector molecules and in particular expression vector molecules. Vectors and expression vectors are generally capable of replication and, if applicable, expression in one or both of a prokaryotic cell or a eukaryotic cell. Preferably, prokaryotic cells include *E. coli, Bacillus* sp and *Pseudomonas* sp. Preferred eukaryotic cells include yeast, fungal, mammalian and insect cells.

Accordingly, another aspect of the present invention contemplates a genetic construct comprising a vector portion and a mammalian and more particularly a human SOCS gene portion, which SOCS gene portion is capable of encoding a SOCS polypeptide or a functional or immunologically interactive derivative thereof.

Preferably, the SOCS gene portion of the genetic construct is operably linked to a promoter on the vector such that said promoter is capable of directing expression of said SOCS gene portion in an appropriate cell.

In addition, the SOCS gene portion of the genetic construct may comprise all or part of the gene fused to another genetic sequence such as a nucleotide sequence encoding glutathione-S-transferase or part thereof.

The present invention extends to such genetic constructs and to prokaryotic or eukaryotic cells comprising same.

The present invention also extends to any or all derivatives of SOCS including mutants, part, fragments, portions, homologues and analogues or their encoding genetic sequence including single or multiple nucleotide or amino acid substitutions, additions and/or deletions to the naturally occurring nucleotide or amino acid sequence. The present invention also extends to mimetics and agonists and antagonists of SOCS.

The SOCS and its genetic sequence of the present invention will be useful in the generation of a range of therapeutic and diagnostic reagents and will be especially useful in the detection of a cytokine involved in a particular cellular response or a receptor for that cytokine. For example, cells expressing SOCS gene such as M1 cells expressing the SOCS1 gene, will no longer be responsive to a particular cytokine such as, in the case of SOCS1, IL-6. Clearly, the present invention further contemplates cells such as M1 cells expressing any SOCS gene such as from SOCS1 to SOCS15. Furthermore, the present invention provides the use of molecules that regulate or potentiate the ability of therapeutic cytokines. For example, molecules which block some SOCS activity, may act to potential therapeutic cytokine activity (eg. G-CSF).

Soluble SOCS polypeptides are also contemplated to be particularly useful in the treatment of disease, injury or abnormality involving cytokine mediated cellular responsiveness such as hyperimmunity, immunosuppression, allergies, hypertension and the like.

A further aspect of the present invention contemplates the use of SOCS or its functional derivatives in the manufacture of a medicament for the treatment of conditions involving cytokine mediated cellular responsiveness.

The present invention further contemplates transgenic mammalian cells expressing a SOCS gene. Such cells are useful indicator cell lines for assaying for suppression of cytokine function. One example is M1 cells expressing a SOCS gene. Such cell lines may be useful for screening for cytokines or screening molecules such as naturally occurring molecules from plants, coral, microorganisms or bio-organically active soil or water capable of acting as cytokine antagonists or agonists.

The present invention further contemplates hybrids between different SOCS from the same or different animal species. For example, a hybrid may be formed between all or a functional part of mouse SOCS1and human SOCS1. Alternatively, the hybrid may be between all or part of mouse SOCS1 and mouse SOCS2. All such hybrids are contemplated herein and are particularly useful in developing pleiotropic molecules.

The present invention further contemplates a range of genetic based diagnostic assays screening for individuals with defective SOCS genes. Such mutations may result in cell types not being responsive to a particular cytokine or resulting in over responsiveness leading to a range of conditions. The SOCS genetic sequence can be readily verified using a range of PCR or other techniques to determine whether a mutation is resident in the gene. Appropriate gene therapy or other interventionist therapy may then be adopted.

The present invention is further described by the following non-limiting Examples.

Examples 1-16 relate to SOCS1, SOCS2 and SOCS3 which were identified on the basis of activity. Examples 17-24 relate to various aspects of SOCS4 to SOCS15 which were cloned initially on the basis of sequence similarity. Examples 25-36 relate to specific aspects of SOCS4 to SOCS15, respectively.

EXAMPLE 1

Cell Culture and Cytokines

The M1 cell line was derived from a spontaneously arising leukaemia in SL mice [Ichikawa, 1969]. Parental M1 cells used in this study have been in passage at the Walter and Eliza Hall Institute for Medical Research, Melbourne, Victoria, Australia, for approximately 10 years. M1 cells were maintained by weekly passage in Dulbecco's modified Eagle's medium (DME) containing 10% (v/v) foetal bovine serum (FCS). Recombinant cytokines are generally available from commercial sources or were prepared by published methods. Recombinant murine LIF was produced in *Escherichia coli* and purified, as previously described [Gearing, 1989]. Purified human oncostatin M was purchased from PeproTech Inc (Rocky Hill, N.J., USA), and purified mouse IFN-γ was obtained from Genzyme Diagnostics (Cambridge, Mass., USA). Recombinant murine thrombopoietin was produced as a FLAGTM-tagged fusion protein in CHO cells and then purified.

EXAMPLE 2

Agar Colony Assays

In order to assay the differentiation of M1 cells in response to cytokines, 300 cells were cultured in 35 mm Petri dishes containing 1 ml of DME supplemented with 20% (v/v) fetal calf serum (FCS), 0.3% (w/v) agar and 0.1 ml of serial dilutions of IL-6, LIF, OSM, IFN-γ, tpo or dexamethasone (Sigma Chemical Company, St Louis, Mich.). After 7 days culture at 37° C. in a fully humidified atmosphere, containing 10% (v/v) $CO_2$ in air, colonies of M1 cells were counted and classified as differentiated if they were composed of dispersed cells or had a corona of dispersed cells around a tightly packed centre.

EXAMPLE 3

Generation of Retroviral Library

A cDNA expression library was constructed from the factor-dependent haemopoietic cell line FDC-P1, essentially as described [Rayner, 1994]. Briefly, cDNA was cloned into the retroviral vector pRUFneo and then transfected into an amphotrophic packaging cell line (PA317). Transiently generated virus was harvested from the cell supernatant at 48 hr posttransfection, and used to infect Y2 ecotropic packaging cells, to generate a high titre virus-producing cell line.

EXAMPLE 4

Retroviral Infection of M1 Cells

Pools of $10^6$ infected Ψ2 cells were irradiated (3000 rad) and cocultivated with $10^6$ M1 cells in DME supplemented with 10% (v/v) FCS and 4 μg/ml Polybrene, for 2 days at 37° C. To select for IL-6-unresponsive clones, retrovirally-infected M1 cells were washed once in DME, and cultured at approximately $2\times10^4$ cells/ml in 1 ml agar cultures containing 400 μg/ml geneticin (GibcoBRL, Grand Island, N.Y.) and 100 ng/ml IL-6. The efficiency of infection of M1 cells was 1-2%, as estimated by agar plating the infected cells in the presence of geneticin only.

EXAMPLE 5

PCR

Genomic DNA from retrovirally-infected M1 cells was digested with SacI and 1 μg of phenol/chloroform extracted DNA was then amplified by polymerase chain reaction (PCR). Primers used for amplification of cDNA inserts from the integrated retrovirus were GAG3 (5' CACGCCGCCCACGTGAAGGC3'[SEQ ID NO:1]), which corresponds to the vector gag sequence approximately 30 bp 5' of the multiple cloning site, and HSVTK (5' TTCGCCAATGACAAGACGCT3'[SEQ ID NO:2]), which corresponds to the pMC1neo sequence approximately 200 bp 3' of the multiple cloning site. The PCR entailed an initial denaturation at 94° C. for 5 min, 35 cycles of denaturation at 94° C. for 1 min, annealing at 56° C. for 2 min, and extension at 72° C. for 3 min, followed by a final 10 min extension. PCR products were gel purified and then ligated into the pGEM-T plasmid (Promega, Madison, Wis.), and sequenced using an ABI PRISM Dye Terminator Cycle Sequencing Kit and a Model 373 Automated DNA Sequencer (Applied Biosystems Inc., Foster City, Calif.).

EXAMPLE 6

Cloning of cDNAs

Independent cDNA clones encoding mouse SOCS1 were isolated from a murine thymus cDNA library essentially as described (Hilton et al, 1994). The nucleotide and predicted amino acid sequences of mouse SOCS1 cDNA were compared to databases using the BLASTN and TFASTA algorithms (Pearson and Lipman, 1988; Pearson, 1990; Altshcul et al, 1990). Oligonucleotides were designed from the ESTs encoding human SOCS1 and mouse SOC-1 and SOCS3 and used to probe commercially available mouse thymus and spleen cDNA libraries. Sequencing was performed using an ABI automated sequencer according to the manufacturer's instructions.

EXAMPLE 7

Southern and Northern Blot Analyses and RT-PCR $^{32}P$-labelled probes were generated using a random decanucleotide labelling kit (Bresatec, Adelaide, South Australia) from a 600 bp PstI fragment encoding neomycin phophotransfease from the plasmid pPGKneo, 1070 bp fragment of the SOCS1 gene obtained by digestion of the 1.4 kbp PCR product with XhoI, SOCS2, SOCS3, CIS and a 1.2 kbp fragment of the chicken glyceraldehyde 3-phosphate dehydrogenase gene [Dugaiczyk, 1983].

Genomic DNA was isolated from cells using a proteinase K-sodium dodecyl sulfate procedure essentially as described. Fifteen micrograms of DNA was digested with either BamHI or SacI, fractionated on a 0.8% (w/v) agarose gel, transferred to GeneScreenPlus membrane (Du Pont NEN, Boston Mass.), prehybridised, hybridised with random-primed $^{2}P$-labelled DNA fragments and washed essentially as described [Sambrook, 1989].

Total RNA was isolated from cells and tissues using Trizol Reagent, as recommended by the manufacturer (GibcoBRL, Grand Island, N.Y.). When required polyA+ mRNA was purified essentially as described [Alexander, 1995]. Northern blots were prehybridised, hybridized with random-primed 32P-labelled DNA fragments and washed as described [Alexander, 1995].

To assess the induction of SOCS genes by IL-6, mice (C57BL6) were injected intravenously with 5 μg IL-6 followed by harvest of the liver at the indicated timepoints after injection. M1 cells were cultured in the presence of 20 ng/ml IL-6 and harvested at the indicated times. For RT-PCR analysis, bone marrow cells were harvested as described (Metacalf et al, 1995) and stimulated for 1 hr at 37° C. with 100 ng/ml of a range of cytokines. RT-PCR was performed on total RNA as described (Metcalf et al, 1995). PCR products were resolved on an agarose gel and Southern blots were hybridised with probes specific for each SOCS family member. Expression of β-actin was assessed to ensure uniformity of amplification.

EXAMPLE 8

DNA Constructs and Transfection

A cDNA encoding epitope-tagged SOCS1 was generated by subcloning the entire SOCS1coding region into the pEF-BOS expression vector [Mizushima, 1990], engineered to encode an inframe FLAG epitope downstream of an initiation methionine (pF-SOCS1). Using electroporation as described previously [Hilton, 1994], M1 cells expressing the thrombopoietin receptor (M1.mpl) were transfected with the 20 μg of Aat II-digested pF-SOCS1 expression plasmid and 2 μg of a Sca I-digested plasmid in which transcription of a cDNA encoding puromycin N-acetyl transferase was driven from the mouse phosphoglycerokinase promoter (pPGK-PuropA). After 48 hours in culture, transfected cells were selected with 20 μg/ml puromycin (Sigma Chemical Company, St Louis Mo.), and screened for expression of SOCS1 by Western blotting, using the M2 anti-FLAG monoclonal antibody according to the manufacturer's instructions (Eastman Kodak, Rochester N.Y.). In other experiments M1 cells were transfected with only the pF-SOCS1 plasmid or a control and selected by their ability to grow in agar in the presence of 100 ng/ml of IL-6.

EXAMPLE 9

Immunoprecipitation and Western Blotting

Prior to either immunoprecipitaion or Western blotting, $10^7$ M1 cells or their derivatives were washed twice, resuspended in 1 ml of DME, and incubated at 37° C. for 30 min. The cells were then stimulated for 4 min at 37° C. with either saline or 100 ng/ml IL-6, after which sodium vanadate (Sigma Chemical Co., St Louis, Mich.) was added to a concentration of 1 mM. Cells were placed on ice, washed once with saline containing 1 mM sodium vanadate, and then solubilised for 5 min on ice with 300 μl % (v/v) Triton X-100, 150 mM NaCl, 2 mM EDTA, 50 mM Tris-HCl pH 7.4, containing Complete protease inhibitors (Boehringer Mannheim, Mannheim, Germany) and 1 mM sodium vanadate. Lysates were cleared by centrifugation and quantitated using a Coomassie Protein Assay Reagent (Pierce, Rockford Ill.).

For immunoprecipitations, equal concentrations of protein extracts (1-2 mg) were incubated for 1 hr or overnight at 4° C. with either 4 μg of anti-gp130 antibody (M20; Santa Cruz Biotechnology Inc., Santa Cruz, Calif.) or 4 μg of anti-phosphotyrosine antibody (4G10; Upstate Biotechnology Inc., Lake Placid N.Y.), and 15 μl packed volume of Protein G Sepharose (Pharmacia, Uppsala, Sweden) [Hilton et al, 1996]. Immunoprecipitates were washed twice in 1% (v/v) NP40, 150 mM NaCl, 50 mM Tris-HCl pH 8.0, containing Complete protease inhibitors (Boehringer Mannheim, Mannheim, Germany and 1 mM sodium vanadate. The samples were heated for 5 min at 95° C. in SDS sample buffer (625 mM Tris-HCl pH 6.8, 0.05% (w/v) SDS, 0.1% (v/v) glycerol, bromophenol blue, 0.125% (v/v) 2-mercaptoethanol), fractionated by SDS-PAGE and immunoblotted as described above.

For Western blotting, 10 μg of protein from a cellular extract or material from an immunoprecipitation reaction was loaded onto 4-15% Ready gels (Bio-Rad Laboratories, Hercules Calif.), and resolved by sodium dodecyl sulfate polyacrylamide gel electrophoresis (SDS-PAGE). Proteins were transferred to PVDF membrane (Micron Separations Inc., Westborough Mass.) for 1 hr at 100 V. The membranes were probed with the following primary antibodies; anti-tyrosine phosphorylated STAT3 (1:1000 dilution; New England Biolabs, Beverly, Mass.); anti-STAT3 (C-20; 1:100 dilution; Santa Cruz Biotechnology Inc., Santa Cruz Calif.); anti-gp130 (M20, 1:100 dilution; Santa Cruz Biotechnology Inc., Santa Cruz Calif.); anti-phosphotyrosine (horseradish peroxidase-conjugated RC20, 1:5000 dilution; Transduction Laboratories, Lexington Ky.); anti-tyrosine phosphorylated MAP kinase and anti-MAP kinase antibodies (1:1000 dilution; New England Biolabs, Beverly, Mass.). Blots were visualised using peroxidase-conjugated secondary antibodies and Enhanced Chemiluminescence (ECL) reagents according to the manafacturer□s instructions (Pierce, Rockford Ill.).

EXAMPLE 10

Electrophoretic Mobility Shift Assays

Assays were performed as described [Novak, 1995], using the high affinity SIF (c-sis-inducible factor) binding site m67 [Wakao, 1994]. Protein extracts were prepared from M1 cells incubated for 4-10 min at 37° C. in 10 ml serum-free DME containing either saline, 100 ng/ml IL-6 or 100 ng/ml IFN-γ. The binding reactions contained 4-6 μg protein (constant within a given experiment), 5 ng $^{32}P$-labelled m67 oligonucleotide, and 800 ng sonicated salmon sperm DNA. For certain experiments, protein samples were preincubated with an excess of unlabelled m67 oligonucleotide, or antibodies specific for either STAT1 (Transduction Laboratories, Lexington, Ky.) or STAT3 (Santa Cruz Biotechnology Inc., Santa Cruz Calif.), as described [Novak, 1995].

Western blots were performed using anti-tyrosine phosphorylated STAT3 or anti-STAT3 (New England Biolabs, Beverly, Mass.) or anti-gp130 (Santa Cruz Biotechnology Inc.) as described (Nicola et al, 1996). EMSA were performed using the m67 oligonucleotide probe, as described (Novak et al, 1995).

EXAMPLE 11

Expression Cloning of a Novel Suppressor of Cytokine Signal Transduction

Figure 1:
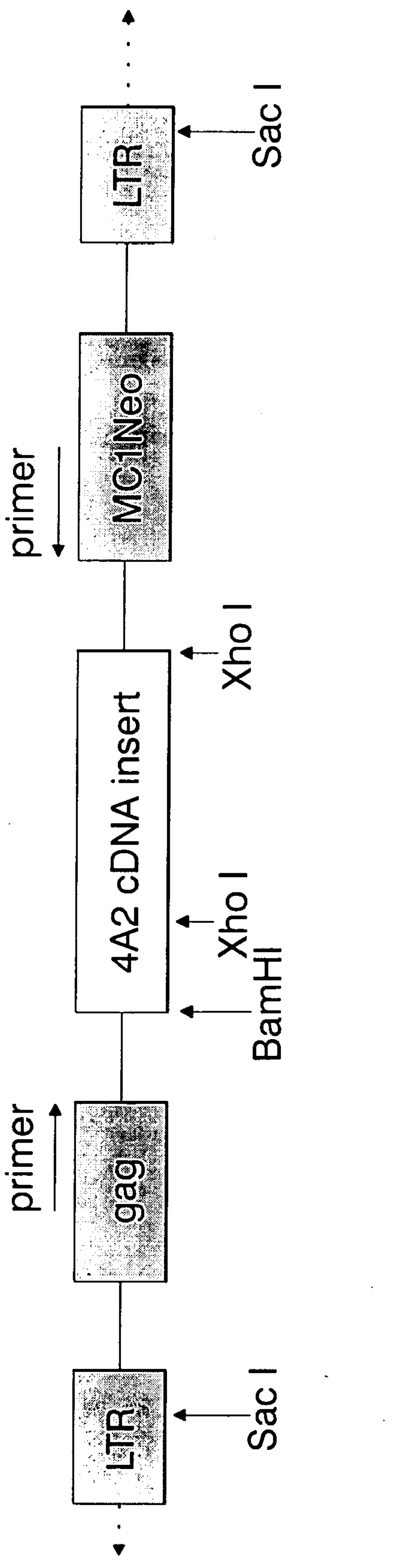
FIG. 1 is a diagrammatic representation showing generation of an IL-6-unresponsive M1 clone by retroviral infection. The RUFneo retrovirus, showing the position of landmark restriction endonuclease cleavage sites, the 4A2 cDNA insert and the position of PCR primer sequences.

In order to identify cDNAs capable of suppressing cytokine signal transduction, an expression cloning approach was adopted. This strategy centred on M1 cells, a monocytic leukaemia cell line that differentiates into mature macrophages and ceases proliferation in response to the cytokines IL-6, LIF, OSM and IFN-γ, and the steroid dexamethasone. Parental M1 cells were infected with the RUFneo retrovirus, into which cDNAs from the factor-dependent haemopoietic cell line FDC-P1 had been cloned. In this retrovirus, transcription of both the neomycin resistance gene and the cloned cDNA was driven off the powerful constitutive promoter present in the retroviral LTR (FIG. 1). When cultured in semi-solid agar, parental M1 cells form large tightly packed colonies. Upon stimulation with IL-6, M1 cells undergo rapid differentiation, resulting in the formation in agar of only single macrophages or small dispersed clusters of cells. Retrovirally-infected M1 cells that were unresponsive to IL-6 were selected in semi-solid agar culture by their ability to form large, tightly packed colonies in the presence of IL-6 and geneticin. A single stable IL-6-unresponsive clone, 4A2, was obtained after examining $10^4$ infected cells.

Figure 2:
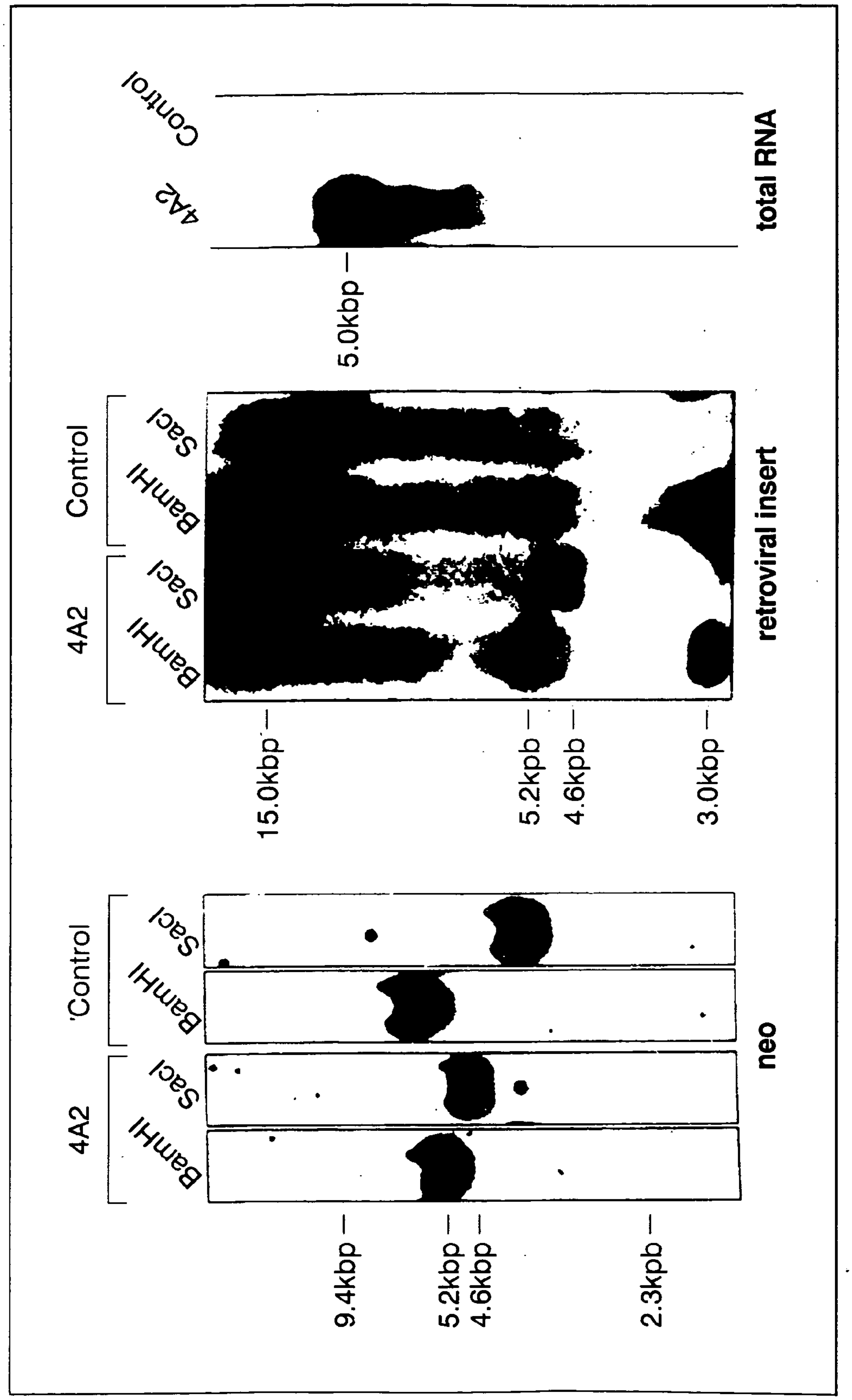
FIG. 2 is a photographic representation of Southern and Northern analysis. (Left and Middle Panels) Southern blot analysis of genomic DNA from clone 4A2 and a control infected M1 clone. DNA was digested with BamHI, to reveal the number of retroviruses carried by each clone, and SacI, to estimate the size of the retroviral cDNA insert. Left panel; probed with neo. Right panel; probed with the XhoI-digested 4A2 PCR product. (Right Panel). Northern blot analysis of total RNA from clone 4A2 and a control infected M1 clone, probed with the XhoI-digested 4A2 PCR product. The two bands represent unspliced and spliced retroviral transcripts, resulting from splice donor and acceptor sites in the retroviral genome.

A fragment of the neomycin phosphotransferase (neo) gene was used to probe a Southern blot of genomic DNA from clone 4A2 and this revealed that the cell line was infected with a single retrovirus containing a cDNA approximately 1.4 kbp in length (FIG. 2). PCR amplification using primers from the retroviral vector which flanked the cDNA cloning site enabled recovery of a 1.4 kbp cDNA insert, which we have named suppressor of cytokine signalling-1, or SOCS1. This PCR product was used to probe a similar Southern blot of4A2 genomic DNA and hybridised to two fragments, one which corresponded to the endogenous SOCS1 gene and the other, which matched the size of the band seen using the neo probe, corresponded to the SOCS1 cDNA cloned into the integrated retrovirus (FIG. 2). The latter was not observed in an M1 cell clone infected with a retrovirus containing an irrelevant cDNA. Similarly, Northern blot analysis revealed that SOCS1mRNA was abundant in the cell line 4A2, but not in the control infected M1 cell clone (FIG. 2).

EXAMPLE 12

SOCS1, SOCS2, SOCS3 and CIS Define a New Family of SH2-Containing Proteins

Figure 3A:
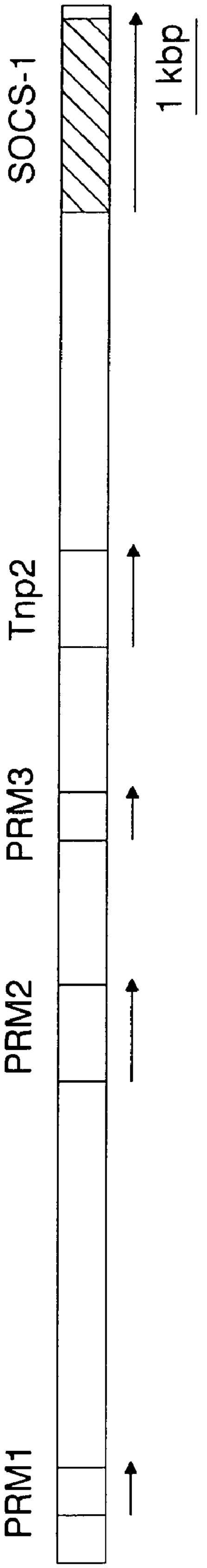

The SOCS1 PCR product was used as a probe to isolate homologous cDNAs from a mouse thymus cDNA library. The sequence of the cDNAs proved to be identical to the PCR product, suggesting that constitutive or over expression, rather than mutation, of the SOCS1 protein was sufficient for generating an IL-6-unresponsive phenotype. Comparison of the sequence of SOCS1 cDNA with nucleotide sequence databases revealed that it was present on mouse and rat genomic DNA clones containing the protamine gene cluster found on mouse chromosome 16. Closer inspection revealed that the 1.4 kb SOCS1 sequence was not homologous to any of the protamine genes, but rather represented a previously unidentified open reading frame located at the extreme 3' end of these clones (FIG. 3A-3B (1)-(3)). There were no regions of discontinuity between the sequences of the SOCS1 cDNA and genomic locus, suggesting that SOCS1 is encoded by a single exon. In addition to the genomic clone containing the protamine genes, a series of murine and human expressed sequenced tags (ESTs) also revealed large blocks of nucleotide sequence identity to mouse SOCS1. The sequence information provided by the human ESTs allowed the rapid cloning of cDNAs encoding human SOCS1.

The mouse and rat SOCS1 gene encodes a 212 amino acid protein whereas the human SOCS1 gene encodes a 211 amino acid protein. Mouse, rat and human SOCS1 proteins share 95-99% amino acid identity (FIG. 9(I)-(III)). A search of translated nucleic acid databases with the predicted amino acid sequence of SOCS1 showed that it was most related to a recently cloned cytokine-inducible immediate early gene product, CIS, and two classes of ESTs. Full length cDNAs from the two classes of ESTs were isolated and found to encode proteins of similar length and overall structure to SOCS1 and CIS. These clones were given the names SOCS2 and SOCS3. Each of the four proteins contains a central SH2 domain and a C-terminal region termed the SOCS motif. The SOCS1 proteins exhibit an extremely high level of amino acid sequence similarity (95-99% identity) amongst different species. However, the forms of the SOCS1, SOCS2, SOCS3 and CIS from the same animal, while clearly defining a new family of SH2-containing proteins, exhibited a lower amino acid identity. SOCS2 and CIS exhibit approximately 38% amino acid identity, while the remaining members of the family share approximately 25% amino acid identity (FIG. 9(I)-(III)). The coding region of the genes for SOCS1 and SOC3 appear to contain no introns while the coding region of the genes for SOCS2 and CIS contain one and two introns, respectively.

The Genbank Accession Numbers for the sequences referred to herein are mouse SOCS1 cDNA (U88325), human SOCS1 cDNA (U88326), mouse SOCS2 cDNA (U88327), mouse SOCS3 cDNA (U88328).

EXAMPLE 13

Constitutive Expression of SOCS1 Suppresses the Action of a Range of Cytokines To formally establish that the phenotype of the 4A2 cell line was directly related to expression of SOCS1, and not to unrelated genetic changes which may have occurred independently in these cells, a cDNA encoding an epitope-tagged version of SOCS1 under the control of the EF1α promoter was transfected into parental M1 cells, and M1 cells expressing the receptor for thrombopoietin, c-mpl (M1.mpl). Transfection of the SOCS1 expression vector into both cell lines resulted in an increase in the frequency of IL-6 unresponsive M1 cells.

Multiple independent clones of M1 cells expression SOCS1, as detected by Western blot, displayed a cytokine-unresponsive phenotype that was indistinguishable from 4A2. Further, if transfectants were not maintained in puromycin, expression of SOCS1 was lost over time and cells regained their cytokine responsiveness. In the absence of cytokine, colonies derived from 4A2 and other SOCS1 expressing clones characteristically grew to a smaller size than colones formed by control M1 cells (FIG. 10).

Figure 4:
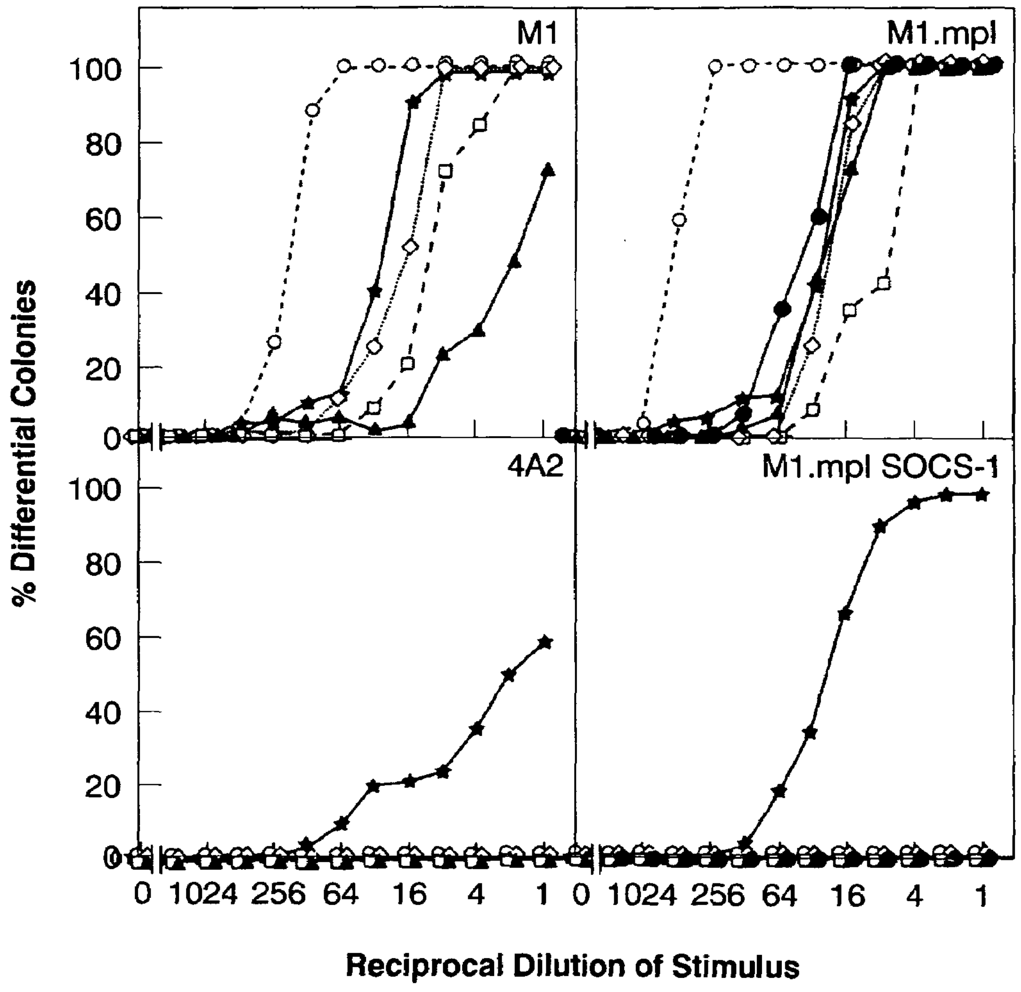
FIG. 4 is a graphical representation of cell differentiation in the presence of cytokines. Semi-solid agar cultures of parental M1 cells (M1 and M1.mpl) and M1 cells expressing SOCS1 (4A2 and M1.mpl.SOCS1), were used and the percentage of colonies which differentiated in response to a titration of 1 mg/ml IL-6 (●), 100 ng/ml LIF (◇), 1 mg/ml OSM (□), 100 ng/ml IFN-γ (▲), 500 ng/ml TPO (●), or $3\times10^{-6}$ M dexamethasone (·X·) determined.
Figure 5:
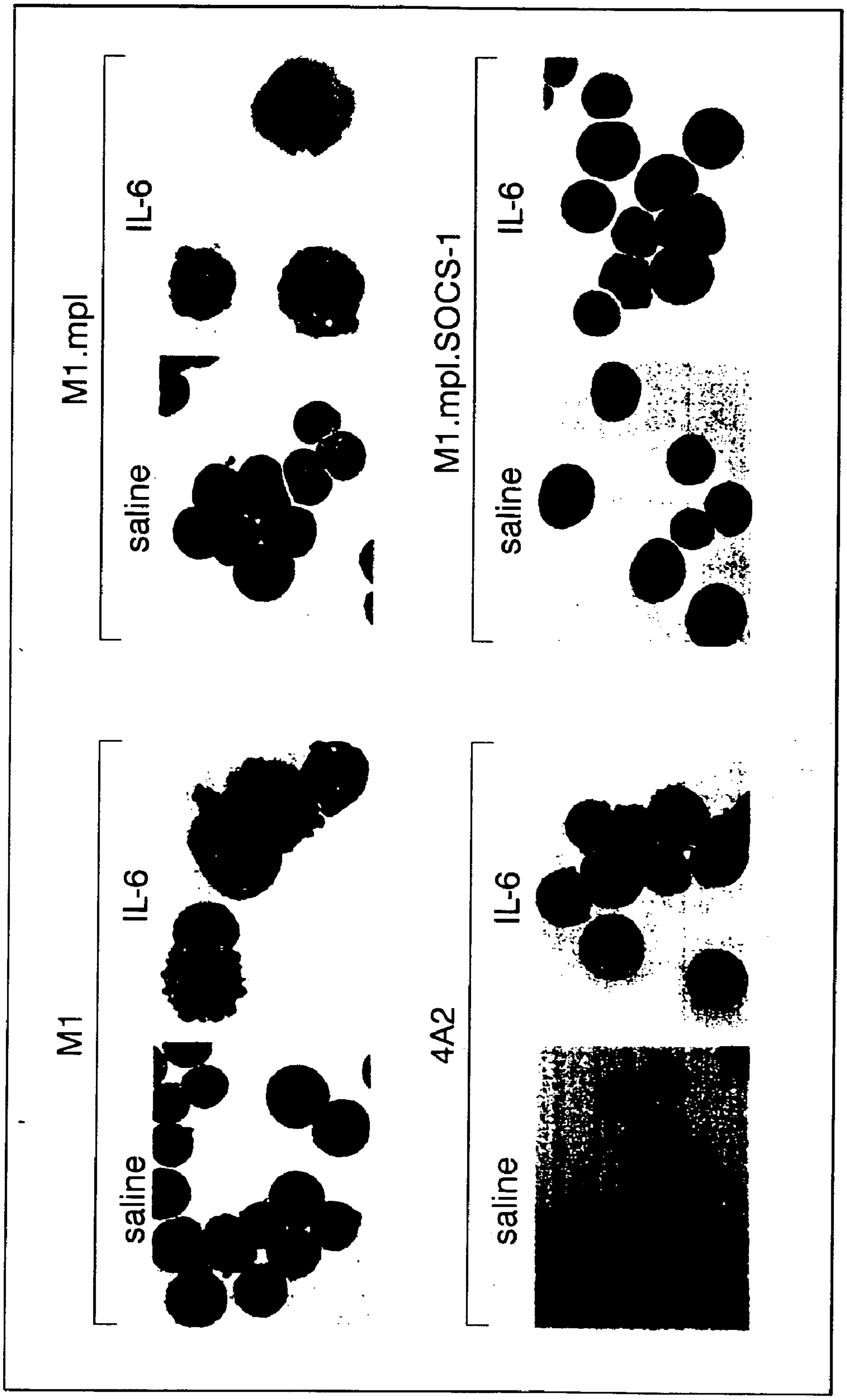
FIG. 5 is a photographic representation of cytospins of liquid cultures of parental M1 cells (M1 and M1.mpl) ) and M1 cells expressing SOCS1 (4A2 and M1.mpl.SOCS1) cultured for 4 days in the presence of 10 ng/ml IL-6 or saline. Unlike parental M1 cells, morphological features consistent with macrophage differentiation are not observed in M1 cells constitutively expressing SOCS1 (4A2 and M1.mpl.SOCS1) when cultured in IL-6.

The effect of constitutive SOCS1 expression on the response of M1 cells to a range of cytokines was investigated using the 4A2 cell line and a clone of M1.mpl cells expressing SOCS1 (M1.mpl.SOCS1). Unlike parental M1 cells and M1.mpl cells, the two cell lines expressing SOCS1 continued to proliferate and failed to form differentiated colonies in response to either IL-6, LIF, OSM, IFN-γ or, in the case of the M1.mpl.SOCS1 cell line, thrombopoietin (FIG. 4). For both cell lines, however, a normal response to dexamethasone was observed, suggesting that SOCS1 specifically affected cytokine signal transduction rather than differentiation per se. Consistent with these data, while parental M1 cells and M1.mpl cells became large and vacuolated in response to IL-6, 4A2 and M1.mpl. SOCS1 cells showed no evidence of morphological differentiation in response to IL-6 or other cytokines (FIG. 5).

EXAMPLE 14

Figure 6:
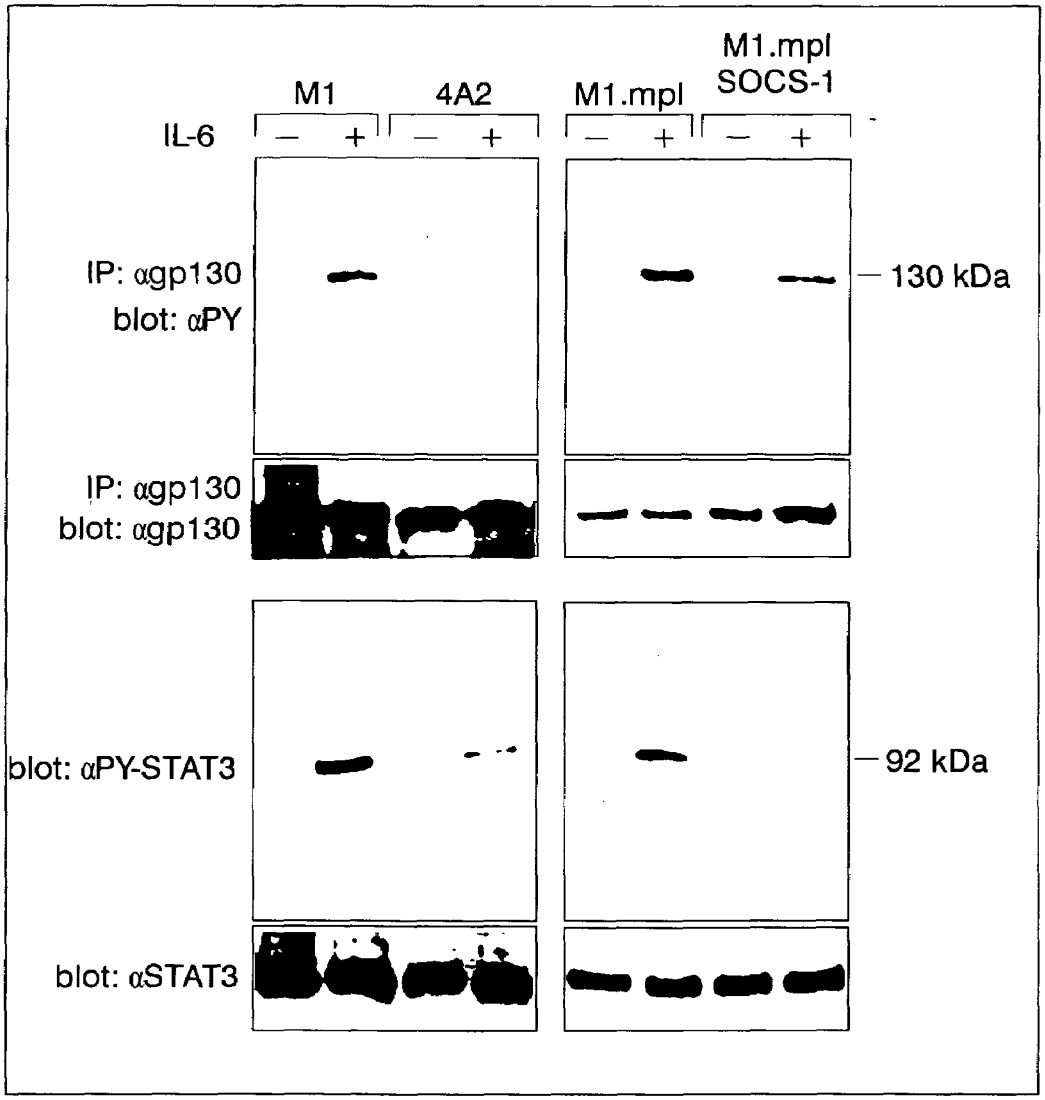
FIG. 6 is a photographic representation showing inhibition of phosphorylation of signalling molecules by SOCS1. Parental M1 cells (M1 and M1.mpl) and M1 cells expressing SOCS1 (4A2 and M1.mpl.SOCS1) were incubated in the absence (−) or presence (+) of 10 ng/ml of IL-6 for 4 minutes at 37° C. Cells were then lysed and extracts were either immunopreciptated using anti-mouse gp130 antibody prior to SDS-PAGE (two upper panels) or were electrophoresed directly (two lower panels). Gels were blotted and the filters were then probed with anti-phosphotyrosine (upper panel), anti-gp130 antibody (second top panel), anti-phospho-STAT3 (second bottom panel) or anti-STAT3 (lower panel). Blots were visualised using peroxidase-conjugated secondary antibodies and Enhanced Chemiluminescence (ECL) reagents.
Figure 7A:
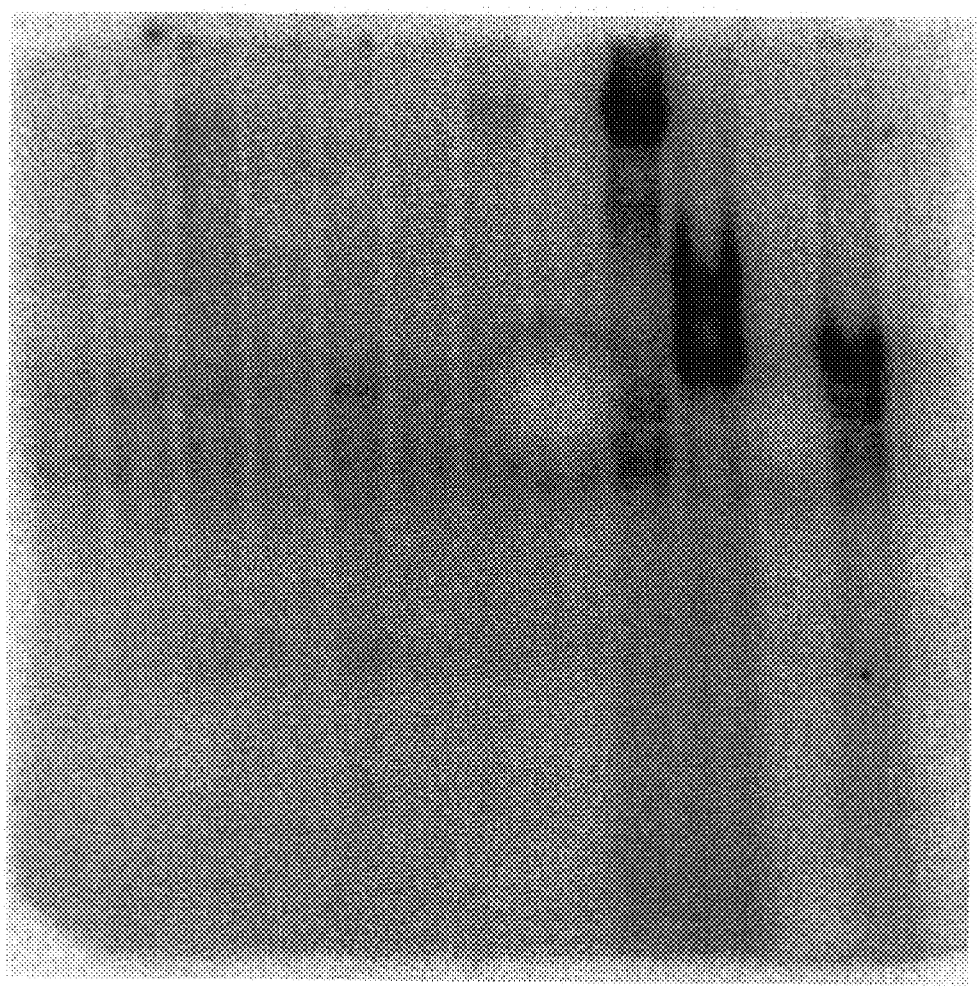
FIG. 7A-B is a representation of protein extracts prepared from (7A) M1 cells or M1 cells expressing SOCS1 (4A2) and (7B) M1.mpl cells or M1.mpl.SOCS1 cells incubated for 10 min at 37° C. in 10 ml serum-free DME containing either saline, 100 ng/ml IL-6 or 100 ng/ml IFN-γ. The binding reactions contained 4-6 μg protein (constant within a given experiment), 5 ng $^{32}$P-labelled m67 oligonucleotide encoding the high affinity SIF (c-sis-inducible factor) binding site, and 800 ng sonicated salmon sperm DNA. For certain experiments, protein samples were preincubated with an excess of unlabelled m67 oligonucleotide, or antibodies specific for either STAT1 or STAT3.
Figure 7B:
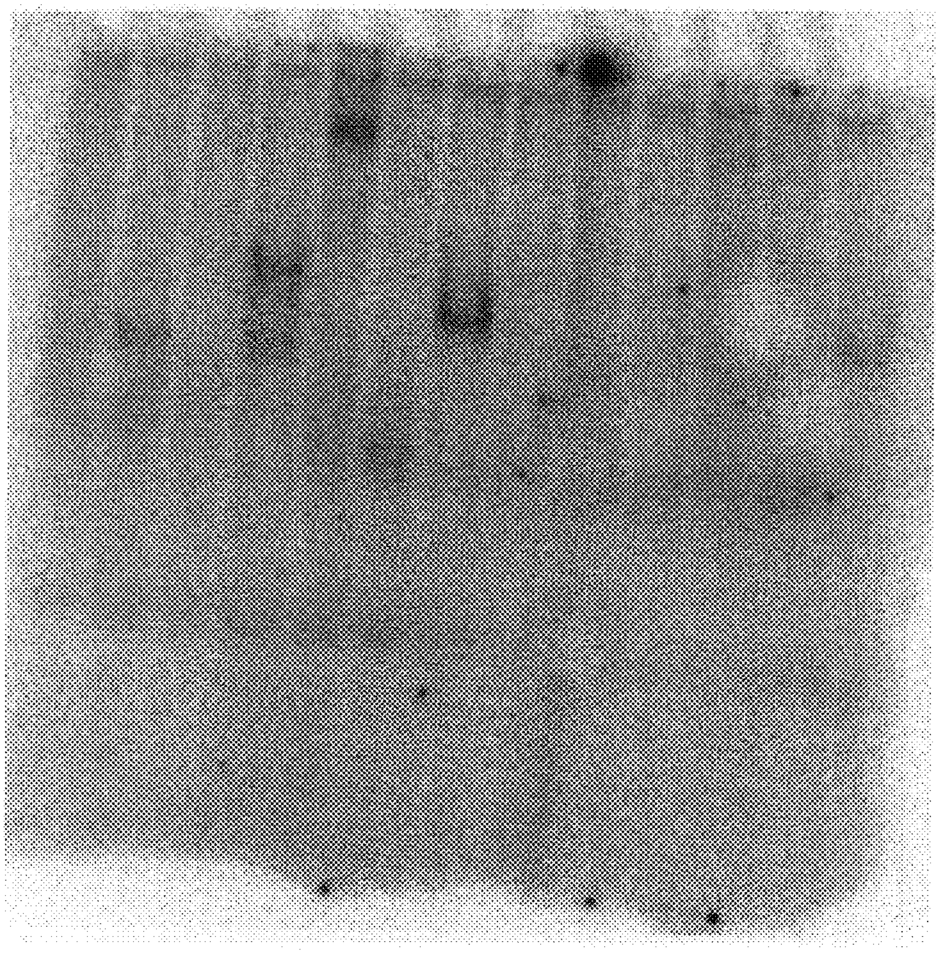

SOCS1 Inhibits a Range of IL-6 Signal Transduction Processes, Including STAT3 Phosphorylation and Activation Phosphorylation of the cell surface receptor component gp130, the cytoplasmic tyrosine kinase JAK1 and the transcription factor STAT3 is thought to play a central role in IL-6 signal transduction. These events were compared in the parental M1 and M1.mpl cell lines and their SOCS1-expressing counterparts. As expected, gp130 was phosphorylated rapidly in response to IL-6 in both parental lines, however, this was reduced five- to ten-fold in the cell lines expressing SOCS1 (FIG. 6). Likewise, STAT3 phosphorylation was also reduced by approximately ten-fold in response to IL-6 in those cell lines expressing SOCS1 (FIG. 6). Consistent with a reduction in STAT3 phosphorylation, activation of specific STAT DNA binding complexes, as determined by electrophoretic mobility shift assay, was also reduced. Notably, there was a reduction in the formation of SIF-A (containing STAT3), SIF-B (STAT1/STAT3 heterodimer) and SIF-C (containing STAT1), the three STAT complexes induced in M1 cells stimulated with IL-6 (FIG. 7A-B). Similarly, constitutive expression of SOCS1 also inhibited IFN-γ-stimulated formation of p91 homodimers (FIG. 7A-B). STAT phosphorylation and activation were not the only cytoplasmic processes to be effected by SOCS1 expression, as the phosphorylation of other proteins, including shc and MAP kinase, was reduced to a similar extent (FIG. 7A-B).

EXAMPLE 15

Transcription of the SOCS1 Gene is Stimulated by IL-6 In Vitro and In Vivo

Figure 8:
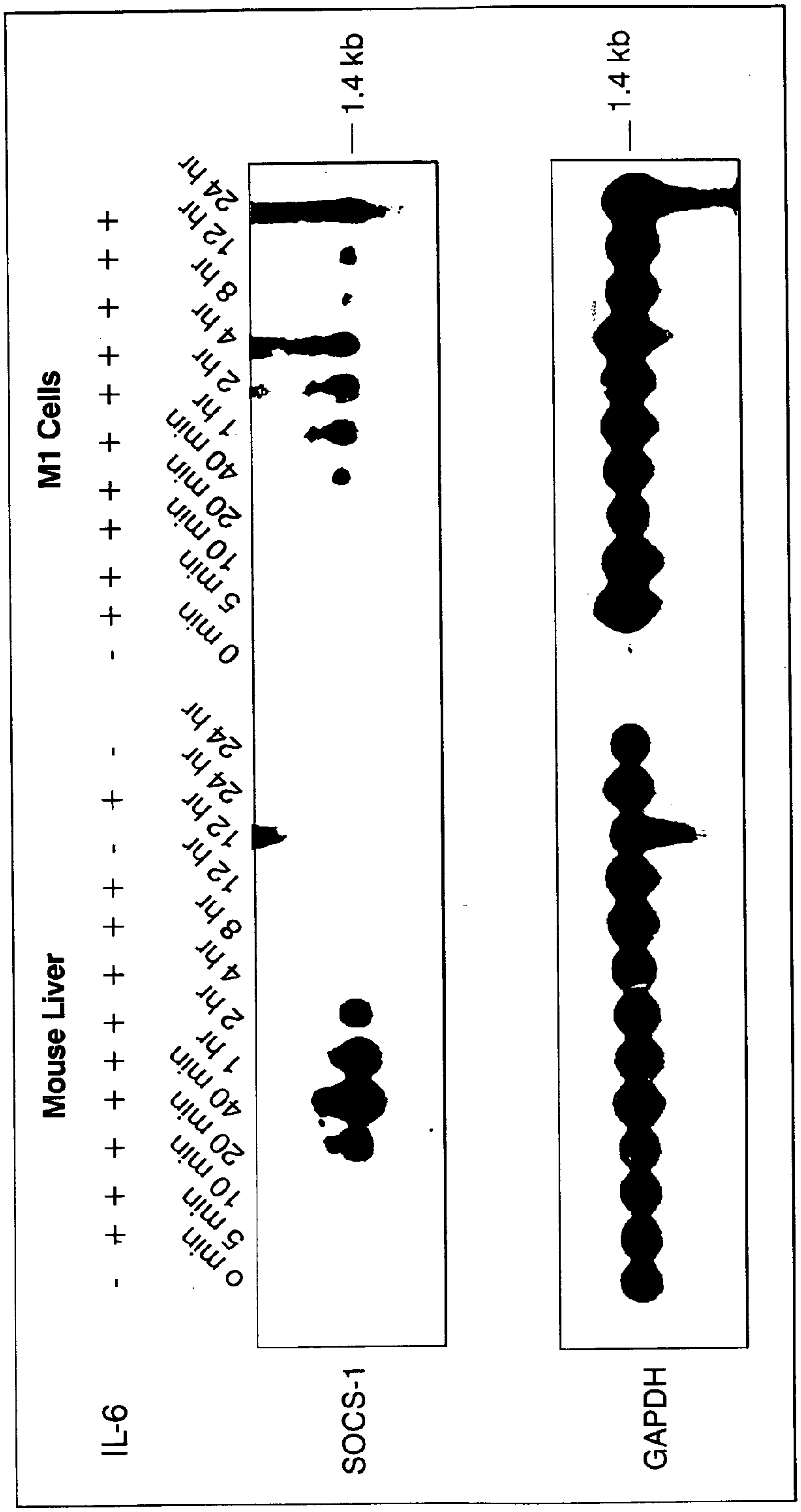
FIG. 8 is a photographic representation of Northern hybridisation. Mice were injected intravenously with 2 μg and after various periods of time, the livers were removed and polyA+ mRNA was purified. M1 cells were stimulated for various lengths of time with 500 ng/ml of IL-6, after which polyA+ mRNA was isolated. mRNA was fractionated by electrophoresis and immobilized on nylon filters. Northern blots were prehybridized, hybridized with random-primed $^{32}$P-labelled SOCS1 or GAPDH DNA fragments, washed and exposed to film overnight.

Although SOCS1 can inhibit cytokine signal transduction when constitutively expressed in M1 cells, this does not necessarily indicate that SOCS1 normally functions to negatively regulate an IL-6 response. In order to investigate this possibility the inventors determined whether transcription of the SOCS1 gene is regulated in the response of M1 cells to IL-6 and, because of the critical role IL-6 plays in regulating the acute phase response to injury and infection, the response of the liver to intravenous injection of 5 mg IL-6. In the absence of IL-6, SOCS1 mRNA was undetectable in either M1 cells or in the liver. However, for both cell types, a 1.4 kb SOCS1 transcript was induced within 20 to 40 minutes by IL-6 (FIG. 8). For M1 cells, where the IL-6 was present throughout the experiment, the level of SOCS1 mRNA remained elevated (FIG. 8). In contrast, IL-6 was administered in vivo by a single intravenous injection and was rapidly cleared from the circulation, resulting in a pulse of IL-6 stimulation to the liver. Consistent with this, transient expression of SOCS1 mRNA was detectable in the liver, peaking approximately 40 minutes after injection and declining to basal levels within 4 hours (FIG. 8).

EXAMPLE 16

Regulation of SOCS Genes

Figure 11A:
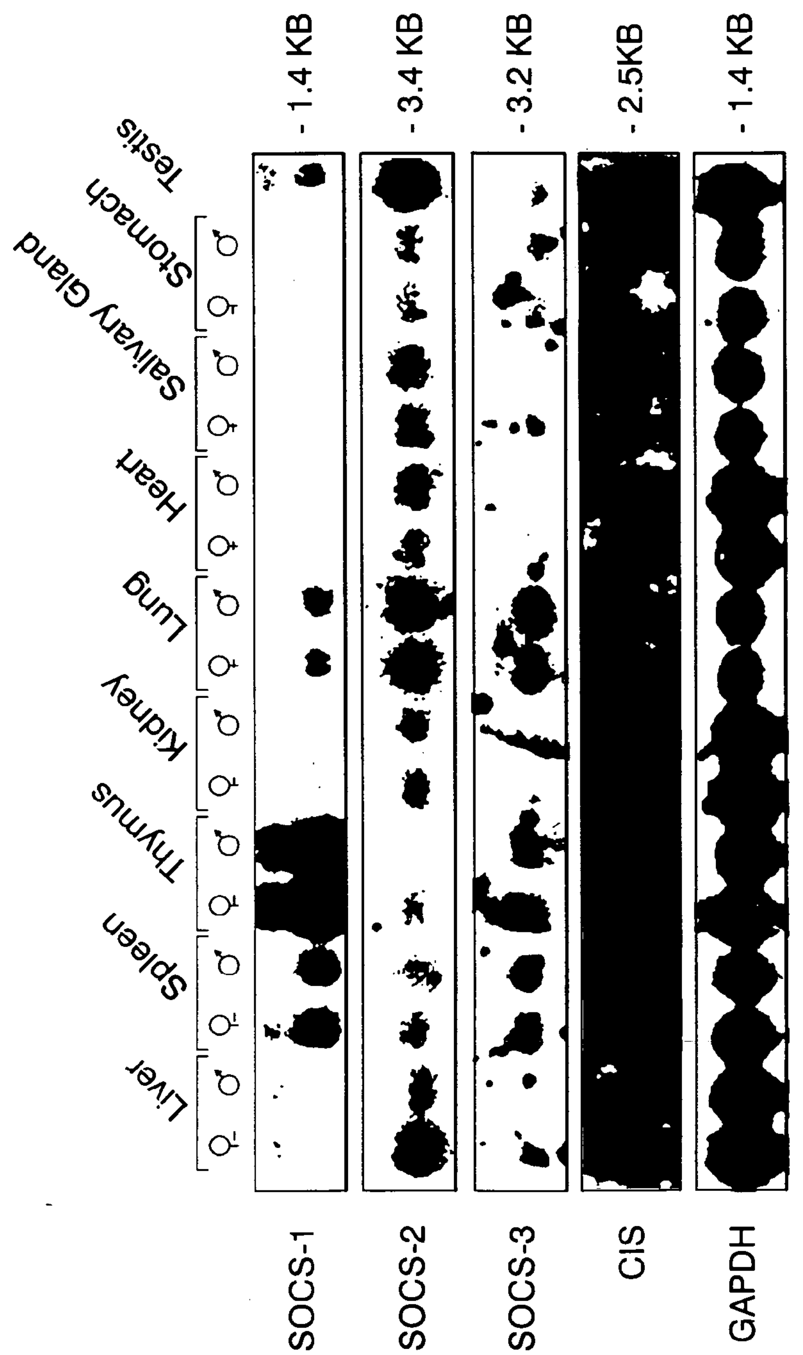
FIG. 11A-11C is a photographic representation showing expression of mRNA for SOCS family members in vitro and in vivo.

Since CIS was cloned as a cytokine-inducible immediate early gene the inventors examined whether SOCS1, SOCS2 and SOCS3 were similarly regulated. The basal pattern of expression of the four SOCS genes was examined by Northern blot analysis of mRNA from a variety of tissues from male and female C57B1/6 mice (FIG. 11A). Constitutive expression of SOCS1 was observed in the thymus and to a lesser extend in the spleen and the lung. SOCS2 expression was restricted primarily to the testis and in some animals the liver and lung; for SOCS3 a low level of expression was observed in the lung, spleen and thymus, while CIS expression was more widespread, including the testis, heart, lung, kidney and, in some animals, the liver.

Figure 11B:
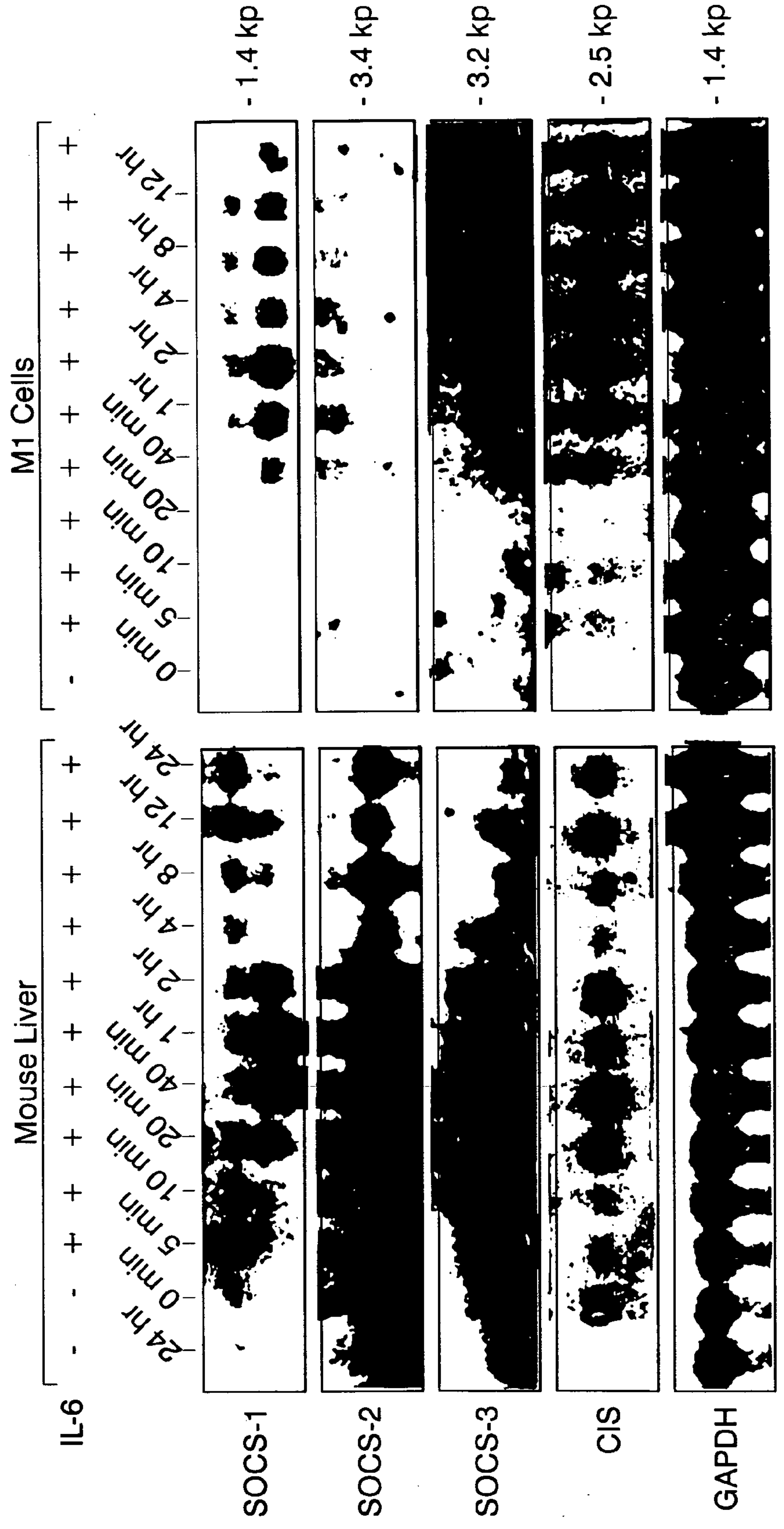

The inventors sought to determine whether expression of the four SOCS genes was regulated by IL-6. Northern blots of mRNA prepared from the livers of untreated and IL-6-injected mice, or from unstimulated and IL-6-stimulated M1 cells, were hybridised with labelled fragments of SOCS1, SOCS2, SOCS3 and CIS cDNAs (FIG. 11B). Expression of all four SOCS genes was increased in the liver following IL-6 injection, however the kinetics of induction appeared to differ. Expression of SOCS1 and SOCS3 was transient in the liver, with mRNA detectable after 20 minutes of IL-6 injection and declining to basal levels within 4 hours for SOCS and 8 hours for SOCS3. Induction of SOCS2 and CIS mRNA in the liver followed similar initial kinetics to that of SOCS1, but was maintained at an elevated level for at least 24 hours. A similar induction of SOCS gene mRNA was observed in other organs, notably the lung and the spleen. In contrast, in M1 cells, while SOCS1 and CIS mRNA were induced by IL-6, no induction of either SOCS2 or SOCS3 expression was detected. This result highlights cell type-specific differences in the expression of the genes of SOCS family members in response to the same cytokine.

Figure 11C:
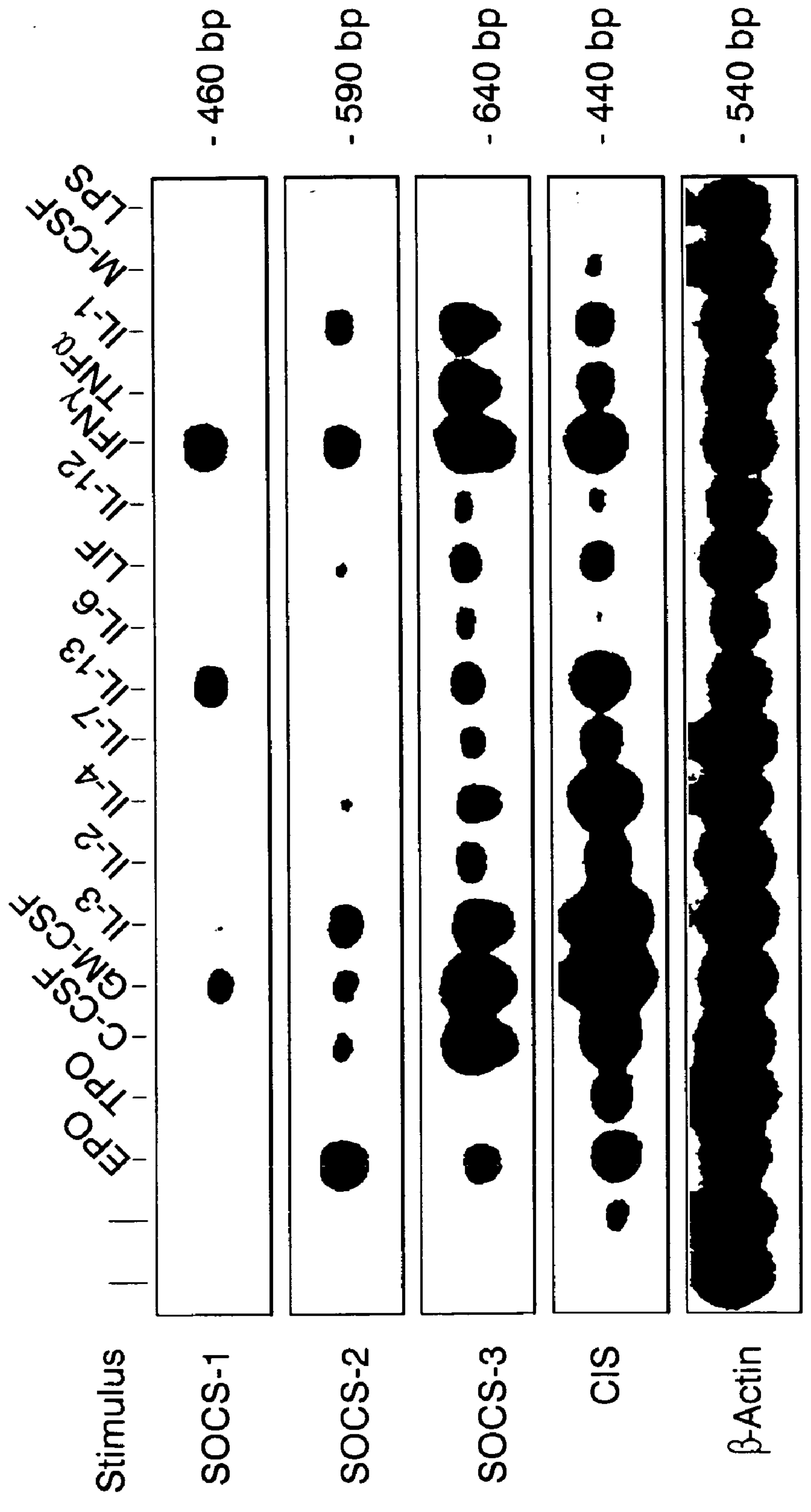

In order to examine the spectrum of cytokines that was capable of inducing transcription of the various members of the SOCS gene family, bone marrow cells were stimulated for an hour with a range of cytokines, after which mRNA was extracted and cDNA was synthesised. PCR was then used to assess the expression of SOCS1, SOCS2, SOCS3 and CIS (FIG. 11C). In the absence of stimulation, little or no expression of any of the SOCS genes was detectable in bone marrow by PCR. Stimulation of bone marrow cells with a broad array of cytokines appeared capable of up regulating mRNA for one or more members of the SOCS family. INFγ, for example, induced expression of all four SOCS genes, while erythropoietin, granulocyte colony-stimulating factor, granulocyte-macrophage colony stimulating factor and interleukin-3 induced expression of SOCS2, SOCS3 and CIS. Interestingly, tumor necrosis factor alpha, macrophage colony-stimulating factor and interleukin-1, which act through receptors that do not fall into the type I cytokine receptor class also appeared capable of inducing expression of SOCS3 and CIS, suggesting that SOCS proteins may play a broader role in regulating signal transduction.

As constitutive expression of SOCS1 inhibited the response of M1 cells to a range of cytokines, the inventors examined whether phosphorylation of the cell surface receptor component gp130 and the transcription factor STAT3, which are though to play a central role in IL-6 signal transduction, were affected. These events were compared in the parental M1 and M1.mpl cell lines and their SOCS1-expressing counterparts. As expected, gp130 was phyosphorylated rapidly in response to IL-6 in both parental lines, however, this was reduced in the cell lines expressing SOCS1 (FIG. 12A). Likewise, STAT3 phosphorylation was also reduced in response to IL-6 in those cell lines expressing SOCS1 (FIG. 12A). Consistent with a reduction in STAT3 phosphorylation, activation of specific STAT/DNA binding complexes, as determined by electrophoretic mobility shift assay, was also reduced. Notably, there was a failure to form SIF-A (containing STAT3) and SIF-B(STAT1/STAT3 heterodimer), the major STAT complexes induced in M1 cells stimulated with IL-6 (FIG. 12B). Similarly, constitutive expression of SOCS1 also inhibited INFγ-stimulating formation of SIF-C (STAT1 homodimer; FIG. 12B). These experiments are consistent with the proposal that SOCS1 inhibits signal transduction upstream of receptor and STAT phosphorylation, potentially at the level of the JAK kinases.

The ability of SOCS1 to inhibit signal transduction and ultimately the biological response to cytokines suggest that, like the SH2-containing phosphatase SHP-1 [Ihle et al, 1994; Yi et al, 1993], the SOCS proteins may play a central role in controlling the intensity and/or duration of a cell's response to a diverse range of extracellular stimuli by suppressing the signal transduction process. The evidence provided here indicates that the SOCS family acts in a classical negative feedback loop for cytokine signal transduction. Like other genes such as OSM, expression of genes encoding the SOCS proteins is induced by cytokines through the activation of STATs. Once expressed, it is proposed that the SOCS proteins inhibit the activity of JAKs and so reduce the phosphorylation of receptors and STATs, thereby suppressing signal transduction and any ensuing biological response. Importantly, inhibition of STAT activation will, over time, lead to a reduction in SOCS gene expression, allowing cells to regain responsiveness to cytokines.

EXAMPLE 17

Database Searches

The NCBI genetic sequence database (Genbank), which encompasses the major database of expressed sequence tags (ESTs) and TIGR database of human expressed sequence tags, were searched for sequences with similarity to a concensus SOCS box sequence using the TFASTA and MOTIF/PATTERN algorithms [Pearson, 1990; Cockwell and Giles, 1989]. Using the software package SRS [Etzold et al, 1996], ESTs that exhibited similarity to the SOCS box (and their partners derived from sequencing the other end of cDNAs) were retrieved and assembled into contigs using Autoassembler (Applied Biosystems, Foster City, Calif.). Consensus nucleotide sequences derived from overlapping ESTs were then used to search the various databases using BLASTN [Altschul et al, 1990]. Again, positive ESTs were retrieved and added to the contig. This process was repeated until no additional ESTs could be recovered. Final consensus nucleotide sequences were then translated using Sequence Navigator (Applied Biosystems, Foster City, Calif.).

EXAMPLE 18 cDNA Cloning

Based on the concensus sequences derived from overlapping ESTs, oligonucleotides were designed that were specific to various members of the SOCS family. As described above, oligonucleotides were labelled and used to screen commerically available genomic and cDNA libraries cloned with λ bacteriophage. Genomic and/or cDNA clones covering the entire coding region of mouse SOCS4, mouse SOCS5 and mouse SOCS6 were isolated. The entire gene for SOCS15 is on the human 12p13 BAC (Genbank Accession Number HSU47924) and the mouse chromosome 6 BAC (Genbank Accession Number AC002393). Partial cDNAs for mouse SOCS7, SOCS9, SOCS10, SOCS11, SOCS12, SOCS13 and SOCS14 were also isolated.

EXAMPLE 19

Northern Blots and rtPCR

Northern blots were performed as described above. The sources of hybridisation probes were as follows; (i) the entire coding region of the mouse SOCS1 cDNA, (ii) a 1059 bp PCR product derived from coding region of SOCS5 upstream of the SH2 domain, (iii) the entire coding region of the mouse SOCS6 cDNA, (iv) a 790 bp PCR product derived from the coding region of a partial SOCS7 cDNA and (v) a 1200 bp PstI fragment of the chicken glyceraldehyde 3-phosphate dehydrogenase (GAPDH) cDNA.

EXAMPLE 20

Additional Members of SOCS Family

SOCS1, SOCS2 and SOCS3 are members of the SOCS protein family identified in Examples 1-16. Each contains a central SH2 domain and a conserved motif at the C-terminus, named the SOCS box. In order to isolate further members of this protein family, various DNA databases were searched with the amino acid sequence corresponding to conserved residues of the SOCS box. This search revealed the presence of human and mouse ESTs encoding twelve further members of the SOCS protein family (FIG. 13A(i)-13F(iii)). Using this sequence information cDNAs encoding SOCS4, SOCS5, SOCS6, SOCS7, SOCS9, SOCS10, SOCS11, SOCS12, SOCS13, SOCS14 and SOCS15 have been isolated. Further analysis of contigs derived from ESTs and cDNAs revealed that the SOCS proteins could be placed into three groups according to their predicted structure N-terminal of the SOCS box. The three groups are those with (i) SH2 domains, (ii) WD-40 repeats and (iii) ankyrin repeats.

EXAMPLE 21

SOCS Protein with SH2 Domains

Eight SOCS proteins with SH2 domains have been identified. These include SOCS1, SOCS2 and SOCS3, SOCS5, SOCS9, SOCS11 and SOCS14 (FIG. 13A(i)-13F(ii)). Full length cDNAs were isolated for mouse SOCS5 and SOCS14 and partial clones encoding mouse SOCS9 and SOCS14. Analysis of primary amino acid sequence and genomic structure suggest that pairs of these proteins (SOCS1 and SOCS3, SOCS2 and CIS, SOCS5 and SOCS14 and SOCS9 and SOCS11) are most closely related (FIG. 13A(i)-13F(ii)). Indeed, the SH2 domains of SOCS5 and SOCS14 are almost identical (FIG. 13B(i)-(ii)), and unlike CIS, SOCS1, SOCS2 and SOCS3, SOCS5 and SOCS14 have an extensive, though less well conserved, N-terminal region preceding their SH2 domains (FIG. 13A(i)-(ii)).

EXAMPLE 22

SOCS Proteins with WD40 Repeats

Four SOCS proteins with WD-40 repeats were identified. As with the SOCS proteins with SH2 domains, pairs of these proteins appeared to be closely related. Full length cDNAs of mouse SOCS4 and SOCS6 were isolated and shown to encode proteins containing eight WD-40 repeats N-terminal of the SOCS box (FIG. 13A(i)-13F(ii)) and SOCS4 and SOCS6 share 65% amino acid similarity. SOCS15 was recognised as an open reading frame upon sequencing BACs from human chromosome 12p13 and the syntenic region of mouse chromosome 6 [Ansari-Lari et al, 1997]. In the human, chimp and mouse, SOCS15 is encoded by a gene with two coding exons that lies within a few hundred base pairs of the 3' end of the triose phosphate isomerase (TPI) gene, but which is encoded on the opposite strand to TPI (9). In addition to a C-terminal SOCS box, the SOCS15 protein contains four WD-40 repeats. Interestingly, within the EST databases, there is a sequence of a nematode, an insect and a fish relative of SOCS15. SOCS15 appears most closely related to SOCS13.

EXAMPLE 23

SOCS Proteins with Ankyrin Repeats

Three SOCS proteins with ankyrin repeats were identified. Analysis of partial cDNAs of mouse SOCS7, SOCS10 and SOCS12 demonstrated the presence of multiple ankyrin repeats.

EXAMPLE 24

Expression Pattern of SOCS Proteins

The expression of mRNA from representative members of each class of SOCS proteins—SOCS1 and SOCS5 from the SH2 domain group, SOCS6 from the WD-40 repeat group and SOCS7 from the ankyrin repeat group was examined. As shown above, SOCS1 mRNA is found in abundance in the thymus and at lower levels in other adult tissues.

Since transcription of the SOCS1 gene is induced by cytokines, the inventors sought to determine whether levels of SOCS5, SOCS6 and SOCS7 mRNA increased upon cytokine stimulation. In the livers of mice injected with IL-6, SOCS1 mRNA is detectable after 20 min and decreases to background levels within 2 hours. In contrast, the kinetics of SOCS5 mRNA expression are quite different, being only detectable 12 to 24 hours after IL-6 injection. SOCS6 mRNA appears to be expressed constitutively while SOCS7 mRNA was not detected in the liver either before injection of IL-6 or at any time after injection.

Expression of these genes was also examined after cytokine stimulation of the factor-dependent cell line FDCP-1 engineered to express bcl-w. Again, while SOCS6 mRNA was expressed constitutively.

EXAMPLE 25

SOCS4

Mouse and human SOCS4 were recognized through searching EST databases using the SOCS box consensus (FIG. 13). Those ESTs derived from mouse and human SOCS4 cDNAs are tabulated below (Tables 4.1 and 4.2). Using sequence information derived from mouse ESTs several oligonucleotides were designed and used to screen, in the conventional manner, a mouse thymus cDNA library cloned into λ-bacteriophage. Two cDNAs encoding mouse SOCS4 were isolated and sequenced in their entirety (FIG. 15) and shown to overlap the mouse ESTs identified in the database (Table 4.1 and FIG. 17). These cDNAs include a region of 5' untranslated region, the entire mouse SOCS4 coding region and a region of 3' untranslated region (FIG. 17). Analysis of the sequence confirms that the SOCS4 cDNA encodes a SOCS Box at its C-terminus and a series of 8 WD-40 repeats before the SOCS Box (FIGS. 17 and 16). The relationship of the two sequence contigs of human SOCS4 (h4.1 and h4.2) to the experimentally determined mouse SOCS4 cDNA sequence is shown in FIG. 17. The nucleotide sequence of the two human contigs is listed in FIG. 18. SEQ ID NO:13 and 14 represent the nucleotide sequence of murine SOCS4 and the corresponding amino acid sequence. SEQ ID NOs: 15 and 16 are SOCS4 cDNA human contigs h4.1 and h4.2, respectively.

EXAMPLE 26

SOCS5

Mouse and human SOCS5 were recognized through searching EST databases using the SOCS box consensus (FIG. 13A(i)-13F(ii)). Those ESTs derived from mouse and human SOCS5 cDNAs are tabulated below (Tables 5.1 and 5.2). Using sequence information derived from mouse and human ESTs, several oligonucleotides were designed and used to screen, in the conventional manner, a mouse thymus cDNA library, a mouse genomic DNA library and a human thymus cDNA library cloned into k-bacteriophage. A single genomic DNA clone (57-2) and (5-3-2) cDNA clone encoding mouse SOCS5 were isolated and sequenced in their entirety and shown to overlap with the mouse ESTs identified in the database (FIGS. 19 and 20A). The entire coding region, in addition to a region of 5' and 3' untranslated regions of mouse SOCS5 appears to be encoded on a single exon (FIG. 19). Analysis of the sequence (FIG. 20) confirms that SOCS5 genomic and cDNA clones encode a protein with a SOCS box at its C-terminus in addition to an SH2 domain (FIG. 19 and 20B). The relationship of the human SOCS5 contig (h5.1; FIG. 21) derived from analysis of cDNA clone 5-94-2 and the human SOCS5 ESTs (Table 5.2) to the mouse SOCS5 DNA sequence is shown in FIG. 19. The nucleotide sequence and corresponding amino acid sequence of murine SOCS5 are shown in SEQ ID NOs: 17 and 18, respectively. The human SOCS5 nucleotide sequence is shown in SEQ ID NO:19.

EXAMPLE 27

SOCS6

Mouse and human SOCS6 were recognized through searching EST databases using the SOCS box consensus (FIG. 13A(i)-13F(ii)). Those ESTs derived from mouse and human SOCS6 cDNAs are tabulated below (Tables 6.1 and 6.2). Using sequence information derived from mouse ESTs, several oligonucleotides were designed and use to screen, in the conventional manner, a mouse thymus cDNA library. Eight cDNA clones (6-1A, 6-2A, 6-5B, 6-4N, 6-18, 6-29, 6-3N, 6-5N) cDNA clone encoding mouse SOCS6 were isolated and sequenced in their entirety and shown to overlap with the mouse ESTs identified in the database (FIGS. 22 and 23A). Analysis of the sequence (FIG. 23) confirms that the mouse SOCS6 cDNA clones encode a protein with a SOCS box at its C-terminus in addition to a eight WD-40 repeats (FIGS. 22 and 23B). The relationship of the human SOCS-6 contigs (h6.1 and h6.2; FIG. 24) derived from analysis of human SOCS6 ESTs (Table 6.2) to the mouse SOCS6 DNA sequence is shown in FIG. 22. The nucleotide and corresponding amino acid sequences of murine SOCS6 are shown in SEQ ID NOs: 20 and 21, respectively. SOCS6 human contigs h6.1 and h6.2 are shown in SEQ ID NOs: 22 and 23, respectively.

EXAMPLE 28

SOCS7

Mouse and human SOCS7 were recognized through searching EST databases using the SOCS box consensus (FIG. 13A(i)-13F(ii)). Those ESTs derived from mouse and human SOCS-7 cDNAs are tabulated below (Tables 7.1 and 7.2). Using sequence information derived from mouse ESTs, several oligonucleotides were designed and use to screen, in the conventional manner, a mouse thymus cDNA library. One cDNA clone (74-10A-11) cDNA clone encoding mouse SOCS7 was isolated and sequenced in its entirety and shown to overlap with the mouse ESTs identified in the database (FIGS. 25 and 26A). Analysis of the sequence (FIG. 26) suggests that mouse SOCS7 encodes a protein with a SOCS box at its C-terminus, in addition to several ankyrin repeats (FIGS. 25 and 26B). The relationship of the human SOCS7 contigs (h7.1 and h7.2; FIG. 27) derived from analysis of human SOCS7 ESTs (Table 7.2) to the mouse SOCS7 DNA sequence is shown in FIG. 25. The nucleotide and corresponding amino acid sequences of murine SOCS7 are shown in SEQ ID NOs: 24 and 25, respectively. The nucleotide sequence of SOCS7 human contigs h7.1 and h7.2 are shown in SEQ ID NOs: 26 and 27, respectively.

EXAMPLE 29

SOCS8

ESTs derived from mouse SOCS8 cDNAs are tabulated below (Table 8.1). As described for other members of the SOCS family, it is possible to isolate cDNAs for mouse SOCS8 using sequence information derived from mouse ESTs. The relationship of the ESTs to the predicted coding region of SOCS8 is shown in FIG. 28. With the nucleotide sequence obtained from the ESTs shown in FIG. 29A and the partial amino acid sequence of SOCS8 shown in FIG. 29B. The nucleotide sequence and corresponding amino acid sequences for murine SOCS8 are shown in SEQ ID NOs:28 and 29, respectively.

EXAMPLE 30

SOCS9

Mouse and human SOCS-9 were recognized through searching EST databases using the SOCS box consensus (FIG. 13). Those ESTs derived from mouse and human SOCS9 cDNAs are tabulated below (Tables 9.1 and 9.2). The relationship of the mouse SOCS9 contigs (m9.1; FIG. 9.2) derived from analysis of the mouse SOCS9 EST (Table 9.1) to the human SOCS-9 DNA contig (h9.1; FIG. 32) derived from analysis of human SOCS9 ESTs (Table 9.2) is shown in FIG. 31. Analysis of the sequence (FIG. 32) indicates that the human SOCS9 cDNA encodes a protein with a SOCS box at its C-terminus, in addition to an SH2 domain (FIG. 30). The nucleotide sequence of muring SOCS9 cDNA is shown in SEQ ID NO:30. The nucleotide sequence of human SOCS9 cDNA is shown in SEQ ID NO:31.

EXAMPLE 31

SOCS10

Mouse and human SOCS10 were recognized through searching EST databases using the SOCS box consensus (FIG. 13A(i)-13F(ii)). Those ESTs derived from mouse and human SOCS10 cDNAs are tabulated below (Table 10.1 and 10.2). Using sequence information derived from mouse ESTs, several oligonucleotides were designed and use to screen, in the conventional manner, a mouse thymus cDNA library. Four cDNA clones (10-9, 10-12, 10-23 and 10-24) encoding mouse SOCS10 were isolated, sequenced in their entirety and shown to overlap with the mouse and human ESTs identified in the database (FIGS. 33 and 34). Analysis of the sequence (FIG. 34) indicates that the mouse SOCS10 cDNA clone is not full length but that it does encode a protein with a SOCS box at its C-terminus, in addition to several ankyrin repeats (FIG. 33). The relationship of the human SOCS10 contigs (h10.1 and h10.2; FIG. 35) derived from analysis of human SOCS10ESTs (Table 10.2) to the mouse SOCS10 DNA sequence is shown in FIG. 33. Comparison of mouse cDNA clones and ESTs with human ESTs suggests that the 3' untranslated regions of mouse and human SOCS10 differ significantly. The nucleotide sequence of murine SOCS10 is shown in SEQ ID NO:32 and the nucleotide sequence of SOCS10 human contigs h10.1 and h10.2 are shown in SEQ ID NOs:33 and 34, respectively.

EXAMPLE 32

SOCS11

Human SOCS11 were recognized through searching EST databases using the SOCS box consensus (FIG. 13A(i)-13F(ii)). Those ESTs derived from human SOCS11 cDNAs are tabulated below (Table 11.1 and 11.2). The relationship of the human SOCS11 contigs (h11.1; FIG. 36A, B), derived from analysis ESTs (Table 11.2) to the predicted encoded protein, is shown in FIG. 37. Analysis of the sequence indicates that the human SOCS11 cDNA encodes a protein with a SOCS box at its C-terminus, in addition to an SH2 domain (FIGS. 37 and 36B). The nucleotide sequence and corresponding amino acid sequence of human SOCS11 are represented in SEQ ID NOs:35 and 36, respectively.

EXAMPLE 33

SOCS12

Mouse and human SOCS-12 were recognized through searching EST databases using the SOCS box consensus (FIG. 13A(i)-13F(ii)). Those ESTs derived from mouse and human SOCS12 cDNAs are tabulated below (Tables 12.1 and 12.2). Using sequence information derived from mouse ESTs, several oligonucleotides were designed and use to screen, in the conventional manner, a mouse thymus cDNA library. Four cDNA clones (10-9, 10-12, 10-23 and 10-24) encoding mouse SOCS12 were isolated, sequenced in their entirety and shown to overlap with the mouse and human ESTs identified in the database (FIGS. 38 and 39). Analysis of the sequence (FIGS. 39 and 40) indicates that the SOCS12 cDNA clone encodes a protein with a SOCS box at its C-terminus, in addition to several ankyrin repeats (FIG. 38). The relationship of the human SOCS12 contigs (h12.1 and h12.2; FIG. 40) derived from analysis of human SOCS12 ESTs (Table 12.2) to the mouse SOCS12 DNA sequence is shown in FIG. 38. Comparison of mouse cDNA clones and ESTs with human ESTs suggests that the 3' untranslated regions of mouse and human SOCS12 differ significantly. The nucleotide sequence of SOCS12 is shown in SEQ ID NO:37. The nucleotide sequence of human SOCS12 contigs h12.1 and h12.2 are shown in SEQ ID NOs:38 and 39, respectively.

EXAMPLE 34

SOCS13

Mouse and human SOCS-13 were recognized through searching EST databases using the SOCS box consensus (FIG. 13A(i)-13F(ii)). Those ESTs derived from mouse and human SOCS13 cDNAs are tabulated below (Tables 13.1 and 13.2). Using sequence information derived from mouse ESTs, several oligonucleotides were designed and use to screen, in the conventional manner, a mouse thymus and a mouse embryo cDNA library. Three cDNA clones (62-1, 62-6-7 and 62-14) encoding mouse SOCS13 were isolated, sequenced in their entirety and shown to overlap with the mouse ESTs identified in the database (FIGS. 41 and 42A). Analysis of the sequence (FIG. 42A-B) indicates that the mouse SOCS13 cDNA encodes a protein with a SOCS box at its C-terminus, in addition to a potential WD-40 repeat (FIGS. 41 and 42B). The relationship of the human SOCS13 contigs (h13.1 and h13.2; FIG. 43) derived from analysis of human SOCS13 ESTs (Table 13.2) to the mouse SOCS13 DNA sequence is shown in FIG. 41. The nucleotide sequence and corresponding amino acid sequence of murine SOCS13 and shown in SEQ ID NOs:40 and 41, respectively. The nucleotide sequence of human SOCS13 contig h13.1 is shown in SEQ ID NO:42.

EXAMPLE 35

SOCS14

Figure 14B:
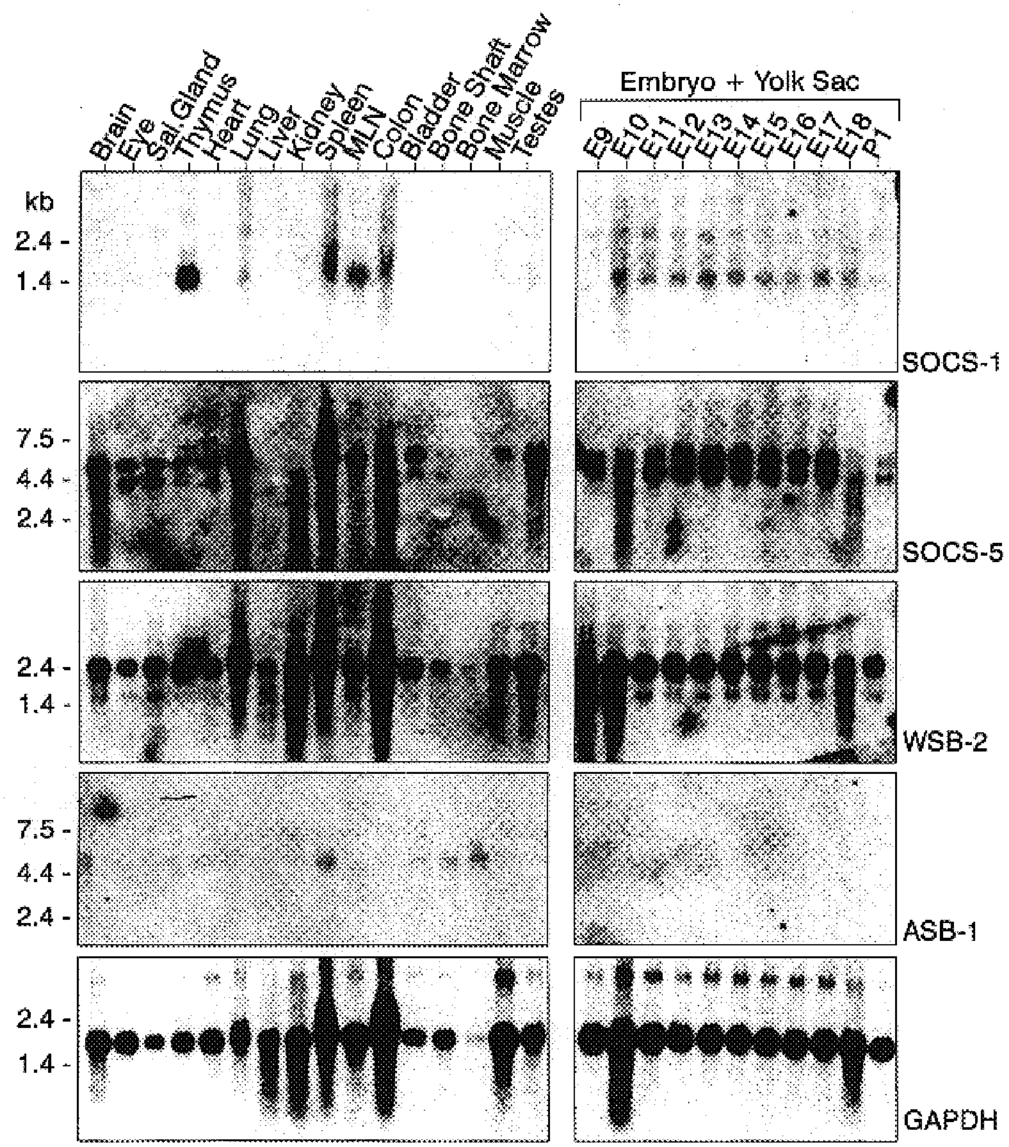

Mouse and human SOCS-14 were recognized through searching EST databases using the SOCS box consensus (FIG. 13A(i)-13F(ii)). Those ESTs derived from mouse and human SOCS14 cDNAs are tabulated below (Tables 14.1 and 14.2). Using sequence information derived from mouse and human ESTs, several oligonucleotides were designed and use to screen, in the conventional manner, a mouse thymus cDNA library, a mouse genomic DNA library and a human thymus cDNA library cloned into λ-bacteriophage. A single genomic DNA clone (57-2) and (5-3-2) cDNA clone encoding mouse SOCS14 were isolated and sequenced in their entirety and shown to overlap with the mouse ESTs identified in the database (FIGS. 44 and 45A). The entire coding region, in addition to a region of 5' and 3' untranslated regions, of mouse SOCS14 appears to be encoded on a single exon (FIG. 44). Analysis of the sequence (FIG. 45A-B) confirms that SOCS14 genomic and cDNA clones encode a protein with a SOCS box at its C-terminus in addition to an SH2 domain (FIGS. 44 and 45B). The relationship of the human SOCS14 contig (h14.1; FIG. 14.3) derived from analysis of cDNA clone 5-94-2 and the human SOCS14 ESTs (Table 14.2) to the mouse SOCS14 DNA sequence is shown in FIG. 44.

The nucleotide sequence and corresponding amino acid sequence of murine SOCS14 are shown in SEQ ID NOs: 43 and 44, respectively.

EXAMPLE 36

SOCS15

Mouse and human SOCS15 were recognized through searching DNA databases using the SOCS box consensus (FIG. 13A(i)-13F(ii)). Those ESTs derived from mouse and human SOCS15 cDNAs are tabulated below (Tables 15.1 and 15.2), as are a mouse and human BAC that contain the entire mouse and human SOCS-15 genes. Using sequence information derived from the ESTs and the BACs it is possible to predict the entire amino acid sequence of SOCS15 and as described for the other SOCS genes it is feasible to design specific oligonucleotide probes to allow cDNAs to be isolated. The relationship of the BACs to the ESTs is shown in FIG. 46 and the nucleotide and predicted amino acid sequence of the SOCS-15, derived from the mouse and human BACs is shown in FIGS. 47A(i)-47B and 48A(i)-48B. The nucleotide sequence and corresponding amino acid sequence of murine SOCS15 are shown in SEQ ID NOs:46 and 47, respectively. The nucleotide and corresponding amino acid sequence of human SOCS15 are shown in SEQ ID NO:48 and 49, respectively.

EXAMPLE 37

SOCS Interaction with JAK2 Kinase

These Examples show interaction between SOCS and JAK2 kinase. Interaction is mediated via the SH2 domain of SOCS1, 2, 3 and CIS. The interaction resulted in inhibition of JAK2 kinase activity by SOCS1 (FIG. 49). General interaction between JAK2 and SOCS1, 2, 3, and CIS is shown in FIG. 50.

The following methods are employed:

Immunoprecipitation: Cos 6 cells were transiently transfected by electroporation and cultured for 48 hours. Cells were then lysed on ice in lysis buffer (50 mM Tris/HCL, pH 7.5, 150 mM NaCl, 1% v/v Triton-X-100, 1 mM EDTA, 1 mM Naf, 1 mM $Na_3VO_4$) with the addition of complete protease inhibitors (Boehringer Mannheim), centrifuged at 4° C. (14,000×g, 10 min) and the supernatant retained for immunoprecipitation. JAK2 proteins were immunoprecipitated using 5 μl anti-JAK2 antibody (UBI). Antigen-antibody complexes were recovered using protein A-Sepharose (30 μl of a 50% slurry).

Western blotting: Immunoprecipitates were analysed by sodium dodecyl sulphate (SDS)—polyacrylamide gel electrophoresis (PAGE) under reducing conditions. Protein was then electrophoretically transferred to nitrocellulose, blocked overnight in 10% w/v skim-milk and washed in PBS/0.1% v/v Tween-20 (Sigma) (wash buffer) prior to incubation with either anti-phosphotyrosine antibody (4G10) (1:5000, UBI), anti-FLAG antibody (1.6 μ/ml) or anti-JAK2 antibody (1:2000, UBI) diluted in wash buffer/1% w/v BSA for 2 hr. Nitrocellulose blots were washed and primary antibody detected with either peroxidase-conjugated sheep anti-rabbit immunoglobulin (1:5000, Silenus) or peroxidase-conjugated sheep anti-mouse immunoglobulin (1:5000, Silenus) diluted in wash buffer/1% w/v BSA. Blots were washed and antibody binding visualised using the enhanced chemiluminescence (ECL) system (Amersham, UK) according to the manufacturers' instructions.

In-vitro kinase assay: An in vitro kinase assy was performed to assess intrinsic JAK2 kinase catalytic activity. JAK2 protein were immunopreciptated as described, washed twice in kinase assay buffer (50 mM NaCl, 5 mM $MgCl_2$, 5 mM MnCl2, 1 mM NaF, 1 mM $Na_3VO_4$, 10 mM HEPES, pH 7.4) and suspended in an equal volume of kinase buffer containing 0.25 μCi/ml (γ-$^{32}$P)-ATP (30 min, room temperature). Excess (γ-$^{32}$P)-ATP was removed and the immunoprecipitates analysed by SDS/PAGE under reducing conditions. Gels were subjected to a mild alkaline hydrolysis by treatment with 1 M KOH (55° C., 2 hours) to remove phosphoserine and phosphothreonine. Radioactive bands were visualised with IMAGEQUANT software on a PhosphorImage system (Molecular Dynamics, Sunnyvale, Calif., USA).

EXAMPLE 38

Making SOCS-1 Knockout Constructs

Diagrams of plasmid constructs and knockout constructs are shown in FIGS. 51-53. The genomic SOCS-1 clone 95-11-10 was digested with the restriction enzymes BamH1 and EcoR1 to obtain a 3.6 Kb DNA fragment 3' of the coding region (SOCS-1 exon), which was used as the 3' arm in the SOCS-1 knockout vectors. The ends of this fragment were then blunted. This fragment was then ligated into the following vectors:

pBgalpAloxNeo and pBgalpAloxNeoTK which had been linearized at the unique Xho 1 site and then blunted. This ligation resulted in the formation of the following vectors:

3'SOCS-1 arm in pBgalpAloxNeo and 3'SOCS-1 arm in pBgalpAloxNeoTK

The 5' arm of the SOCS-1 knockout vectors was constructed by using PCR to generate a 2.5 Kb PCR product from the genomic SOCS-1 clone 95-11-10 just 5' of the SOCS-1 coding region (SOCS-1 exon). The oligo's used to generate this product were:

```
5' oligo (sense) (2465)
                                    [SEQ ID NO:49]
AGCT AGA TCT GGA CCC TAG AAT GGC AGC

3' oligo (antisense) (2466)
                                    [SEQ ID NO:50]
AGCT AG ATC TGC CAT CCT ACT CGA GGG GCC AGC TGG
```

The PCR product was then digested with the restriction enzyme BglII, to generate BglII ends to the PCR product. This 5' SOCS-1 PCR product, with Bg1II, ends was then ligated as follows: 3'SOCS-1 arm in pBgalpAloxNeo and 3'SOCS-1 arm in pBgalpAloxNeoTK, which had been linearized with the unique restriction enzyme BamH1. This resulted in the following vectors being formed:

5'&3'SOCS-1 arms in pBgalpAloxNeo and 5'&3'SOCS-1 arms in pBgalpAloxNeoTK

These were the final SOCS-1 knockout constructs. Both these constructs lacked the entire SOCS-1 coding region (SOCS-1 EXON), being replaced with portions of the Bgal, B globin polyA, PGK promoter, neomycin and PGK polyA sequences. The 5'&3' SOCS-1 arms in pBgalpAloxNeoTK vector also contained the tymidine kinase gene sequence, between the neomycin and PGK poly A sequences.

The vectors: 5'&3'SOCS-1 arms in pBgalpAloxNeo and 5'&3'SOCS-1 arms in pBgalpAloxNeoTK were linearized with the unique restriction enzyme Not1 and then transfected into Embryonic stem cells by electroporation. Clones which were resistant to neomycin were selected and analysed by southern blot to determine if they contained the correctly integrated SOCS-1 targeting sequence. In order to determine if correct integration had occurred, genomic DNA from the neomycin resistant clones was digested with the restriction enzyme EcoR1. The digested DNA was then blotted onto nylon filters and probed with a 1.5 Kb EcoR1/Hind III DNA fragment, which was further 5' of the 5'arm sequence used in the knockout constructs. The band sizes expected for correct integration were:

Wild type SOCS-1 allele 5.4 Kb

SOCS-1 knockout allele 8.2 Kb in 5'&3'SOCS-1 arms in pBgalpAloxNeo or 11 Kb in 5'&3'SOCS-1 arms in pBgalpAloxNeoTK transfomed cells.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

TABLE 4.1

Summary of ESTs derived from mouse SOCS-4 cDNAs

| SOCS | Species | EST name | End | EST no | Library source | Contig |
|---|---|---|---|---|---|---|
| SOCS-4 | Mouse | mc65f04 | 5' | EST0549700 | d13.5–14.5 mouse embryo | m4.1 |
| | | mf42e06 | 5' | EST0593477 | d13.5–14.5 mouse embryo | m4.1 |
| | | mp10c10 | 5' | EST0747905 | d8.5 mouse embryo | m4.1 |
| | | mr81g09 | 5' | EST0783081 | d13 embryo | m4.1 |
| | | mt19h12 | 5' | EST0816531 | spleen | m4.1 |

TABLE 4.2

Summary of ESTs derived from human SOCS-4 cDNAs

| SOCS | Species | EST name | End | EST no | Library source | Contig |
|---|---|---|---|---|---|---|
| SOCS-4 | Human | 27b5 | 5' | EST0534081 | retina | h4.2 |
| | | 30d2 | 5' | EST0534315 | retina | h4.2 |
| | | J0159F | 5' | EST0461188 | foetal heart | h4.2 |
| | | J3802F | 5' | EST0461428 | foetal heart | h4.2 |
| | | EST19523 | 5' | EST0958884 | retina | h4.2 |
| | | EST81149 | 5' | EST1011015 | placenta | h4.2 |
| | | EST180909 | 5' | EST0951375 | Jurkat T-lymphocyte | h4.2 |
| | | EST182619 | 5' | EST0953220 | Jurkat T-lymphocyte | h4.1 |
| | | ya99h09 | 3' | EST0103262 | placenta | h4.2 |
| | | ye70c04 | 5' | EST0172673 | foeatl liver/spleen | h4.2 |
| | | yh53c09 | 5' | EST0197390 | placenta | h4.2 |
| | | | 3' | EST0197391 | | h4.2 |
| | | yh77g11 | 5' | EST0203418 | placenta | h4.2 |
| | | | 3' | EST0203419 | | h4.1 |
| | | yh87h05 | 5' | EST0204888 | placenta | h4.1 |
| | | | 3' | EST0204773 | | h4.1 |
| | | yi45h07 | 5' | EST0246604 | placenta | h4.2 |
| | | yj04e06 | 5' | EST0258541 | placenta | h4.1 |
| | | | 3' | EST0258285 | | h4.1 |
| | | yq12h06 | 5' | EST0309968 | foetal liver spleen | h4.2 |
| | | yq56a06 | 3' | EST0346924 | foetal liver spleen | h4.2 |
| | | yq60e02 | 5' | EST0347259 | foetal liver spleen | h4.2 |
| | | | 3' | EST0347209 | | h4.2 |
| | | yq92g03 | 5' | EST0355932 | foetal liver spleen | h4.2 |
| | | | 3' | EST0355884 | | h4.2 |
| | | yq97h06 | 5' | EST0357618 | foetal liver spleen | h4.2 |
| | | | 3' | EST0357416 | | h4.2 |
| | | yr90f01 | 5' | EST0372402 | foetal liver spleen | h4.2 |
| | | yt69c03 | 5' | EST0338395 | foetal liver spleen | h4.2 |
| | | | 3' | EST0338303 | | h4.2 |
| | | yv30a08 | 3' | EST0458506 | foetal liver spleen | h4.2 |
| | | yv55f07 | 5' | EST0465391 | foetal liver spleen | h4.2 |
| | | | 3' | EST0463331 | | h4.2 |
| | | yv57h09 | 5' | EST0464336 | foetal liver spleen | h4.2 |
| | | | 3' | EST0458765 | | h4.2 |
| | | yv87h02 | 5' | EST0388085 | melanocyte | h4.2 |
| | | yv98e11 | 5' | EST0400679 | melanocyte | h4.2 |
| | | | 3' | EST0400680 | | h4.2 |
| | | yw68d10 | 5' | EST0441370 | placenta (8–9 wk) | h4.2 |
| | | yw82a03 | 5' | EST0463005 | placenta (8–9 wk) | h4.2 |
| | | | 3' | EST0433678 | | h4.1 |
| | | yx08a07 | 3' | EST0407016 | melanoocyte | h4.1 |
| | | yx72h06 | 5' | EST0435158 | melanoocyte | h4.2 |
| | | | 3' | EST0422871 | melanoocyte | h4.1 |
| | | yx76b09 | 5' | EST0434011 | melanoocyte | h4.2 |
| | | yy37h08 | 5' | EST0451704 | melanoocyte | h4.2 |
| | | yy66b02 | 5' | EST0505446 | multiple sclerosis lesion | h4.2 |
| | | za81f08 | 5' | EST0511777 | foetal lung | h4.2 |
| | | zb18f07 | 3' | EST0485315 | foetal lung | h4.1 |
| | | zc06e08 | 5' | EST0540473 | parathyroid tumor | h4.1 |
| | | | 3' | EST0540354 | | h4.1 |
| | | zd14g06 | 3' | EST0564666 | foetal heart | h4.1 |
| | | zd51h12 | 3' | EST0578099 | foetal heart | h4.1 |
| | | zd52b09 | 5' | EST0582012 | foetal heart | h4.1 |
| | | | 3' | EST0581958 | | h4.1 |
| | | ze25g11 | 3' | EST0679543 | foetal heart | h4.1 |
| | | ze69f02 | 5' | EST0635563 | retina | h4.2 |
| | | | 3' | EST0635472 | | h4.1 |
| | | zf54f03 | 5' | EST0680111 | retina | h4.2 |
| | | zh96e07 | 5' | EST0616241 | foetal liver spleen | h4.2 |
| | | | 3' | EST0615745 | | h4.2 |
| | | zv66h12 | 5' | EST1043265 | 8–9w foetus | h4.2 |
| | | zs83a08 | 5' | EST0920072 | germinal centre B cell | h4.1 |
| | | | 3' | EST0920016 | | h4.1 |
| | | zs83g08 | 5' | EST0920121 | germinal centre B cell | h4.1 |
| | | | 3' | EST0920122 | | h4.1 |

TABLE 5.1

Summary of ESTs derived from mouse SOCS-5 cDNAs

| SOCS | Species | EST name | End | EST no | Library source | Contig |
|---|---|---|---|---|---|---|
| SOCS-5 | Mouse | mc55a01 | 5' | EST0541556 | d13.5–14.5 mouse embryo | m5.1 |
| | | mh98f09 | 5' | EST0638237 | placenta | m5.1 |
| | | my26h12 | 5' | EST0859939 | mixed organs | m5.1 |
| | | ve24e06 | 5' | EST0819106 | heart | m5.1 |

TABLE 5.2

Summary of ESTs derived from human SOCS-5 cDNAs

| SOCS | Species | EST name | End | EST no | Library source | Contig |
|---|---|---|---|---|---|---|
| SOCS-5 | Human | EST15B103 | ? | EST0258029 | adipose tissue | h5.1 |
| | | EST15B105 | ? | EST0258028 | adipose tissue | h5.1 |
| | | EST27530 | 5' | EST0965892 | cerebellum | h5.1 |
| | | zf50f01 | 5' | EST0679820 | retina | h5.1 |

TABLE 6.1

Summary of ESTs derived from mouse SOCS-6 cDNAs

| SOCS | Species | EST name | End | EST no | Library source | Contig |
|---|---|---|---|---|---|---|
| SOCS-6 | Mouse | mco4c05 | 5' | EST0525832 | d19.5 embryo | m6.1 |
| | | md48a03 | 5' | EST0566730 | d13.5–14.5 embryo | m6.1 |
| | | mf31d03 | 5' | EST0675970 | d13.5–14.5 embryo | m6.1 |
| | | mh26b07 | 5' | EST0628752 | d13.5–14.5 placenta | m6.1 |
| | | mh78e11 | 5' | EST0637608 | d13.5–14.5 placenta | m6.1 |
| | | mh88h09 | 5' | EST0644383 | d13.5–14.5 placenta | m6.1 |
| | | mh94h07 | 5' | EST0638078 | d13.5–14.5 placenta | m6.1 |
| | | mi27h04 | 5' | EST0644252 | d13.5–14.5 embryo | m6.1 |
| | | mj29c05 | 5' | EST0664093 | d13.5–14.5 embryo | m6.1 |
| | | mp66g04 | 5' | EST0757905 | thymus | m6.1 |
| | | mw75g03 | 5' | EST0847938 | liver | m6.1 |
| | | va53b05 | 5' | EST0901540 | d12.5 embryo | m6.1 |
| | | vb34h02 | 5' | EST0930132 | lymph node | m6.1 |
| | | vc55d07 | 3' | EST1057735 | 2 cell embryo | m6.1 |
| | | vc59e05 | 3' | EST1058201 | 2 cell embryo | m6.1 |
| | | vc67d03 | 3' | EST1057849 | 2 cell embryo | m6.1 |
| | | vc68d10 | 3' | EST1058663 | 2 cell embryo | m6.1 |
| | | vc97h01 | 3' | EST1059343 | 2 cell embryo | m6.1 |
| | | vc99c08 | 3' | EST1059410 | 2 cell embryo | m6.1 |
| | | vd07h03 | 3' | EST1058173 | 2 cell embryo | m6.1 |
| | | vd08c01 | 3' | EST1058275 | 2 cell embryo | m6.1 |
| | | vd09b12 | 3' | EST1058632 | 2 cell embryo | m6.1 |
| | | vd19b02 | 3' | EST1059723 | 2 cell embryo | m6.1 |
| | | vd29a04 | 3' | ? none found | | m6.1 |
| | | vd46d06 | 3' | ? none found | | m6.1 |

TABLE 6.2

Summary of ESTs derived from human SOCS-5 cDNAs

| SOCS | Species | EST name | End | EST no | Library source | Contig |
|---|---|---|---|---|---|---|
| SOCS-6 | Human | yf61e08 | 5' | EST0184387 | d73 infant brain | h6.1 |
| | | yf93a09 | 5' | EST0186084 | d73 infant brain | h6.1 |
| | | yg05f12 | 5' | EST0191486 | d73 infant brain | h6.1 |
| | | yg41f04 | 5' | EST0195017 | d73 infant brain | h6.1 |
| | | yg45c02 | 5' | EST0185308 | d73 infant brain | h6.1 |
| | | yh11f10 | 5' | EST0236705 | d73 infant brain | h6.1 |
| | | yh13b05 | 5' | EST0237191 | d73 infant brain | h6.1 |
| | | | 3' | EST0236958 | | h6.2 |
| | | zc35a12 | 5' | EST0555518 | senescent fibroblasts | h6.1 |
| | | ze02h08 | 5' | EST0603826 | foetal heart | h6.1 |
| | | | 3' | EST0603718 | | h6.2 |

TABLE 6.2-continued

Summary of ESTs derived from human SOCS-5 cDNAs

| SOCS | Species | EST name | End | EST no | Library source | Contig |
|---|---|---|---|---|---|---|
| | | zl09a03 | 5' | EST0773936 | pregnant uterus | h6.1 |
| | | | 3' | EST0773892 | | h6.1 |
| | | zl69e10 | 5' | EST0683363 | colon | h6.1 |
| | | zn39d08 | 5' | EST0718885 | endothelial cell | h6.1 |
| | | zo39e06 | 5' | EST0785947 | endothelial cell | h6.1 |

TABLE 7.1

Summary of ESTs derived from mouse SOCS-7 cDNAs

| SOCS | Species | EST name | End | EST no | Library source | Contig |
|---|---|---|---|---|---|---|
| SOCS-7 | Mouse | mj39a01 | 5' | EST0665627 | d13.5/ 14.5 embryo | m7.1 |
| | | vi52h07 | 5' | EST1267404 | d7.5 embryo | m7.1 |

TABLE 9.1

Summary of ESTs derived from mouse SOCS-9 cDNAs

| SOCS | Species | EST name | End | EST no | Library source | Contig |
|---|---|---|---|---|---|---|
| | Mouse | me65d05 | 5' | EST0585211 | d13.5/ 14.5 embryo | m9.1 |

TABLE 7.2

Summary of ESTs derived from human SOCS-5 cDNAs

| SOCS | Species | EST name | End | EST no | Library source | Contig |
|---|---|---|---|---|---|---|
| SOCS-7 | HUMAN | STS WI-30171 | | (G21563) | Chromosome 2 | h7.2 |
| | | EST00939 | 5' | EST0000906 | hippocampus | h7.1 |
| | | EST12913 | 3' | EST0944382 | uterus | h7.2 |
| | | yc29b05 | 3' | EST0128727 | liver | h7.2 |
| | | yp49f10 | 3' | EST0301914 | retina | h7.2 |
| | | zt10f03 | 5' | EST0922932 | germinal centre B cell | h7.2 |
| | | | 3' | EST0921231 | | h7.1 |
| | | zx73g04 | 3' | EST1102975 | ovarian tumour | h7.1 |

TABLE 8.1

Summary of ESTs derived from mouse SOCS-8 cDNAs

| SOCS | Species | EST name | End | EST no | Library source | Contig |
|---|---|---|---|---|---|---|
| SOCS-8 | Mouse | mj16e09 | r1 | EST0666240 | d13.5/ 14.5 embryo | m8.1 |
| | | vj27a029 | r1 | EST1155973 | heart | m8.1 |

TABLE 9.2

Summary of ESTs derived from human SOCS-5 cDNAs

| SOCS | Species | EST name | End | EST no | Library source | Contig |
|---|---|---|---|---|---|---|
| SOCS-9 | Human | CSRL-83f2-u | | (B06659) | chromsome 11 | h9.1 |
| | | EST114054 | 5' | EST0939759 | placenta | h9.1 |
| | | yy06b07 | 3' | EST0434504 | melanocyte | h9.1 |
| | | yy06g06 | 5' | EST0443783 | melanocyte | h9.1 |
| | | zr40c09 | 5' | EST0832461 | melanocyte, heart, uterus | h9.1 |
| | | zr72h01 | 5' | EST0892025 | melanocyte, | h9.1 |

TABLE 9.2-continued

Summary of ESTs derived from human SOCS-5 cDNAs

| SOCS | Species | EST name | End | EST no | Library source | Contig |
|---|---|---|---|---|---|---|
| | | | | | heart, uterus | |
| | | | 3' | EST0892026 | | h9.1 |
| | | yx92c08 | 5' | EST0441160 | melanocyte | h9.1 |
| | | yx93b08 | 5' | EST0441260 | melanocyte | h9.1 |
| | | hfe0662 | 5' | EST0889611 | foetal heart | h9.1 |

TABLE 10.1

Summary of ESTs derived from mouse SOCS-10 cDNAs

| SOCS | Species | EST name | End | EST no | Library source | Contig |
|---|---|---|---|---|---|---|
| | Mouse | mb14d12 | 5' | EST0549887 | d19.5 embryo | m10.1 |
| | | mb40f06 | 5' | EST0515064 | d19.5 embryo | m10.1 |
| | | mg89b11 | 5' | EST0630631 | d13.5–14.5 embryo | m10.1 |
| | | mq89e12 | 5' | EST0776015 | heart | m10.1 |
| | | mp03g12 | 5' | EST0741991 | heart | m10.1 |
| | | vh53c11 | 5' | EST1154634 | mammary gland | m10.1 |

TABLE 10.2

Summary of ESTs derived from human SOCS-5 cDNAs

| SOCS | Species | EST name | End | EST no | Library source | Contig |
|---|---|---|---|---|---|---|
| SOCS-10 | Human | aa48h10 | 3' | EST1135220 | germinal centre B cell | h10.2 |
| | | zp35h01 | 3' | EST0819137 | muscle | h10.2 |
| | | zp97h12 | 5' | EST0835442 | muscle | h10.2 |
| | | | 3' | EST0831211 | | h10.2 |
| | | zq08h01 | 5' | EST0835907 | muscle | h10.1 |
| | | zr34g05 | 5' | EST0834251 | melanocyte, heart, uterus | h10.2 |
| | | | 3' | EST0834440 | | h10.2 |
| | | EST73000 | 5 | EST1004491 | ovary | h10.2 |
| | | HSDHEI005 | ? | EST0013906 | heart | h10.2 |

TABLE 11.1

Summary of ESTs derived from human SOCS-5 cDNAs

| SOCS | Species | EST name | End | EST no | Library source | Contig |
|---|---|---|---|---|---|---|
| SOCS-11 | Human | zt24h06 | r1 | EST0925023 | ovarian tumor | 11.1 |
| | | zr43b02 | r1 | EST0873006 | melanocyte, heart, | 11.1 |

TABLE 11.1-continued

Summary of ESTs derived from human SOCS-5 cDNAs

| SOCS | Species | EST name | End | EST no | Library source | Contig |
|---|---|---|---|---|---|---|
| | | | | | uterus | |
| | | | s1 | EST0872954 | | 11.1 |

TABLE 12.1

Summary of ESTs derived from mouse SOCS-12 cDNAs

| SOCS | Species | EST name | End | EST no | Library source | Contig |
|---|---|---|---|---|---|---|
| SOCS-12 | Mouse | EST03803 | 5' | EST1054173 | day 7.5 emb ectoplacental cone | m12.1 |
| | | mt18f02 | 5' | EST0817652 | 3NbMS spleen | m12.1 |
| | | mz60g10 | 5' | EST0890872 | lymph node | m12.1 |
| | | va05c11 | 5' | EST0909449 | lymph node | m12.1 |

TABLE 12.2

Summary of ESTs derived from human SOCS-5 cDNAs

| SOCS | Species | EST name | End | EST no | Library source | Contig |
|---|---|---|---|---|---|---|
| SOCS-12 | Human | STS-SHGC-13867 | | | Chromosome 2 | h12.2 |
| | | EST177695 | 5' | EST0948071 | Jurkat cells | h12.1 |
| | | EST64550 | 5' | EST0997367 | Jurkat cells | h12.1 |
| | | EST76868 | 5' | EST1007291 | pineal body | h12.2 |
| | | PMY2369 | 5' | EST1115998 | KG-1 | h12.1 |
| | | yb38f04 | 5' | EST0108807 | foetal spleen | h12.1 |
| | | | 3' | | | h12.2 |
| | | yg74e12 | 5' | EST0224407 | d73 brain | h12.1 |
| | | yh13g04 | 5' | EST0237226 | d73 brain | h12.1 |
| | | | 3' | EST0236992 | | h12.2 |
| | | yh48b06 | 5' | yh48b06 | placenta | h12.2 |
| | | yh53a05 | 5' | EST0197282 | placenta | h12.2 |
| | | | 3' | EST0197486 | | h12.2 |
| | | yn48h09 | 5' | EST0278258 | brain | h12.2 |
| | | | 3' | EST0278259 | | h12.2 |
| | | yn90a09 | 3' | EST0302557 | brain | h12.2 |
| | | yo08f03 | 5' | EST0301790 | brain | h12.2 |
| | | | 3' | EST0302059 | | h12.2 |
| | | yo11e01 | 3' | ? none found | | h12.2 |
| | | yo63b12 | 5' | EST0303606 | breast | h12.2 |
| | | | 3' | EST0304085 | | h12.2 |
| | | yq56g02 | 3' | EST0346935 | foetal liver spleen | h12.1 |
| | | zh57c04 | 3' | EST0594201 | foetal liver spleen | h12.2 |
| | | zh79h01 | 3' | EST0598945 | foetal liver spleen | h12.2 |
| | | zh99a11 | 3' | EST0618570 | foetal liver spleen | h12.2 |
| | | zo92h12 | 5' | EST0803392 | ovarian cancer | h12.1 |
| | | | 3' | EST0803393 | | h12.2 |
| | | zs48c01 | 5' | EST0925714 | germinal centre B cell | h12.1 |
| | | | 3' | EST0925530 | | h12.2 |
| | | zs45h02 | 3' | EST0932296 | germinal centre B cell | h12.2 |

TABLE 13.1

Summary of ESTs derived from mouse SOCS-13 cDNAs

| SOCS | Species | EST name | End | EST no | Library source | Contig |
|---|---|---|---|---|---|---|
| SOCS-13 | Mouse | ma39c09 | 5' | EST0517875 | day 19.5 embryo | m13.1 |
| | | me60c05 | 5' | EST0584950 | day 13.5/14.5 embryo | m13.1 |
| | | mi78g05 | 5' | EST0653834 | day 19.5 embryo | m13.1 |
| | | mk10c11 | 5' | EST0735158 | day 19.5 embryo | m13.1 |
| | | mo48g12 | 5' | EST0745111 | day 10.5 embryo | m13.1 |
| | | mp94a01 | 5' | EST0762827 | thymus | m13.1 |
| | | vb57c07 | 5' | EST1028976 | day 11.5 embryo | m13.1 |
| | | vh07c11 | 5' | EST1117269 | mammary gland | m13.1 |

TABLE 13.2

Summary of ESTs derived from human SOCS-13 cDNAs

| SOCS | Species | EST name | End | EST no | Library source | Contig |
|---|---|---|---|---|---|---|
| SOCS-13 | Human | EST59161 | 5' | EST0992726 | infant brain | h13.1 |

TABLE 14.1

Summary of ESTs derived from mouse SOCS-14 cDNAs

| SOCS | Species | EST name | End | EST no | Library source | Contig |
|---|---|---|---|---|---|---|
| SOCS-14 | mouse | mi75e03 | 5' | EST0651892 | d19.5 embryo | m14.1 |
| | | vd29h11 | 5' | EST1067080 | 2 cell embryo | m14.1 |
| | | vd53g07 | 5' | EST1119627 | 2 cell embryo | m14.1 |

TABLE 15.1

Summary of ESTs derived from mouse SOCS-15 cDNAs

| SOCS | Species | EST name | End | EST no | Library source | Contig |
|---|---|---|---|---|---|---|
| SOCS-15 | Mouse | mh29b05 | 5' | EST0628834 | placenta | m15.1 |
| | | mh98h09 | 5' | EST0638243 | placenta | m15.1 |
| | | ml45a02 | 5' | EST0687171 | testis | m15.1 |
| | | mu43a10 | 5' | EST851588 | thymus | m15.1 |
| | | my38c09 | 5' | EST878461 | pooled organs | m15.1 |
| | | vj37h07 | 5' | EST1174791 | diaphragm | m15.1 |
| | | AC002393 | | | Chromo-some 6 BAC | m15.1 |

TABLE 15.2

Summary of ESTs derived from human SOCS-15 cDNAs

| SOCS | Species | EST name | End | EST no | Library source | Contig |
|---|---|---|---|---|---|---|
| SOCS-15 | Human | EST98889 | 5' | EST1026568 | thyroid | h15.1 |
| | | ne48bo5 | 3' | EST1138057 | colon tumour | h15.1 |
| | | yb12h12 | 5' | EST0098885 | placenta | h15.1 |
| | | | 3' | EST0098886 | | h15.1 |
| | | HSU47924 | | | Chromosome 12 BAC | h15.1 |

BIBLIOGRAPHY

Alexander W S, Metcalf D and Dunn A R (1995). *Embo Journal* 14, 5569-78.

Altschul, S. F. Gish, W. Miller, W. Myers, E. W. & Lipman, D. J. (1990) *J. Mol. Biol.* 215, 403-10.

Ansari-Lari, M. A., Shen, Y., Munzy, D. M., Lee, W. and Gibbs, R. A. (1997) *Genome. Res.* 7, 268-280.

Bazan J F (1990). [Review]. *Immunology Today* 11, 350-4.

Bork, P. (1993) *Proteins: Struct. Funct. Genet.* 17, 363-374.

Cockwell, L. Y. and Giles, I. G. (1989) *Comp. Appl. Biosci.* 5, 227-232.

Cutler R L, Liu L, Damen J E and Krystal G (1993). *Journal of Biological Chemistry* 268, 21463-5.

Darnell J Jr., Kerr I M and Stark GR (1994). *Science* 264, 1415-21.

David M, Petricoin E3, Benjamin C, Pine R, Weber M J and Larner A C (1995). *Science* 269, 1721-3.

David M, Wong L, Flavell R, Thompson S A, Wells A, Lamer A C and Johnson G R (1996). *Journal of Biological Chemistry* 271, 9185-8.

Dugaiczyk A, Haron J A, Stone E M, Dennison O E, Rothblum K N and Schwartz R J (1983). *Biochemistry* 22, 1605-13.

Durbin J E, Hackenmiller R, Simon M C and Levy D E (1996). *Cell* 84, 443-50.

Etzold, T., Ulyanov, A. and Argos, P. (1996) *Methods Enzymol.* 266, 114-28.

Gearing D P, Nicola N A, Metcalf D, Foote S, Willson T A, Gough N M and Williams L (1989). *BioTechnology* 7, 1157-1161.

Gupta S, Yan H, Wong L H, Ralph S, Krolewski J and Schindler C (1996). *Embo Journal* 15, 1075-84.

Hilton D J (1994). An introduction to cytokine receptors, p8-16 in *Guidebook to Cytokines and Their Receptors*, Eds: N. A. Nicola. Oxford University Press: Oxford.

Hilton D J, Hilton A A, Raicevic A, Rakar S, Harrison-Smith M, Gough N M, Begley C G, Metcalf D, Nicola N A and Willson T A (1994). *Embo Journal* 13, 4765-75.

Hilton D J, Watowich S S, Katz L and Lodish H F (1996). *J. Biol. Chem.* 271, 4699-4708.

Ichikawa Y (1969). *Journal of Cellular Physiology* 74, 223-34.

Ihle J N (1995). *Nature* 377, 591-4.

Ihle J N, Witthuhn B A, Quelle F W, Yamamoto K and Silvennoinen O (1995). *Annual Review of Immunology* 13, 369-98.

Kaplan M H, Schindler U, Smiley S T and Grusby M J (1996a). *Immunity* 4, 313-9.

Kaplan M H, Sun Y L, Hoey T and Grusby M J (1996b). *Nature* 382, 174-179.

Levy D E and Stark G R (1996). *Molecular & Cellular Biology* 16, 369-75.

Metcalf D, Wilson T A, Hilton D J, DiRago L and Mifsud S. (1995) *Leukaemia* 9, 1556-1564.

Meraz M A, White J M, Sheehan K C, Bach E A, Rodig S J, Dighe A S, Kaplan D H, Riley J K, Greenlund A C, Campbell D, Carver-Moore K, DuBois R N, Clark R, Aguet M and Schreiber R D (1996). *Cell* 84, 431-42.

Mizushima S and Nagata S (1990). *Nucleic Acids Research* 18, 5322.

Murakami M, Narazaki M, Hibi M, Yawata H, Yasukawa K, Hamaguchi M, Taga T and Kishimoto T (1991). *Proc. Natl. Acad. Sci. USA* 88, 11349-11353.

Neer, E. J., Schmidt, C. J., Nambudripad, R. and Smith, T. F. (1994) *Nature* 371, 297-300.

Nicola N A((1994). *Guidebook to Cytokines and Their Receptors*. Oxford University Press: Oxford.

Nicola, N V, Viney E, Hilton D J, Roberts B and Wilson T. (1996) *Growth Factors* 13, 141-149.

Novak U, Harpur A G, Paradiso L, Kanagasundaram V, Jaworowski A, Wilks A F and Hamilton J A (1995). *Blood* 86, 2948-56.

Pearson W R and Lipman D J. (1988) *Proc. Natl. Acad. Sci. USA* 85, 2444-8.

Pearson W R. (1990) *Methods Enzymol.* 183, 63-98.

Rayner J R and Gonda T J (1994). *Molecular & Cellular Biology* 14, 880-7.

Sambrook J, Fritsch E F and Maniatis T (1989). *Molecular Cloning, A Laboratory Manual.* Cold Spring Harbour Laboratory Press, Cold Spring Harbour USA.

Sato N, Sakamaki K, Terada N, Arai K and Miyajima A (1993). *Embo Journal* 12, 4181-9.

Shimoda K, van Deursen J, Sangster M Y, Sarawar S R, Carson R T, Tripp R A, Chu C, Quelle F W, Nosaka T, Vignali D A, Doherty P C, Grosveld G, Paul W E and Ihle J N (1996). *Nature* 380, 630-3.

Shual K, Ziemiecki A, Wilks A F, Harpur A G, Sadowski H B, Gilman M Z and Darnell J E (1993). *Nature* 366, 580-3.

Sprang S R and Bazan J F (1993). *Curr. Opin. Structural Biol.* 3, 815-827.

Takeda K, Tanaka T, Shi W, Matsumoto M, Minami M, Kashiwamura S, Nakanishi K, Yoshida N, Kishimoto T and Akira S (1996). *Nature* 380, 627-30.

Thierfelder W E, Vandeursen J M, Yamamoto K, Tripp R A, Sarawar S R, Carson R T, Sangster M Y, Vignali D D A, Doherty P C, Grosveld G C and Ihle J N (1996). *Nature* 382, 171-174.

Wakao H, Gouilleux F and Groner B (1994). *Embo Journal* 13, 2182-91.

Wen Z, Zhong Z and Darnell J Jr. (1995). *Cell* 82, 241-50.

Yi T, Mui A L, Krystal G and Ihle J N (1993). *Molecular & Cellular Biology* 13, 7577-86.

Yoshimura A, Ohkubo T, Kiguchi T, Jenkins N A, Gilbert D J, Copeland N G, Hara T and Miyajima A (1995). *Embo Journal* 14, 2816-26.

The invention claimed is:

1. An isolated nucleic acid molecule encoding a protein, wherein said protein comprises a suppressor of cytokine signaling (SOCS) box which comprises the amino acid sequence as set forth in SEQ ID NO: 53, and wherein said protein suppresses the signal transduction mediated by a cytokine.

2. The isolated nucleic acid molecule of claim 1, wherein said protein comprises the amino acid sequence as set forth in SEQ ID NO: 6.

3. The isolated nucleic acid molecule of claim 1, comprising the nucleotide sequence as set forth in SEQ ID NO: 5.

4. An isolated nucleic acid molecule encoding a protein, wherein said protein comprises a SOCS box which comprises an amino acid sequence having at least 80% identity with SEQ ID NO: 53, and wherein said protein suppresses the signal transduction mediated by a cytokine.

5. The isolated nucleic acid molecule of claim 4, wherein said protein is further characterized as comprising an amino acid sequence having at least 80% identity with SEQ ID NO: 6.

6. An isolated nucleic acid molecule consisting of the nucleotide sequence as set forth in SEQ ID NO: 3.

7. An expression vector comprising the nucleic acid molecule of any one of claims 1-6.

8. A host cell comprising the expression vector of claim 7.

9. A method of producing a SOCS protein, said method comprising culturing the host cell of claim 8 under conditions allowing the expression of said SOCS protein, and isolating said SOCS protein.

10. An isolated protein comprising the amino acid sequence as set forth in SEQ ID NO: 6.

11. An isolated protein comprising a SOCS box which comprises an amino acid sequence having at least 80% identity with SEQ ID NO: 53, and wherein said protein suppresses the signal transduction mediated by a cytokine.

12. The isolated protein of claim 11, wherein said protein is further characterized as comprising an amino acid sequence having at least 80% identity with SEQ ID NO: 6.

* * * * *

```
                      SEQUENCE LISTING


<160> NUMBER OF SEQ ID NOS: 68

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:Primer

<400> SEQUENCE: 1

cacgccgccc acgtgaaggc                                              20


<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:Primer

<400> SEQUENCE: 2

ttcgccaatg acaagacgct                                              20


<210> SEQ ID NO 3
<211> LENGTH: 1235
<212> TYPE: DNA
<213> ORGANISM: Mus musculus
<220> FEATURE:
<221> NAME/KEY: CDS
<222> LOCATION: (161)..(799)

<400> SEQUENCE: 3

cgaggctcaa gctccgggcg gattctgcgt gccgctctcg ctccttgggg tctgttggcc     60

ggcctgtgcc acccggacgc ccggctcact gcctctgtct cccccatcag cgcagccccg    120

gacgctatgg cccacccctc cagctggccc ctcgagtagg                          160

atg gta gca cgc aac cag gtg gca gcc gac aat gcg atc tcc ccg gca      208
Met Val Ala Arg Asn Gln Val Ala Ala Asp Asn Ala Ile Ser Pro Ala
  1               5                  10                  15

gca gag ccc cga cgg cgg tca gag ccc tcc tcg tcc tcg tct tcg tcc      256
Ala Glu Pro Arg Arg Arg Ser Glu Pro Ser Ser Ser Ser Ser Ser Ser
             20                  25                  30

tcg cca gcg gcc ccc gtg cgt ccc cgg ccc tgc ccg gcg gtc cca gcc      304
Ser Pro Ala Ala Pro Val Arg Pro Arg Pro Cys Pro Ala Val Pro Ala
         35                  40                  45

cca gcc cct ggc gac act cac ttc cgc acc ttc cgc tcc cac tcc gat      352
Pro Ala Pro Gly Asp Thr His Phe Arg Thr Phe Arg Ser His Ser Asp
     50                  55                  60

tac cgg cgc atc acg cgg acc agc gcg ctc ctg gac gcc tgc ggc ttc      400
Tyr Arg Arg Ile Thr Arg Thr Ser Ala Leu Leu Asp Ala Cys Gly Phe
```

-continued 65 70 75 80 tat tgg gga ccc ctg agc gtg cac ggg gcg cac gag cgg ctg cgt gcc 448
Tyr Trp Gly Pro Leu Ser Val His Gly Ala His Glu Arg Leu Arg Ala
85 90 95 gag ccc gtg ggc acc ttc ttg gtg cgc gac agt cgt caa cgg aac tgc 496
Glu Pro Val Gly Thr Phe Leu Val Arg Asp Ser Arg Gln Arg Asn Cys
100 105 110 ttc ttc gcg ctc agc gtg aag atg gct tcg ggc ccc acg agc atc cgc 544
Phe Phe Ala Leu Ser Val Lys Met Ala Ser Gly Pro Thr Ser Ile Arg
115 120 125 gtg cac ttc cag gcc ggc cgc ttc cac ttg gac ggc agc cgc gag acc 592
Val His Phe Gln Ala Gly Arg Phe His Leu Asp Gly Ser Arg Glu Thr
130 135 140 ttc gac tgc ctt ttc gag ctg ctg gag cac tac gtg gcg gcg ccg cgc 640
Phe Asp Cys Leu Phe Glu Leu Leu Glu His Tyr Val Ala Ala Pro Arg
145 150 155 160 cgc atg ttg ggg gcc ccg ctg cgc cag cgc cgc gtg cgg ccg ctg cag 688
Arg Met Leu Gly Ala Pro Leu Arg Gln Arg Arg Val Arg Pro Leu Gln
165 170 175 gag ctg tgt cgc cag cgc atc gtg gcc gcc gtg ggt cgc gag aac ctg 736
Glu Leu Cys Arg Gln Arg Ile Val Ala Ala Val Gly Arg Glu Asn Leu
180 185 190 gcg cgc atc cct ctt aac ccg gta ctc cgt gac tac ctg agt tcc ttc 784
Ala Arg Ile Pro Leu Asn Pro Val Leu Arg Asp Tyr Leu Ser Ser Phe
195 200 205 ccc ttc cag atc tga ccggctg ccgctgtgcc gcagcattaa gtgggggcgc 836
Pro Phe Gln Ile
210 cttattattt cttattatta attattatta tttttctgga accacgtggg agccctcccc 896 gcctgggtcg gagggagtgg ttgtggaggg tgagatgcct cccacttctg gctggagacc 956 tcatcccacc tctcaggggt gggggtgctc ccctcctggt gctccctccg ggtccccccct 1016 ggttgtagca gcttgtgtct ggggccagga cctgaattcc actcctacct ctccatgttt 1076 acatattccc agtatctttg cacaaaccag gggtcgggga gggtctctgg cttcattttt 1136 ctgctgtgca gaatatccta ttttatattt ttacagccag tttaggtaat aaactttatt 1196 atgaaagttt ttttttaaaa gaaaaaaaaa aaaaaaaaa 1235

<210> SEQ ID NO 4
<211> LENGTH: 212
<212> TYPE: PRT
<213> ORGANISM: Mus musculus

<400> SEQUENCE: 4

Met Val Ala Arg Asn Gln Val Ala Ala Asp Asn Ala Ile Ser Pro Ala
1 5 10 15

Ala Glu Pro Arg Arg Arg Ser Glu Pro Ser Ser Ser Ser Ser Ser Ser
20 25 30

Ser Pro Ala Ala Pro Val Arg Pro Arg Pro Cys Pro Ala Val Pro Ala
35 40 45

Pro Ala Pro Gly Asp Thr His Phe Arg Thr Phe Arg Ser His Ser Asp
50 55 60

Tyr Arg Arg Ile Thr Arg Thr Ser Ala Leu Leu Asp Ala Cys Gly Phe
65 70 75 80

Tyr Trp Gly Pro Leu Ser Val His Gly Ala His Glu Arg Leu Arg Ala
85 90 95

Glu Pro Val Gly Thr Phe Leu Val Arg Asp Ser Arg Gln Arg Asn Cys

-continued

```
            100                 105                 110

Phe Phe Ala Leu Ser Val Lys Met Ala Ser Gly Pro Thr Ser Ile Arg
        115                 120                 125

Val His Phe Gln Ala Gly Arg Phe His Leu Asp Gly Ser Arg Glu Thr
    130                 135                 140

Phe Asp Cys Leu Phe Glu Leu Leu Glu His Tyr Val Ala Ala Pro Arg
145                 150                 155                 160

Arg Met Leu Gly Ala Pro Leu Arg Gln Arg Arg Val Arg Pro Leu Gln
                165                 170                 175

Glu Leu Cys Arg Gln Arg Ile Val Ala Ala Val Gly Arg Glu Asn Leu
            180                 185                 190

Ala Arg Ile Pro Leu Asn Pro Val Leu Arg Asp Tyr Leu Ser Ser Phe
        195                 200                 205

Pro Phe Gln Ile
    210


<210> SEQ ID NO 5
<211> LENGTH: 1121
<212> TYPE: DNA
<213> ORGANISM: Mus musculus
<220> FEATURE:
<221> NAME/KEY: CDS
<222> LOCATION: (223)..(819)

<400> SEQUENCE: 5

gcgatctgtg ggtgacagtg tctgcgagag actttgccac accattctgc cggaatttgg      60

agaaaaagaa ccagccgctt ccagtcccct ccccctccgc caccatttcg gacaccctgc     120

acactctcgt tttggggtac cctgtgactt ccaggcagca cgcgaggtcc actggcccca     180

gctcgggcga ccagctgtct gggacgtgtt gactcatctc cc atg acc ctg cgg       234
                                                Met Thr Leu Arg
                                                1

tgc ctg gag ccc tcc ggg aat gga gcg gac agg acg cgg agc cag tgg       282
Cys Leu Glu Pro Ser Gly Asn Gly Ala Asp Arg Thr Arg Ser Gln Trp
  5                  10                  15                  20

ggg acc gcg ggg ttg ccg gag gaa cag tcc ccc gag gcg gcg cgt ctg       330
Gly Thr Ala Gly Leu Pro Glu Glu Gln Ser Pro Glu Ala Ala Arg Leu
                25                  30                  35

gcg aaa gcc ctg cgc gag ctc agt caa aca gga tgg tac tgg gga agt       378
Ala Lys Ala Leu Arg Glu Leu Ser Gln Thr Gly Trp Tyr Trp Gly Ser
            40                  45                  50

atg act gtt aat gaa gcc aaa gag aaa tta aaa gag gct cca gaa gga       426
Met Thr Val Asn Glu Ala Lys Glu Lys Leu Lys Glu Ala Pro Glu Gly
        55                  60                  65

act ttc ttg att aga gat agt tcg cat tca gac tac cta cta act ata       474
Thr Phe Leu Ile Arg Asp Ser Ser His Ser Asp Tyr Leu Leu Thr Ile
     70                  75                  80

tcc gtt aag acg tca gct gga ccg act aac ctg cgg att gag tac caa       522
Ser Val Lys Thr Ser Ala Gly Pro Thr Asn Leu Arg Ile Glu Tyr Gln
 85                  90                  95                 100

gat ggg aaa ttc aga ttg gat tct atc ata tgt gtc aag tcc aag ctt       570
Asp Gly Lys Phe Arg Leu Asp Ser Ile Ile Cys Val Lys Ser Lys Leu
                105                 110                 115

aaa cag ttt gac agt gtg gtt cat ctg att gac tac tat gtc cag atg       618
Lys Gln Phe Asp Ser Val Val His Leu Ile Asp Tyr Tyr Val Gln Met
            120                 125                 130

tgc aag gat aaa cgg aca ggc cca gaa gcc cca cgg aat ggg act gtt       666
Cys Lys Asp Lys Arg Thr Gly Pro Glu Ala Pro Arg Asn Gly Thr Val
        135                 140                 145
```

-continued

```
cac ctg tac ctg acc aaa cct ctg tat aca tca gca ccc act ctg cag      714
His Leu Tyr Leu Thr Lys Pro Leu Tyr Thr Ser Ala Pro Thr Leu Gln
    150                 155                 160

cat ttc tgt cga ctc gcc att aac aaa tgt acc ggt acg atc tgg gga      762
His Phe Cys Arg Leu Ala Ile Asn Lys Cys Thr Gly Thr Ile Trp Gly
165                 170                 175                 180

ctg cct tta cca aca aga cta aaa gat tac ttg gaa gaa tat aaa ttc      810
Leu Pro Leu Pro Thr Arg Leu Lys Asp Tyr Leu Glu Glu Tyr Lys Phe
                185                 190                 195

cag gta taagtatttc tctctctttt tcgttttttt ttaaaaaaaa aaaaacacat       866
Gln Val

gcctcatata gactatctcc gaatgcagct atgtgaaaga gaacccagag gccctcctct    926

ggataactgc gcagaattct ctcttaagga cagttgggct cagtctaact taaaggtgtg    986

aagatgtagc taggtatttt aaagttcccc ttaggtagtt ttagctgaat gatgctttct   1046

ttcctatggc tgctcaagat caaatggccc ttttaaatga aacaaaacaa aacaaaacaa   1106

aaaaaaaaaa aaaaa                                                    1121


<210> SEQ ID NO 6
<211> LENGTH: 198
<212> TYPE: PRT
<213> ORGANISM: Mus musculus

<400> SEQUENCE: 6

Met Thr Leu Arg Cys Leu Glu Pro Ser Gly Asn Gly Ala Asp Arg Thr
  1               5                  10                  15

Arg Ser Gln Trp Gly Thr Ala Gly Leu Pro Glu Glu Gln Ser Pro Glu
            20                  25                  30

Ala Ala Arg Leu Ala Lys Ala Leu Arg Glu Leu Ser Gln Thr Gly Trp
        35                  40                  45

Tyr Trp Gly Ser Met Thr Val Asn Glu Ala Lys Glu Lys Leu Lys Glu
    50                  55                  60

Ala Pro Glu Gly Thr Phe Leu Ile Arg Asp Ser Ser His Ser Asp Tyr
 65                  70                  75                  80

Leu Leu Thr Ile Ser Val Lys Thr Ser Ala Gly Pro Thr Asn Leu Arg
                85                  90                  95

Ile Glu Tyr Gln Asp Gly Lys Phe Arg Leu Asp Ser Ile Ile Cys Val
            100                 105                 110

Lys Ser Lys Leu Lys Gln Phe Asp Ser Val Val His Leu Ile Asp Tyr
        115                 120                 125

Tyr Val Gln Met Cys Lys Asp Lys Arg Thr Gly Pro Glu Ala Pro Arg
    130                 135                 140

Asn Gly Thr Val His Leu Tyr Leu Thr Lys Pro Leu Tyr Thr Ser Ala
145                 150                 155                 160

Pro Thr Leu Gln His Phe Cys Arg Leu Ala Ile Asn Lys Cys Thr Gly
                165                 170                 175

Thr Ile Trp Gly Leu Pro Leu Pro Thr Arg Leu Lys Asp Tyr Leu Glu
            180                 185                 190

Glu Tyr Lys Phe Gln Val
        195


<210> SEQ ID NO 7
<211> LENGTH: 2187
<212> TYPE: DNA
<213> ORGANISM: Mus musculus
<220> FEATURE:
```

-continued

```
<221> NAME/KEY: CDS
<222> LOCATION: (18)..(695)

<400> SEQUENCE: 7

cgctggctcc gtgcgcc atg gtc acc cac agc aag ttt ccc gcc gcc ggg         50
                   Met Val Thr His Ser Lys Phe Pro Ala Ala Gly
                    1               5                   10

atg agc cgc ccc ctg gac acc agc ctg cgc ctc aag acc ttc agc tcc        98
Met Ser Arg Pro Leu Asp Thr Ser Leu Arg Leu Lys Thr Phe Ser Ser
            15                  20                  25

aaa agc gag tac cag ctg gtg gtg aac gcc gtg cgc aag ctg cag gag       146
Lys Ser Glu Tyr Gln Leu Val Val Asn Ala Val Arg Lys Leu Gln Glu
        30                  35                  40

agc gga ttc tac tgg agc gcc gtg acc ggc ggc gag gcg aac ctg ctg       194
Ser Gly Phe Tyr Trp Ser Ala Val Thr Gly Gly Glu Ala Asn Leu Leu
    45                  50                  55

ctc agc gcc gag ccc gcg ggc acc ttt ctt atc cgc gac agc tcg gac       242
Leu Ser Ala Glu Pro Ala Gly Thr Phe Leu Ile Arg Asp Ser Ser Asp
 60                 65                  70                  75

cag cgc cac ttc ttc acg ttg agc gtc aag acc cag tcg ggg acc aag       290
Gln Arg His Phe Phe Thr Leu Ser Val Lys Thr Gln Ser Gly Thr Lys
                80                  85                  90

aac cta cgc atc cag tgt gag ggg ggc agc ttt tcg ctg cag agt gac       338
Asn Leu Arg Ile Gln Cys Glu Gly Gly Ser Phe Ser Leu Gln Ser Asp
            95                  100                 105

ccc cga agc acg cag cca gtt ccc cgc ttc gac tgt gta ctc aag ctg       386
Pro Arg Ser Thr Gln Pro Val Pro Arg Phe Asp Cys Val Leu Lys Leu
        110                 115                 120

gtg cac cac tac atg ccg cct cca ggg acc ccc tcc ttt tct ttg cca       434
Val His His Tyr Met Pro Pro Pro Gly Thr Pro Ser Phe Ser Leu Pro
    125                 130                 135

ccc acg gaa ccc tcg tcc gaa gtt ccg gag cag cca cct gcc cag gca       482
Pro Thr Glu Pro Ser Ser Glu Val Pro Glu Gln Pro Pro Ala Gln Ala
140                 145                 150                 155

ctc ccc ggg agt acc ccc aag aga gct tac tac atc tat tct ggg ggc       530
Leu Pro Gly Ser Thr Pro Lys Arg Ala Tyr Tyr Ile Tyr Ser Gly Gly
                160                 165                 170

gag aag att ccg ctg gta ctg agc cga cct ctc tcc tcc aac gtg gcc       578
Glu Lys Ile Pro Leu Val Leu Ser Arg Pro Leu Ser Ser Asn Val Ala
            175                 180                 185

acc ctc cag cat ctt tgt cgg aag act gtc aac ggc cac ctg gac tcc       626
Thr Leu Gln His Leu Cys Arg Lys Thr Val Asn Gly His Leu Asp Ser
        190                 195                 200

tat gag aaa gtg acc cag ctg cct gga ccc att cgg gag ttc ctg gat       674
Tyr Glu Lys Val Thr Gln Leu Pro Gly Pro Ile Arg Glu Phe Leu Asp
    205                 210                 215

cag tat gat gct cca ctt taaggagcaa aagggtcaga ggggggcctg              722
Gln Tyr Asp Ala Pro Leu
220                 225

ggtcggtcgg tcgcctctcc tccgaggcac atggcacaag cacaaaaatc cagccccaac    782

ggtcggtagc tcccagtgag ccaggggcag attggcttct tcctcaggcc ctccactccc    842

gcagagtaga gctggcagga cctggaattc gtctgagggg agggggagct gccacctgct    902

ttcccccctc ccccagctcc agcttctttc aagtggagcc agccggcctg gcctggtggg    962

acaatacctt tgacaagcgg actctcccct ccccttcctc cacacccccct ctgcttccca  1022

agggaggtgg ggacacctcc aagtgttgaa cttagaactg caaggggaat cttcaaactt   1082

tcccgctgga acttgtttgc gctttgattt ggtttgatca agagcaggca cctgggggaa   1142
```

-continued

```
ggatggaaga gaaaagggtg tgtgaagggt ttttatgctg gccaaagaaa taaccactcc   1202

cactgcccaa cctaggtgag gagtggtggc tcctggctct ggggagagtg gcaaggggtg   1262

acctgaagag agctatactg gtgccaggct cctctccatg ggcagctaa tgaaacctcg    1322

cagatccctt gcaccccaga accctccccg ttgtgaagag gcagtagcat ttagaaggga   1382

gacagatgag gctggtgagc tggccgcctt ttccaacacc gaagggaggc agatcaacag   1442

atgagccatc ttggagccca ggtttcccct ggagcagatg gagggttctg ctttgtctct   1502

cctatgtggg gctaggagac tcgccttaaa tgccctctgt cccagggatg gggattggca   1562

cacaaggagc caaacacagc caataggcag agagttgagg gattcaccca ggtggctaca   1622

ggccagggga agtggctgca ggggagagac ccagtcactc caggagactc ctgagttaac   1682

actgggaaga cattggccag tcctagtcat ctctcggtca gtaggtccga gagcttccag   1742

gccctgcaca gccctccttt ctcacctggg gggaggcagg aggtgatgga gaagccttcc   1802

catgccgctc acaggggcct cacgggaatg cagcagccat gcaattacct ggaactggtc   1862

ctgtgttggg gagaaacaag ttttctgaag tcaggtatgg ggctgggtgg ggcagctgtg   1922

tgttggggtg gctttttttct ctctgttttg aataatgttt acaatttgcc tcaatcactt  1982

ttataaaaat ccacctccag cccgcccctc tccccactca ggccttcgag gctgtctgaa   2042

gatgcttgaa aaactcaacc aaatcccagt tcaactcaga ctttgcacat atatttatat   2102

ttatactcag aaaagaaaca tttcagtaat ttataataaa agagcactat tttttaatga   2162

aaaaaaaaaa aaaaaaaaaa aaaaa                                          2187
```

<210> SEQ ID NO 8
<211> LENGTH: 225
<212> TYPE: PRT
<213> ORGANISM: Mus musculus

<400> SEQUENCE: 8

```
Met Val Thr His Ser Lys Phe Pro Ala Ala Gly Met Ser Arg Pro Leu
  1               5                  10                  15

Asp Thr Ser Leu Arg Leu Lys Thr Phe Ser Ser Lys Ser Glu Tyr Gln
             20                  25                  30

Leu Val Val Asn Ala Val Arg Lys Leu Gln Glu Ser Gly Phe Tyr Trp
         35                  40                  45

Ser Ala Val Thr Gly Gly Glu Ala Asn Leu Leu Leu Ser Ala Glu Pro
     50                  55                  60

Ala Gly Thr Phe Leu Ile Arg Asp Ser Ser Asp Gln Arg His Phe Phe
 65                  70                  75                  80

Thr Leu Ser Val Lys Thr Gln Ser Gly Thr Lys Asn Leu Arg Ile Gln
                 85                  90                  95

Cys Glu Gly Gly Ser Phe Ser Leu Gln Ser Asp Pro Arg Ser Thr Gln
            100                 105                 110

Pro Val Pro Arg Phe Asp Cys Val Leu Lys Leu Val His His Tyr Met
        115                 120                 125

Pro Pro Pro Gly Thr Pro Ser Phe Ser Leu Pro Pro Thr Glu Pro Ser
    130                 135                 140

Ser Glu Val Pro Glu Gln Pro Pro Ala Gln Ala Leu Pro Gly Ser Thr
145                 150                 155                 160

Pro Lys Arg Ala Tyr Tyr Ile Tyr Ser Gly Gly Glu Lys Ile Pro Leu
                165                 170                 175

Val Leu Ser Arg Pro Leu Ser Ser Asn Val Ala Thr Leu Gln His Leu
            180                 185                 190
```

-continued

```
Cys Arg Lys Thr Val Asn Gly His Leu Asp Ser Tyr Glu Lys Val Thr
        195                 200                 205

Gln Leu Pro Gly Pro Ile Arg Glu Phe Leu Asp Gln Tyr Asp Ala Pro
    210                 215                 220

Leu
225


<210> SEQ ID NO 9
<211> LENGTH: 1094
<212> TYPE: DNA
<213> ORGANISM: Homo sapiens

<400> SEQUENCE: 9

ctccggctgg ccccttctgt aggatggtag cacacaacca ggtggcagcc gacaatgcag     60

tctccacagc agcagagccc cgacggcggc cagaaccttc ctcctcttcc tcctcctcgc    120

ccgcggcccc cgcgcgcccg cggccgtgcc ccgcggtccc ggccccggcc cccggcgaca    180

cgcacttccg cacattccgt tcgcacgccg attaccggcg catcacgcgc gccagcgcgc    240

tcctggacgc ctgcggattc tactgggggc ccctgagcgt gcacggggcg cacgagcggc    300

tgcgcgccga gcccgtgggc accttcctgg tgcgcgacag ccgccagcgg aactgctttt    360

tcgcccttag cgtgaagatg gcctcgggac ccacgagcat ccgcgtgcac tttcaggccg    420

gccgctttca cctggatggc agccgcgaga gcttcgactg cctcttcgag ctgctggagc    480

actacgtggc ggcgccgcgc cgcatgctgg gggccccgct gcgccagcgc cgcgtgcggc    540

cgctgcagga gctgtgccgc cagcgcatcg tggccaccgt gggccgcgag aacctggctc    600

gcatccccct caaccccgtc ctccgcgact acctgagctc cttccccttc cagatttgac    660

cggcagcgcc cgccgtgcac gcagcattaa ctgggatgcc gtgttatttt gttattactt    720

gcctggaacc atgtgggtac cctccccggc ctgggttgga gggagcggat gggtgtaggg    780

gcgaggcgcc tcccgccctc ggctggagac gaggccgcag accccttctc acctcttgag    840

ggggtcctcc ccctcctggt gctccctctg ggtccccctg gttgttgtag cagcttaact    900

gtatctggag ccaggacctg aactcgcacc tcctacctct tcatgtttac atatacccag    960

tatctttgca caaaccaggg gttgggggag ggtctctggc tttatttttc tgctgtgcag   1020

aatcctattt tatatttttt aaagtcagtt taggtaataa actttattat gaaagttttt   1080

tttttaaaa aaaa                                                     1094


<210> SEQ ID NO 10
<211> LENGTH: 211
<212> TYPE: PRT
<213> ORGANISM: Homo sapiens

<400> SEQUENCE: 10

Met Val Ala His Asn Gln Val Ala Ala Asp Asn Ala Val Ser Thr Ala
  1               5                  10                  15

Ala Glu Pro Arg Arg Arg Pro Glu Pro Ser Ser Ser Ser Ser Ser Ser
            20                  25                  30

Pro Ala Ala Pro Ala Arg Pro Arg Pro Cys Pro Ala Val Pro Ala Pro
        35                  40                  45

Ala Pro Gly Asp Thr His Phe Arg Thr Phe Arg Ser His Ala Asp Tyr
    50                  55                  60

Arg Arg Ile Thr Arg Ala Ser Ala Leu Leu Asp Ala Cys Gly Phe Tyr
 65                  70                  75                  80
```

-continued

```
Trp Gly Pro Leu Ser Val His Gly Ala His Glu Arg Leu Arg Ala Glu
                85                  90                  95

Pro Val Gly Thr Phe Leu Val Arg Asp Ser Arg Gln Arg Asn Cys Phe
            100                 105                 110

Phe Ala Leu Ser Val Lys Met Ala Ser Gly Pro Thr Ser Ile Arg Val
        115                 120                 125

His Phe Gln Ala Gly Arg Phe His Leu Asp Gly Ser Arg Glu Ser Phe
    130                 135                 140

Asp Cys Leu Phe Glu Leu Leu Glu His Tyr Val Ala Ala Pro Arg Arg
145                 150                 155                 160

Met Leu Gly Ala Pro Leu Arg Gln Arg Arg Val Arg Pro Leu Gln Glu
                165                 170                 175

Leu Cys Arg Gln Arg Ile Val Ala Thr Val Gly Arg Glu Asn Leu Ala
            180                 185                 190

Arg Ile Pro Leu Asn Pro Val Leu Arg Asp Tyr Leu Ser Ser Phe Pro
        195                 200                 205

Phe Gln Ile
    210
```

<210> SEQ ID NO 11
<211> LENGTH: 2807
<212> TYPE: DNA
<213> ORGANISM: Rattus norvegicus

<400> SEQUENCE: 11

```
ggaaaccgag gcggggagac caggaggcct tggcctcaga gcttcagagt cgcgtggcag     60

caaacagaga aacctgtaga gggcagtgtg cgtcacttag ctcagggaag ctgcacgcga    120

aactcacccg ccttcattca taaacatcgt cagctaggca cctactcctg ggctttcagg    180

acaaactgaa tcacgaaacc acagtgtcct taaaataggt ctgaccgcct gaatccctgg    240

ccaaggtgtg tacggggcat gggagccctt gtgcagagat gcttgcagga gccttgaggg    300

gctctgtaag acagaggcta ggaagacaaa gttgggggct acagcttctt gtcctgcccg    360

gggcctcagt ttcttcggtt gcccacgtag gagtgcagag agtccagccc ctggggaccc    420

aacccaaccc cgcccagttt ccgaggaact cgtccgggag cgggggcgcc cctcccgcac    480

cgccttaggc ttcctttgaa gcctctgcgg tcaggccacc gcttcctggg aagcccaagc    540

caaggccagg ccgagtggcc aacgggaggg gcccgcgcgc gattctggag gagggcggcg    600

gccccacagg tctccagggc tggctagccg ggctcctaga gcggagactg ccaaggcctt    660

cgggtcctgg gcaggaagga tcctggcagg gaggagttgc ttggggggtg ggggggaaag    720

gctccaggcg cggtggagct ctgaccagga gaatgcacac actcggaggg gaggaggcgt    780

gtcagcccca agctagcatc ccacccgggg agcagcgatg tggggcgaag gtagccagag    840

caaaagagca ggcaccaggt gacacgaaac agaagattcc gggtagagcc agaaccccag    900

aagtcccatt cagggaaggt gcgaggcgag aacgagttag gtggaccctc tccaggggca    960

gccaaagaaa tctaaagaga acccgaagga cttgccggaa agagaaaccg aaagcggcgg   1020

tgggcgggat cggtgggcgg ggcctccctg gtttaagagc ttgatgcagg ggcgggcagc   1080

agcagagaga actgcggccg tggcagcggc acggctcccg gccccggagc atgcgcgaca   1140

gcagccccgg aacccccagc cgcggcgccc cgcgtcccgc cgccaggtga gccgaggcag   1200

ctgcgaagga gcaggcggga ggggatggga ggaaggggag cagagcctgg caggactatc   1260

ctcgcagact gcatggcggg gtcgtggatg ctatgcctct ggcgcccgcc ccaccggctg   1320
```

-continued

```
gcccaggcgg cccctcgcgc gcgcggggcg ccgtcagccc ctcctctccg gccctgagcc   1380

cggatcgtcc gcccgggttc cagttcccgg cgtggccagt aggcggcaac cgcgaggcgg   1440

caagccaccc agcggggacg gcctggagtc gggcccctct ccacgccccc ttctccacgc   1500

gcgcggggag gcagggctcc accgccagtc tggaagggtt ccacatacag gaacggccta   1560

cttcgcagat gagcccaccg aggctcaggc tccgggcgga ttctgcgtgt caccctcgct   1620

ccttggggtc cgctggccgg cctgtgccac ccggacgccc ggttcactgc ctctgtctcc   1680

cccatcagcg cagccccgga cgctatggcc cacccctcca gctggcccct cgagtaggat   1740

ggtagcacgt aaccaggtgg aagccgacaa tgcgatctcc ccggcatcag agccccgacg   1800

gcggccagag ccatcctcgt cctcgtcttc gtcctcgccg gcggccccgg cgcgtccccg   1860

gccctgcccg gtggtcccgg ccccggctcc gggcgacact cacttccgca ccttccgctc   1920

ccactctgat accggcgca tcacgcggac cagcgctctc ctggacgcct gcggcttcta   1980

ctggggaccc ctgagcgtgc atggggcgca cgaacggctg cgttccgaac ccgtgggcac   2040

cttcttggtg cgcgacagtc gccagcggaa ctgcttcttc gcgctcagcg tgaagatggc   2100

ttcgggcccc acgagcattc gtgtgcactt ccaggccggc cgcttccacc tggacggcaa   2160

ccgcgagacc ttcgactgcc tcttcgagct gctggagcac tacgtggcgg cgccgcgccg   2220

catgttgggg gccccactgc gccagcgccg cgtgcggccg ctgcaggagc tgtgtcgcca   2280

gcgcatcgtg gccgccgtgg gtcgcgagaa cctggcacgc atccctctta acccggtact   2340

ccgtgactac ctgagttcct tccccttcca gatctgaccg gctgccgccg tgcccgcaga   2400

attaagtggg agcgccttat tatttcttat tattaattat tattattttt ctggaaccac   2460

gtgggagccc tccccgccta ggtcggaggg agtgggtgtg gagggtgaga tccctcccac   2520

ttctggctgg agaccttatc ccgcctctcg gggggcctcc cctcctggtg ctccctcccg   2580

gtccccctgg ttgtagcagc ttgtgtctgg ggccaggacc tgaactccac gcctacctct   2640

ccatgtttac atgttcccag tatctttgca caaaccaggg gtgggggagg gtctctggct   2700

tcatttttct gctgtgcaga atattctatt ttatattttt acatccagtt tagataataa   2760

actttattat gaaagttttt ttttttaaag aaacaaagat ttctaga                 2807
```

<210> SEQ ID NO 12
<211> LENGTH: 212
<212> TYPE: PRT
<213> ORGANISM: Rattus norvegicus

<400> SEQUENCE: 12

```
Met Val Ala Arg Asn Gln Val Glu Ala Asp Asn Ala Ile Ser Pro Ala
  1               5                  10                  15

Ser Glu Pro Arg Arg Arg Pro Glu Pro Ser Ser Ser Ser Ser Ser Ser
             20                  25                  30

Ser Pro Ala Ala Pro Ala Arg Pro Arg Pro Cys Pro Val Val Pro Ala
         35                  40                  45

Pro Ala Pro Gly Asp Thr His Phe Arg Thr Phe Arg Ser His Ser Asp
     50                  55                  60

Tyr Arg Arg Ile Thr Arg Thr Ser Ala Leu Leu Asp Ala Cys Gly Phe
 65                  70                  75                  80

Tyr Trp Gly Pro Leu Ser Val His Gly Ala His Glu Arg Leu Arg Ser
                 85                  90                  95

Glu Pro Val Gly Thr Phe Leu Val Arg Asp Ser Arg Gln Arg Asn Cys
            100                 105                 110
```

-continued

```
Phe Phe Ala Leu Ser Val Lys Met Ala Ser Gly Pro Thr Ser Ile Arg
        115                 120                 125

Val His Phe Gln Ala Gly Arg Phe His Leu Asp Gly Asn Arg Glu Thr
    130                 135                 140

Phe Asp Cys Leu Phe Glu Leu Leu Glu His Tyr Val Ala Ala Pro Arg
145                 150                 155                 160

Arg Met Leu Gly Ala Pro Leu Arg Gln Arg Arg Val Arg Pro Leu Gln
                165                 170                 175

Glu Leu Cys Arg Gln Arg Ile Val Ala Ala Val Gly Arg Glu Asn Leu
            180                 185                 190

Ala Arg Ile Pro Leu Asn Pro Val Leu Arg Asp Tyr Leu Ser Ser Phe
        195                 200                 205

Pro Phe Gln Ile
    210


<210> SEQ ID NO 13
<211> LENGTH: 1611
<212> TYPE: DNA
<213> ORGANISM: Mus musculus
<220> FEATURE:
<221> NAME/KEY: CDS
<222> LOCATION: (263)..(1525)

<400> SEQUENCE: 13

cgaattccgg gcgggctgtg tgagtctgtg agtggaaggc gcgccggctc ttttgtctga     60

gtgtgacccg gtggctttgt tccaggcatt ccggtgattt cctccgggca gtccgcagaa    120

gccgcagcgg ccgcccgcgc tctctctgca gtctccacac ccgggagagc ctgagcccgc    180

gtcacgcccc tcagcccccg ctgagtccct tctctgttgt cgcgtccgaa tcgagttccc    240

ggaatcagac ggtgccccat ag atg gcc agc ttt ccc ccg agg gtt aac gag     292
                         Met Ala Ser Phe Pro Pro Arg Val Asn Glu
                         1               5                   10

aaa gag atc gtg aga tca cgt act ata ggg gaa ctc ttg gct cca gca      340
Lys Glu Ile Val Arg Ser Arg Thr Ile Gly Glu Leu Leu Ala Pro Ala
                15                  20                  25

gct cct ttt gac aag aaa tgt ggt ggt gag aac tgg acg gtt gct ttt      388
Ala Pro Phe Asp Lys Lys Cys Gly Gly Glu Asn Trp Thr Val Ala Phe
            30                  35                  40

gct cct gat ggt tcc tac ttt gcg tgg tca caa gga tat cgc ata gtg      436
Ala Pro Asp Gly Ser Tyr Phe Ala Trp Ser Gln Gly Tyr Arg Ile Val
        45                  50                  55

aag ctt gtc ccg tgg tcc cag tgc cgt aag aac ttt ctt ttg cat ggt      484
Lys Leu Val Pro Trp Ser Gln Cys Arg Lys Asn Phe Leu Leu His Gly
    60                  65                  70

tcc aaa aat gtt acc aat tca agc tgt cta aaa ttg gca aga caa aac      532
Ser Lys Asn Val Thr Asn Ser Ser Cys Leu Lys Leu Ala Arg Gln Asn
75                  80                  85                  90

agt aat ggt ggt cag aaa aac aag cct cct gag cac gtt ata gac tgt      580
Ser Asn Gly Gly Gln Lys Asn Lys Pro Pro Glu His Val Ile Asp Cys
                95                  100                 105

gga gac ata gtc tgg agt ctt gct ttt ggg tct tca gtt cca gaa aaa      628
Gly Asp Ile Val Trp Ser Leu Ala Phe Gly Ser Ser Val Pro Glu Lys
            110                 115                 120

cag agt cgt tgc gtt aat ata gaa tgg cat cgg ttc cga ttt gga cag      676
Gln Ser Arg Cys Val Asn Ile Glu Trp His Arg Phe Arg Phe Gly Gln
        125                 130                 135

gat cag cta ctc ctt gcc aca gga tta aac aat ggt cgc atc aaa atc      724
Asp Gln Leu Leu Leu Ala Thr Gly Leu Asn Asn Gly Arg Ile Lys Ile
```

-continued

```
    140                 145                 150

tgg gat gta tat aca gga aaa ctc ctc ctt aat ttg gta gac cac att      772
Trp Asp Val Tyr Thr Gly Lys Leu Leu Leu Asn Leu Val Asp His Ile
155                 160                 165                 170

gaa atg gtt aga gat tta act ttt gct cca gat ggg agc tta ctc ctt      820
Glu Met Val Arg Asp Leu Thr Phe Ala Pro Asp Gly Ser Leu Leu Leu
                175                 180                 185

gta tca gct tca aga gac aaa act cta aga gtg tgg gac ctg aaa gat      868
Val Ser Ala Ser Arg Asp Lys Thr Leu Arg Val Trp Asp Leu Lys Asp
            190                 195                 200

gat gga aac atg gtg aaa gta ttg cgg gca cat cag aat tgg gtg tac      916
Asp Gly Asn Met Val Lys Val Leu Arg Ala His Gln Asn Trp Val Tyr
        205                 210                 215

agt tgt gca ttc tct ccc gac tgt tct atg ctg tgt tca gtg ggc gcc      964
Ser Cys Ala Phe Ser Pro Asp Cys Ser Met Leu Cys Ser Val Gly Ala
    220                 225                 230

agt aaa gca gtt ttc ctt tgg aat atg gat aaa tac acc atg att agg     1012
Ser Lys Ala Val Phe Leu Trp Asn Met Asp Lys Tyr Thr Met Ile Arg
235                 240                 245                 250

aag ctg gaa ggt cat cac cat gat gtt gta gct tgt gac ttt tct cct     1060
Lys Leu Glu Gly His His His Asp Val Val Ala Cys Asp Phe Ser Pro
                255                 260                 265

gat gga gca ttg cta gct act gca tcc tat gac act cgt gtg tat gtc     1108
Asp Gly Ala Leu Leu Ala Thr Ala Ser Tyr Asp Thr Arg Val Tyr Val
            270                 275                 280

tgg gat cca cac aat gga gac ctt ctg atg gag ttt ggg cac ctg ttt     1156
Trp Asp Pro His Asn Gly Asp Leu Leu Met Glu Phe Gly His Leu Phe
        285                 290                 295

ccc tcg ccc act cca ata ttt gct gga gga gca aat gac cga tgg gtg     1204
Pro Ser Pro Thr Pro Ile Phe Ala Gly Gly Ala Asn Asp Arg Trp Val
    300                 305                 310

aga gct gtg tct ttc agt cat gat gga ctg cat gtt gcc agc ctt gct     1252
Arg Ala Val Ser Phe Ser His Asp Gly Leu His Val Ala Ser Leu Ala
315                 320                 325                 330

gat gat aaa atg gtg agg ttc tgg aga atc gat gag gat tgt ccg gta     1300
Asp Asp Lys Met Val Arg Phe Trp Arg Ile Asp Glu Asp Cys Pro Val
                335                 340                 345

caa gtt gca cct ttg agc aat ggt ctt tgc tgt gcc ttt tct act gat     1348
Gln Val Ala Pro Leu Ser Asn Gly Leu Cys Cys Ala Phe Ser Thr Asp
            350                 355                 360

ggc agt gtt tta gct gct ggg aca cat gat gga agt gtg tat ttt tgg     1396
Gly Ser Val Leu Ala Ala Gly Thr His Asp Gly Ser Val Tyr Phe Trp
        365                 370                 375

gcc act cca agg caa gtc cct agc ctt caa cat ata tgt cgc atg tca     1444
Ala Thr Pro Arg Gln Val Pro Ser Leu Gln His Ile Cys Arg Met Ser
    380                 385                 390

atc cga aga gtg atg tcc acc caa gaa gtc caa aaa ctg cct gtt cct     1492
Ile Arg Arg Val Met Ser Thr Gln Glu Val Gln Lys Leu Pro Val Pro
395                 400                 405                 410

tcc aaa ata ttg gcg ttt ctc tcc tac cgc ggt tag a ctgaagactg        1539
Ser Lys Ile Leu Ala Phe Leu Ser Tyr Arg Gly
                415                 420

cctttcctgg taggcctgcc agacagagcg ccctttacaa gacacacctc aagctttacc   1599

tcgtgccgaa tt                                                       1611
```

<210> SEQ ID NO 14
<211> LENGTH: 421
<212> TYPE: PRT
<213> ORGANISM: Mus musculus -continued

<400> SEQUENCE: 14

```
Met Ala Ser Phe Pro Pro Arg Val Asn Glu Lys Glu Ile Val Arg Ser
  1               5                  10                  15

Arg Thr Ile Gly Glu Leu Leu Ala Pro Ala Ala Pro Phe Asp Lys Lys
             20                  25                  30

Cys Gly Gly Glu Asn Trp Thr Val Ala Phe Ala Pro Asp Gly Ser Tyr
         35                  40                  45

Phe Ala Trp Ser Gln Gly Tyr Arg Ile Val Lys Leu Val Pro Trp Ser
     50                  55                  60

Gln Cys Arg Lys Asn Phe Leu Leu His Gly Ser Lys Asn Val Thr Asn
 65                  70                  75                  80

Ser Ser Cys Leu Lys Leu Ala Arg Gln Asn Ser Asn Gly Gly Gln Lys
                 85                  90                  95

Asn Lys Pro Pro Glu His Val Ile Asp Cys Gly Asp Ile Val Trp Ser
            100                 105                 110

Leu Ala Phe Gly Ser Ser Val Pro Glu Lys Gln Ser Arg Cys Val Asn
        115                 120                 125

Ile Glu Trp His Arg Phe Arg Phe Gly Gln Asp Gln Leu Leu Leu Ala
    130                 135                 140

Thr Gly Leu Asn Asn Gly Arg Ile Lys Ile Trp Asp Val Tyr Thr Gly
145                 150                 155                 160

Lys Leu Leu Leu Asn Leu Val Asp His Ile Glu Met Val Arg Asp Leu
                165                 170                 175

Thr Phe Ala Pro Asp Gly Ser Leu Leu Leu Val Ser Ala Ser Arg Asp
            180                 185                 190

Lys Thr Leu Arg Val Trp Asp Leu Lys Asp Asp Gly Asn Met Val Lys
        195                 200                 205

Val Leu Arg Ala His Gln Asn Trp Val Tyr Ser Cys Ala Phe Ser Pro
    210                 215                 220

Asp Cys Ser Met Leu Cys Ser Val Gly Ala Ser Lys Ala Val Phe Leu
225                 230                 235                 240

Trp Asn Met Asp Lys Tyr Thr Met Ile Arg Lys Leu Glu Gly His His
                245                 250                 255

His Asp Val Val Ala Cys Asp Phe Ser Pro Asp Gly Ala Leu Leu Ala
            260                 265                 270

Thr Ala Ser Tyr Asp Thr Arg Val Tyr Val Trp Asp Pro His Asn Gly
        275                 280                 285

Asp Leu Leu Met Glu Phe Gly His Leu Phe Pro Ser Pro Thr Pro Ile
    290                 295                 300

Phe Ala Gly Gly Ala Asn Asp Arg Trp Val Arg Ala Val Ser Phe Ser
305                 310                 315                 320

His Asp Gly Leu His Val Ala Ser Leu Ala Asp Asp Lys Met Val Arg
                325                 330                 335

Phe Trp Arg Ile Asp Glu Asp Cys Pro Val Gln Val Ala Pro Leu Ser
            340                 345                 350

Asn Gly Leu Cys Cys Ala Phe Ser Thr Asp Gly Ser Val Leu Ala Ala
        355                 360                 365

Gly Thr His Asp Gly Ser Val Tyr Phe Trp Ala Thr Pro Arg Gln Val
    370                 375                 380

Pro Ser Leu Gln His Ile Cys Arg Met Ser Ile Arg Arg Val Met Ser
385                 390                 395                 400

Thr Gln Glu Val Gln Lys Leu Pro Val Pro Ser Lys Ile Leu Ala Phe
```

-continued

```
            405                 410                 415

Leu Ser Tyr Arg Gly
            420
```

<210> SEQ ID NO 15
<211> LENGTH: 783
<212> TYPE: DNA
<213> ORGANISM: Homo sapiens

<400> SEQUENCE: 15

```
ctgtcttcct ccgcagcgcg aggctgggta cagggtctat tgtctgtggt tgactccgta      60

ctttggtctg aggccttcgg gagctttccc gaggcagtta gcagaagccg cagcgaccgc     120

ccccgcccgt ctcctctgtc cctgggcccg ggagacaaac ttggcgtcac gccctcagcg     180

gtcgccactc tcttctctgt tgttgggtcc gcatcgtatt cccggaatca gacggtgccc     240

catagatggc cagctttccc ccgagggtca acgagaaaga gatcgtgaga tcacgtacta     300

taggtgaact tttagctcct gcagctcctt ttgacaagaa atgtggtcgt gaaaattgga     360

ctgttgcttt tgctccagat ggttcatact ttgcttggtc acaaggacat cgcacagtaa     420

agcttgttcc gtggtcccag tgccttcaga actttctctt gcatggcacc aagaatgtta     480

ccaattcaag cagtttaaga ttgccaagac aaaatagtga tggtggtcag aaaaataagc     540

ctcgtgacat attatagact gtggagatat agtctggagt cttgcttttg ggtcatcagt     600

tccagaaaaa cagagtcgct gtgtaaatat agaatggcat cgcttcagat ttggacaaga     660

tcagctactt cttgctacag ggttgaacaa tgggcgtatc aaaatatggg atgtatatca     720

ggaaactcct ccttaacttg gtagatcata ctgaagtggt cagagattta acttttgctc     780

cag                                                                   783
```

<210> SEQ ID NO 16
<211> LENGTH: 1122
<212> TYPE: DNA
<213> ORGANISM: Homo sapiens

<400> SEQUENCE: 16

```
ctctgtatgt ctgaatgaag ctataacatt tgccttttta ttgcaggttt tcctttggaa      60

tatggataaa tacaccatga tacggaaact agaaggacat caccatgatg tggtagcttg     120

tgacttttct cctgatggag cattactggc tactgcatct tatgatactc gagtatatat     180

ctgggatcca cataatggag acattctgat ggaatttggg cacctgtttc ccccacctac     240

tccaatattt gctggaggag caaatgaccg gtgggtacga tctgtatctt ttagccatga     300

tggactgcat gttgcaagcc ttgctgatga taaaatggtg aggttctgga gaattgatga     360

ggattatcca gtgcaagttg cacctttgag caatggtctt tgctgtgcct tctctactga     420

tggcagtgtt ttagctgctg ggacacatga cggaagtgtg tatttttggg ccactccacg     480

gcaggtccct agcctgcaac atttatgtcg catgtcaatc cgaagagtga tgcccaccca     540

agaagttcag gagctgccga ttccttccaa gcttttggag tttctctcgt atcgtattta     600

gaagattctg ccttccctag tagtagggac tgacagaata cacttaacac aaacctcaag     660

ctttactgac ttcaattatc tgtttttaaa gacgtagaag atttatttaa tttgatatgt     720

tcttgtactg cattttgatc agttgagctt ttaaaatatt atttatagac aatagaagta     780

tttctgaaca tatcaaatat aaattttttt aaagatctaa ctgtgaaaac atacatacct     840

gtacatattt agatataagc tgctatatgt tgaatggacc cttttgcttt tctgattttt     900
```

-continued

```
agttctgaca tgtatatatt gcttcagtag agccacaata tgtatctttg ctgtaaagtg    960

caaggaaatt ttaaattctg ggacactgag ttagatggta aatactgact tacgaaagtt   1020

gaattgggtg aggcgggcaa atcacctgag gtcagcagtt tgagactagc ctggcaaaca   1080

tgatgaaacc ctgtctctac taaaaataca aaaaaaaaaa aa                      1122


<210> SEQ ID NO 17
<211> LENGTH: 2544
<212> TYPE: DNA
<213> ORGANISM: Mus musculus
<220> FEATURE:
<221> NAME/KEY: UNSURE
<222> LOCATION: (320)
<223> OTHER INFORMATION: Xaa is unsure
<220> FEATURE:
<221> NAME/KEY: UNSURE
<222> LOCATION: (451)
<223> OTHER INFORMATION: Xaa is unsure
<220> FEATURE:
<221> NAME/KEY: CDS
<222> LOCATION: (423)..(2030)

<400> SEQUENCE: 17

cggcacgagc cgggctccgt ccggaggaag cgaggctgcg ccgccggccc ggcaggagcg     60

gaggacggga mgcgcgggcg gtcgcgctcg ccctgtcgct gactgcgctg ccccggccca    120

tccttgcctg gccgcaggtg ccctggatga ggccgccgcg cgtgtcccgg ccgctgagtg    180

tcccccgcgg tcgcccggcg cctgccctca agcggccgcc tctccttgcc cgggtccccg    240

ttttcccccg gcgcagtcct cctccggtgg gcgcctccgc acctcggcgc aggcggcacg    300

gccctcgggc cgggatggat ccgccgggaa gaggaagaca agccggggcg ttgagcccct    360

gcgcacggtg ccgccgcgcg tagtgggagc ttactcgcag taggctctcg ctcttctaat    420

ca atg gat aaa gtg ggg aaa atg tgg aac aac tta aaa tac aga tgc       467
   Met Asp Lys Val Gly Lys Met Trp Asn Asn Leu Lys Tyr Arg Cys
     1               5                  10                  15

cag aat ctc ttc agc cac gag gga gga agc cgt aat gag aac gtg gag      515
Gln Asn Leu Phe Ser His Glu Gly Gly Ser Arg Asn Glu Asn Val Glu
                20                  25                  30

atg aac ccc aac aga tgt ccg tct gtc aaa gag aaa agc atc agt ctg      563
Met Asn Pro Asn Arg Cys Pro Ser Val Lys Glu Lys Ser Ile Ser Leu
            35                  40                  45

gga gag gca gct ccc cag caa gag agc agt ccc tta aga gaa aat gtt      611
Gly Glu Ala Ala Pro Gln Gln Glu Ser Ser Pro Leu Arg Glu Asn Val
        50                  55                  60

gcc tta cag ctg gga ctg agc cct tcc aag acc ttt tcc agg cgg aac      659
Ala Leu Gln Leu Gly Leu Ser Pro Ser Lys Thr Phe Ser Arg Arg Asn
    65                  70                  75

caa aac tgt gcc gca gag atc cct caa gtg gtt gaa atc agc atc gag      707
Gln Asn Cys Ala Ala Glu Ile Pro Gln Val Val Glu Ile Ser Ile Glu
 80                  85                  90                  95

aaa gac agt gac tcg ggt gcc acc cca gga acg agg ctt gca cgg aga      755
Lys Asp Ser Asp Ser Gly Ala Thr Pro Gly Thr Arg Leu Ala Arg Arg
                100                 105                 110

gac tcc tac tcg cgg cac gcc ccg tgg gga gga aag aag aaa cat tcc      803
Asp Ser Tyr Ser Arg His Ala Pro Trp Gly Gly Lys Lys Lys His Ser
            115                 120                 125

tgt tcc aca aag acc cag agt tca ttg gat acc gag aaa aag ttt ggt      851
Cys Ser Thr Lys Thr Gln Ser Ser Leu Asp Thr Glu Lys Lys Phe Gly
        130                 135                 140

aga act cga agc ggc ctt cag agg cga gag cgg cgc tat gga gtc agc      899
Arg Thr Arg Ser Gly Leu Gln Arg Arg Glu Arg Arg Tyr Gly Val Ser
```

-continued

```
    145                 150                 155

tcc atg cag gac atg gac agc gtt tct agc cgc gcg gtc ggg agc cgc       947
Ser Met Gln Asp Met Asp Ser Val Ser Ser Arg Ala Val Gly Ser Arg
160                 165                 170                 175

tcc ctg agg cag agg ctc cag gac acg gtg ggt ttg tgt ttt ccc atg       995
Ser Leu Arg Gln Arg Leu Gln Asp Thr Val Gly Leu Cys Phe Pro Met
                180                 185                 190

aga act tac agc aag cag tca aag cca ctc ttt tcc aat aaa aga aaa      1043
Arg Thr Tyr Ser Lys Gln Ser Lys Pro Leu Phe Ser Asn Lys Arg Lys
            195                 200                 205

ata cat ctt tct gaa tta atg ctg gag aaa tgc cct ttt cct gct ggc      1091
Ile His Leu Ser Glu Leu Met Leu Glu Lys Cys Pro Phe Pro Ala Gly
        210                 215                 220

tcg gat tta gca caa aag tgg cat ttg att aaa cag cat acc gcc cct      1139
Ser Asp Leu Ala Gln Lys Trp His Leu Ile Lys Gln His Thr Ala Pro
    225                 230                 235

gtg agc cca cac tca aca ttt ttt gat aca ttt gat cca tca ctg gtg      1187
Val Ser Pro His Ser Thr Phe Phe Asp Thr Phe Asp Pro Ser Leu Val
240                 245                 250                 255

tct aca gaa gat gaa gaa gat agg ctt cgc gag aga aga cgg ctt agt      1235
Ser Thr Glu Asp Glu Glu Asp Arg Leu Arg Glu Arg Arg Arg Leu Ser
                260                 265                 270

atc gaa gaa ggg gtg gat ccc cct ccc aac gca caa ata cac acc ttt      1283
Ile Glu Glu Gly Val Asp Pro Pro Pro Asn Ala Gln Ile His Thr Phe
            275                 280                 285

gaa gct act gca cag gtc aac cca ttg tat aag ctg gga cca aag tta      1331
Glu Ala Thr Ala Gln Val Asn Pro Leu Tyr Lys Leu Gly Pro Lys Leu
        290                 295                 300

gct cct ggg atg aca gag ata agt gga gat ggt tct gca att cca caa      1379
Ala Pro Gly Met Thr Glu Ile Ser Gly Asp Gly Ser Ala Ile Pro Gln
    305                 310                 315

gcs aat tgt gac tca gaa gag gat tca acc acc cta tgt ctg cag tca      1427
Xaa Asn Cys Asp Ser Glu Glu Asp Ser Thr Thr Leu Cys Leu Gln Ser
320                 325                 330                 335

cgg agg cag aag cag cgc cag gtg tcc ggg gac agc cac gcg cac gtt      1475
Arg Arg Gln Lys Gln Arg Gln Val Ser Gly Asp Ser His Ala His Val
                340                 345                 350

agc aga cag gga gct tgg aaa gtt cat acg cag atc gat tac ata cac      1523
Ser Arg Gln Gly Ala Trp Lys Val His Thr Gln Ile Asp Tyr Ile His
            355                 360                 365

tgc ctc gtg cca gat ttg ctt cag atc aca ggg aat ccc tgt tac tgg      1571
Cys Leu Val Pro Asp Leu Leu Gln Ile Thr Gly Asn Pro Cys Tyr Trp
        370                 375                 380

ggc gtg atg gac cga tac gag gcc gaa gcc ctt cta gaa ggg aaa ccg      1619
Gly Val Met Asp Arg Tyr Glu Ala Glu Ala Leu Leu Glu Gly Lys Pro
    385                 390                 395

gaa ggc acg ttc ttg ctc agg gac tct gca cag gag gac tac ctc ttc      1667
Glu Gly Thr Phe Leu Leu Arg Asp Ser Ala Gln Glu Asp Tyr Leu Phe
400                 405                 410                 415

tct gtg agc ttc cgc cgc tac aac agg tct ctg cac gcc cgg atc gag      1715
Ser Val Ser Phe Arg Arg Tyr Asn Arg Ser Leu His Ala Arg Ile Glu
                420                 425                 430

cag tgg aac cac aac ttc agc ttc gat gcc cat gac ccc tgc gtg ttt      1763
Gln Trp Asn His Asn Phe Ser Phe Asp Ala His Asp Pro Cys Val Phe
            435                 440                 445

cac tcc tcc acw gtc acg ggg ctt ctc gaa cac tat aaa gac ccc agc      1811
His Ser Ser Xaa Val Thr Gly Leu Leu Glu His Tyr Lys Asp Pro Ser
        450                 455                 460

tct tgc atg ttt ttt gaa ccg ttg cta acg ata tca ctg aat aga act      1859
```

-continued

```
Ser Cys Met Phe Phe Glu Pro Leu Leu Thr Ile Ser Leu Asn Arg Thr
    465                 470                 475

ttc cct ttc agc ctg cag tat atc tgc cgc gca gtg atc tgc aga tgc     1907
Phe Pro Phe Ser Leu Gln Tyr Ile Cys Arg Ala Val Ile Cys Arg Cys
480                 485                 490                 495

act acg tat gat ggg att gac ggg ctc ccg cta ccg tcg atg tta cag     1955
Thr Thr Tyr Asp Gly Ile Asp Gly Leu Pro Leu Pro Ser Met Leu Gln
                500                 505                 510

gat ttt tta aaa gag tat cat tat aaa caa aaa gtt agg gtt cgc tgg     2003
Asp Phe Leu Lys Glu Tyr His Tyr Lys Gln Lys Val Arg Val Arg Trp
            515                 520                 525

tta gaa cga gar cca gtc aaa gca aag taactcctgt ccccaaaggg          2050
Leu Glu Arg Xaa Pro Val Lys Ala Lys
        530                 535

cactaactaa gtctgctcct cccgtgcatc mgaactgcac ccataggrag gcagtcagct   2110

gctaggattt cccacccaga atgggagctt agtcattagc ctctgcccta tggggtccgc   2170

tgttcctcag acaaaggtgc ctagggacag caagatggct tgcaggtgtt cggtgggctg   2230

tgacaactga gggaggcaac tctggggcat ttgctatgaa gaattctatt tcttaccgaa   2290

gaacaaatta ttaatattgg atgggtattt caatagtgtg actaatgttt gaaattattt   2350

tttctaagaa tttttctata accttcagaa aaagtagtga tgtttgtagt tactataaat   2410

caagctttga aagttcaaaa caaacaagtt aaataaaaga ctaccttcct tttagagaaa   2470

acaaatgcaa gttttcccag ccacaggcat tgtgcactgt taatgttagc ttgttatcag   2530

ctcctttctc ctcc                                                     2544


<210> SEQ ID NO 18
<211> LENGTH: 536
<212> TYPE: PRT
<213> ORGANISM: Mus musculus
<220> FEATURE:
<221> NAME/KEY: UNSURE
<222> LOCATION: (320)
<223> OTHER INFORMATION: Xaa is unsure
<220> FEATURE:
<221> NAME/KEY: UNSURE
<222> LOCATION: (451)
<223> OTHER INFORMATION: Xaa is unsure
<220> FEATURE:
<221> NAME/KEY: UNSURE
<222> LOCATION: (531)
<223> OTHER INFORMATION: Xaa is unsure

<400> SEQUENCE: 18

Met Asp Lys Val Gly Lys Met Trp Asn Asn Leu Lys Tyr Arg Cys Gln
  1               5                  10                  15

Asn Leu Phe Ser His Glu Gly Gly Ser Arg Asn Glu Asn Val Glu Met
            20                  25                  30

Asn Pro Asn Arg Cys Pro Ser Val Lys Glu Lys Ser Ile Ser Leu Gly
        35                  40                  45

Glu Ala Ala Pro Gln Gln Glu Ser Ser Pro Leu Arg Glu Asn Val Ala
     50                  55                  60

Leu Gln Leu Gly Leu Ser Pro Ser Lys Thr Phe Ser Arg Arg Asn Gln
 65                  70                  75                  80

Asn Cys Ala Ala Glu Ile Pro Gln Val Val Glu Ile Ser Ile Glu Lys
                 85                  90                  95

Asp Ser Asp Ser Gly Ala Thr Pro Gly Thr Arg Leu Ala Arg Arg Asp
            100                 105                 110

Ser Tyr Ser Arg His Ala Pro Trp Gly Gly Lys Lys Lys His Ser Cys
```

-continued

```
        115                 120                 125

Ser Thr Lys Thr Gln Ser Ser Leu Asp Thr Glu Lys Lys Phe Gly Arg
    130                 135                 140

Thr Arg Ser Gly Leu Gln Arg Arg Glu Arg Arg Tyr Gly Val Ser Ser
145                 150                 155                 160

Met Gln Asp Met Asp Ser Val Ser Ser Arg Ala Val Gly Ser Arg Ser
                165                 170                 175

Leu Arg Gln Arg Leu Gln Asp Thr Val Gly Leu Cys Phe Pro Met Arg
            180                 185                 190

Thr Tyr Ser Lys Gln Ser Lys Pro Leu Phe Ser Asn Lys Arg Lys Ile
        195                 200                 205

His Leu Ser Glu Leu Met Leu Glu Lys Cys Pro Phe Pro Ala Gly Ser
    210                 215                 220

Asp Leu Ala Gln Lys Trp His Leu Ile Lys Gln His Thr Ala Pro Val
225                 230                 235                 240

Ser Pro His Ser Thr Phe Phe Asp Thr Phe Asp Pro Ser Leu Val Ser
                245                 250                 255

Thr Glu Asp Glu Glu Asp Arg Leu Arg Glu Arg Arg Arg Leu Ser Ile
            260                 265                 270

Glu Glu Gly Val Asp Pro Pro Pro Asn Ala Gln Ile His Thr Phe Glu
        275                 280                 285

Ala Thr Ala Gln Val Asn Pro Leu Tyr Lys Leu Gly Pro Lys Leu Ala
    290                 295                 300

Pro Gly Met Thr Glu Ile Ser Gly Asp Gly Ser Ala Ile Pro Gln Xaa
305                 310                 315                 320

Asn Cys Asp Ser Glu Glu Asp Ser Thr Thr Leu Cys Leu Gln Ser Arg
                325                 330                 335

Arg Gln Lys Gln Arg Gln Val Ser Gly Asp Ser His Ala His Val Ser
            340                 345                 350

Arg Gln Gly Ala Trp Lys Val His Thr Gln Ile Asp Tyr Ile His Cys
        355                 360                 365

Leu Val Pro Asp Leu Leu Gln Ile Thr Gly Asn Pro Cys Tyr Trp Gly
    370                 375                 380

Val Met Asp Arg Tyr Glu Ala Glu Ala Leu Leu Glu Gly Lys Pro Glu
385                 390                 395                 400

Gly Thr Phe Leu Leu Arg Asp Ser Ala Gln Glu Asp Tyr Leu Phe Ser
                405                 410                 415

Val Ser Phe Arg Arg Tyr Asn Arg Ser Leu His Ala Arg Ile Glu Gln
            420                 425                 430

Trp Asn His Asn Phe Ser Phe Asp Ala His Asp Pro Cys Val Phe His
        435                 440                 445

Ser Ser Xaa Val Thr Gly Leu Leu Glu His Tyr Lys Asp Pro Ser Ser
    450                 455                 460

Cys Met Phe Phe Glu Pro Leu Leu Thr Ile Ser Leu Asn Arg Thr Phe
465                 470                 475                 480

Pro Phe Ser Leu Gln Tyr Ile Cys Arg Ala Val Ile Cys Arg Cys Thr
                485                 490                 495

Thr Tyr Asp Gly Ile Asp Gly Leu Pro Leu Pro Ser Met Leu Gln Asp
            500                 505                 510

Phe Leu Lys Glu Tyr His Tyr Lys Gln Lys Val Arg Val Arg Trp Leu
        515                 520                 525

Glu Arg Xaa Pro Val Lys Ala Lys
    530                 535
```

-continued

```
<210> SEQ ID NO 19
<211> LENGTH: 1221
<212> TYPE: DNA
<213> ORGANISM: Homo sapiens

<400> SEQUENCE: 19

gattaaacag catacagctc ctgtgagccc acattcaaca ttttttgata ctttgatcca      60

tctttggttt ctacagaaga tgaagaagat aggcttagag agagaaggcg gcttagtatt     120

gaagaagggg ttgatccccc tcccaatgca caaatacata catttgaagc tactgcacag     180

gttaatccat tattaaactg ggaccaaaat tagctcctgg aatgactgaa ataagtgggg     240

acagttctgc aattccacaa gctaattgtg actcggaaga ggatacaacc accctgtgtt     300

gcagtcacgg aggcagaagc agcgtcagat atctggagac agccataccc atgttagcag     360

acagggagct tggaaagtcc acacacagat tgattacata cactgcttcg tgcctgattt     420

gcttcaaatt acagggaatc cctgttactg gggagtgatg gaccgttatg aagcagaagc     480

ccttctcgaa gggaaacctg aaggcacgtt tttgctcagg gactctgcgc aagaggacta     540

cttcttctct gtgagcttcc gccgatacaa cagatccctg catgcccgaa ttgagcagtg     600

gaatcacaac tttagtttcg acgcccatga cccgtgtgta tttcactcct ccactgtaac     660

gggactttta gaacattata aagatcccag ttcgtgcatg ttttttgaac cattgcttac     720

tatatcacta aataggactt tcccttttag cctgcagtat atctgtcgcg cggtaatctg     780

caggtgcact acgtatgatg gaattgatgg gctccctcta ccctcaatgt tacaggattt     840

tttaaaagag tatcattata aacaaaaagt tagagttcgc tggttggaac gagaaccagt     900

caaggcaaag taaactctcc ggtccccaaa gggtgttaac taggtccgct ttcatgtgca     960

tcagacagta cacctatagc aagcacacgt agcagtgtta ggctttttca tacagtatgt    1020

aagcttagtg ttagtatctg tcagatgcta cctgctgtta cttattcaga taaacatggt    1080

gcctattgga acaatagcgg atagagctac aggtgttcag taagactaca aaaacatttt    1140

gcctatttcg ctaacagttt ggtttttaat ggctgtggta tttgagtgag gcaactctgg    1200

ggcatttgtt atgaagaaat g                                              1221


<210> SEQ ID NO 20
<211> LENGTH: 2369
<212> TYPE: DNA
<213> ORGANISM: Mus musculus
<220> FEATURE:
<221> NAME/KEY: CDS
<222> LOCATION: (116)..(1327)

<400> SEQUENCE: 20

ggcacgaggc ggtggtggcg gcggcgggcg cggccgcggc ggggcgggcg cggaatgaag      60

gcccacggcc ctgggggctg aggcgcccgc cgcctggggc gggccgcgcg tcctc atg      118
                                                             Met
                                                               1

gag gcc gga gag gag ccg ctg ctg ctg gct gaa ctc aag cct ggg cgc      166
Glu Ala Gly Glu Glu Pro Leu Leu Leu Ala Glu Leu Lys Pro Gly Arg
              5                  10                  15

ccc cac cag ttc gac tgg aag tca agc tgc gag acc tgg agc gtg gcc      214
Pro His Gln Phe Asp Trp Lys Ser Ser Cys Glu Thr Trp Ser Val Ala
         20                  25                  30

ttc tcg cca gac ggt tcc tgg ttc gcc tgg tct caa gga cac tgc gtg      262
Phe Ser Pro Asp Gly Ser Trp Phe Ala Trp Ser Gln Gly His Cys Val
     35                  40                  45
```

-continued

```
gtc aag ctg gtc ccc tgg ccc tta gag gaa cag ttc atc cct aaa gga      310
Val Lys Leu Val Pro Trp Pro Leu Glu Glu Gln Phe Ile Pro Lys Gly
 50                  55                  60                  65

ttc gaa gcc aag agc cga agc agc aag aat gac cca aaa gga cgg ggc      358
Phe Glu Ala Lys Ser Arg Ser Ser Lys Asn Asp Pro Lys Gly Arg Gly
                 70                  75                  80

agt ctg aag gag aag acg ctg gac tgt ggc cag att gtg tgg ggg ctg      406
Ser Leu Lys Glu Lys Thr Leu Asp Cys Gly Gln Ile Val Trp Gly Leu
             85                  90                  95

gcc ttc agc ccg tgg ccc tct cca ccc agc agg aaa ctc tgg gca cgt      454
Ala Phe Ser Pro Trp Pro Ser Pro Pro Ser Arg Lys Leu Trp Ala Arg
        100                 105                 110

cac cat ccc cag gcg cct gat gtt tct tgc ctg atc ctg gcc aca ggt      502
His His Pro Gln Ala Pro Asp Val Ser Cys Leu Ile Leu Ala Thr Gly
    115                 120                 125

ctc aac gat ggg cag atc aag att tgg gag gta cag aca ggc ctc ctg      550
Leu Asn Asp Gly Gln Ile Lys Ile Trp Glu Val Gln Thr Gly Leu Leu
130                 135                 140                 145

ctt ctg aat ctt tct ggc cac caa gac gtc gtg aga gat ctg agc ttc      598
Leu Leu Asn Leu Ser Gly His Gln Asp Val Val Arg Asp Leu Ser Phe
                150                 155                 160

acg ccc agc ggc agt ttg att ttg gtc tct gca tcc cgg gat aag aca      646
Thr Pro Ser Gly Ser Leu Ile Leu Val Ser Ala Ser Arg Asp Lys Thr
            165                 170                 175

ctt cga att tgg gac ctg aat aaa cac ggt aag cag atc cag gtg tta      694
Leu Arg Ile Trp Asp Leu Asn Lys His Gly Lys Gln Ile Gln Val Leu
        180                 185                 190

tcc ggc cat ctg cag tgg gtt tac tgc tgc tcc atc tcc cct gac tgt      742
Ser Gly His Leu Gln Trp Val Tyr Cys Cys Ser Ile Ser Pro Asp Cys
    195                 200                 205

agc atg ctg tgc tct gca gct ggg gag aag tcg gtc ttt ctg tgg agc      790
Ser Met Leu Cys Ser Ala Ala Gly Glu Lys Ser Val Phe Leu Trp Ser
210                 215                 220                 225

atg cgg tcc tac aca cta atc cgg aaa cta gaa ggc cac caa agc agt      838
Met Arg Ser Tyr Thr Leu Ile Arg Lys Leu Glu Gly His Gln Ser Ser
                230                 235                 240

gtt gtc tcc tgt gat ttc tct cct gat tca gcc ttg ctt gtc aca gct      886
Val Val Ser Cys Asp Phe Ser Pro Asp Ser Ala Leu Leu Val Thr Ala
            245                 250                 255

tcg tat gac acc agt gtg att atg tgg gac ccc tac acc ggc gcg agg      934
Ser Tyr Asp Thr Ser Val Ile Met Trp Asp Pro Tyr Thr Gly Ala Arg
        260                 265                 270

ctg agg tca ctt cat cac aca caa ctt gaa ccc acc atg gat gac agt      982
Leu Arg Ser Leu His His Thr Gln Leu Glu Pro Thr Met Asp Asp Ser
    275                 280                 285

gac gtc cac atg agc tcc ctg agg tcc gtg tgc ttc tca cct gaa ggc     1030
Asp Val His Met Ser Ser Leu Arg Ser Val Cys Phe Ser Pro Glu Gly
290                 295                 300                 305

ttg tat ctc gct acg gtg gca gat gac agg ctg ctc agg atc tgg gct     1078
Leu Tyr Leu Ala Thr Val Ala Asp Asp Arg Leu Leu Arg Ile Trp Ala
                310                 315                 320

ctg gaa ctg aag gct ccg gtt gcc ttt gct ccg atg acc aat ggt ctt     1126
Leu Glu Leu Lys Ala Pro Val Ala Phe Ala Pro Met Thr Asn Gly Leu
            325                 330                 335

tgc tgc acg ttc ttc cca cac ggt gga att att gcc aca ggg acg aga     1174
Cys Cys Thr Phe Phe Pro His Gly Gly Ile Ile Ala Thr Gly Thr Arg
        340                 345                 350

gat ggc cat gtc cag ttc tgg aca gct ccc cgg gtc ctg tcc tca ctg     1222
Asp Gly His Val Gln Phe Trp Thr Ala Pro Arg Val Leu Ser Ser Leu
```

-continued

```
    355                 360                 365

aag cac tta tgc agg aaa gcc ctc cga agt ttc ctg aca acg tat caa      1270
Lys His Leu Cys Arg Lys Ala Leu Arg Ser Phe Leu Thr Thr Tyr Gln
370                 375                 380                 385

gtc cta gca ctg cca atc ccc aag aag atg aaa gag ttc ctc aca tac      1318
Val Leu Ala Leu Pro Ile Pro Lys Lys Met Lys Glu Phe Leu Thr Tyr
                390                 395                 400

agg act ttc tagcagtgcc ggctccccca cctcctgcag cagcagcagt              1367
Arg Thr Phe

acaagggact ggctaggatg gagtcaggca gctcacactg gaccagtgtg gaccttcctt   1427

cctcccatgg catgtgcaag taggtctgcg tgaccccact tctgtggtgc cggccttacc   1487

tcgtcttcat ccgtggtgag cagccttcgt cagtctagtt gtgttgaagc caagtgcagt   1547

tgtggatgtt gctggggtaa taaaggcaag cgggctccag agcctctctg gtggcggcca   1607

agccacactc ccttaactgg gaagtacctg ccacgtaggg catttctgct gcctatttcc   1667

agccagcggc tgcatggttt gaagttcctc cgttgtggtc agaagaactc tggtgtttgg   1727

ttccctgctc agctgcgcgt ggactgggct gagctcctca ccatacacta gtgccggctt   1787

ttgtttcctg taaacagtgg ttgcatgtgt agagaagtaa caagcgagta ttcagatcat   1847

acgaggaggc gttcctcggt gcatgacggt cagatggcca tttatcagca tatttatttg   1907

tattttctca gcacatagta aggtacaact gtgttttctc aattgtctcg aaaaaacaga   1967

gttcttaagt ggcccagttg tggagccaag tctaagtcgt gtggagtcag tgctgacatc   2027

actggcttgt gctgtctgtc acatgtgttt gtctctgctg cttgacctca tgggatgtac   2087

cctccagttc aactgcccaa aacagacagc cccttccaag caccgttctt tgacagcggt   2147

agcagctacc tattcaagac gcctcacaca aaatctgcct tagaaagtta atatatttta   2207

aattatttta aaagaaactc aacatcttat tctttggcct ttcttaattg atgctttatg   2267

gaggcagtgt taacattgta cagtgtatgc atagaggagt ctcctctatt tgaagaacaa   2327

tgcaaaatga ggctttcatt gaagggaaaa aaaaaaaaaa aa                       2369


<210> SEQ ID NO 21
<211> LENGTH: 404
<212> TYPE: PRT
<213> ORGANISM: Mus musculus

<400> SEQUENCE: 21

Met Glu Ala Gly Glu Glu Pro Leu Leu Leu Ala Glu Leu Lys Pro Gly
  1               5                  10                  15

Arg Pro His Gln Phe Asp Trp Lys Ser Ser Cys Glu Thr Trp Ser Val
             20                  25                  30

Ala Phe Ser Pro Asp Gly Ser Trp Phe Ala Trp Ser Gln Gly His Cys
         35                  40                  45

Val Val Lys Leu Val Pro Trp Pro Leu Glu Glu Gln Phe Ile Pro Lys
     50                  55                  60

Gly Phe Glu Ala Lys Ser Arg Ser Ser Lys Asn Asp Pro Lys Gly Arg
 65                  70                  75                  80

Gly Ser Leu Lys Glu Lys Thr Leu Asp Cys Gly Gln Ile Val Trp Gly
                 85                  90                  95

Leu Ala Phe Ser Pro Trp Pro Ser Pro Pro Ser Arg Lys Leu Trp Ala
            100                 105                 110

Arg His His Pro Gln Ala Pro Asp Val Ser Cys Leu Ile Leu Ala Thr
        115                 120                 125
```

-continued

```
Gly Leu Asn Asp Gly Gln Ile Lys Ile Trp Glu Val Gln Thr Gly Leu
    130                 135                 140

Leu Leu Leu Asn Leu Ser Gly His Gln Asp Val Val Arg Asp Leu Ser
145                 150                 155                 160

Phe Thr Pro Ser Gly Ser Leu Ile Leu Val Ser Ala Ser Arg Asp Lys
                165                 170                 175

Thr Leu Arg Ile Trp Asp Leu Asn Lys His Gly Lys Gln Ile Gln Val
            180                 185                 190

Leu Ser Gly His Leu Gln Trp Val Tyr Cys Cys Ser Ile Ser Pro Asp
        195                 200                 205

Cys Ser Met Leu Cys Ser Ala Ala Gly Glu Lys Ser Val Phe Leu Trp
    210                 215                 220

Ser Met Arg Ser Tyr Thr Leu Ile Arg Lys Leu Glu Gly His Gln Ser
225                 230                 235                 240

Ser Val Val Ser Cys Asp Phe Ser Pro Asp Ser Ala Leu Leu Val Thr
                245                 250                 255

Ala Ser Tyr Asp Thr Ser Val Ile Met Trp Asp Pro Tyr Thr Gly Ala
            260                 265                 270

Arg Leu Arg Ser Leu His His Thr Gln Leu Glu Pro Thr Met Asp Asp
        275                 280                 285

Ser Asp Val His Met Ser Ser Leu Arg Ser Val Cys Phe Ser Pro Glu
    290                 295                 300

Gly Leu Tyr Leu Ala Thr Val Ala Asp Asp Arg Leu Leu Arg Ile Trp
305                 310                 315                 320

Ala Leu Glu Leu Lys Ala Pro Val Ala Phe Ala Pro Met Thr Asn Gly
                325                 330                 335

Leu Cys Cys Thr Phe Phe Pro His Gly Gly Ile Ile Ala Thr Gly Thr
            340                 345                 350

Arg Asp Gly His Val Gln Phe Trp Thr Ala Pro Arg Val Leu Ser Ser
        355                 360                 365

Leu Lys His Leu Cys Arg Lys Ala Leu Arg Ser Phe Leu Thr Thr Tyr
    370                 375                 380

Gln Val Leu Ala Leu Pro Ile Pro Lys Lys Met Lys Glu Phe Leu Thr
385                 390                 395                 400

Tyr Arg Thr Phe


<210> SEQ ID NO 22
<211> LENGTH: 1246
<212> TYPE: DNA
<213> ORGANISM: Homo sapiens

<400> SEQUENCE: 22

gacactgcat cgtcaaactg atcccctggc cgttggagga gcagttcatc cctaaagggt     60

ttgaagccaa aagccgaagt agcaaaaatg agacgaaagg gcggggcagc ccaaaagaga    120

agacgctgga ctgtggtcag attgtctggg ggctggcctt cagcctgtgc tttccccacc    180

cagcaggaag ctctgggcac gccaccaccc ccaagtgccc gatgtctctt gcctggttct    240

tgctacggga ctcaacgatg ggcagatcaa gatctgggag gtgcagacag ggctcctgct    300

tttgaatctt tccggccacc aagatgtcgt gagagatctg agcttcacac ccagtggcag    360

tttgattttg gtctccgcgt cacgggataa gactcttcgc atctgggacc tgaataaaca    420

cggtaaacag attcaagtgt tatcgggcca cctgcagtgg gtttactgct gttccatctc    480

cccagactgc agcatgctgt gctctgcagc tggagagaag tcggtctttc tatggagcat    540
```

-continued

```
gaggtcctac acgttaattc ggaagctaga gggccatcaa agcagtgttg tctcttgtga    600

cttctccccc gactctgccc tgcttgtcac ggcttcttac gataccaatg tgattatgtg    660

ggacccctac accggcgaaa ggctgaggtc actccaccac acccaggttg accccgccat    720

ggatgacagt gacgtccaca ttagctcact gagatctgtg tgcttctctc cagaaggctt    780

gtaccttgcc acggtggcag atgacagact cctcaggatc tgggccctgg aactgaaaac    840

tcccattgca tttgctccta tgaccaatgg gctttgctgg cacatttttt ccacatggtg    900

gagtcattgc cacagggaca agagatggcc acgtccagtt ctggacagct cctagggtcc    960

tgtcctcact gaagcactta tgccggaaag cccttcgaag tttcctaaca acttaccaag   1020

tcctagcact gccaatcccc aagaaaatga aagagttcct cacatacagg actttttaag   1080

caacaccaca tcttgtgctt ctttgtagca gggtaaatcg tcctgtcaaa gggagttgct   1140

ggaataatgg gccaaacatc tggtcttgca ttgaaatagc atttctttgg gattgtgaat   1200

agaatgtagc aaaaccagat tccagtgtac tagtcatgga tttttc                  1246


<210> SEQ ID NO 23
<211> LENGTH: 422
<212> TYPE: DNA
<213> ORGANISM: Homo sapiens

<400> SEQUENCE: 23

accatggttc caagtcctct cccctgtggt caagttgccc gaatgttggg cccaagtgcc     60

ttttcctcct tgggcctccc cttctgacct gcaggacagt tttccggagc ccatttggta    120

tgaggtatta attagcctta actaaattac aggggactca gaggccgtgc tcctgaccga    180

tccagacact attttttttt ttttttttta acaatggtgt gcatgtgcag gaaatgacaa    240

atttgtatgt cagattatac aaggatgtat tcttaaaccg catgactatt cagatggcta    300

ctgagttatc agtggccatt tattagcatc atatttattt gtattttctc aacagatgtt    360

aaggtacaac tgtgtttttc tcgattatct aaaaaccata gtacttaaat tgaaaaaaaa    420

aa                                                                   422


<210> SEQ ID NO 24
<211> LENGTH: 2019
<212> TYPE: DNA
<213> ORGANISM: Mus musculus
<220> FEATURE:
<221> NAME/KEY: UNSURE
<222> LOCATION: (1981)
<223> OTHER INFORMATION: N is unsure
<220> FEATURE:
<221> NAME/KEY: UNSURE
<222> LOCATION: (1992)
<223> OTHER INFORMATION: N is unsure
<220> FEATURE:
<221> NAME/KEY: UNSURE
<222> LOCATION: (2000)
<223> OTHER INFORMATION: N is unsure

<400> SEQUENCE: 24

ggcacgaggc ggggtcaggg cggaggctga ggaccaagta ggcatggcgg agggcgggac     60

cggccccgat ggacgggccg gcccgggacc cgcaggtcct aatctgaagg agtggctgag    120

ggagcagttc tgtgaccatc cactggagca ctgtgacgat acaagactcc atgatgcagc    180

ctatgtaggg gacctccaga ccctcaggaa cctactgcaa gaggagagct accggagccg    240

catcaatgag aagtctgtct ggtgctgcgg ctggcttccc tgcacaccac tgaggatcgc    300

agccactgca ggccatggga actgtgtgga cttcctcata cgcaaagggg ccgaggtgga    360
```

-continued

```
cctggtggat gtcaaggggc agactgccct gtatgtggct gtagtgaacg ggcacttgga    420

gagcactgag atccttttgg aagctggtgc tgatcccaac ggcagccggc accaccgcag    480

cactcctgtg taccatgcct ytcgtgtggg tagggacgac atcctgaagg ctcttatcag    540

gtatggggca gatgttgatg tcaaccatca tctgaattct gacacccggc cccctttttc    600

acggcggcta acctccttgg tggtctgtcc tctatacatc agtgctgcct accataacct    660

tcagtgcttc aggctgctct tgcaggctgg ggcaaatcct gacttcaatt gcaatggccc    720

tgtcaacacc caggagttct acaggggatc ccctgggtgt gtcatggatg ctgtcctgcg    780

ccatggctgt gaagcagcct tcgtgagtct gttggtagag tttggagcca acctgaacct    840

ggtgaagtgg gaatccctgg gcccagaggc aagaggcaga agaaagatgg atcctgaggc    900

cttgcaggtc tttaaagagg ccagaagtat tcccaggacc ttgctgagtt tgtgccgggt    960

ggctgtgaga agagctcttg gcaaataccg actgcatctg gttccctcgc tgccgctgcc   1020

agaccccata aagaagtttt tgctttatga gtagcattca catgcagtgc tgactgcaat   1080

gtggaagccg atcacctgca gtgaaaactg acacagactc tggcatcctg ggaaccatgg   1140

cctgtgctgc cagcttgatc cttggctgtc agtgaagaaa aaacggctgt gttctcttgg   1200

actgtgattc tatctcaggt gcttgggcca tcgaacgctc cttgagtcat tgtcaactga   1260

gaggcacata caaacttaat tttgttcctc ttcagtctct ctgttttgga ttcttcctgg   1320

caatgtgtgc agcatgggct gagcctggtg attgccctag tggggaaggc tttttctcc   1380

aggctatgca tctatttatg ttcctacttt gcaatttatt gttcttttaa ggcttgatat   1440

caaaacagaa agaggtttgt taagaaaaga tatagggaga aaggaattcc ggttccgtgc   1500

acttgctagc ctgctttcct tgcctgggtt tgtctgtcta tgctgcctgg tgcacatccc   1560

ttctctttgc tgccactgtt ctattttggg agttgtcttc cgtctaagat ggcttctggg   1620

gttctatctt attgcacaga ggtcccagaa cagtgttcat agggcaccat ctgctctgcc   1680

aagggttttc tgatgtctta ccctggggat cttcagacag tggttacctt taggagaccc   1740

acctggaact aaccattaag tgactgccca cattcagatc agggaccatc ttaatagtac   1800

tcactgccag tcctcacaag agaagatgac acgggtgctc tcttcagaca ctcccataca   1860

ggaagttgga aaatgtcttg gtcacctggg ttgttcccag gctacaactt cttggtgttc   1920

cactaaracc agratatcct agttttttgg gttgactgtt ccctccccac tttccttgaa   1980

ncccaatgcc cntttgtktn ggttgcttcc ctaaaaktt                          2019


<210> SEQ ID NO 25
<211> LENGTH: 350
<212> TYPE: PRT
<213> ORGANISM: Mus musculus
<220> FEATURE:
<221> NAME/KEY: UNSURE
<222> LOCATION: (167)
<223> OTHER INFORMATION: Xaa is unsure

<400> SEQUENCE: 25

Ala Arg Gly Gly Val Arg Ala Glu Ala Glu Asp Gln Val Gly Met Ala
  1               5                  10                  15

Glu Gly Gly Thr Gly Pro Asp Gly Arg Ala Gly Pro Gly Pro Ala Gly
             20                  25                  30

Pro Asn Leu Lys Glu Trp Leu Arg Glu Gln Phe Cys Asp His Pro Leu
         35                  40                  45

Glu His Cys Asp Asp Thr Arg Leu His Asp Ala Ala Tyr Val Gly Asp
```

-continued

```
     50                  55                  60

Leu Gln Thr Leu Arg Asn Leu Leu Gln Glu Glu Ser Tyr Arg Ser Arg
 65                  70                  75                  80

Ile Asn Glu Lys Ser Val Trp Cys Cys Gly Trp Leu Pro Cys Thr Pro
                 85                  90                  95

Leu Arg Ile Ala Ala Thr Ala Gly His Gly Asn Cys Val Asp Phe Leu
            100                 105                 110

Ile Arg Lys Gly Ala Glu Val Asp Leu Val Asp Val Lys Gly Gln Thr
        115                 120                 125

Ala Leu Tyr Val Ala Val Val Asn Gly His Leu Glu Ser Thr Glu Ile
    130                 135                 140

Leu Leu Glu Ala Gly Ala Asp Pro Asn Gly Ser Arg His His Arg Ser
145                 150                 155                 160

Thr Pro Val Tyr His Ala Xaa Arg Val Gly Arg Asp Asp Ile Leu Lys
                165                 170                 175

Ala Leu Ile Arg Tyr Gly Ala Asp Val Asp Val Asn His His Leu Asn
            180                 185                 190

Ser Asp Thr Arg Pro Pro Phe Ser Arg Arg Leu Thr Ser Leu Val Val
        195                 200                 205

Cys Pro Leu Tyr Ile Ser Ala Ala Tyr His Asn Leu Gln Cys Phe Arg
    210                 215                 220

Leu Leu Leu Gln Ala Gly Ala Asn Pro Asp Phe Asn Cys Asn Gly Pro
225                 230                 235                 240

Val Asn Thr Gln Glu Phe Tyr Arg Gly Ser Pro Gly Cys Val Met Asp
                245                 250                 255

Ala Val Leu Arg His Gly Cys Glu Ala Ala Phe Val Ser Leu Leu Val
            260                 265                 270

Glu Phe Gly Ala Asn Leu Asn Leu Val Lys Trp Glu Ser Leu Gly Pro
        275                 280                 285

Glu Ala Arg Gly Arg Arg Lys Met Asp Pro Glu Ala Leu Gln Val Phe
    290                 295                 300

Lys Glu Ala Arg Ser Ile Pro Arg Thr Leu Leu Ser Leu Cys Arg Val
305                 310                 315                 320

Ala Val Arg Arg Ala Leu Gly Lys Tyr Arg Leu His Leu Val Pro Ser
                325                 330                 335

Leu Pro Leu Pro Asp Pro Ile Lys Lys Phe Leu Leu Tyr Glu
            340                 345                 350
```

<210> SEQ ID NO 26
<211> LENGTH: 419
<212> TYPE: DNA
<213> ORGANISM: Homo sapiens

<400> SEQUENCE: 26

```
gcatccatgg cggagggcgg cagcacgacg ggcgggcagg gccgggctcc gcaggtcgta     60

atctgaagga gtggctgagg gagcaatttt gtgatcatcc gctggagcac tgtgaggaca    120

cgaggctcca tgatgcagct tacgtcgggg acctccagac cctcaggagc ctattgcaag    180

aggagagcta ccggagccgc atcaacgaga agtctgtctg gtgctgtggc tggctcccct    240

gcacaccgtt gcgaatcgcg gccactgcag gccatgggag ctgtgtggac ttcctcatcc    300

ggaagggggc cgaggtggat ctggtggacg taaaaggaca gacggccctg tatgtggctg    360

tggtgaacgg gcacctagag agtacccaga tccttctcga agctggcgcg gaccccaac     419
```

-continued

<210> SEQ ID NO 27
<211> LENGTH: 595
<212> TYPE: DNA
<213> ORGANISM: Homo sapiens

<400> SEQUENCE: 27

```
gaggaagaag aaaagtggac cctgaggcct tgcaggtctt taaagaggcc agaagtgttc     60

ccagaacctt gctgtgtctg tgccgtgtgg ctgtgagaag agctcttggc aaaaccggct    120

tcatctgatt ccttcgctgc ctctgccaga ccccataaag aagtttctac tccatgagta    180

gactccaagt gctgcggttg attccagtga gggagaaagt gatctgcagg gaggtggaca    240

ccgagccctg agtgctgtgc tgctgctggt ctcctgatgg ctgttgctgc agaagatgtc    300

ctcgtagact gtcattgctc ctcaggtgcc tgggccgctg aacagtcctt gggtcattgt    360

cagctgagag gcttatacta aagttattat tgtttttccc aagttctctg ttctggattt    420

tcagttgcat attaatgtaa cgggccatgg ggtatgtaca tgtaggggct gaggttggag    480

gcctactaat ttcctgtagg gaagactccc agcacttctg gaactgtgct tctctttatt    540

tttctacttc tcaatttgat ggttcgatta aagccttcta gtatctcaat gaaaa          595
```

<210> SEQ ID NO 28
<211> LENGTH: 896
<212> TYPE: DNA
<213> ORGANISM: Mus musculus
<220> FEATURE:
<221> NAME/KEY: CDS
<222> LOCATION: (4)..(396)
<220> FEATURE:
<221> NAME/KEY: UNSURE
<222> LOCATION: (551)
<223> OTHER INFORMATION: n is unsure
<220> FEATURE:
<221> NAME/KEY: UNSURE
<222> LOCATION: (651)
<223> OTHER INFORMATION: n is unsure

<400> SEQUENCE: 28

```
ctg atg tcc gca att ctg aag gtt gga cac cac tgc tgg ctg cct gtg       48
    Met Ser Ala Ile Leu Lys Val Gly His His Cys Trp Leu Pro Val
      1               5                  10                  15

aca tcc gct gtc aat ccc caa agg atg ctg agg cca cca cca acc gct       96
Thr Ser Ala Val Asn Pro Gln Arg Met Leu Arg Pro Pro Pro Thr Ala
                20                  25                  30

gtt ttc aac tgt gcc gct tgc tgc tgt ctg tgg ggg cag atg ctg atg      144
Val Phe Asn Cys Ala Ala Cys Cys Cys Leu Trp Gly Gln Met Leu Met
            35                  40                  45

aat aca tac cgt gta gtt cag ctt cct gag gag gcc aag ggc ttg gtg      192
Asn Thr Tyr Arg Val Val Gln Leu Pro Glu Glu Ala Lys Gly Leu Val
        50                  55                  60

cca cca gag att cta cag aag tac cat gga ttc tac tct tcc ctc ttt      240
Pro Pro Glu Ile Leu Gln Lys Tyr His Gly Phe Tyr Ser Ser Leu Phe
     65                  70                  75

gcc ttg gtg agg cag ccc agg tcg ctg cag cat ctc tgc cgt tgt gcg      288
Ala Leu Val Arg Gln Pro Arg Ser Leu Gln His Leu Cys Arg Cys Ala
 80                  85                  90                  95

ctc cgc agt cac ctg gag ggc tgt ctg ccc cat gca cta ccg cgc ctt      336
Leu Arg Ser His Leu Glu Gly Cys Leu Pro His Ala Leu Pro Arg Leu
                100                 105                 110

ccc ctg cca ccg cgc atg ctc cgc ttt ctg cag ctg gac ttt gag gat      384
Pro Leu Pro Pro Arg Met Leu Arg Phe Leu Gln Leu Asp Phe Glu Asp
            115                 120                 125

ctg ctc tac taggcttgct gccctgtgaa caaagcagac cccaccccca              433
```

-continued

```
Leu Leu Tyr
        130

ccccaagggc atctctcagc aatgaatgat gcaaggcggt ctgtcttcaa gtcaggagtg    493

gacgccttga tccacacttg agagaagagg ccagatcagc accyggctgg tagtgatngc    553

agagggcacc tgtgcagatc tgtgtgcgca ctggaaatct ctaggctgaa ggcyagagca    613

aatggtgcar gtgttagtcc ttgggangag agacagangg tgagaaagca agacagaggt    673

gagagtgcac atgtcaagtg gtagattgcc ttaaaagaaa gctaaaaaaa gaaaaagatt    733

cgggcgaact tctttagggg taatgctgca gcgtgttaaa ctgactgacc agcgtccata    793

tctttggacc cttcccgggt gaaaaagccc cttcatcctc cagcgctccc caagggtgct    853

tagcaatacc gggtgctttt ctgccgcaaa gtgagttacc aaa                      896


<210> SEQ ID NO 29
<211> LENGTH: 130
<212> TYPE: PRT
<213> ORGANISM: Mus musculus

<400> SEQUENCE: 29

Met Ser Ala Ile Leu Lys Val Gly His His Cys Trp Leu Pro Val Thr
  1               5                  10                  15

Ser Ala Val Asn Pro Gln Arg Met Leu Arg Pro Pro Pro Thr Ala Val
             20                  25                  30

Phe Asn Cys Ala Ala Cys Cys Cys Leu Trp Gly Gln Met Leu Met Asn
         35                  40                  45

Thr Tyr Arg Val Val Gln Leu Pro Glu Glu Ala Lys Gly Leu Val Pro
     50                  55                  60

Pro Glu Ile Leu Gln Lys Tyr His Gly Phe Tyr Ser Ser Leu Phe Ala
 65                  70                  75                  80

Leu Val Arg Gln Pro Arg Ser Leu Gln His Leu Cys Arg Cys Ala Leu
                 85                  90                  95

Arg Ser His Leu Glu Gly Cys Leu Pro His Ala Leu Pro Arg Leu Pro
            100                 105                 110

Leu Pro Pro Arg Met Leu Arg Phe Leu Gln Leu Asp Phe Glu Asp Leu
        115                 120                 125

Leu Tyr
    130


<210> SEQ ID NO 30
<211> LENGTH: 436
<212> TYPE: DNA
<213> ORGANISM: Mus musculus

<400> SEQUENCE: 30

gtgggggcgt catcatgacc tcctctaggg ctctgcaaca tgactcctgt ggtgcaaatc     60

aacaaattgt tcactgatga atccacaagg atctctgggc ctacaaccag gtcctggtcc    120

acatgactgt cgtcttcgga gaaggcacca ctcgcccccg gcaggtacgg ctgacacctc    180

catgggagaa gacgtatcca ggcagcagct gcgcggccct tcaagagggc acatcccgtc    240

atctaaaggc acggtgtact gaaggtagtc ctgagacatg agtccgatta ctacaggcac    300

gtgttcctcc aggtggaggc tcaggtcccc gggtgagctg gggctgcagc gggactcagg    360

gcgcggctct ggctgcaggt ctcgcagctc cctgggctgt agctcccgca gatccttgcg    420

cacaccgttg actggt                                                    436
```

-continued

<210> SEQ ID NO 31
<211> LENGTH: 2180
<212> TYPE: DNA
<213> ORGANISM: Homo sapiens

<400> SEQUENCE: 31
ttaatagtac ctacatagta gaaaattata actccacttt aaaacaatgt tttctttcta 60
ttcaaatcaa tttaaaactt tttataaaca ttaatgttgc aagagaatcc agtccattta 120
tgaaaattag ttgacaatca agttcaccca agaaaatgtt gactaagcta aagaaatcac 180
agataaaaca ttttaccaaa aggataggta acacacaaaa aaatgctatc acaggaagct 240
atgatcatct aatatttctt taataataat tctagttcca taggttttca tgttatgcca 300
atttgtaccc gagtttaatt acagaaaagg caacaatttc taaattggtg gtatacattt 360
ctttacaatt ttttaatgta aggccattta ttaaaataga caaactagaa gatgaaaacg 420
aaggcaacag aaaaattcaa cttttcacaa ccaaaagaat tagcacaacc ttagaaataa 480
tttagaaaaa agtgttgtta aaagatatgt tgcagatctc cgttccatta cccaagatta 540
tgtcaattca cgattctaaa taaatctttt taaagtaaga gattaaaaac tcatcttcag 600
tgtatatgta aattccgtgg ttttatcaca caggtatgtt tattcaacac tgctttggaa 660
atggaccatt taaaaggaca tggcaatttc cattctgtta agtttcattc aacctttact 720
taggggttga ttaccacatg aaatgtgctt ttaatgcata aaaatcacag tggattagcc 780
agcaaaaggg actgggcggg gggggcattg aggagaattt gataattcac attgtgatta 840
ttctgcacat tgatgaaaca taattcacac ctctaaaacc tcaagacttc cctttttttaa 900 agaaccaaaa taaacccaag acaccttgct gacacttccc cacccctaaa caaactgatg 960
actcttttac acataaaact gaaatagtta tggcagcaaa agattttgat ggcaatgaaa 1020
gtttgtaaac tgtatttcaa tctcttgttc ttattcccaa agtgcaagat gcagggttct 1080
caatctttca gtagtgcttc tcctgtaaat aatccttcat tttgtttggc aaaggcagtt 1140
tctgaattaa gtctattctg gtatactgac gtataacaaa acgacacagg tactgcaacg 1200
agcgcaccta tgaaccccgg aacactggtt ggcaagttct gacggaagtg cagattccag 1260
gcagcgagac cttgaataac aaaaagctcc cattttcaga gtccctgatt gaatgctcca 1320
attagatcaa ctatggacgt atgtccttcc acatcggctg ttcataaaag ctaaacctac 1380
catttgagtg ctcaattcta gtgtgaagtg ttttaccatg ggagcgaaag tcacagctta 1440
aaaggtaacg gtcgtcagaa ctgtcccgaa caagaaaaga accatctggc acgtttgcta 1500
gcttcccttc tgcctcccaa cgtgtgattg gtccccagta ccatccttgc tttgcaagtt 1560
ttttcagctc ctctgtaagg cttgtcacaa ccatgggacc actactttgc actgagtcat 1620
aaactcttgc aaccccagga gcagagttcg gatcaaaatt caaatgacag cgcataactt 1680
tcagccacgt ggggctttct gtccagtgag tccactgaaa gttccccttt gggatttgga 1740
ttattcctgc attggagtaa ccaatggtga agattggagg gacatccatc gtgaacccgc 1800
tctccggggt tctgcaacat gactcccgtg gtgccaatca acaagccatt caccggactg 1860
atccacgaag atctctgggg cgacaactag gtcctggtct acctgactct catcctcggg 1920
gaaagcgcgc cctcccactt gaggaggaac cgcagagact tccatgggag aagagctgtc 1980
cagacaatag ctccgtgatc cttccaaagg atacatcccc tcatctaaag gcacagtata 2040
ctgaatgtag tcctgaggca taagtccaat aacgacaggc acatgttcat ccaggtgaag 2100
atgcaggtct ccattatgag aagccgagct cttcagtgaa ttggcttgct cctggcacgt 2160

-continued

```
ggtctcagac tggaggtcgt                                                2180


<210> SEQ ID NO 32
<211> LENGTH: 2649
<212> TYPE: DNA
<213> ORGANISM: Mus musculus

<400> SEQUENCE: 32

ggcacgaggc tgtgtccagc acacagagag ggcccggcca tctgctttgg ttcagagccc      60

tgtgtctgtc tgtcacttag actcttcctc ccggctcgca gctcaccctc catcctcctt     120

actggctcca gcatgactcg cttctcttat gcagagtact ttgctctgtt tcactctggc     180

tctgcacctt ccaggtcccc ttcgtctccc gagaacccac cggcccgcgc acccctgggt     240

ctgttccaag ggtcatgcca gaagtatagc agcaacctgt tcaagacctc ccagatggcg     300

gctatggacc ccgtgctgaa ggccatcaag gaaggggatg aagaggcctt gaagatcatg     360

atccaggatg ggaagaatct tgcagagccc aacaaggagg gctggctgcc gctccacgag     420

gctgcctact atggccagct gggctgcctg aaagtcctgc agcaagccta cccagggacc     480

attgaccaac gcacactgca ggaagagaca gcattatacc tggccacatg cagagaacac     540

ctggattgcc tcctgtcgct gctccaggcg ggggcagagc ctgacatctc taacaaatcc     600

agggagactc cactttacaa agcctgtgag cgcaagaacg cggaggcggt gaggatattg     660

gtgcgataca acgcagacgc caaccaccgc tgtaacaggg gctggaccgc actgcacgag     720

tctgtctccc gcaatgacct ggaggtcatg gagatcctag tgagtggcgg ggccaaggtg     780

gaggccaaga atgtctacag catcacccct ttgtttgtgg ctgcccagag tgggcagctg     840

gaggccctga ggttcctggc caagcatggt gcagacatca acacgcaggc cagtgacagt     900

gcatcagccc tctacgaggc cagcaagaat gagcatgaag acgtggtaga gtttcttctc     960

tctcagggcg ccgatgctaa caaagccaac aaggacggcc tgctccccct gcatgttgcc    1020

tccaagaagg gcaactatag aatagtgcag atgctgctgc ctgtgaccag ccgcacgcgc    1080

gtgcgccgta gcggcatcag cccgctgcac ctagcggccg agcgcaacca cgacgcggtg    1140

ctggaggcgc tgctggccgc gcgcttcgac gtgaacgcac ctctggctcc cgagcgcgcc    1200

cgcctctacg aggaccgccg cagttctgcg ctctacttcg ctgtggtcaa caacaatgtg    1260

tacgccaccg agctgttgct gctggcgggc gcggacccca accgcgatgt catcagccct    1320

ctgctcgtgg ccatccgcca cggctgcctg cgcaccatgc agctgctgtt ggaccatggc    1380

gccaacatcg acgcctacat cgccactcac cccaccgcct ttccagccac catcatgttt    1440

gccatgaagt gcctgtcgtt actcaagttc cttatggacc tcggctgcga tggcgagccc    1500

tgcttctcct gcctgtacgg caacgggccg caccacccgc cccgcgacct ggccgcttcc    1560

acgacgcacc cgtggacgac aaggcaccta gcgtggtgca gttctgtgag ttcctgtcgg    1620

ccccggaagt gagccgctgg gcgggaccca tcatcgatgt cctcctggac tatgtgggca    1680

acgtgcagct gtgctcccgg ctgaaggagc acatcgacag ctttgaggac tgggctgtca    1740

tcaaggagaa ggcagaacct ccgagacctc tggctcacct ctgccggctg cgggttcgga    1800

aggccatagg aaaataccgg ataaaactcc tggacacact gccgcttccc ggcaggctaa    1860

tcagatactt gaaatatgag aatacacagt aaccagcctg gagaggagat gtggccttca    1920

gactgtttcc gggacgcccc aggtggcctg catccaggac cccctggggt cagaacaggt    1980

gtgaccttgc tggttctttg ctggagcttc acccaaagtg agaacctgat gtggggagtg    2040

gacgtggaac ctctgctttc acactgtcag cggatcgcag acccgctctg cttctggcca    2100
```

tagccagaga ccttcaacct ggggccaggg gagagctggt ctgggcaagg tggcccaggc 2160
aggaatcctg gccttaagct ggagaacttg taggaatccc tcactggacc ctcagctttc 2220
aggctgcgag ggagacgccc agcccaagta ttttatttcc gtgacacaat aacgttgtat 2280
cagaaaaaaa aaaaaacatg ggcgcagctt attccttagt agggtattta cttgcatgcg 2340
cgcttaaagc tactggaaac atgcgttcca ctatgcttga gaatcccctt gcactggtaa 2400
acgagagccg acgtgcttca aggttggatt tttggttgcc cctttggcgt tccgcgggtt 2460
tgtccgacgt aattgacccc gtgtttttgtc actttcgagt gttccgacta ttggggggct 2520
tttggttgtc cccaaaattg tgggtggtgt gcggacgcca cgagaagtgg ttcatgggcg 2580
ataatcatta ctggagaatg tagagcggcg gttttacgaa taaatatttt ttaagccgcc 2640
ttcccaaaa 2649

<210> SEQ ID NO 33
<211> LENGTH: 495
<212> TYPE: DNA
<213> ORGANISM: Homo sapiens

<400> SEQUENCE: 33
cctcctgaga gttcgccggc ccgggcccaa tgggttgttc caaggggtca tgcagaaata 60
cagcagcagc ttgttcaaga cctcccagct ggcgcctgcg gacccccttga taaaggccat 120 caaggatgcg atgaagaggc cttgaagacc atgatcaagg aagggaagaa tctcgcagag 180
cccaacaagg agggctggct gccgctgcac gaggccgcat actatggcca ggtgggctgc 240
ctgaaagtcc tgcagcgagc gtacccaggg accatcgacc agcgcaccct gcaggaggaa 300
acagccgttt acttggcaac gtgcaggggc cacctggact gtctcctgtc actgctccaa 360
gcaggggcag agcgggacat ctccaacaaa tcccgagaga accgctctac aaagcctgtg 420
agcgcaagaa cgcggaagcc gtgaagattc ttggtgcagc acaacgcaga caccaacaac 480
gctgcaaccg ggctg 495

<210> SEQ ID NO 34
<211> LENGTH: 709
<212> TYPE: DNA
<213> ORGANISM: Homo sapiens

<400> SEQUENCE: 34
gtgcagctct gctcgcggct gaaggaacac atcgacagct ttgaggactg ggccgtcatc 60
aaggagaagg cagaacctcc aagacctctg gctcaccttt gccgactgcg ggttcgaaag 120
gccattggga aataccgtat aaaactccta gacaccttgc cgctcccagg caggctgatt 180
agatacctga aatacgagaa cacccagtaa ctggggccac ggggagagag gagtagcccc 240
tcagactctt cttactaagt ctcaggacgt cggtgttccc aactccaagg ggacctggtg 300
acagacgagg ctgcaggctg cctccctctc agcctggaca gctaccagga tctcactggg 360
tctcagggcc cagagctttg gccagagcag agaacagaat gtgtcaagga gaagaatcat 420
ttgtttacaa actgatgagc agatcccaga ccttctctac cttcaggaat ggcagaaacc 480
tctattcctg gggccagggc agagcttgag gtgttctggg gaaggtggtg ctcagagcct 540
tccctgtgcc cctccacttg ttctggaaaa ctcaccactt gacttcagag ctttctctcc 600
aaagactaag atgaagacgt ggcccaaggt agggggtagg gggagcctgg gtcttggagg 660
gctttgttaa gtattaatat aataaatgtt acacatgtga aaaaaaaaa 709

-continued

<210> SEQ ID NO 35
<211> LENGTH: 848
<212> TYPE: DNA
<213> ORGANISM: Homo sapiens
<220> FEATURE:
<221> NAME/KEY: CDS
<222> LOCATION: (1)..(624)

<400> SEQUENCE: 35

```
ttg gag aag tgt ggt tgg tat tgg ggg cca atg aat tgg gaa gat gca       48
Leu Glu Lys Cys Gly Trp Tyr Trp Gly Pro Met Asn Trp Glu Asp Ala
  1               5                  10                  15

gag atg aag ctg aaa ggg aaa cca gat ggt tct ttc ctg gta cga gac       96
Glu Met Lys Leu Lys Gly Lys Pro Asp Gly Ser Phe Leu Val Arg Asp
             20                  25                  30

agt tct gat cct cgt tac atc ctg agc ctc agt ttc cga tca cag ggt      144
Ser Ser Asp Pro Arg Tyr Ile Leu Ser Leu Ser Phe Arg Ser Gln Gly
         35                  40                  45

atc acc cac cac act aga atg gag cac tac aga gga acc ttc agc ctg      192
Ile Thr His His Thr Arg Met Glu His Tyr Arg Gly Thr Phe Ser Leu
     50                  55                  60

tgg tgt cat ccc aag ttt gag gac cgc tgt caa tct gtt gta gag ttt      240
Trp Cys His Pro Lys Phe Glu Asp Arg Cys Gln Ser Val Val Glu Phe
 65                  70                  75                  80

att aag aga gcc att atg cac tcc aag aat gga aag ttt ctc tat ttc      288
Ile Lys Arg Ala Ile Met His Ser Lys Asn Gly Lys Phe Leu Tyr Phe
                 85                  90                  95

tta aga tcc agg gtt cca gga ctg cca cca act cct gtc cag ctg ctc      336
Leu Arg Ser Arg Val Pro Gly Leu Pro Pro Thr Pro Val Gln Leu Leu
            100                 105                 110

tat cca gtg tcc cga ttc agc aat gtc aaa tcc ctc cag cac ctt tgc      384
Tyr Pro Val Ser Arg Phe Ser Asn Val Lys Ser Leu Gln His Leu Cys
        115                 120                 125

aga ttc cgg ata cga cag ctc gtc agg ata gat cac atc cca gat ctc      432
Arg Phe Arg Ile Arg Gln Leu Val Arg Ile Asp His Ile Pro Asp Leu
    130                 135                 140

cca ctg cct aaa cct ctg atc tct tat atc cga aag ttc tac tac tat      480
Pro Leu Pro Lys Pro Leu Ile Ser Tyr Ile Arg Lys Phe Tyr Tyr Tyr
145                 150                 155                 160

gat cct cag gaa gag gta tac ctg tct cta aag gaa gcg cag cgt cag      528
Asp Pro Gln Glu Glu Val Tyr Leu Ser Leu Lys Glu Ala Gln Arg Gln
                165                 170                 175

ttt cca aac aga agc aag agg tgg aac cct cca cgt agc gag ggg ctc      576
Phe Pro Asn Arg Ser Lys Arg Trp Asn Pro Pro Arg Ser Glu Gly Leu
            180                 185                 190

cct gct ggt cac cac caa ggg cat ttg gtt gcc aag ctc cag ctt tga      624
Pro Ala Gly His His Gln Gly His Leu Val Ala Lys Leu Gln Leu
        195                 200                 205

agaaccaaat taagctacca tgaaaagaag aggaaaagtg agggaacagg aaggttggga    684

ttctctgtgc agagactttg gttccccacg caagccctgg ggcttggaag aagcacatga    744

ccgtactctg cgtggggctc cacctcacac ccacccctgg gcatcttagg actggagggg    804

ctccttggaa aactggaaga agtctcaaca ctgtttcttt ttca                     848
```

<210> SEQ ID NO 36
<211> LENGTH: 207
<212> TYPE: PRT
<213> ORGANISM: Homo sapiens

<400> SEQUENCE: 36

-continued

```
Leu Glu Lys Cys Gly Trp Tyr Trp Gly Pro Met Asn Trp Glu Asp Ala
  1             5                  10                  15

Glu Met Lys Leu Lys Gly Lys Pro Asp Gly Ser Phe Leu Val Arg Asp
            20                  25                  30

Ser Ser Asp Pro Arg Tyr Ile Leu Ser Leu Ser Phe Arg Ser Gln Gly
        35                  40                  45

Ile Thr His His Thr Arg Met Glu His Tyr Arg Gly Thr Phe Ser Leu
    50                  55                  60

Trp Cys His Pro Lys Phe Glu Asp Arg Cys Gln Ser Val Val Glu Phe
 65                  70                  75                  80

Ile Lys Arg Ala Ile Met His Ser Lys Asn Gly Lys Phe Leu Tyr Phe
                85                  90                  95

Leu Arg Ser Arg Val Pro Gly Leu Pro Pro Thr Pro Val Gln Leu Leu
            100                 105                 110

Tyr Pro Val Ser Arg Phe Ser Asn Val Lys Ser Leu Gln His Leu Cys
        115                 120                 125

Arg Phe Arg Ile Arg Gln Leu Val Arg Ile Asp His Ile Pro Asp Leu
    130                 135                 140

Pro Leu Pro Lys Pro Leu Ile Ser Tyr Ile Arg Lys Phe Tyr Tyr Tyr
145                 150                 155                 160

Asp Pro Gln Glu Glu Val Tyr Leu Ser Leu Lys Glu Ala Gln Arg Gln
                165                 170                 175

Phe Pro Asn Arg Ser Lys Arg Trp Asn Pro Pro Arg Ser Glu Gly Leu
            180                 185                 190

Pro Ala Gly His His Gln Gly His Leu Val Ala Lys Leu Gln Leu
        195                 200                 205
```

<210> SEQ ID NO 37
<211> LENGTH: 464
<212> TYPE: DNA
<213> ORGANISM: Mus musculus

<400> SEQUENCE: 37

```
gttccaagcc taacccatct ttgtcgtttg gaaattcggg ccagtctaaa agcagagcac     60

cttcactctg acattttcat ccatcagttg ccacttccca gaagtctgca gaactatttg    120

ctctatgaag aggttttaag aatgaatgag attctagaac cagcagctaa tcaggatgga    180

gaaaccagca aggccacctg acacaggtcc tttaattctg tttagtcaca aaagacggct    240

tgtgtgactg tttggatttg gtgatcaaat gtccatgttt acagttgctt ttcccagttt    300

gtgtctttcc caatattgtg aaccttatcc atcttgcctt actcagtttt atttctagtg    360

cactttgttg tgtattattt gtttacctga ccattttcta ctttattctg ctaataaact    420

gtaattctga aaaaaaaaaa aaaaaaaaaa aaaaaaaaaa aaaa                     464
```

<210> SEQ ID NO 38
<211> LENGTH: 747
<212> TYPE: DNA
<213> ORGANISM: Homo sapiens

<400> SEQUENCE: 38

```
ggggatcgaa agcgggggct tctgggacgc agctctggag acgcggcctc ggaccagcca     60

tttcggtgta gaagtggcag cacggcagac tggtcaaaca aatggatttt acagaggctt    120

acgcggacac gtgctctaca gttggacttg ctgccaggga aggcaatgtt aaagtcttaa    180

ggaaactgct caaaaagggc cgaagtgtcg atgttgctga taacagggga tggatgccaa    240
```

-continued

```
ttcatgaagc agcttatcac aactctgtag aatgtttgca aatgttaatt aatgcagatt    300

catctgaaaa ctacattaag atgaagacct ttgaaggttt ctgtgctttg catctcgctg    360

caagtcaagg acattggaaa atcgtacaga ttcttttaga agctggggca gatcctaatg    420

caactacttt agaagaaacg acaccattgt tttagctgt tgaaaatgga cagatagatg     480

tgttaaggct gttgcttcaa cacggagcaa atgttaatgg atcccattct atgtgtggat    540

ggaactcctt gcaccaggct tcttttcagg aaaatgctga gatcataaaa ttgcttctta    600

gaaaaggagc aaacaaggaa tgccaggatg actttggaat cacaccttta tttgtggctg    660

ctcagtatgg ccaagctaga aagctttgaa gcatacttat ttcatccggg tgcaaatgtc    720

aattgtcaag ccttggacaa agctacc                                        747
```

<210> SEQ ID NO 39
<211> LENGTH: 1018
<212> TYPE: DNA
<213> ORGANISM: Homo sapiens

<400> SEQUENCE: 39

```
cacaaatggg accatacaaa aatcttggac ttgttaataa ccacttacta accgggacct     60

gtgacactgg gctaaacaaa gtaagtccct gtttactcag cagtgtttgg gggacatgaa    120

ggattgccta gaaatattac tccggaatgg tctacagccc agacgcccag gcgtgccttg    180

tttttggatt cagttctcct gtgtgcatgg ctttccaaaa ggaggtggag ctgtagttct    240

ttggaattgt gaacattctt ttgaaatatg gagcccagat aaatgaactt catttggcat    300

actgcctgaa gtacgagaag ttttcgatat ttcgctactt tttgaggaaa ggttgctcat    360

tgggaccatg gaaccatata tatgaatttg taaatcatgc aattaaagca caagcaaaat    420

ataaggagtg gttgccacat cttctggttg ctggatttga cccactgatt ctactgtgca    480

attcttggat tgactcagtc agcattgaca cccttatctt cactttggag tttactaatt    540

ggaagacact tgcaccagct gttgaaagga tgctctctgc tcgtgcctca aacgcttgga    600

ttctacagca acatattgcc cactgttcca tccctgaccc atctttgtcg tttggaaatt    660

cggtccagtc taaaatcaga acgtctacgg tctgacagtt atattagtca gctgccactt    720

cccagaagcc tacataatta tttgctctat gaagacgttc tgaggatgta tgaagttcca    780

gaactggcag ctattcaaga tggataaatc agtgaaacta cttaacacag ctaatttttt    840

tctctgaaaa atcatcgaga caaaagagcc acagagtaca agtttttatg attttatagt    900

caaaagatga ttattgattg tcagataggt taggttttgg ggggccagta gttcagtgag    960

aatgtttatg tttacaacta gccttcccag taaaaaaaaa aaaaaaaaaa aaaaaaa      1018
```

<210> SEQ ID NO 40
<211> LENGTH: 1897
<212> TYPE: DNA
<213> ORGANISM: Mus musculus

<400> SEQUENCE: 40

```
cggggggctg ggacctgggg cgtaaccgtc tctaccacga cggcaagaac cagccaagta     60

aaacataccc agcctttctg gagccggacg agacattcat tgtccctgac tccttttttcg   120

tggccctgga catgratgat gggaccttaa gtttcatcgt ggatggacag tacatgggag    180

tggctttccg gggactcaag ggtaaaaagc tgtatcctgt agtgagtgcc gtctggggcc    240

actgtgagat ccgcatgcgc tacttgaacg gacttgatcc tgagcccctg ccactcatgg    300

acctgtgccg gcgttcggtg cgcctagcgc tgggaaaaga gcgcctgggt gccatccccg    360
```

-continued

```
ctctgccgct acctgcctcc ctcaaagcct acctcctcta ccagtgatcc acatcccagg    420
accgccatac gacagccatc tggtgccaar tcactgagcc cgttggggtc cgccgacccc    480
tgcgcctggg atggaagccc acctcagcca tgggcagacg tgccccctca tcctaccggc    540
tgcctctgct gggggaacct atgccaacgg acttctccct tcccaacact ggctgaagca    600
gcagcaccca ggcccttccc tgaaccagat gcagagaata aactatgaaa acctctctca    660
ggcgccttct gctctcaggt ggagtgggct gccccccact ctctgcagag agaggctaca    720
cccacctggg gggtcctggg aggtaagact agtaggaggt gccagggctg artccaaaag    780
caggaatggc caggamcagg ccatacagat gaagctcagg atgtcacata ccatggacam    840
tgagacagaa ccccaggttg gamttccctt gggccaacga gtgccagctt taatgtcagc    900
tgcmggtgct ctgtggcctg tatttattct ttaaacagta gcaaaggcca tttatttatt    960
ccacttagaa aggaaacctt ggtgggtggy ttccctcgat gtgctttccc ccacctccct   1020
ggaatgtgtg tgccacacct gtccttgtcc caggccagga ctgtggcaca tgagctggtg   1080
tgcacagata cacgtatgtc gtcgtgcatg acccctgact agttcctaag tagccctgca   1140
ccaagcacca gagcagaccc caagagaggc ccgtgcaagt ccccatgtcc ccaggtccct   1200
gcttctgttg ccttgggact catacaccgg cacacgtgtt tcagcctctt gacttccatg   1260
agcttcgaat tttgcccccg attcttctga tatttcccat tggcatcctc caaagctctg   1320
ggcctggagg gcattaggac acatggaatg agtggggtct ccagcccctg ggaaagccac   1380
tggcaaggca ggattagaaa gaccaagagc agggtggggc gccatgaagc ctgtatgcct   1440
ctcaggctca agaccccgcc acacacccac tcaagcctca gaagtggtgt gtagggcagc   1500
cccaggagag gaatgcctgt cctagcagca cgtacatgga gcaccccaca tgtgctccag   1560
ccctctggct gtttctcttg ctctagaatc aactccctac attgggaatg tagccatttg   1620
gtagaggact tgcctagcct gcaggaagct cacgttccat cccctgcacc aaggagaatc   1680
aaagctcagg aggctgaggc aggaggattg ctgtcagtgg tgtacagagg tcatggccat   1740
cctgggctat attaaacctt gtcctttaag aaaaagaaaa gaaatcaact tccattgaat   1800
ctgagttctg ctcatttctg cacaggtaca atagatgact tkatttgttg aaaaatgktt   1860
aatatattta cmtatatata tatttgtaag aagcatt                            1897
```

<210> SEQ ID NO 41
<211> LENGTH: 134
<212> TYPE: PRT
<213> ORGANISM: Mus musculus
<220> FEATURE:
<221> NAME/KEY: UNSURE
<222> LOCATION: (45)
<223> OTHER INFORMATION: Xaa is unsure

<400> SEQUENCE: 41

```
Gly Gly Trp Asp Leu Gly Arg Asn Arg Leu Tyr His Asp Gly Lys Asn
  1               5                  10                  15

Gln Pro Ser Lys Thr Tyr Pro Ala Phe Leu Glu Pro Asp Glu Thr Phe
             20                  25                  30

Ile Val Pro Asp Ser Phe Phe Val Ala Leu Asp Met Xaa Asp Gly Thr
         35                  40                  45

Leu Ser Phe Ile Val Asp Gly Gln Tyr Met Gly Val Ala Phe Arg Gly
     50                  55                  60

Leu Lys Gly Lys Lys Leu Tyr Pro Val Val Ser Ala Val Trp Gly His
 65                  70                  75                  80
```

-continued

```
Cys Glu Ile Arg Met Arg Tyr Leu Asn Gly Leu Asp Pro Glu Pro Leu
                85                  90                  95

Pro Leu Met Asp Leu Cys Arg Arg Ser Val Arg Leu Ala Leu Gly Lys
            100                 105                 110

Glu Arg Leu Gly Ala Ile Pro Ala Leu Pro Leu Pro Ala Ser Leu Lys
        115                 120                 125

Ala Tyr Leu Leu Tyr Gln
    130
```

<210> SEQ ID NO 42
<211> LENGTH: 265
<212> TYPE: DNA
<213> ORGANISM: Homo sapiens

<400> SEQUENCE: 42

```
aagggtaaaa aactgtatcc tgtagtgagt gccgtctggg gccactgtag atccgaatgc     60

gctacttgaa cggactcgat cccgagactg ccgctcatgg atttgtgccg tcgctcggtg    120

cgcctggccc tggggaggga gcgcctgggg gagaaccaca cctgccgctg ccggcttccc    180

tcaaggccta cctcctctac cagtgacgtt cgccatcata ccgccagcgc gacagccacc    240

tggtgccaac tcactgagcc gcctg                                          265
```

<210> SEQ ID NO 43
<211> LENGTH: 2438
<212> TYPE: DNA
<213> ORGANISM: Mus musculus

<400> SEQUENCE: 43

```
aagtggcggc ggtccctgga gagcaggcgg aggcagcggc aagtctgact ctgggctgac     60

cgtggagccg gggcgggggc tgacagccag gcctccgcct ggcgggagcc gcacgaggag    120

cgggagtggc cgggcctctc ttccgcgctt gagcgagcgc cgggtgatgg cggtggtgat    180

ggcggcaggc gctcggacag ctccgcttga gctgagctcg gagagatccg tccagaaagt    240

gcccagaaga aacttcctct tagaaaagct gaaaaacaca rtatttataa cactggaaat    300

tgtaaagaat ttgtttaaaa tggctgaaaa caatagtaaa aatgtagatg tacggcctaa    360

aacaagtcgg agtcgaagtg ctgacaggaa ggatggttat gtgtggagtg gaaagaagtt    420

gtcttggtcc aaaaagagtg agagttgttc tgaatctgaa gccataggta ctgttgagaa    480

tgttgaaatt cctctaagaa gccaagaaag gcagcttagc tgttcgtcca ttgagttgga    540

cttagatcat tcctgtgggc atagattttt aggccgatcc cttaaacaga aactgcaaga    600

tgcggtgggg cagtgttttc caataaagaa ttgtagtggc cgacactctc cagggcttcc    660

atctaaaaga aagattcata tcagtgaact catgttagat aagtgccctt tcccacctcg    720

ctcagattta gcctttaggt ggcattttat taaacgacac actgttccta tgagtcccaa    780

ctcagatgaa tgggtgagtg cagacctgtc tgagaggaaa ctgagagatg ctcagctgaa    840

acgaagaaac acagaagatg acataccctg tttctcacat accaatggcc agccttgtgt    900

cataactgcc aacagtgctt cgtgtacagg tggtcacata actggttcta tgatgaactt    960

ggtcacaaac aacagcatag aagacagtga catggattca gaggatgaaa ttataacgct   1020

gtgcacaagc tccagaaaaa ggaataagcc caggtgggaa atggaagagg agatcctgca   1080

gttggaggca cctcctaagt tccacaccca gatcgactac gtccactgcc ttgttccaga   1140

cctccttcag atcagtaaca atccgtgcta ctggggtgtc atggacaaat atgcagccga   1200
```

-continued

```
agctctgctg gaaggaaagc cagagggcac ctttttactt cgagattcag cgcaggaaga   1260
ttatttattc tctgttagtt ttagacgcta cagtcgttct cttcatgcta gaattgagca   1320
gtggaatcat aactttagct ttgatgccca tgatccttgt gtcttccatt ctcctgatat   1380
tactgggctc ctggaacact ataaggaccc cagtgcctgt atgttctttg agccgctctt   1440
gtccactccc ttaatccgga cgttcccctt ttccttgcag catatttgca gaacggttat   1500
ttgtaattgt acgacttacg atggcatcga tgcccttccc attccttcgc ctatgaaatt   1560
gtatctgaag gaataccatt ataaatcaaa agttaggtta ctcaggattg atgtgccaga   1620
gcagcagtga tgcggagagg ttagaatgtc gacctgcata catattttca tttaatattt   1680
tatttttctt atgcctcttt gaatttttgt acaaaggcag ttgaatcaaa taaaactgtg   1740
ccctaagttt taattccaga tcaatttatt ttttttatga tacacttgtt atatattttt   1800
aagcaggtgt ttggttttgt ttttaccata taaatttaca tatggtccag gcatatttac   1860
aatttcaagg cattgcatat acatttgaat attctgtatt ttttaaataa tcttttgttc   1920
tttcctatgt gtgaaatatt ttgctaatct atgctatcag tattcttgta tgaccgaata   1980
gttacctatt ctcttttcat cttgaagatt ttcagtaaag agtgttgtaa tcaatccatt   2040
ataatgtaat tgacttttgt aatttgccaa taggagtgtt aaacaacaaa atgatttaaa   2100
atgaaactta atgtattttc attttaaata ttaactaaac caagtttgtt tgttagttat   2160
tctagccaat aagaaaagag aatgtagcat cctagaggtg tatttgttct gcagtttggc   2220
aggaccgtca gttagtccaa ataaacatcc cctcagcgtg gaggcgaatg gaacctgtgc   2280
tcctttctta cgggaagctt tgcaaagcaa aatagcaggg ttacaagctt ggagttgtta   2340
aggcaactag agttttctct attaatttat agactgttgt tgcacctact tagctctttt   2400
ttgggaactc tagttcccag gggaaaatac ctcgtgcc                           2438
```

```
<210> SEQ ID NO 44
<211> LENGTH: 542
<212> TYPE: PRT
<213> ORGANISM: Mus musculus
<220> FEATURE:
<221> NAME/KEY: UNSURE
<222> LOCATION: (94)
<223> OTHER INFORMATION: Xaa is unsure

<400> SEQUENCE: 44

Ser Gly Gly Gly Pro Trp Arg Ala Gly Gly Gly Ser Gly Lys Ser Asp
  1               5                  10                  15

Ser Gly Leu Thr Val Glu Pro Gly Arg Gly Leu Thr Ala Arg Pro Pro
             20                  25                  30

Pro Gly Gly Ser Arg Thr Arg Ser Gly Ser Gly Arg Ala Ser Leu Pro
         35                  40                  45

Arg Leu Ser Glu Arg Arg Val Met Ala Val Val Met Ala Ala Gly Ala
     50                  55                  60

Arg Thr Ala Pro Leu Glu Leu Ser Ser Glu Arg Ser Val Gln Lys Val
 65                  70                  75                  80

Pro Arg Arg Asn Phe Leu Leu Glu Lys Leu Lys Asn Thr Xaa Phe Ile
                 85                  90                  95

Thr Leu Glu Ile Val Lys Asn Leu Phe Lys Met Ala Glu Asn Asn Ser
            100                 105                 110

Lys Asn Val Asp Val Arg Pro Lys Thr Ser Arg Ser Arg Ser Ala Asp
        115                 120                 125

Arg Lys Asp Gly Tyr Val Trp Ser Gly Lys Lys Leu Ser Trp Ser Lys
```

-continued

```
        130                 135                 140

Lys Ser Glu Ser Cys Ser Glu Ser Glu Ala Ile Gly Thr Val Glu Asn
145                 150                 155                 160

Val Glu Ile Pro Leu Arg Ser Gln Glu Arg Gln Leu Ser Cys Ser Ser
                165                 170                 175

Ile Glu Leu Asp Leu Asp His Ser Cys Gly His Arg Phe Leu Gly Arg
            180                 185                 190

Ser Leu Lys Gln Lys Leu Gln Asp Ala Val Gly Gln Cys Phe Pro Ile
        195                 200                 205

Lys Asn Cys Ser Gly Arg His Ser Pro Gly Leu Pro Ser Lys Arg Lys
    210                 215                 220

Ile His Ile Ser Glu Leu Met Leu Asp Lys Cys Pro Phe Pro Pro Arg
225                 230                 235                 240

Ser Asp Leu Ala Phe Arg Trp His Phe Ile Lys Arg His Thr Val Pro
                245                 250                 255

Met Ser Pro Asn Ser Asp Glu Trp Val Ser Ala Asp Leu Ser Glu Arg
            260                 265                 270

Lys Leu Arg Asp Ala Gln Leu Lys Arg Arg Asn Thr Glu Asp Asp Ile
        275                 280                 285

Pro Cys Phe Ser His Thr Asn Gly Gln Pro Cys Val Ile Thr Ala Asn
    290                 295                 300

Ser Ala Ser Cys Thr Gly Gly His Ile Thr Gly Ser Met Met Asn Leu
305                 310                 315                 320

Val Thr Asn Asn Ser Ile Glu Asp Ser Asp Met Asp Ser Glu Asp Glu
                325                 330                 335

Ile Ile Thr Leu Cys Thr Ser Ser Arg Lys Arg Asn Lys Pro Arg Trp
            340                 345                 350

Glu Met Glu Glu Glu Ile Leu Gln Leu Glu Ala Pro Pro Lys Phe His
        355                 360                 365

Thr Gln Ile Asp Tyr Val His Cys Leu Val Pro Asp Leu Leu Gln Ile
    370                 375                 380

Ser Asn Asn Pro Cys Tyr Trp Gly Val Met Asp Lys Tyr Ala Ala Glu
385                 390                 395                 400

Ala Leu Leu Glu Gly Lys Pro Glu Gly Thr Phe Leu Leu Arg Asp Ser
                405                 410                 415

Ala Gln Glu Asp Tyr Leu Phe Ser Val Ser Phe Arg Arg Tyr Ser Arg
            420                 425                 430

Ser Leu His Ala Arg Ile Glu Gln Trp Asn His Asn Phe Ser Phe Asp
        435                 440                 445

Ala His Asp Pro Cys Val Phe His Ser Pro Asp Ile Thr Gly Leu Leu
    450                 455                 460

Glu His Tyr Lys Asp Pro Ser Ala Cys Met Phe Phe Glu Pro Leu Leu
465                 470                 475                 480

Ser Thr Pro Leu Ile Arg Thr Phe Pro Phe Ser Leu Gln His Ile Cys
                485                 490                 495

Arg Thr Val Ile Cys Asn Cys Thr Thr Tyr Asp Gly Ile Asp Ala Leu
            500                 505                 510

Pro Ile Pro Ser Pro Met Lys Leu Tyr Leu Lys Glu Tyr His Tyr Lys
        515                 520                 525

Ser Lys Val Arg Leu Leu Arg Ile Asp Val Pro Glu Gln Gln
    530                 535                 540
```

<210> SEQ ID NO 45

-continued

<211> LENGTH: 5000
<212> TYPE: DNA
<213> ORGANISM: Mus musculus

<400> SEQUENCE: 45
ccctctgggc aagccgcccc ccccccaccc atctaccaca cacacacaca cacacacaca 60
cacacattca gaccttgggg caaaaacaaa gcaaaataac aacaacaaaa acactgcctg 120
tggaaagtcc ttacttcagg aaggttggca gatgaggagc aagggaacat tttatcagga 180
ctgccacaaa ggagtctttt tttttaatgg tttttcaaga cagggtttct ctgtatagcc 240
ctggctgtcc tggagctcac tttgtagacc aggctggcct cgaactcaga aattcgcctg 300
cctctgcctc ctgagtgctg ggattaaagg cgtgcagcac catgtccaac tggcattttc 360
tcaattaagg ttcgttcctt tcagataact ctaggttctg ggtcaagctg acacaaggct 420
acacagcaca gtttgtatgc cacattcagt tcagaagaca cccaacctcc ctggaactgg 480
aacttatgca catttgtgag cttccacttg ggagtgggaa cctgaactgg gtcctctgca 540
agagcagccg tgctcttaac tgctgagcca tttcagcagc ctcacatcag aattaagtta 600
gaaattagcc gggtatgaat catacctta gaatcctagc atctgaaagc agagctaaga 660
gaaacaggga ttcaagacca gctcttggct acagagcccg tcctgtccta ggatgggcta 720
caagagacta tttcaaagcc atccaaacaa caataactac aacaacaaca aggttaaaat 780
taggctgggc acagggtaca cacctttaat gccaacactc aggaggcaga ggcaggctga 840
tcagtgtgag tttgagttca acgtggtcta catagggagt tctaggccag cagaggttac 900
agtctctctc tctctctctc tctctctctc tctctcacac acacacacac acacacacac 960
acacacacac acacacacgg tggcattatg ggattttttt gggataaggt ttctctgtct 1020
agccctggca tagattcact ctgtagacta ggctagcctt gaactcagag atccgcctgc 1080
ctctgcctcc caagtgctgg gattataggt gttgcaccac cactgcccag ccactttggg 1140
atttttgaac tgttatcaag aggctttcga ggaggtcaaa cttcaacagc aacctctcca 1200
tgataatgta gctaatgatc aaacgacact caaaacttaa cccttaaagc acacatccac 1260
cagacagcgt gcccactcgt agttccatta ctcaggaggc tgaagcagga ggatgaagga 1320
ctaaggcttc agcaacctag ggagccgcag gggacagtag tctcaatccc tacattctcc 1380
tgaacacagg agcaggagtt caggaagggt gtcaaggccg cttactgatc ttagggcctc 1440
aggaatgact agctcaggca gagagagcaa aggtctccag tggagaagtc tacacacaca 1500
cacacacaca cacacacaca cacacacaca cagaatccaa ggcgatgacg tcatcaaagg 1560
gttaattcta gtctgggatg gggggggaggg tggggcacgc agctgtcagg tggctttgga 1620
aaaataaact gctgaagagt ctgacgccag ggagtcctgg gagggacaag aggttaccca 1680
ctcaaagagt gtgctccaca aagcatgcgc gcttgtccac gtctggagtc gtcacttatt 1740
ttttgcctgg attctttgta gccggtgggt tctcaaggcg gtaagtggtg tggccgccgt 1800
ggtctgggag gtgacgatag ggttaatcgt ccacagagcc caggggcgga gcgcgggcgg 1860
gcgtccgcag ccccgctgga gccggaagca gtggctggtc aggggcgctt ctagccttcc 1920
ctatctgtac ttccacagag gtctctgcga gctaggggga cagtgaggtg cggggtaggg 1980
gcccggcgtt agagccagca aggggacggt tcacggtaag gtctgaggga gagagagctc 2040
ctgagaaact tggggggcgc gacacagata gggtgaaagc agagtgatag acctgggatg 2100
gttaggggac caagggaaga ccaggctggt tggcatacac cggtgaacgg atgggagtcc 2160
tagggaaaga tgatgcgcct aacagtcctt tctgtctcca caccactcca ggggacgatc 2220

-continued

```
cggagctcaa ctttcaaaag cgagacgccc cagcaagcct gttttgagaa gttcttcagc   2280
ggctctcctc atgggccaga cggccctggc aaggggcagc agcagcaccc ctacctcgca   2340
ggctctgtac tcggacttct ctcctcccga gggcttggag gagctcctgt ctgctccccc   2400
tcctgacctg gttgcccaac ggcaccacgg ctggaacccc aaggattgct ccgagaacat   2460
cgatgtcaag gaaggggtc tgtgctttga gcggcgccct gtggcccaga gcactgatgg    2520
agtccggggg aaacggggct attcgagagg tctgcacgcc tgggagatca gctggcccct   2580
ggagcaaagg ggcacacacg ccgtggtggg cgtggccacc gccctcgccc cgctgcaggc   2640
tgaccactat gcggcgcttt tgggcagcaa cagcgagtcc tggggctggg atattgggcg   2700
gggaaaattg tatcatcaga gtaagggcct cgaggccccc cagtatccag ctggacctca   2760
gggtgagcag ctagtggtgc cagagagact gctggtggtt ctggacatgg aggaggggac   2820
tcttggctac tctattgggg gcacgtacct gggaccagcc ttccgtggac tgaaggggag   2880
gaccctctat ccctctgtaa gtgctgtttg gggccagtgc caggtccgca tccgctacat   2940
gggcgaaaga agaggtgaga tacggactag gtgtggggag atcactactc ttggcaatgg   3000
tttgggctgg aaactcatgg ttggagcaca ggaagtaggc ttcttgtcac tttggcctgt   3060
cacttagatg gccttggatc tagcttcact cccaatccct attggatgtg atgcacaaat   3120
tcagagcctt tgggtctccc tcagctgagg tggcggtgga aatggaggaa gaaggaaggg   3180
tgcctgagca ggatctcaag ttcaaggatg cctggagttg cttacttacc ttgtcttcct   3240
tctctctccg cagtggagga accacaatcc cttctgcacc tgagccgcct gtgtgtgcgc   3300
catgctctgg gggacacccg gctgggtcaa atatccactc tgcctttgcc ccctgccatg   3360
aagcgctatc tgctctacaa atgacccagt agtacagggt gtgctggcac cctaccgtgg   3420
ggacaggtgg agaggcaccc gctggcctag acaactttaa aaagctggtg aagctggggg   3480
ggggggctg gaccccttca cctccccttc tcacaggagc aagacatata gaaatgatat    3540
taaacaccat ggcagcctgg gacaaagagg tttttgaagt aaaaaatgag atgtattgtc   3600
acaacctgtt tcattattgt tttttgtttt gttttacact cccccacccc aggctagagc   3660
cccatcactg tcttaaggaa ttatgacaac ccacaaagct caggcccagg tgtttatttc   3720
ccttacatgt aggatggttc acaaacacaa tacaggggct ttggcaccgt gggggagggg   3780
actatcccag gcctcttagg gtctcatgta taccgaattc agacccgaaa gctctgaatt   3840
tctgcatcag acatccagta gaacttggga gtgaagctag agccaaggcc atctaagtga   3900
caggccaaag tgacacgaag cccacttcct gtgctccaac catgagtttc cagcccaaac   3960
caatggaagg tgatttcact tgtcagggcc caaagggaca gtcagttcta ctccctcccc   4020
tcactaggag ccaccttggt gacagttgat tctacccact gtaagtggta aagggattgg   4080
cctggtccca accataatag ggcggtggaa acggctcagg agggtacagc gtggattagg   4140
ccacaagatg gggcagatga tgtcatcaga agcatgtgac cggtgggagc agttactaaa   4200
cttctgggca acctagtcca tgctatgcag gcaggtagag ggatgggcag tgctcattgt   4260
ttggcattga tgatgtccac aaattcaggc ttgagagatg cgccacccac aaggaagccg   4320
tccacgtcag gctggcttgc cagctctttg caggttgctc cagtcacaga acctgtacca   4380
ggaacaagaa gacagtttgg tcaggtctat gatcagaaca cttaagcccc acctctctgt   4440
gcaaggcagc ctcagtctgt cttagcccat ttccgtctta gctagagcca aagccactca   4500
cctccataaa tgatccgggt gctctgagcc accccatcat tgacattgga tttcagccat   4560
```

-continued

```
ccccggagct tctcgtgtac ttcctgtgcc tagaaggagg aggcagagct actaagtaag   4620

ctccttccta tctatcattc aaggagtaaa aaccactggt tctcacatag agttgagttt   4680

ccagaaaagc cccgggacca gagagtggca aggctccaat cccaccaggc ttggaatgaa   4740

catttttggc aaagtcactc tccttggtga gtttgggggc cctctgtctc taaaggggct   4800

tggatgggct ccatagctgt gtgagtctgt taaagccgga caggctgagg agctctgggt   4860

agttacctgc tgaggggttg ccgtcttgcc agtcccaatg gcccacacag gttcataggc   4920

caggaccacc ttgctccagt ctttcacatt atctgtgggg cagagaggag agtgagtagg   4980

aaggagctga cccgccaagc                                                5000
```

```
<210> SEQ ID NO 46
<211> LENGTH: 264
<212> TYPE: PRT
<213> ORGANISM: Mus musculus

<400> SEQUENCE: 46

Met Gly Gln Thr Ala Leu Ala Arg Gly Ser Ser Ser Thr Pro Thr Ser
1               5                   10                  15

Gln Ala Leu Tyr Ser Asp Phe Ser Pro Pro Glu Gly Leu Glu Glu Leu
            20                  25                  30

Leu Ser Ala Pro Pro Pro Asp Leu Val Ala Gln Arg His His Gly Trp
        35                  40                  45

Asn Pro Lys Asp Cys Ser Glu Asn Ile Asp Val Lys Glu Gly Gly Leu
    50                  55                  60

Cys Phe Glu Arg Arg Pro Val Ala Gln Ser Thr Asp Gly Val Arg Gly
65                  70                  75                  80

Lys Arg Gly Tyr Ser Arg Gly Leu His Ala Trp Glu Ile Ser Trp Pro
                85                  90                  95

Leu Glu Gln Arg Gly Thr His Ala Val Val Gly Val Ala Thr Ala Leu
            100                 105                 110

Ala Pro Leu Gln Ala Asp His Tyr Ala Ala Leu Leu Gly Ser Asn Ser
        115                 120                 125

Glu Ser Trp Gly Trp Asp Ile Gly Arg Gly Lys Leu Tyr His Gln Ser
    130                 135                 140

Lys Gly Leu Glu Ala Pro Gln Tyr Pro Ala Gly Pro Gln Gly Glu Gln
145                 150                 155                 160

Leu Val Val Pro Glu Arg Leu Leu Val Val Leu Asp Met Glu Glu Gly
                165                 170                 175

Thr Leu Gly Tyr Ser Ile Gly Gly Thr Tyr Leu Gly Pro Ala Phe Arg
            180                 185                 190

Gly Leu Lys Gly Arg Thr Leu Tyr Pro Ser Val Ser Ala Val Trp Gly
        195                 200                 205

Gln Cys Gln Val Arg Ile Arg Tyr Met Gly Glu Arg Arg Val Glu Glu
    210                 215                 220

Pro Gln Ser Leu Leu His Leu Ser Arg Leu Cys Val Arg His Ala Leu
225                 230                 235                 240

Gly Asp Thr Arg Leu Gly Gln Ile Ser Thr Leu Pro Leu Pro Pro Ala
                245                 250                 255

Met Lys Arg Tyr Leu Leu Tyr Lys
            260

<210> SEQ ID NO 47
<211> LENGTH: 5615
<212> TYPE: DNA
```

-continued

<213> ORGANISM: Homo sapiens

<400> SEQUENCE: 47
gtactttctt tatatctcca taatttttatt tactattact acatgataca ttatttttata 60
aaagtctttg taacctcctt aaggattcac tgcttaatct ccagtgctta gcacaaatca 120
ttaaatgcga accagaaact cttccaaatg tgttacatct ataacctcat tggattctca 180
ctaccaaccc catgcaatag atactaatgt gatctctgtc ttacagagga agaaacaggc 240
acagggaggt tcagtaattt gcccaaggtc atacacacac tggccttcag gtattcatgc 300
ccggggagtc tggtcccaca gctggcatgt ttgccattat attatattgc ctccttatag 360
tgtcggcact cattaagcac attgacagct atgcttggtg agtgactact atgtacccag 420
ctctgtgcta catgctttac ctggattatt tcaactgcac aacaaccctg tgaggtaact 480
accatcattg ctcctatttt acataacaga aaactacaga aatctggggc tgggcgtagt 540
ggctcatgcc tgaaatccca gcactttggg agaccctgtc tctaaaaaaa atttttttttt 600
ggccggacgt ggtggctcac acctgtaatc tcagcacttt gggaggctaa ggcaggcaga 660
tcacaaggtc aggagttcta gaccagcctg gccaacatgg caaaaccctg tgtctactaa 720
aaatacaaaa aatagctagg cgtggtggca ggtgcctgta atcccagcta ctcaggaggc 780
tgaggcagga gaatcccctg aacctgggag atggaggtta cagagagccg agatcgtgcc 840
gctgcactcc agcctgggca acaagagcaa gactctgtct cgaaaaaaat aaaaataaaa 900
ataaaaatat tttttaaaa attagctggg tgtggtagca catgcctgta gtcccagcta 960
cttgggaggc tgaggtagga ggatcacttg agcccaggag gtcaaggctg cagtgggctg 1020
tgatggcgcc actgcactct agccttggtg acagcaagac cctgtctcaa aaaaaaaaaa 1080
aagagaaatc gggcaacttc cccaagatcg cgcagttaac tagtggcata gcttcactca 1140
aactcgaagt cttaatcagg acactctacc aaatgagatc aacggctcag taatggattg 1200
gcatccagta tgaagactgg accagcaggg agaactatga tgcgtacagc ctagagcctg 1260
aagcagattt cacagcctca gaggtggcac aggctgactc acaacccggg gcagaaaggg 1320
accagcccag aaacagtgac ccagaatcac agggaagtag aaatgggatt cggcacaatg 1380
aagcccctcc ttgaccccat gctccttacc ctcaggggcg caggagttag tcgctcaggc 1440
ggctcaaagg tcttgacggt ggagaacacc atccccaggg attcccgacg cggtgatgcc 1500
atcaaagcgt taattctgag atgggcctgc ccgggtgcgg actctgccgc agcaagagaa 1560
gggttaactg ccccgggcct tcgccgtggg ggcggggcct cggggagggt cacagcccgg 1620
gactgagacc cgaggttaac cgcccggggt gggctccacg gggcggggc atgctctccg 1680
cggctgctgc cggtatagag cggtaactgc ccaggagggg gcggggcccc acaggggcgt 1740
ggcctcggag ctgcacggcc gtgggcggcg atgagagggt taagccccag agggccctgg 1800
aggggcgggg ccgcgggacg ggctcggccc aagggaggag ctgggggcgg aagcggccgg 1860
cggtctgcgc cctgcgcgcc tcggcttctt tccgcccggc tccttcagag gcccggcgac 1920
ctccagggct gggaagtcaa ccgaggttcg ggggcagcgg cgagggctcc gggcgagtaa 1980
gggggatggt ccatgctgag gcccaaatgg ggcgaactcg cgagagtctc tggcgacctg 2040
gatcagatgg ggcgagggca gatgaagggc ccaggagctt tggggcagcg aggagggagg 2100
agcgggcccg ttggcaaact tgggtgaaag gatggggtac ctgggtgacg agcccccgcc 2160
aggattctgc tcttcacgcc ccttttctcc cagctccctt ccaggtcaat ccaaactgga 2220
gctcaacttt cagaagagaa agacgcccca gcaagcctct ttcggggagt cctctagctc 2280

-continued

```
ctcacctcca tgggccagac agctctggca gggggcagca gcagcacccc cacgccacag   2340
gccctgtacc ctgacctctc ctgtcccgag ggcttggaag agctgctgtc tgcacccccct   2400
cctgacctgg gggcccagcg gcgccacggt tggaacccca aagactgttc agagaacatc   2460
gaggtcaagg aaggagggtt gtactttgag cggcggcccg tggcccagag cactgatggg   2520
gcccggggta agaggggcta ttcaaggggc ctgcacgcct gggagatcag ctggccccta   2580
gagcagaggg gcacgcatgc cgtggtgggc gtggccacgg ccctcgcccc gctgcagact   2640
gaccactacg cggcgctgct gggcagcaac agcgagtcgt ggggctggga catcgggcgg   2700
gggaagctgt accatcagag caaggggccc ggagcccccc agtatccagc gggaactcag   2760
ggtgagcagc tggaggtgcc agagagactg ctggtggttc tggacatgga ggagggaact   2820
ctgggctacg ctattggggg cacctacctg gggccagcat tccgcggact gaagggcagg   2880
accctctatc cggcagtaag cgctgtctgg ggccagtgcc aggtccgcat ccgctacctg   2940
ggcgaaagga gaggtgaggc ctggggcaga cgtggggaga actttctgtc cctggtggca   3000
gtggtttggg atggaaactc ttctgacaag agcagagggg atggaccttc atccagcctg   3060
cctcaacctc tgttcagtgc tgggaaaggc taggggtctt cacagctgtt atttaattta   3120
acccaacagc aatagaggtg aaacaggctt gagaaagcaa ctttctcaag ttctcttggc   3180
cagtaaatgg tgaaccttca gaatggaggg aggaactgca gggatgagag aattcaggag   3240
atatcaaccc ctgagcaaga ggtgcaaagc gttaggtact gggtttgatg tacaggtcca   3300
aaagaaggat gggcagagcc aggtacccag gctgtatacc ggattccctg ggctctaacc   3360
tgtctctgtg ccacatacct acttccttcc tcagccacac ctctggatgg agacactggg   3420
gccctgggca ccagggagga gagcagtgga ggaggcaggg ccttagggtg gggcagcagg   3480
ggaggagcct ccccaggaac tgactgggtc cagggcttgg agctgctctc tgcagttgtg   3540
tgggctgtag agtggagggc catccctcct cacctcagcc ccagctccca agcctctgga   3600
gtcaaagcct gggccagctc caccactgtc agagccacct tggcctgttg tttagagggc   3660
cttagccagc tcttcacccc cagctctgac tagggatgtg tgaaatctta tctgggaggc   3720
agaacttccg ggtatctcaa attccccttt cagccaggtg ggcacactcg aagcaggaaa   3780
gcagaaaggc atctgagtag gaccccgtag tttgaggaca tctggctggt ggctgcaccc   3840
atacttacat tcccctcctt ctctctccca gcggagccac actcccttct gcacctgagc   3900
cgcctgtgtg tgcgccacaa cctgggggat acccggctcg gccaggtgtc tgccctgccc   3960
ttgcccccctg ccatgaagcg ctacctgctc taccagtgag ccctgtgata ccacagactg   4020
tgctgaggtc ttgccaccac ccctcccctt ggggaggtgg ggaggcactg ctggcctaga   4080
ccagctgctg aaagctggtg aggctgagcc cctaccccaa cccaagctct gcggaaatca   4140
acagccccag agccacttgg agggaggaag aaagggagcc ggcgttcaag gctatgacag   4200
tctgctacgc aaaacatttt ttcaagtaaa aatagtaaga gatgttgtta tagaaacctg   4260
ttcttgtttt tttttttttc ttgcacaaat gatcatttat atagctgcct caaaaaggaa   4320
gattatctgg gcaagtccag tgaaggcaga caaaccacaa gacctagtgc caggtttatt   4380
ccctcacatg ggtggttcac atacacagca cagaggcacg ggcaccatgg gagagggcag   4440
cactcctgcc ttctgagggg atcttggcct cacggtgtaa gaagggagag gatggtttct   4500
cttctgccct cactagggcc tagggaaccc aggagcaaat cccaccacgc cttccatctc   4560
tcagccaagg agaagccacc ttggtgacgt ttagttccaa ccattatagt aagtggagaa   4620
```

-continued

```
gggattggcc tggtcccaac cattacaggg tgaagatata aacagtaaag gaagatacag   4680

tttggatgag gccacaggaa ggagcagatg acaccatcag aagcatatgc agggaaaggg   4740

cagttactgg gcttctgggc tgcttagtcc ctggcttggc aggaagggta gggaagatgg   4800

atggggctca ttgtttggca ttgatgatgt ccacgaattc gggcttgagg gaagcaccac   4860

ccacaaggaa gccatccaca tcaggctggc tggccagctc cttgcaggtt gccccagtca   4920

cagagcctgg gaagggagca gaacaagggc ttggtcaaga atgggatgag tctgccccat   4980

ccccacctcc atgtccgagg gctcagtcta gtcctcagcc cactccacct cagccgggaa   5040

ccaaagccac tcacctccat aaatgatacg ggtgctctga gccaccgcat cagagacgtt   5100

ggacttcagc catcctcgga gcttctcgtg tacttcctgg gcctagaaca agaagctggc   5160

ctaagtaaga ccttttctgc ctctctaaga ggaaaaatca ctggcaccag tggacactta   5220

gtgtggtttc tgactgagtc agagtaccag ggctctgatc caagccaggc cctggactgg   5280

atgcccttgg acaagtcact gtctctgggt tcaaggtctc tgtgtctttg aaataagggg   5340

ttgccccatg tgggctgtgt ctgtccaaac ctattgaggc aggctgggat gagggcaggg   5400

ctcctgggcc cggttacctg ttggggtgtt gcagtcttgc cagtaccaat ggcccacaca   5460

ggctcatagg ccaggacgac cttgctccag tccttcacgt tatctgcagg gcagagatac   5520

agatggaggg aagggtgaac aagaaagagc tctccagcca ggttctccgg agtacgaaga   5580

acggtggcct actgcccccct agtggacatt ggggg                              5615
```

```
<210> SEQ ID NO 48
<211> LENGTH: 263
<212> TYPE: PRT
<213> ORGANISM: Homo sapiens

<400> SEQUENCE: 48

Met Gly Gln Thr Ala Leu Ala Gly Gly Ser Ser Ser Thr Pro Thr Pro
1               5                   10                  15

Gln Ala Leu Tyr Pro Asp Leu Ser Cys Pro Glu Gly Leu Glu Glu Leu
            20                  25                  30

Leu Ser Ala Pro Pro Pro Asp Leu Gly Ala Gln Arg Arg His Gly Trp
        35                  40                  45

Asn Pro Lys Asp Cys Ser Glu Asn Ile Glu Val Lys Glu Gly Gly Leu
    50                  55                  60

Tyr Phe Glu Arg Arg Pro Val Ala Gln Ser Thr Asp Gly Ala Arg Gly
65                  70                  75                  80

Lys Arg Gly Tyr Ser Arg Gly Leu His Ala Trp Glu Ile Ser Trp Pro
                85                  90                  95

Leu Glu Gln Arg Gly Thr His Ala Val Val Gly Val Ala Thr Ala Leu
            100                 105                 110

Ala Pro Leu Gln Thr Asp His Tyr Ala Ala Leu Leu Gly Ser Asn Ser
        115                 120                 125

Glu Ser Trp Gly Trp Asp Ile Gly Arg Gly Lys Leu Tyr His Gln Ser
    130                 135                 140

Lys Gly Pro Gly Ala Pro Gln Tyr Pro Ala Gly Thr Gln Gly Glu Gln
145                 150                 155                 160

Leu Glu Val Pro Glu Arg Leu Leu Val Val Leu Asp Met Glu Glu Gly
                165                 170                 175

Thr Leu Gly Tyr Ala Ile Gly Gly Thr Tyr Leu Gly Pro Ala Phe Arg
            180                 185                 190

Gly Leu Lys Gly Arg Thr Leu Tyr Pro Ala Val Ser Ala Val Trp Gly
```

-continued

```
        195                 200                 205

Gln Cys Gln Val Arg Ile Arg Tyr Leu Gly Glu Arg Arg Ala Glu Pro
    210                 215                 220

His Ser Leu Leu His Leu Ser Arg Leu Cys Val Arg His Asn Leu Gly
225                 230                 235                 240

Asp Thr Arg Leu Gly Gln Val Ser Ala Leu Pro Leu Pro Pro Ala Met
                245                 250                 255

Lys Arg Tyr Leu Leu Tyr Gln
            260


<210> SEQ ID NO 49
<211> LENGTH: 28
<212> TYPE: DNA
<213> ORGANISM: Artificial Sequence
<220> FEATURE:
<223> OTHER INFORMATION: Description of Artificial Sequence:Primer

<400> SEQUENCE: 49

agctagatct ggaccctaca atggcagc                                          28


<210> SEQ ID NO 50
<211> LENGTH: 36
<212> TYPE: DNA
<213> ORGANISM: Artificial Sequence
<220> FEATURE:
<223> OTHER INFORMATION: Description of Artificial Sequence:Primer

<400> SEQUENCE: 50

agctagatct gccatcctac tcgaggggcc agctgg                                 36


<210> SEQ ID NO 51
<211> LENGTH: 128
<212> TYPE: PRT
<213> ORGANISM: Mus musculus
<220> FEATURE:
<221> NAME/KEY: UNSURE
<222> LOCATION: (1)
<223> OTHER INFORMATION: Xaa is Leu, Ile, Val, Met, Ala or Pro
<220> FEATURE:
<221> NAME/KEY: UNSURE
<222> LOCATION: (2)
<223> OTHER INFORMATION: Xaa is any amino acid residue
<220> FEATURE:
<221> NAME/KEY: UNSURE
<222> LOCATION: (3)
<223> OTHER INFORMATION: Xaa is Pro, Thr or Ser
<220> FEATURE:
<221> NAME/KEY: UNSURE
<222> LOCATION: (4)
<223> OTHER INFORMATION: Xaa is Leu, Ile, Val, Met, Ala or Pro
<220> FEATURE:
<221> NAME/KEY: UNSURE
<222> LOCATION: (5)
<223> OTHER INFORMATION: Xaa is any amino acid
<220> FEATURE:
<221> NAME/KEY: UNSURE
<222> LOCATION: (6)
<223> OTHER INFORMATION: Xaa is any amino acid
<220> FEATURE:
<221> NAME/KEY: UNSURE
<222> LOCATION: (7)
<223> OTHER INFORMATION: Xaa is Leu, Ile, Val, Met, Ala, Phe, Tyr or Trp
<220> FEATURE:
<221> NAME/KEY: UNSURE
<222> LOCATION: (8)
<223> OTHER INFORMATION: Xaa is Cys, Thr or Ser
<220> FEATURE:
<221> NAME/KEY: UNSURE
<222> LOCATION: (9)
<223> OTHER INFORMATION: Xaa is Arg, Lys or His
```

-continued

<220> FEATURE:
<221> NAME/KEY: UNSURE
<222> LOCATION: (10)
<223> OTHER INFORMATION: Xaa is any amino acid
<220> FEATURE:
<221> NAME/KEY: UNSURE
<222> LOCATION: (11)
<223> OTHER INFORMATION: Xaa is any amino acid
<220> FEATURE:
<221> NAME/KEY: UNSURE
<222> LOCATION: (12)
<223> OTHER INFORMATION: Xaa is Leu, Ile, Val, Met, Ala or Pro
<220> FEATURE:
<221> NAME/KEY: UNSURE
<222> LOCATION: (13)
<223> OTHER INFORMATION: Xaa is any amino acid
<220> FEATURE:
<221> NAME/KEY: UNSURE
<222> LOCATION: (14)
<223> OTHER INFORMATION: Xaa is any amino acid
<220> FEATURE:
<221> NAME/KEY: UNSURE
<222> LOCATION: (15)
<223> OTHER INFORMATION: Xaa is any amino acid
<220> FEATURE:
<221> NAME/KEY: UNSURE
<222> LOCATION: (16)
<223> OTHER INFORMATION: Xaa is Leu, Ile, Val, Met, Ala, Pro, Gly, Cys,
Thr or Ser
<220> FEATURE:
<221> NAME/KEY: UNSURE
<222> LOCATION: (17)..(66)
<223> OTHER INFORMATION: Xaa can be any amino acid or no amino acid.
Position 17-66 can be 1-50 amino acids.
<220> FEATURE:
<221> NAME/KEY: UNSURE
<222> LOCATION: (67)
<223> OTHER INFORMATION: Xaa is Leu, Ile, Val, Met, Ala or Pro
<220> FEATURE:
<221> NAME/KEY: UNSURE
<222> LOCATION: (68)
<223> OTHER INFORMATION: Xaa is any amino acid
<220> FEATURE:
<221> NAME/KEY: UNSURE
<222> LOCATION: (69)
<223> OTHER INFORMATION: Xaa is any amino acid
<220> FEATURE:
<221> NAME/KEY: UNSURE
<222> LOCATION: (70)
<223> OTHER INFORMATION: Xaa is Leu, Ile, Val, Met, Ala or Pro
<220> FEATURE:
<221> NAME/KEY: UNSURE
<222> LOCATION: (72)
<223> OTHER INFORMATION: Xaa is Leu, Ile, Val, Met, Ala, Pro or Gly
<220> FEATURE:
<221> NAME/KEY: UNSURE
<222> LOCATION: (73)
<223> OTHER INFORMATION: Xaa is Pro or Asn
<220> FEATURE:
<221> NAME/KEY: UNSURE
<222> LOCATION: (74)..(123)
<223> OTHER INFORMATION: Xaa can be any amino acid or no amino acid.
Position 74-123 can be 0-50 amino acids.
<220> FEATURE:
<221> NAME/KEY: UNSURE
<222> LOCATION: (124)
<223> OTHER INFORMATION: Xaa is Leu, Ile, Val, Met, Ala or Pro
<220> FEATURE:
<221> NAME/KEY: UNSURE
<222> LOCATION: (125)..(126)
<223> OTHER INFORMATION: Xaa is any amino acid
<220> FEATURE:
<221> NAME/KEY: UNSURE
<222> LOCATION: (127)
<223> OTHER INFORMATION: Xaa is Tyr or Phe
<220> FEATURE:
<221> NAME/KEY: UNSURE
<222> LOCATION: (128)
<223> OTHER INFORMATION: Xaa is Leu, Ile, Val, Met, Ala or Pro -continued

<400> SEQUENCE: 51

```
Xaa Xaa Xaa Xaa Xaa Xaa Xaa Xaa Xaa Xaa Xaa Xaa Xaa Xaa Xaa Xaa
  1               5                  10                  15

Xaa Xaa Xaa Xaa Xaa Xaa Xaa Xaa Xaa Xaa Xaa Xaa Xaa Xaa Xaa Xaa
             20                  25                  30

Xaa Xaa Xaa Xaa Xaa Xaa Xaa Xaa Xaa Xaa Xaa Xaa Xaa Xaa Xaa Xaa
         35                  40                  45

Xaa Xaa Xaa Xaa Xaa Xaa Xaa Xaa Xaa Xaa Xaa Xaa Xaa Xaa Xaa Xaa
     50                  55                  60

Xaa Xaa Xaa Xaa Xaa Xaa Pro Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Xaa Xaa Xaa
                 85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125
```

<210> SEQ ID NO 52
<211> LENGTH: 34
<212> TYPE: PRT
<213> ORGANISM: Mus musculus or Rattus norvegicus

<400> SEQUENCE: 52

```
Val Arg Pro Leu Gln Glu Leu Cys Arg Gln Arg Ile Val Ala Ala Val
  1               5                  10                  15

Gly Arg Glu Asn Leu Ala Arg Ile Pro Leu Asn Pro Val Leu Arg Asp
             20                  25                  30

Tyr Leu
```

<210> SEQ ID NO 53
<211> LENGTH: 32
<212> TYPE: PRT
<213> ORGANISM: Mus musculus

<400> SEQUENCE: 53

```
Ala Pro Thr Leu Gln His Phe Cys Arg Leu Ala Ile Asn Lys Cys Thr
  1               5                  10                  15

Gly Thr Ile Trp Gly Leu Pro Leu Pro Thr Arg Leu Lys Asp Tyr Leu
             20                  25                  30
```

<210> SEQ ID NO 54
<211> LENGTH: 33
<212> TYPE: PRT
<213> ORGANISM: Mus musculus

<400> SEQUENCE: 54

```
Val Ala Thr Leu Gln His Leu Cys Arg Lys Thr Val Asn Gly His Leu
  1               5                  10                  15

Asp Ser Tyr Glu Lys Val Thr Gln Leu Pro Gly Pro Ile Arg Glu Phe
             20                  25                  30

Leu
```

<210> SEQ ID NO 55
<211> LENGTH: 34
<212> TYPE: PRT
<213> ORGANISM: Homo sapiens -continued

<400> SEQUENCE: 55

Val Arg Pro Leu Gln Glu Leu Cys Arg Gln Arg Ile Val Ala Thr Val
1 5 10 15

Gly Arg Glu Asn Leu Ala Arg Ile Pro Leu Asn Pro Val Leu Arg Asp
20 25 30

Tyr Leu

<210> SEQ ID NO 56
<211> LENGTH: 34
<212> TYPE: PRT
<213> ORGANISM: Mus musculus

<400> SEQUENCE: 56

Val Pro Ser Leu Gln His Ile Cys Arg Met Ser Ile Arg Arg Val Met
1 5 10 15

Ser Thr Gln Glu Val Gln Lys Leu Pro Val Pro Ser Lys Ile Leu Ala
20 25 30

Phe Leu

<210> SEQ ID NO 57
<211> LENGTH: 34
<212> TYPE: PRT
<213> ORGANISM: Mus musculus

<400> SEQUENCE: 57

Pro Phe Ser Leu Gln Tyr Ile Cys Arg Ala Val Ile Cys Arg Cys Thr
1 5 10 15

Thr Tyr Asp Gly Ile Asp Gly Leu Pro Leu Pro Ser Met Leu Gln Asp
20 25 30

Phe Leu

<210> SEQ ID NO 58
<211> LENGTH: 37
<212> TYPE: PRT
<213> ORGANISM: Mus musculus

<400> SEQUENCE: 58

Pro Arg Thr Leu Leu Ser Leu Cys Arg Val Ala Val Arg Arg Ala Leu
1 5 10 15

Gly Lys Tyr Arg Leu His Leu Val Pro Ser Leu Pro Leu Pro Asp Pro
20 25 30

Ile Lys Lys Phe Leu
35

<210> SEQ ID NO 59
<211> LENGTH: 37
<212> TYPE: PRT
<213> ORGANISM: Mus musculus

<400> SEQUENCE: 59

Pro Arg Ser Leu Gln His Leu Cys Arg Cys Ala Leu Arg Ser His Leu
1 5 10 15

Glu Gly Cys Leu Pro His Ala Leu Pro Arg Leu Pro Leu Pro Pro Arg
20 25 30

Met Leu Arg Phe Leu
35

<210> SEQ ID NO 60
<211> LENGTH: 34

-continued

<212> TYPE: PRT
<213> ORGANISM: Homo sapiens

<400> SEQUENCE: 60

```
Val Arg Ser Leu Gln Tyr Leu Cys Arg Phe Val Ile Cys Gln Tyr Thr
  1               5                  10                  15

Arg Ile Asp Leu Ile Gln Lys Leu Pro Leu Pro Asn Lys Met Lys Asp
             20                  25                  30

Tyr Leu
```

<210> SEQ ID NO 61
<211> LENGTH: 37
<212> TYPE: PRT
<213> ORGANISM: Mus musculus

<400> SEQUENCE: 61

```
Pro Arg Pro Leu Ala His Leu Cys Arg Leu Arg Val Arg Lys Ala Ile
  1               5                  10                  15

Gly Lys Tyr Arg Ile Lys Leu Leu Asp Thr Leu Pro Leu Pro Gly Arg
             20                  25                  30

Leu Ile Arg Tyr Leu
         35
```

<210> SEQ ID NO 62
<211> LENGTH: 34
<212> TYPE: PRT
<213> ORGANISM: Homo sapiens

<400> SEQUENCE: 62

```
Val Lys Ser Leu Gln His Leu Cys Arg Phe Arg Ile Arg Gln Tyr Thr
  1               5                  10                  15

Arg Ile Asp His Ile Pro Asp Leu Pro Leu Pro Lys Pro Leu Ile Ser
             20                  25                  30

Tyr Ile
```

<210> SEQ ID NO 63
<211> LENGTH: 40
<212> TYPE: PRT
<213> ORGANISM: Mus musculus

<400> SEQUENCE: 63

```
Val Pro Ser Leu Thr His Leu Cys Arg Leu Glu Ile Arg Ala Ser Leu
  1               5                  10                  15

Lys Ala Glu His Leu His Ser Asp Ile Phe Ile His Gln Leu Pro Leu
             20                  25                  30

Pro Arg Ser Leu Gln Asn Tyr Leu
         35                  40
```

<210> SEQ ID NO 64
<211> LENGTH: 37
<212> TYPE: PRT
<213> ORGANISM: Mus musculus

<400> SEQUENCE: 64

```
Pro Leu Pro Leu Met Asp Leu Cys Arg Arg Ser Val Arg Leu Ala Leu
  1               5                  10                  15

Gly Lys Glu Arg Leu Gly Ala Ile Pro Ala Leu Pro Leu Pro Ala Ser
             20                  25                  30

Leu Lys Ala Tyr Leu
         35
```

-continued

<210> SEQ ID NO 65
<211> LENGTH: 34
<212> TYPE: PRT
<213> ORGANISM: Mus musculus

<400> SEQUENCE: 65

```
Pro Phe Ser Leu Gln His Ile Cys Arg Thr Val Ile Cys Asn Cys Thr
  1               5                  10                  15

Thr Tyr Asp Gly Ile Asp Ala Leu Pro Ile Pro Ser Pro Met Lys Leu
             20                  25                  30

Tyr Leu
```

<210> SEQ ID NO 66
<211> LENGTH: 37
<212> TYPE: PRT
<213> ORGANISM: Mus musculus

<400> SEQUENCE: 66

```
Pro Gln Ser Leu Leu His Leu Ser Arg Leu Cys Val Arg His Ala Leu
  1               5                  10                  15

Gly Asp Thr Arg Leu Gly Gln Ile Ser Thr Leu Pro Leu Pro Pro Ala
             20                  25                  30

Met Lys Arg Tyr Leu
         35
```

<210> SEQ ID NO 67
<211> LENGTH: 37
<212> TYPE: PRT
<213> ORGANISM: Homo sapiens

<400> SEQUENCE: 67

```
Pro His Ser Leu Leu His Leu Ser Arg Leu Cys Val Arg His Asn Leu
  1               5                  10                  15

Gly Asp Thr Arg Leu Gly Gln Val Ser Ala Leu Pro Leu Pro Pro Ala
             20                  25                  30

Met Lys Arg Tyr Leu
         35
```

<210> SEQ ID NO 68
<211> LENGTH: 34
<212> TYPE: PRT
<213> ORGANISM: Mus musculus

<400> SEQUENCE: 68

```
Leu Ser Ser Leu Lys His Leu Cys Arg Lys Ala Leu Arg Ser Phe Leu
  1               5                  10                  15

Thr Thr Tyr Gln Val Leu Ala Leu Pro Ile Pro Lys Lys Met Lys Glu
             20                  25                  30

Phe Leu
```